(12) United States Patent
de Naria et al.

(10) Patent No.: US 8,288,510 B2
(45) Date of Patent: Oct. 16, 2012

(54) ISOLATED PEPTIDES HAVING PHOSPHOLIPASE INHIBITORY ACTIVITY

(75) Inventors: Leonardo de Naria, Frederiksberg (DK); Ming Li, Beijing (CN); Christian Isak Joergensen, Bagsvaerd (DK); Kim Borch, Birkeroed (DK); Tom Anton Busk Nielsen, Chiba (JP); Jesper Vind, Vaerloese (DK)

(73) Assignee: Novozymes A/S, Bagsvaerd (DK)

( * ) Notice: Subject to any disclaimer, the term of this patent is extended or adjusted under 35 U.S.C. 154(b) by 57 days.

(21) Appl. No.: 12/433,266

(22) Filed: Apr. 30, 2009

(65) Prior Publication Data

US 2009/0275083 A1 Nov. 5, 2009

Related U.S. Application Data

(60) Provisional application No. 61/050,317, filed on May 5, 2008.

(30) Foreign Application Priority Data

Apr. 30, 2008 (EP) ..................................... 08155438

(51) Int. Cl.
- *A61K 38/00* (2006.01)
- *A61K 38/04* (2006.01)
- *C07K 5/00* (2006.01)
- *C07K 7/00* (2006.01)
- *C07K 16/00* (2006.01)
- *C07K 17/00* (2006.01)

(52) U.S. Cl. ........................................ 530/324; 530/326

(58) Field of Classification Search .................. None
See application file for complete search history.

(56) References Cited

U.S. PATENT DOCUMENTS

| 7,312,062 | B2 * | 12/2007 | Bojsen et al. | 435/196 |
| 7,632,669 | B2 * | 12/2009 | Bojsen et al. | 435/198 |
| 7,851,176 | B2 * | 12/2010 | Bojsen et al. | 435/18 |
| 2010/0291262 | A1 * | 11/2010 | Bojsen et al. | 426/18 |

FOREIGN PATENT DOCUMENTS

| WO | WO 98/26057 | 6/1998 |
| WO | WO 02/055679 | 7/2002 |

OTHER PUBLICATIONS

Hruby. Designing Peptide Receptor Agonists and Antagonists. Nature Reviews. Drug Discovery. Nov. 2002. vol. 1, pp. 847-857.*
Nagao et al, Journal of Molecular Catalysis, vol. 17, pp. 125-132 (2002).
Nagao et al, Journal Biochem, vol. 124, pp. 1124-1129 (1998).
Nagao et al, Journal of Bioscience and Bioengineering, vol. 89, No. 5, pp. 446-450 (2000).
Nagao et al, Journal Biochem, vol. 116, pp. 536-540 (1994).
Voigt et al, The Plant Journal, vol. 42, pp. 364-375 (2005).
Minning et al, Alignment Display SA862926_0009(fasta3).PRT 269 aa for WO 02/055679 (2002).

* cited by examiner

*Primary Examiner* — Marcela M Cordero Garcia
(74) *Attorney, Agent, or Firm* — Kristin J. McNamara

(57) ABSTRACT

The invention provides for isolated peptides having phospholipase inhibitory activity, polypeptides comprising phospholipase inhibitory activity and lipases capable of being inhibited by the isolated peptides and/or polypeptides comprising phospholipase inhibitory activity. The invention also relates to nucleic acid constructs, recombinant expression vectors, and recombinant host cells comprising the polynucleotides as well as methods for producing and using the peptides and the polypeptides having lipase inhibitory activity.

23 Claims, 11 Drawing Sheets

FIGURE 1

```
SEQID01     .MLLLPLLSA ITLAVASPV. ALDDYVNSLE ERAVGVTTTD FSNFKFYIQH
SEQID02     .MRLLSLLSV VTLAVASPL. SVEEYAKALD ERAVSVSTTD FGNFKFYIQH
SEQID03     .MRLLPALSV VGVASAASI. ..KSYLHAFE ERAVTVTSQN LANFKFYVQH
SEQID04     .MLLLPLLSA ITLAVASPV. ALEDYANSLE DRAVGVSTTD FGNFKFYIQH
SEQID05     .......... .......... .......... ..AVGVTSTD FTNFKFYIQH
SEQID06     .MRVLSLLSV ATFAVASPL. SVEDYAKALD ERAVAVSNGD FGNFKFYIQH
SEQID07     MHLILSILSI IAFTAAGPVP SVDENTRVLE HRALTVTTQD LSNFRFYLQH
SEQID08     MHLILSILSI IAFTTAGPVP SVDENTRVLE HRAVTVTTQD LSNFRFYLQH
SEQID09     MRSSLVLFFV SAWTALASP. .......... .IRREVSQDL FNQFNLFAQY

SEQID01     GAAAYC..NS EAAAGSKITC SNNGCPTVQG NGATIVTSFV GSKTG.IGGY
SEQID02     GAAAYC..NS EAPAGAKVTC SGNGCPTVQS NGATIVASFT GSKTG.IGGY
SEQID03     ATAAYC..NY DRAAGALISC SSN.CPSIES NAAKIVGSFG GEDTG.IAGY
SEQID04     GAAAYC..NS DASAGSKITC SNNGCPTIQS NGVTVVSSFI GSKTG.IGGY
SEQID05     GAAAYC..NS GTAAGAKITC SNNGCPTIES NGVTVVASFT GSKTG.IGGY
SEQID06     GAASYC..NS NAAAGAKITC GNNGCPTVQS NGATIVASFT GSKTG.IGGY
SEQID07     ADAAYC..NF NTAVGKPVHC SAGNCPDIEK DAAIVVGSVV GTKTG.IGAY
SEQID08     ADAAYC..NF DTAVGKPVHC SAGNCPDVEQ DAAIVVGSVV GTKTG.IGAY
SEQID09     SAAAYCGKNN DAPAGTNITC TGNACPEVEK ADATFLYSFE DSGVGDVTGF

SEQID01     VATDSARKEI VVSFRGSINI RNWLTNLDFG QEDCS.LVSG CGVHSGFQRA
SEQID02     VATDPTRKEI VVSFRGSINI RNWLTNLDFD QDDCS.LTSG CGVHSGFQNA
SEQID03     VSTDATRKEI VVSIRGSINV RNWITNLDFV WSSCSDLSSN CKAHAGFKDA
SEQID04     VATDPIRKEI VVSIRGSSNI RNWLTNLDFG QSDCS.LVSG CGVHTGFQNA
SEQID05     VSTDSSRKEI VVAIRGSSNI RNWLTNLDFD QSDCS.LVSG CGVHSGFQNA
SEQID06     VSTDSSRKEI VLSVRGSINI RNWLTNLDFG QEDCS.LTSG CGVHSGFQNA
SEQID07     VATDNARKEI VVSVRGSINV RNWITNFNFG QKTCE.LVAG CGVHTGFLDA
SEQID08     VATDNARKEI VVSVRGSINV RNWITNFNFG QKTCD.LVAG CGVHTGFLDA
SEQID09     LALDNTNKLI VLSFRGSRSI ENWIGNLNFD LKEINDICSG CRGHDGFTSS

SEQID01     WNEISSQATA AVASARKANP SFNVISTGHS LGGAVAVLAA ANLRVGGTPV
SEQID02     WNEISAAATA AVAKARKANP SFKVVSVGHS LGGAVATLAG ANLRVGGTPL
SEQID03     WDEISTAAKA AVVSAKKANP SYTIVATGHS LGGAVATLAA AYIRAAGYSV
SEQID04     WNEIANQVTA AVAKAQKANP SFKVISTGHS LGGAVAVLAG ANLRVGGTPV
SEQID05     WAEISAQASA AVAKARKANP SFKVVATGHS LGGAVATLSA ANLRAAGTPV
SEQID06     WKEISAAATA AVAKARKANP SFKVIATGHS LGGAVATLAG ANLRVGGTPV
SEQID07     WEEVAANVKA AVSAAKTANP TFKFVVTGHS LGGAVATIAA AYLRKDGFPF
SEQID08     WEEVAANIKA AVSAAKTANP TFKFVATGHS LGGAVATIAA AYLRKDGFPF
SEQID09     WRSVADTLRQ KVEDAVREHP DYRVVFTGHS LGGALATVAG ADLRGNGYDI

SEQID01     DIYTYGSPRV GNAQLSAFVS NQAGG.EYRV THADDPVPRL PPLIFGYRHT
SEQID02     DIYTYGSPRV GNTQLAAFVS NQAGG.EFRV TNAKDPVPRL PPLIFGYRHT
SEQID03     DLYTFGSPRV GNDYFANFVT SQAGA.EYRV THLDDPVPRL PPILFGYRHT
SEQID04     DIYTYGAPRV GNAQLSAFIS NQAGG.EYRI THAADPVPRL PPLIFGYRHT
SEQID05     DIYTYGAPRV GNAALSAFIS NQAGG.EFRV THDKDPVPRL PPLIFGYRHT
SEQID06     DIYTYGSPRV GNSQLAGFIS NQAGG.EFRV TNAKDPVPRL PPLVFGYRHT
SEQID07     DLYTYGSPRV GNDFFANFVT QQTGA.EYRV THGDDPVPRL PPIVFGYRHT
SEQID08     DLYTYGSPRV GNDFFTNFVT QQTGA.EYRV THGDDPVPRL PPIVFGYRHT
SEQID09     DVFSYGAPRV GNRAFAEFLT VQTGGTLYRI THTNDIVPRL PPREFGYSHS

SEQID01     TPEFWLSGGG GDKVDYTISD VKVCEGAANL GCNGGTLGLD IAAHLHYFQA
SEQID02     SPEYWLSGSG GDKIDYTIND VKVCEGAANL QCNGGTLGLD IDAHLHYFQA
SEQID03     SPEYWLSNGG ATTTTYSLSD IVVCEGIANT DCNAGTLGLD IIAHLIYFQD
SEQID04     SPEFWLSGGS GSTIDYTIDS VKVCEGAANL GCNGGTLGLD IIAHLHYFQA
```

FIGURE 1 cont.

```
SEQID05    TPEYWLSGGG  GDKVDYAISD  VKVCEGAANL  MCNGGTLGLD  IDAHLHYFQA
SEQID06    SPEYWLSGAG  GDKVDYTIND  IKVCEGAANL  KCNGGTLGLD  IDAHLHYFQE
SEQID07    SPEYWLDGGP  LDK.DYTVTE  IKVCEGMANV  MCNGGTIGLD  ILAHITYFQS
SEQID08    SPEYWLDGGP  LDK.DYTVSE  IKVCEGMANV  MCNGGTIGLD  ILAHITYFQS
SEQID09    SPEYWIKSG.  .TLVPVTRND  IVKIEGIDAT  GGNNQPNIPD  IPAHLWYFGL

SEQID01    TDACNAGGFS  WR..RYRSA.  .ESVDKRAT.  MTDAELEKKL  NSYVQMDKEY
SEQID02    TDACSAGGIS  WR..RYRSAK  RESISERAT.  MTDAELEKKL  NSYVEMDKEY
SEQID03    TSACN.TGFT  WK........  .......RDT  LSDAELEEMV  NKWAEQDVEY
SEQID04    TDACNVLSIS  WR..RYRSAS  VEGVDKRAT.  MTDAELEKKL  NSYVELDKEY
SEQID05    TDACNAGGFS  WR..RYRSAK  RESIDKRAT.  MTDAQLEAKL  NSYVAMDQEY
SEQID06    TDACSGGGIS  WRSRRYRSAK  REDISERAAP  MTDAELEKKL  NNYVEMDKEY
SEQID07    MATCAPIAIP  WK........  ........RD  MSDEELEKKL  TQYSEMDQEF
SEQID08    MATCAPIAIP  WK........  ........RD  MSDEELEKKL  TQYSEMDQEF
SEQID09    IGTCL.....  ..........  ..........  ..........  ..........

SEQID01    VKNNQARS..  ........
SEQID02    IKTHA.....  ........
SEQID03    VANLTTTASK  RWKGAVAN
SEQID04    VKNHQNRS..  ........
SEQID05    VKTHQNRT..  ........
SEQID06    VKNNAARTS.  ........
SEQID07    VKQMT.....  ........
SEQID08    VKQMT.....  ........
SEQID09    ..........  ........
```

FIGURE 2

Alpha-beta sequences

Plectasin (SEQ. ID. NO:11) PDB file 1ZFU, model 1.

```
............aaaAAAaaa......bBBb....bBBb.
GFGCNGPWDEDDMQCHNHCKSIKGYKGGYCAKGGFVCKCY
```

Monellin (SEQ. ID. NO: 12) PDB file 1IV7

```
.bBBBb...a aaAAAAAAAA AAAaaa....  ...bBBBBBB BBBBBBb... ....bBBBBB
GEWEIIDIGP FTQNLGKFAV DEENKIGQYG RLTFNKVIRP CMKKTIYENE GFREIKGYEY BBBBBb..bB BBBBBBBb.. ...bBBBBBb ......
QLYVYASDKL FRADISEDYK TRGRKLLRFN GPVPPP
```

Protegrin (SEQ. ID. NO: 13) PDB file 1KWI

```
.aaaAAAAAA AAAAAaaa.. ..bBBBBBBb .......... ....bBBBBB BBBBb.b...
ALSYREAVLR AVDRLNEQSS EANLYRLLEL DGTPKPVSF TVKETVCPRP TRQPPELCDF ........... ....bBBBBB Bb....
KENGRVKQCV GTVTLDPLDI TCNEVQ
```

Barnase (SEQ. ID. NO: 14) PDB file 1BRN

```
......aaaA AAAAaaa... ...bb.aaaa aa........ .aaaa....b BBBBBb....
AQVINTFDGV ADYLQTYHKL PDNYITKSEA QALGWVASKG NLADVAPGKS IGGDIFSNRE ........... bBBBb..... ......bBBB b....bBBb. .......bb..
GKLPGKSGRT WREADINYTS GFRNSDRILY SSDWLIYKTT DHYQTFTKIR
```

Cystatins (SEQ. ID. NO: 15) PDB file 1RN7

```
........... ....bBb... .aaaAAAAAA AAAAaaa... ...bBBBBBB BBBBBBBb..
GSASAQSRTL AGGIHATDLN DKSVQRALDF AISEYNKVIN KDEYYSRPLQ VMAAYQQIVG bBBBBBBBBB BBBb.b.... ........... .....bBBBB BBBBBb.... bBBBBBBBBB
GVNYYFNVKF GRTTCTKSQP NLDNCPFNDQ PKLKEEEFCS FQINEVPWED KISILNYKCR b.
KV
```

FIGURE 2 cont.

All-alpha sequences

Apolipoprotein E (SEQ. ID. NO: 16) PDB file 1LE4

```
.aaaAAAAAA AAAAAAaaa. .aaaaaa... .aaaAAAAAA AAAAAAAAAA AAaaa.....
QRWELALGRF WDYLRWVQTL SEQVQEELLS SQVTQELRAL MDETMKELKA YKSELEEQLT .....aaaAA AAAAAAAAAA AAAAAAAAAA AAAAAAAAAa aa.....aaa AAAAAAAAAA
PVAEETRARL SKELQAAQAR LGADMEDVRG RLVQYRGEVQ AMLGQSTEEL RVRLASHLRK AAAAAAAAAA AAAAaaa..
LRKRLLRDAD DLQKRLAVY
```

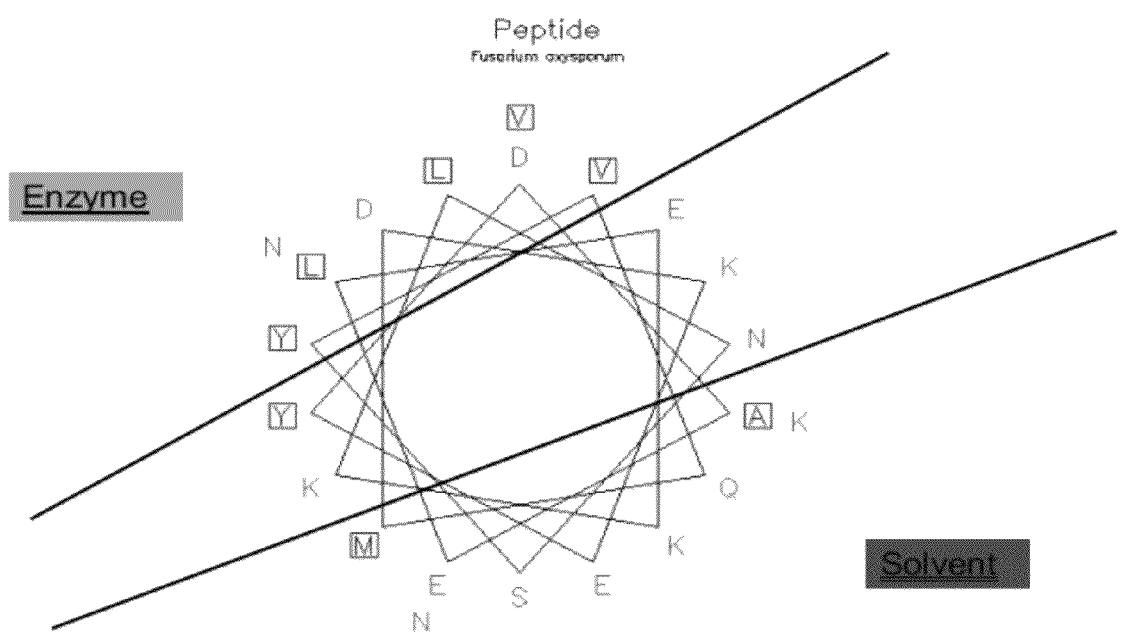

FIGURE 7

Monellin 1, MON1 variant

GEWEIIDIGP ETKLVGYVAV DEEYVIGQYG RLTFNKVIRP CMKKTIYEEN
FREIKGYEYQ LYVYASDKLF RADASRDYKT GGGKLLRFNG PVPPP

Monellin 2, MON2 variant

GEWEIIDIGP YTNLLGALAV DEENHIGQYG RLTVNKVIRP CMKKTIYEEN
FREIKGYEYQ LYVYASDKLF RADISEDYKT GGGKLLRFNG PVPPP

FIGURE 8
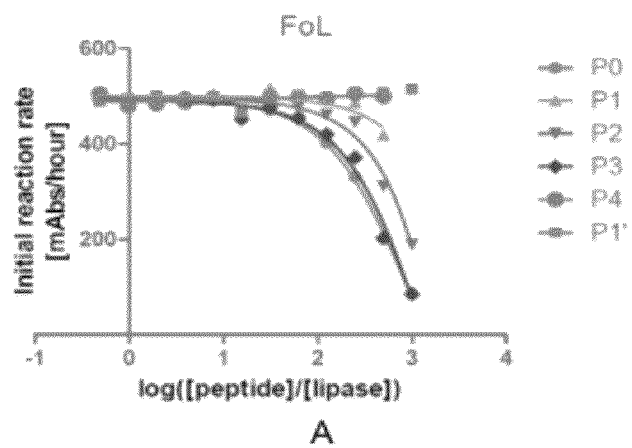
A
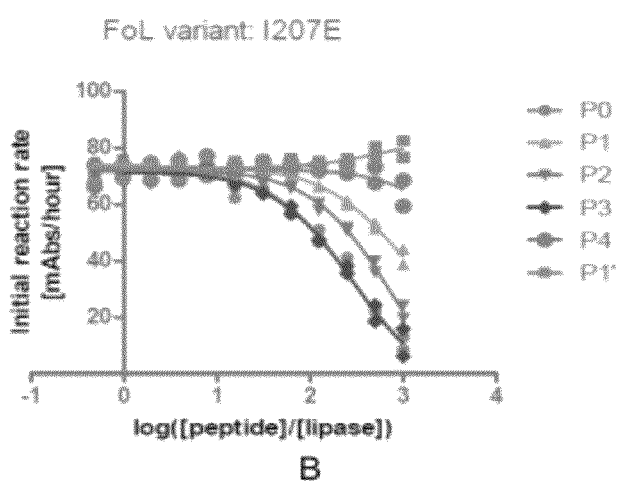
B
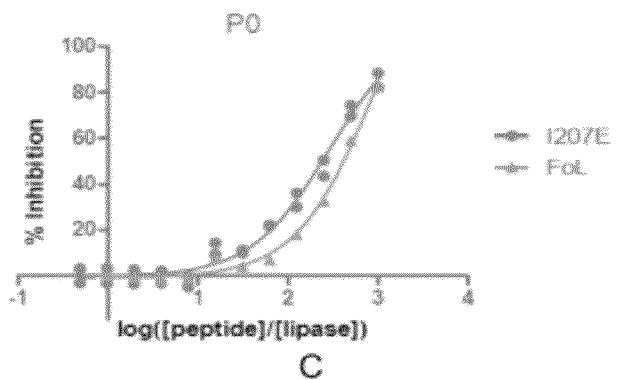
C

ISOLATED PEPTIDES HAVING PHOSPHOLIPASE INHIBITORY ACTIVITY

CROSS-REFERENCE TO RELATED APPLICATIONS

This application claims priority or the benefit under 35 U.S.C. 119 of European application no. 08155438.8 filed Apr. 30, 2008 and U.S. provisional application No. 61/050,317 filed May 5, 2008, the contents of which are fully incorporated herein by reference.

REFERENCE TO SEQUENCE LISTING

This application contains a sequence listing in computer readable form. The computer readable form is incorporated herein by reference.

FIELD OF THE INVENTION

The present invention relates to the field of lipases. In particular, it relates to isolated peptides having phospholipase inhibitory activity and isolated polynucleotides encoding the peptides. The invention also relates to nucleic acid constructs, vectors, and host cells comprising the polynucleotides as well as methods for producing and using the peptides. It furthermore relates to polypeptides having phospholipase inhibitory activity and lipases capable of being inhibited by such peptides and/or polypeptides.

BACKGROUND OF THE INVENTION

Lipases (EC 3.1.1.3) hydrolyze ester bonds of triacylglycerols and catalyze esterification and transesterification (acidolysis, alcoholysis, and interesterification) in a non-aqueous system. Some lipases, such as phospholipases, hydrolyze ester bonds in phospholipids which are polar lipids that are of great importance for the structure and function of cell membranes and are the most abundant of membrane lipids. A 26 amino acid C-terminal peptide of *Fusarium heterosporum* phospholipase was described by Nagao et al., 1998, J. Biochem. 124:1124-29 to play an important role in increasing the thermostability of the lipase without the peptide having an effect on the enzymatic activity.

In light of the broad use of lipids such as e.g. as digestives, for the production of flavours, in dough and baked products of dough, as diagnostic reagents, ingredients of detergent, as catalysts of optical resolutions, etc. it would be desirable to have a mean of controlling the enzymatic activity of lipases. Furthermore, control of the lipolytic activity is desirable from a production point of view due to the option of making enzyme productions that are reproducible regarding their enzymatic activity.

SUMMARY OF THE INVENTION

It is an object of the present invention to provide peptides having lipase inhibitory activity and polynucleotides encoding the peptides, as well as nucleic acid constructs, vectors, and host cells comprising the polynucleotides and methods for producing and using the peptides. It is furthermore an object of the invention to provide polypeptides having lipase inhibitory activity and lipases capable of being inhibited by such peptides and/or polypeptides.

The present invention relates to an isolated peptide having phospholipase inhibitory activity, selected from: (a) an isolated peptide comprising an amino acid sequence having at least 65%, at least 70%, at least 75%, at least 80%, at least 85%, at least 90%, at least 95%, at least 97%, or 100% identity to the residues 289-310 of SEQ ID NO: 1 or the residues 154-175 of SEQ ID. NO: 9; (b) an isolated peptide encoded by a polynucleotide that hybridizes under medium stringency conditions or high stringency conditions with a peptide coding sequence of SEQ ID NO: 1 or the complementary stand of said peptide coding sequence of SEQ ID NO: 1; (c) an isolated peptide encoded by a polynucleotide comprising a nucleotide sequence having at least 65%, at least 70%, at least 75%, at least 80%, at least 85%, at least 90%, at least 95%, at least 97%, or 100% identity to the residues 289-310 of SEQ ID NO: 1; or (d) an isolated peptide comprising a motif with the following amino acid sequence: $M_1T_2D_3X_4X_5L_6E_7X_8K_9L_{10}N_{11}X_{12}Y_{13}V_{14}X_{15}X_{16}D_{17}X_{18}E_{19}Y_{20}X_{21}K_{22}$ (SEQ ID NO: 32) where $X_4$, $X_5$, $X_8$, $X_{12}$, $X_{15}$, $X_{16}$, $X_{18}$, and $X_{21}$ independently may be any amino acid, wherein the size of the peptide is less than 60 amino acids (aa).

The present invention also relates to polypeptides comprising the peptide and a lipase, wherein said lipase has a phospholipase activity below 50 PHLU/mg, below 45 PHLU/mg, below 40 PHLU/mg, below 35 PHLU/mg, below 30 PHLU/mg, blow 25 PHLU/mg, below 20 PHLU/mg, below 15 PHLU/mg, below 10 PHLU/mg, below 5 PHLU/mg or below 1 PHLU/mg, and/or shows no phospholipase activity in a plate assay.

The present invention also relates to polypeptides having phospholipase inhibitory activity, wherein a parent protein with at least three solvent accessible residues of an alpha-helix localized at the surface of said protein has been amended in the alpha-helix at at least one of the solvent accessible residues corresponding to position $D_3$, $L_6$, $L_{10}$, $Y_{13}$, $V_{14}$, $D_{17}$, and $X_{21}$ and/or the edge residues corresponding to position $E_7$, $K_9$, $N_{11}$, $X_{18}$, and $Y_{20}$ of the motif.

The present invention also relates to isolated polynucleotide's, nucleic acid constructs, recombinant expression vectors, recombinant host cells comprising the peptides or the polypeptides and methods of producing the isolated peptides or polypeptides having phospholipase inhibitory activity.

The present invention also relates to use of the peptides or the polypeptides for inhibiting the enzymatic activity of a lipase upon binding of the peptides or the polypeptides to said lipase.

The present invention also relates to lipases having a phospholipase activity below 50 PHLU/mg, below 45 PHLU/mg, below 40 PHLU/mg, below 35 PHLU/mg, below 30 PHLU/mg, blow 25 PHLU/mg, below 20 PHLU/mg, below 15 PHLU/mg, below 10 PHLU/mg, below 5 PHLU/mg or below 1 PHLU/mg, and/or shows no phospholipase activity in a plate assay which is capable of being inhibited by the peptide, wherein said lipase comprises at least one alteration which independently is an insertion, a deletion or a substitution, whereby the activity of said lipase is inhibited upon binding of at least one of (a) the isolated peptide having phospholipase inhibitory activity; or (b) the peptide having phospholipase inhibitory activity comprised in the polypeptide.

BRIEF DESCRIPTION OF THE FIGURES

FIG. 1 shows the sequence alignment of phospholipases to *F. oxysporum*

FIG. 2 shows alpha-beta and all-alpha protein sequences

FIG. 3 shows the solvent accessibility of the residues from the *F. oxysporum* alpha-helix FIG. 7 shows Monellin variant 1, MON1 and Monellin variant 2, MON2 sequences FIG. 8 shows the change in initial reaction rate for various peptides

SEQUENCE LIST

Figure 4:
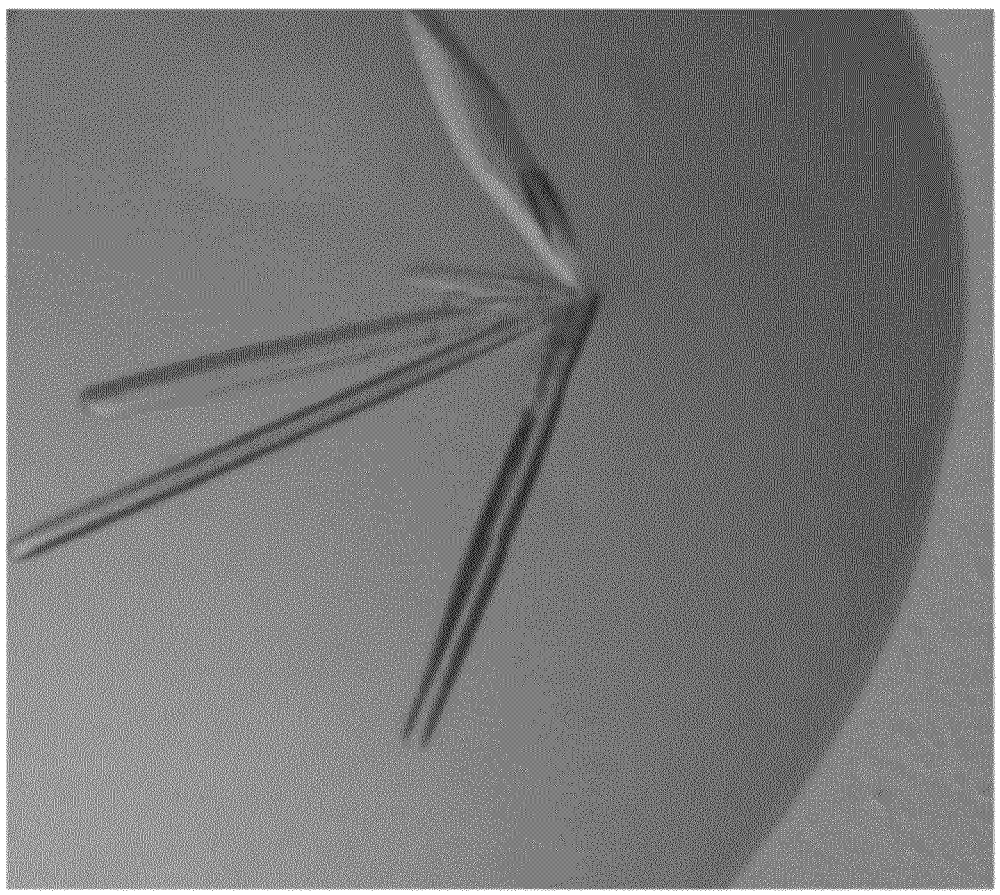
FIG. 4 shows a crystal of GZEL
Figure 5:
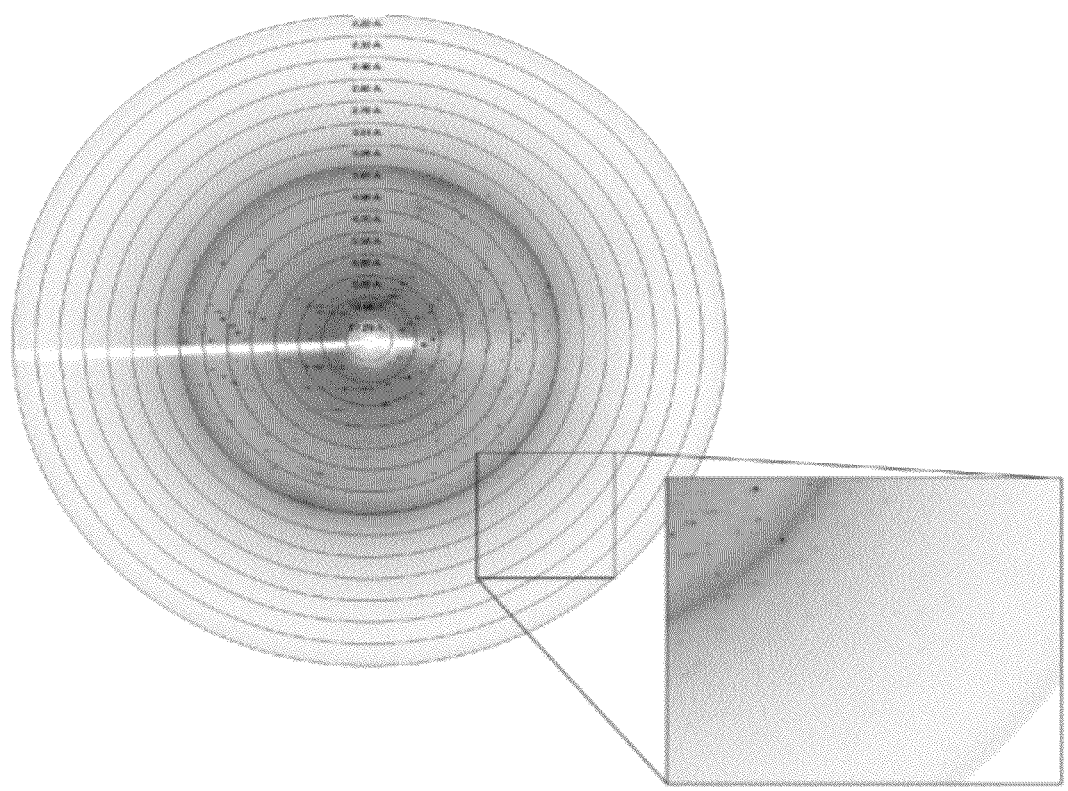
FIG. 5 shows a typical diffraction pattern of GZEL crystals

SEQ ID No. 1: *Fusarium oxysporum*, FoL
SEQ ID No. 2: *Fusarium graminearium*
SEQ ID No. 3: *Nectria* lipase 1
SEQ ID No. 4: *Nectria* lipase 2
SEQ ID No. 5: *Fusarium heterosporum*
SEQ ID No. 6: *Fusarium semitectum*.
SEQ ID No. 7: *Fusarium solani* LipC
SEQ ID No. 8: *Fusarium solani* LipD
SEQ ID No. 9: *Thermomyces lanuginosus*, TLL
SEQ ID No. 10: *Fusarium venenatum* PLA2, FVPLA2
SEQ ID No. 11: Plectasin
SEQ ID No. 12: Monellin
SEQ ID No. 13: Protegrin
SEQ ID No. 14: Barnase
SEQ ID No. 15: Cystatins
SEQ ID No. 16: Apolipoprotein E Definitions Phospholipase activity: The term "phospholipase activity" is defined herein as a phospholipolytic (EC number 3.1.1.4) activity that converts phospholipids into fatty acids and other lipophilic substances. For purposes of the present invention, phospholipase activity is determined according to the procedures described for PHLU and the plate assay described in the paragraph "Materials and Methods" below.

Phospholipase inhibitory activity: The term "phospholipase inhibitory activity" is defined herein as the activity that inhibits the phospholipase activity. The peptides of the present invention have at least 20%, at least 40%, at least 50%, at least 60%, at least 70%, at least 80%, at least 90%, at least 95%, or 100% of the phospholipase inhibitory activity of the mature polypeptide of SEQ ID NO: 1.

Isolated peptide/polypeptide: The term "isolated peptide" or "isolated polypeptide" as used herein refers to a peptide or a polypeptide respectively that is isolated from a source. In certain aspects, the peptide/polypeptide is at least 1% pure, at least 5% pure, at least 10% pure, at least 20% pure, at least 40% pure, at least 60% pure, at least 80% pure, or at least 90% pure, as determined by SDS-PAGE or HPLC. Peptide purity is determined by HPLC.

Identity: The relatedness between two amino acid sequences or between two nucleotide sequences is described by the parameter "identity". For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows: (Identical Residues×100)/(Length of Alignment–Total Number of Gaps in Alignment). For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNA-FULL (EMBOSS version of NCBI NUC4.4) substitution matrix. The output of Needle labeled "longest identity" (obtained using the –nobrief option) is used as the percent identity and is calculated as follows: (Identical Deoxyribonucleotides×100)/(Length of Alignment–Total Number of Gaps in Alignment).

Homologous sequence: The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219). The degree of homology may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45). In the present invention, corresponding (or homologous) positions in the lipase sequences of *Fusarium graminearium, Nectria* lipase, *Fusarium solani, Fusarium semitectum, Fusarium oxysporum, Fusarium heterosporum*, and *Thermomyces lanoginosus* (synonym: *Humicola lanuginose*) are defined by the alignment shown in FIG. 1. To find the homologous positions in lipase sequences not shown in the alignment, the sequence of interest is aligned to the sequences shown in FIG. 1. The new sequence is aligned to the present alignment in FIG. 1 by using the GAP alignment to the most homologous sequence found by the GAP program. The following settings are used for polypeptide sequence comparison: GAP creation penalty of 3.0 and GAP extension penalty of 0.1.

Isolated polynucleotide: The term "isolated polynucleotide" as used herein refers to a polynucleotide that is isolated from a source. In certain aspects, the polynucleotide is at least 1% pure, at least 5% pure, at least 10% pure, at least 20% pure, at least 40% pure, at least 60% pure, at least 80% pure, or at least 90% pure, as determined by agarose electrophoresis.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic or recombinant nucleotide sequence.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, pro-peptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Alteration: The term "alteration" means herein any chemical alteration of the polypeptide consisting of the mature polypeptide of SEQ ID NO: 1; or a homologous sequence thereof; as well as genetic manipulation of the DNA encoding such a polypeptide. The alteration can be a substitution, a deletion and/or an insertion of one or more (several) amino acids as well as replacements of one or more (several) amino acid side chains. In describing the amended amino acid sequences according to the invention, the following nomenclature is used for ease of reference: "Original amino acid: position:substituted amino acid(s)". According to this nomenclature, for instance the substitution of glutamic acid (E) for glycine (G) in position 195 is shown as G195E. A deletion of glycine in the same position is shown as G195*, and insertion of an additional amino acid residue such as lysine (K) is shown as G195GK. Where a specific lipase contains a "deletion" in comparison with other lipases and an insertion is made in such a position this is indicated as *36D for insertion of an aspartic acid (D) in position 36. Multiple mutations are separated by pluses, i.e.: R170Y+G195E, representing mutations in positions 170 and 195 substituting tyrosine (Y) and glutamic acid (E) for arginine (R) and glycine (G), respectively. X231 indicates the amino acid in a parent polypeptide corresponding to position 231, when applying the described alignment procedure. X231R indicates that the amino acid is replaced with R. For SEQ ID NO: 2 X is T, and X231R thus indicates a substitution of T in position 231 with R. Where the amino acid in a position (e.g. 231) may be substituted by another amino acid selected from a group of amino acids, e.g. the group consisting of R and P and Y, this will be indicated by X231R/P/Y. In all cases, the accepted IUPAC single letter or triple letter amino acid abbreviation is employed.

Whether a given amino acid residue is on the surface of the enzyme may be determined according to W. Kabsch and C. Sander (1983). Biopolymers 22, pp. 2577-2637. Dictionary of protein secondary structure: pattern recognition of hydrogen-bonded and geometrical features, for example if its solvent accessible surface as calculated with the program DSSP is over 30 Å$^2$.

DETAILED DESCRIPTION OF THE INVENTION

The inventors have found that a peptide, which may be isolated from the C-terminal of *Fusarium oxysporum* or *Fusarium graminearium* (*Gibberella zeae*) is able to bind to the lipase. They have furthermore shown that the peptide of *Fusarium oxysporum* has phospholipase inhibitory activity. It is thus suggested that a similar C-terminal peptide isolated from any suitable phospholipase such as e.g., *Nectria* lipase, *Nectria haematococca* (*Fusarium eumartii*), *Fusarium solani, Fusarium culmorum, Fusarium semitectum* and *Fusarium heterosporum*, may be used for inhibiting phospholipase activity.

In a first aspect, the invention relates to an isolated peptide having phospholipase inhibitory activity, selected from: (a) an isolated peptide comprising an amino acid sequence having at least 65%, at least 70%, at least 75%, at least 80%, at least 85%, at least 90%, at least 95%, at least 97%, or 100% identity to the residues 289-310 of SEQ ID NO: 1 or the residues 154-175 of SEQ ID. NO: 9; (b) an isolated peptide encoded by a polynucleotide that hybridizes under medium stringency conditions or high stringency conditions with a peptide coding sequence of SEQ ID NO: 1 or the complementary stand of said peptide coding sequence of SEQ ID NO: 1; (c) an isolated peptide encoded by a polynucleotide comprising a nucleotide sequence having at least 65%, at least 70%, at least 75%, at least 80%, at least 85%, at least 90%, at least 95%, at least 97%, or 100% identity to the residues 289-310 of SEQ ID NO: 1; or (d) an isolated peptide comprising a motif with the following amino acid sequence: $M_1T_2D_3X_4X_5L_6E_7X_8K_9L_{10}N_{11}X_{12}Y_{13}V_{14}X_{15}X_{16}D_{17}X_{18}E_{19}Y_{20}X_{21}K_{22}$ (SEQ ID NO: 32) where $X_4$, $X_5$, $X_8$, $X_{12}$, $X_{15}$, $X_{16}$, $X_{18}$, and $X_{21}$ independently may be any amino acid, wherein the size of the peptide is less than 60 amino acids (aa).

In another aspect, the invention relates to the peptide which has a length of less than 55 aa, less than 50 aa, less than 45 aa, less than 40 aa, less than 35 aa, or less than 30 aa.

In another aspect, the invention relates to the peptide which has a length of at least 15 aa, at least 20 aa, or at least 25 aa.

In another aspect, the invention relates to the peptide wherein said peptide has a secondary structure of an alpha-helix.

In another aspect, the invention relates to the peptide wherein the amino acid at each of the positions $X_4$, $X_5$, $X_8$, $X_{12}$, $X_{15}$, $X_{16}$, $X_{18}$, and $X_{21}$ present in the motif independently are selected whereby $X_4$ is A or E; $X_5$ is E or Q; $X_8$ is K or A; $X_{12}$ is S or N; $X_{15}$ is E, Q or A; $X_{16}$ is L or M; $X_{18}$ is K or Q; and $X_{21}$ is I or V.

The peptide of *Fusarium oxysporum* lipase (FoL) may be altered to improve or reduce the capacity of said peptide of inhibiting the lipase. Examples of such alterations are shown in Table 1.

TABLE 1

Alterations in the peptide having phospholipase inhibitory activity derived from *Fusarium oxysporum* lipase corresponding to residues 289-310 of SEQ ID NO: 1 to obtain an improved or reduced inhibition of the wild type lipase by the changed peptide.

| Original amino acid | Improved inhibition | Reduced inhibition |
|---|---|---|
| D291 | D291E | |
| L294 | | L294A |
| E295 | E295T, S | |
| K297 | K297R | |
| L298 | | L298A |
| N299 | N299D, E | |
| Y301 | Y301W | |
| D305 | | D305A |
| K306 | K306R | |
| Y308 | Y308E, D | |
| V309 | V309I, N, Q | |

In another aspect, the invention relates to the peptide which compared to SEQ ID NO: 1 comprises at least one amino acid substitution at a position corresponding to FoL residues D291; L294; E295; K297; L298; N299; Y301; D305; K306; Y308; or V309.

In another aspect, the invention relates to the peptide which compared to SEQ ID NO: 1 comprises at least one amino acid substitution corresponding to FoL residues D291E; L294A; E295T,S; K297R; L298A; N299D,E; Y301W; D305A; K306R; Y308E,D; or V309I,N,Q.

It is contemplated that alterations in the peptide in some cases may result in a change and in other cases may result in no change in the binding between peptide and lipase. A change may lead to improved or reduced binding which accordingly may result in improved or reduced inhibition of the lipase by the peptide.

The interaction between the peptide and the lipase may in addition to the alterations in the peptide also be influenced by changes in the lipase. Such alterations may contribute to an improved inhibition or a reduced inhibition. Examples of alterations in the amino acid sequence of the *Fusarium oxysporum* lipase is shown in Table 2.

TABLE 2

Alterations in the *Fusarium oxysporum* lipase corresponding to residues 1-316 of SEQ ID NO: 1 to obtain an improved or reduced inhibition of the changed lipase by the wild type peptide.

| Original amino acid | Improved inhibition | Reduced inhibition |
|---|---|---|
| L92 | L92D, E | L92W |
| R96 | | R96E, D, A |
| L203 | | L203W, K, M |
| I207 | I207D, E | |
| R211 | | R211H |
| L243 | | L243W, K |
| L250 | L250D, E | L250R |
| L252 | L252S, T | |

In another aspect, the invention relates to an isolated polynucleotide encoding the peptide.

In another aspect, the invention relates to a nucleic acid construct comprising the polynucleotide operationally linked to at least one control sequence that directs the production of the peptide in an expression host.

In another aspect, the invention relates to a recombinant expression vector comprising the nucleic acid construct.

In another aspect, the invention relates to a recombinant host cell comprising the nucleic acid construct or the recombinant expression vector.

In another aspect, the invention relates to a method of preparing the isolated peptide comprising the steps: (a) cultivating a host cell comprising the nucleic acid construct comprising the polynucleotide encoding at least one copy of the peptide under conditions conductive for production of the peptide; and (b) recovering the peptide.

Alternatively the peptides of the invention may be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The particular sequence and the manner of preparation will be determined by convenience, economics, purity required, and the like.

The peptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In another aspect, the invention relates to use of the peptide for inhibiting the enzymatic activity of a lipase upon binding of the peptide to said lipase.

Some lipases which are not classified as phospholipases and it is desirable to derive a variant with phospholipase activity from a parent lipolytic enzyme having no or very little phospholipase activity, e.g. corresponding to a ratio of phospholipase activity to lipase activity below or below 50 PHLU/mg, below 45 PHLU/mg, below 40 PHLU/mg, below 35 PHLU/mg, below 30 PHLU/mg, blow 25 PHLU/mg, below 20 PHLU/mg, below 15 PHLU/mg, below 10 PHLU/mg, below 5 PHLU/mg or below 1 PHLU/mg, and/or shows no phospholipase activity in a plate assay.

In a further aspect, the invention relates to a polypeptide comprising the peptide and a lipase, wherein said lipase has a phospholipase activity below 50 PHLU/mg, below 45 PHLU/mg, below 40 PHLU/mg, below 35 PHLU/mg, below 30 PHLU/mg, blow 25 PHLU/mg, below 20 PHLU/mg, below 15 PHLU/mg, below 10 PHLU/mg, below 5 PHLU/mg or below 1 PHLU/mg, and/or shows no phospholipase activity in a plate assay.

In another aspect, the invention relates to the polypeptide comprising a lipase which is at least 70%, at least 75%, at least 80%, at least 85%, at least 90%, at least 95%, at least 97%, or 100% identical to *Thermomyces lanuginosus* (SEQ ID NO: 9).

Lipases which do not naturally comprise a peptide having inhibitory activity may be altered for the purpose of obtaining lipase variants that are inhibited by the isolated peptide of the invention. These lipase variants may be inhibited by either of (a) the isolated peptide, (b) the peptide which is attached to such lipase variants or (c) a polypeptide comprising peptides having inhibitory activity. The binding interaction between the peptide and the lipase variants may be further modified by amending the amino acid sequence of the peptide.

*Thermomyces lanuginosus* lipase (TLL) has essentially no phospholipase activity and there is currently no information indicating that this lipase comprises any C- or N-terminal peptides to control and/or inhibit its activity. This lipase has a structure that makes it suitable for introducing amino acid alterations that will render TLL susceptible for binding of the *Fusarium oxysporum* lipase (FoL) peptide and thereby inhibiting its lipolytic activity. Examples of such alterations are disclosed in Table 3 (A). The interaction of TLL and isolated peptides of the invention may further be optimized by introduction of alterations in the peptide. Examples of alterations in the C-terminal peptide of the FoL are shown in Table 3 (B).

TABLE 3

(A) Alterations in the *Thermomyces lanuginosus* lipase (TLL) corresponding to residues 1-269 of SEQ ID NO: 9 to generate a lipase that is inhibited by the wild type FoL peptide, and (B) Alterations in the peptide having phospholipase inhibitory activity derived from *Fusarium oxysporum* lipase (FoL) corresponding to residues 288-317 of SEQ ID NO: 1 to obtain an improved inhibition of TLL.

| (A) Alterations in TLL | (B) Alterations in the FoL peptide |
|---|---|
| E87R | L294V |
| I90L | Q303N, T |
| G91T | M304A, S, G |
| I202P | K306A |
| R209L | |
| E210I | |
| T244L | |
| Substitution of the TLL residues 248-255 (NQPNIP-DI) (SEQ ID NO: 19) with the FoL residues 246-254 (NGGTLGLDI) (SEQ ID NO: 20) | |
| Substitution of the TLL residues 248-253 (NQPNIP) (SEQ ID NO: 21) with the FoL residues 247-252 (GGTLGL) (SEQ ID NO: 22) | |

It is contemplated that where TLL residues is substituted with FoL residues all the residues may be substituted, or alternatively at least one residue selected from the TLL sequence may be substituted with the corresponding residue selected from the FoL sequence according to the following alignments:

| Alignment A | Alignment B |
|---|---|
| N Q P N I P - D I_ (SEQ ID NO: 19) | N Q P N I P |
| N G G T L G L D I (SEQ ID NO: 20) | G G T L G L |

In another aspect, the invention relates to the polypeptide wherein the lipase comprises at least one alteration which independently is an insertion, a deletion or a substitution.

In another aspect, the invention relates to the polypeptide wherein the at least one alteration of the lipase comprises one or more amino acid substitutions corresponding to the residues E87R, I90L, G91T, I202P, R209L, E210I, or T244L of *Thermomyces lanuginosus* (SEQ ID NO: 9).

In another aspect, the invention relates to the polypeptide wherein the lipase comprises a substitution of the residues corresponding to 248-255 of *Thermomyces lanuginosus* (SEQ ID NO: 9) with the residues 246-254 of *Fusarium oxysporum* (SEQ ID NO: 1), or 248-253 of *Thermomyces lanuginosus* (SEQ ID NO: 9) with the residues 247-252 of *Fusarium oxysporum* (SEQ ID NO: 1).

In a further aspect, the invention relates to a polypeptide having phospholipase inhibitory activity, wherein a protein with at least three solvent accessible residues of an alpha-helix localized at the surface of said protein has been amended in the alpha-helix at at least one of the solvent accessible residues corresponding to position $D_3$, $L_6$, $L_{10}$, $Y_{13}$, $V_{14}$, $D_{17}$, and $X_{21}$ and/or the edge residues corresponding to position $E_7$, $K_9$, $N_{11}$, $X_{18}$, and $Y_{20}$ of the motif of the invention as described.

In another aspect, the invention relates to the polypeptide wherein the protein has an amino acid sequence which is at least 70%, at least 75%, at least 80%, at least 85%, at least 90%, at least 95%, at least 97%, or 100% identical to the Plectasin (SEQ ID NO: 11); Monellin (SEQ ID NO: 12); Protegrin (SEQ ID NO: 13); Barnase (SEQ ID NO: 14); Cytostatins (SEQ ID NO: 15); or Apolipoprotein E (SEQ ID NO: 16).

Proteins suitable for generating a polypeptide having phospholipase inhibitory activity must comprise at least one alpha-helix which is exposed to the surface of the protein. It is necessary that the some of the amino acids comprised in the alpha helix are solvent accessible to be able to bind to a lipase and exert its inhibitory effect. The size of the alpha helix may be 22 amino acids or 20, 18, 16, 14, 12, or 10 amino acids. In addition to the at least one alpha-helix other secondary structure elements such as e.g. beta-strands may be present. Based on their secondary structures three main groups of proteins may be defined: an All-alpha group, an all beta-group and an Alpha-beta group. FIG. 2 shows examples of proteins belonging to the Alpha-beta group such as e.g. plectasin, monellin, protegrin, barnase, and cystatins and examples of proteins belonging to the All-alpha group such as apolipoprotein E. The amino acid sequence are shown in the second line and the first line refers to the secondary structure as calculated by the programme Dictionary of Secondary Structure Prediction (DSSP) where a/A indicate alpha-helices and b/B indicate beta-strands.

The alpha-helix of the phospholipase inhibitory peptide may be superimposed and aligned with the alpha-helix of the selected protein (underlined) in a two-step procedure as illustrated below for monellin:

Select the direction, either parallel or anti-parallel of the sequences to be aligned, ----→ Phospholipase inhibitory peptide ----→ Monellin (parallel)

←---- Monellin (Anti-parallel)

Once the direction is selected there are several possibilities of aligning the sequences of the alpha-helices. The most optimal alignment is the one comprising the maximum length in common and the minimum number of troubles (clashes).

----→ Phospholipase inhibitory peptide

----→ Monellin

----→ Monellin

----→ Monellin

After identifying the most optimal alignment, modifications in the protein alpha-helix may be made to change the amino acid residues to the alpha-helix of the phospholipase inhibitory peptide. An example is shown in FIG. 3 wherein the peptide of Fol is drawn to illustrate which part of the alpha-helix and which amino acid residues are facing the enzyme and which is facing the solvent. In particular, residues that are facing the surface of the scaffold protein and are solvent accessible and accordingly may be involved in the contact and in the inhibition of a lipase must be considered. These residues are corresponding to position $D_3$, $L_6$, $L_{10}$, $Y_{13}$, $V_{14}$, $D_{17}$, and $X_{21}$ of the motif: $M_1T_2D_3X_4 X_5L_6E_7 X_8K_9L_{10} N_{11}X_{12}Y_{13}V_{14}X_{15}X_{16}D_{17}X_{18}E_{19}Y_{20}X_{21}K_{22}$. Optionally, residues that are found at the edge of the surface of the protein and are potentially solvent accessible and accordingly may be involved in the contact and in the inhibition of a lipase should also be considered. These residues are corresponding to position $E_7$, $K_9$, $N_{11}$, $X_{18}$, and $Y_{20}$ of the motif.

Finally, parts outside the alpha-helix in the protein are analyzed to identify if there are other and/or new clashes that may affect binding of the alpha-helix of the scaffold protein to the lipase or affect the accommodation of the alpha-helix within the protein. Such residues are then optionally changed to maximize the phospholipase inhibitory effect. These are the mutations outside the helix.

In another aspect, the invention relates to a method of preparing the polypeptide of the invention comprising a step of attaching the peptide to a lipase, wherein said lipase has a phospholipase activity below 50 PHLU/mg, below 45 PHLU/mg, below 40 PHLU/mg, below 35 PHLU/mg, below 30 PHLU/mg, blow 25 PHLU/mg, below 20 PHLU/mg, below 15 PHLU/mg, below 10 PHLU/mg, below 5 PHLU/mg or below 1 PHLU/mg, and/or shows no phospholipase activity in a plate assay.

In another aspect, the invention relates to a method of preparing a polypeptide comprising the steps: (a) selecting a protein having an alpha-helix localized at the surface of the protein whereby at least three, at least four, at least five, or at least six residues of said alpha-helix is solvent accessible; (b) aligning the alpha-helix of the protein with the peptide; (c) identifying the residues in the alpha-helix of the protein that are solvent accessible corresponding to position $D_3$, $L_6$, $L_{10}$, $Y_{13}$, $V_{14}$, $D_{17}$, and $X_{21}$ of the motif; (d) altering at least one, at least two, at least three, at least four, at least five, at least six or at least seven of the amino acids in the protein identified in step (c); (e) testing the polypeptide for phospholipase inhibitory activity; (f) selecting the polypeptide having phospholipase inhibitory activity; and (g) producing the polypeptide selected in (f).

In another aspect, the invention relates to the method further identifying in step (c) the residues in the alpha-helix of the protein that are potentially solvent accessible corresponding to position $E_7$, $K_9$, $N_{11}$, $X_{18}$, and $Y_{20}$ of the motif.

In another aspect, the invention relates to the method further comprising a step of making at least one alteration at one or more positions in the protein.

In another aspect, the invention relates to use of the polypeptide, for inhibiting the enzymatic activity of a lipase upon binding of the peptide comprised in the polypeptide to said lipase.

In a further aspect, the invention relates to a lipase having a phospholipase activity below 50 PHLU/mg, below 45 PHLU/mg, below 40 PHLU/mg, below 35 PHLU/mg, below 30 PHLU/mg, blow 25 PHLU/mg, below 20 PHLU/mg, below 15 PHLU/mg, below 10 PHLU/mg, below 5 PHLU/mg or below 1 PHLU/mg, and/or shows no phospholipase activity in a plate assay which is capable of being inhibited by the peptide, wherein said lipase comprises at least one alteration which independently is an insertion, a deletion or a substitution, whereby the activity of said lipase is inhibited upon binding of at least one of (a) the isolated peptide having phospholipase inhibitory activity; or (b) the peptide having phospholipase inhibitory activity comprised in the polypeptide.

In another aspect, the invention relates to the lipase wherein said lipase is at least 70%, at least 75%, at least 80%, at least 85%, at least 90%, at least 95%, at least 97%, or 100% identical to *Thermomyces lanuginosus* (SEQ ID. NO: 9).

In another aspect, the invention relates to the lipase wherein the at least one alteration is a substitution corresponding to the residues L92; R96; L203; I207; R211; L243; L250; or L252 of *Thermomyces lanuginosus* (SEQ ID NO: 9).

In another aspect, the invention relates to the lipase wherein the at least one alteration is a substitution corresponding to the residues L92D,E,W; R96E,D,A; L203W,K,M; I207D,E; R211 H; L243W,K L250D,E,R; and L252S,T of *Thermomyces lanuginosus* (SEQ ID NO: 9).

Materials and Methods

Phospholipase Activity (PHLU)

Phospholipase activity (PHLU) is measured as the release of free fatty acids from lecithin. 50 µl 4% L-alpha-phosphatidylcholine (plant lecithin from Avanti), 5 mM $CaCl_2$ in 50 mM HEPES, pH 7 is added 50 µl enzyme solution diluted to an appropriate concentration in 50 mM HEPES, pH 7. The samples are incubated for 10 min at 30° C. and the reaction stopped at 95° C. for 5 min prior to centrifugation (5 min at 7000 rpm). Free fatty acids are determined using the NEFA C kit from Wako Chemicals GmbH; 25 µl reaction mixture is added 250 µl Reagent A and incubated 10 min at 37° C. Then 500 µl Reagent B is added and the sample is incubated again, 10 min at 37° C. The absorption at 550 nm is measured using an HP 8452A diode array spectrophotometer. Samples are run in at least in duplicates. Substrate and enzyme blinds (pre-heated enzyme samples (10 min at 95° C.)+substrate) are included. Oleic acid is used as a fatty acid standard. 1 PHLU equals the amount of enzyme capable of releasing 1 µmol of free fatty acid/min at these conditions. Specific phospholipase activity (PHLU/mg) is calculated at the phospholipase activity (PHLU) per amount protein (mg).

Plate assay: 50 ml 2% agarose is dissolved by heating in purified water for 5 minutes and subsequently cooled to 60-63° C. 50 ml 2% plant L-alpha-Phosphatidylcholine 95% in 0.2M NaOAc, 10 mM $CaCl_2$, pH 5.5 at 60° C. in 30 min. is blended for 15 sec. with ultrathorax. Equal volumes of 2% agarose and 2% Lecithin are mixed. 250 µl 4 mg/ml crystal violet in purified water is added as indicator. The mixture is poured into appropriate petri dishes (e.g. 30 ml in 14 cm Ø dish), and appropriate holes (3-5 mm) are made in the agar for application of enzyme solution. The enzyme sample is diluted to a concentration corresponding to $OD_{280}=0.5$ and 10 microliter and applied into holes in the agarose/lecithin-matrix. Plates are incubated at 30° C. and reaction zones in the plates are identified after approximately 4-5 hours and/or after approximately 20 hours incubation. The *Humicola lanuginosa* lipase is used as a control, and the presence of a larger clearing zone than the control is taken as a positive result for phospholipase activity.

EXAMPLES

The present invention is further described by the following examples that should not be construed as limiting the scope of the invention.

Example 1

GZEL Crystal Structure

Protein expression and purification: The *Gibberella zeae/Fusarium graminearum* lipase (GZEL) gene was amplified by PCR and further confirmed by sequencing. Then the GZEL gene was expressed in yeast with a significant protein band shown on SDS-PAGE after Comassie staining. And the activity was detected against the olive oil/Bright Green plate at pH 7. The positive candidate clones showed dark green zones around the holes.

The culture supernatant separated from cells by centrifugation and the pH of supernatant was adjusted to pH 7.0. The supernatant was then filtrated and applied into Ni-Sepharose FF equilibrated with 25 mM Tris-HCl at pH 7.0 with 0.3 M NaCl. The target protein was eluted by imidazole at a gradient from 0M to 1M. Fractions from the column were analyzed for activity. Fractions with enzyme activity were pooled and concentrated. Then the samples were loaded into a gel filtration column Superdex 75 equilibrated by 25 mM Tris-HCl at pH 8.0 with 0.15 M NaCl. The eluted active lipase was concentrated and dialyzed with 25 mM Tris-HCl at pH 8.0. The lipase was checked by SDS-PAGE and the pure fractions were prepared for crystallization trails.

Crystallization: The freshly prepared protein was concentrated to 10 mg/ml and crystallized by the hanging drop vapor diffusion method at 291K. The initial crystallization conditions were screened using several Crystal Screen Kits (Hampton Research screen kit 1 and 2, Index screen kit, MembFac screen kit). One microliter of protein solution was mixed with 1 microliter of reservoir solution and equilibrated against 200 microliter of reservoir solution. Small crystals could be found in many different conditions within three days. Many of the crystals are hollow sticks and have poor diffraction quality. Fine shaped and good quality crystals were selected from the condition with 0.2 M Ammonium Sulfate, 0.1 M Bis-Tris (pH 5.5), 25% w/v PEG3350 within 2-4 days (see FIG. 3), which can reach their final volumes of about 50*50*200 micrometer with the space group $P2_12_12_1$.

Data collection and processing: A 2.8 Å resolution set of diffraction data sets were collected at 100K from a single GZEL derivative crystal using an in-house Rigaku MM-007 generator and a Mar345dtb detector. The beam was focused by osmic mirrors. For a more detailed analysis, flash-cooled crystals were used. Crystals were immersed in cryoprotectant for 5-10 sec., picked up with a loop and flash-cooled in a stream of nitrogen gas cooled to 100K. The cryoprotectant was prepared by adding 25% glycerol to the mother liquor reservoir. The crystal form belongs to space group $P2_12_12_1$ (a=78.4, b=91.0, c=195.8, $\alpha=\beta=\gamma=90°$) with four GZEL molecules per asymmetric unit and a VM of 2.6 Å3 Da-1 (Matthews 1968), corresponding to a solvent content of 48%. Processing of diffraction images and scaling of the integrated intensities were performed using the HKL2000 software package (Otwinowski et al. 1997).

Results: Initially, although we have obtained dozens of GZEL crystals in many conditions of the screening kits, they are unsuitable for X-ray diffraction. Many of the crystals are hollow fibre. Therefore, further crystallization optimization was performed and better crystals were obtained in the following condition: 0.2 M Ammonium Sulfate, 0.1 M Bis-Tris, pH 5.5, 25% w/v PEG3350. Drops containing 2 µl protein solution and 2 µl of reservoir solution were equilibrated against 200 microliter of reservoir solution. Crystals grown from the optimized reservoir solution (0.2 M Ammonium Sulfate, 0.1 M Bis-Tris, pH 5.5, 25% w/v PEG3350) were more suitable for X-ray diffraction and diffracted to 2.8 Å. A set of data was subsequently collected from one single crystal (see FIG. 4 showing a typical diffraction pattern of GZEL crystals. The exposure time was 300 seconds, detector distance was 150 millimeter and oscillation range per frame was 10). There are four molecules per asymmetric unit. Complete datacollection statistics are given in Table 4. The structure of GZEL has been determined and is disclosed in appendix 1.

References: Matthews, B. W., Solvent content of protein crystals. J. Mol. Biol., 1968. 33: p. 491-497. Otwinowski, Z. and W. Minor, Processing of X-ray diffraction data collected in oscillation mode, in Macromolecular Crystallography, part A, C. W. Carter Jr. and R. M. Sweet, Editors. 1997, Academic Press. p. 307-326.

TABLE 4

Data collection and processing statistics. $R_{merge} = 100\Sigma|I_i - <I>|/\Sigma I_i$, where $I_i$ is the intensity of the observation.

| | |
|---|---|
| Space group | $P2_12_12_1$, |
| Unit-cell parameters | a = 78.4 Å, b = 91.0 Å, c = 195.8 Å, |
| | $\alpha = \beta = \gamma = 90°$. |
| Resolution range (Å) | 50.0-2.8 (2.9-2.8)$^a$ |
| Total reflections | 326163 |
| Unique reflections | 34080 |
| Average I/σ (I) | 9.6 (8.0)$^a$ |
| $R_{merge}$ (%) | 10.1 (48.0)$^a$ |
| Data completeness$_{(\%)}$ | 97.7 (92.3)$^a$ |

Example 2

Peptide Binding to GZEL

There are four GZEL-peptide complexes in the asymmetric unit of the crystal structure. The four complexes were refined independently from each other. They constitute four different entities. In this four different complexes the peptide sits in exactly the same way with respect to the lipase core domain, see Table 5 below. This provides another set of evidence for a specific binding of the peptide to the lipase core.

TABLE 5

GZEL-peptide C_alpha root mean square deviation upon optimal superimposion. An in-house program designed superimpose optimally two sets of protein atomic coordinates was used on each of the four GZEL-peptide pairs. The entries on the table show the residual (root mean square deviation) of the C_alpha atoms upon superimposion in Angstroms.

| | A | B | C | D |
|---|---|---|---|---|
| A | 0.00 | 0.44 | 0.52 | 0.51 |
| B | 0.44 | 0.00 | 0.49 | 0.47 |
| C | 0.52 | 0.49 | 0.00 | 0.48 |
| D | 0.51 | 0.47 | 0.48 | 0.00 |

Example 3

Preparation of FoL Devoid of Peptide for Binding Experiments

FoL was purified from a Pilot fermentation LVF 57 UF concentrate PPW6523. PPW6523 was 0.22 µm filtered and loaded onto a butyl-sepharose fast flow column, washed with 1.8M $NH_4$acetate and eluted with MilliQ $H_2O$. Datasheet on purified FoL: 2003-04317-01. On an isoelectric focusing gel IEF pH 3-10 (Novex precast) 20070628 the sample gave a single band. N-terminal sequencing of the band showed only one sequence—the expected FoL N-terminus showing that C-terminal peptide was not bound.

Example 4

Inhibition Assay

The substrate used for these experiments was para-nitropenyl (p-NP) butyrate purchased from Sigma Aldrich. A substrate stock solution was prepared by adding 18 μL of p-NP Butyrate to 1 ml of 2-propanol giving a 100 mM stock solution. The working solution was prepared by diluting 10 μL stock solution in final volume of 1 ml 50 mM Tris pH 7 buffer. 45 μL of the FoL 1 mg/ml in 50 mM Tris buffer pH 7 was preincubated with two concentrations of the peptide and control was carried out in absence of peptide using the same buffer. After pre-incubation for 5 minutes at room temperature the enzyme solution was diluted in 50 mM Tris pH 7 buffer and 100 μL diluted enzyme solution was mixed with the 100 μL substrate solution and reaction was followed in microtiter plate spectrophotometer under constant shaking at room temperature. Table 6 below shows the color development over time monitored at $A_{405}$ (every 30 sec. for 10 minutes) of p-nitrophenol, one of the degradation products of p-NP butyrate, liberated by the enzyme which was preincubated with the peptide in two different concentrations and a control which was treated exactly the same way in the absence of peptide.

TABLE 6

Data for the activity of FoL enzyme with and without peptide. The activity of FoL demonstrated that addition of the peptide caused an inhibition of the activity, determined as a reduced color development. FoL with peptide gave the lowest color development, whereas FoL with 5x diluted peptide had a higher color development, whereas the control sample, FoL with water, had the highest color development.

| Time (seconds) | 45 μL FoL + 5 μL peptide | 45 μL FoL + 5 μL 5x diluted peptide | 45 μL FoL + 5 μL MilliQ water |
| --- | --- | --- | --- |
| 0   | 0.03 | 0.05 | 0.06 |
| 30  | 0.18 | 0.12 | 0.19 |
| 60  | 0.22 | 0.23 | 0.28 |
| 90  | 0.29 | 0.32 | 0.38 |
| 120 | 0.38 | 0.42 | 0.49 |
| 150 | 0.45 | 0.52 | 0.59 |
| 180 | 0.54 | 0.60 | 0.70 |
| 210 | 0.62 | 0.69 | 0.81 |
| 240 | 0.70 | 0.79 | 0.91 |
| 270 | 0.77 | 0.88 | 1.00 |
| 300 | 0.83 | 0.96 | 1.08 |
| 330 | 0.89 | 1.03 | 1.15 |
| 360 | 0.95 | 1.09 | 1.21 |
| 390 | 1.00 | 1.15 | 1.27 |
| 420 | 1.06 | 1.22 | 1.33 |
| 450 | 1.10 | 1.26 | 1.37 |
| 480 | 1.15 | 1.31 | 1.41 |
| 510 | 1.19 | 1.36 | 1.45 |
| 540 | 1.23 | 1.40 | 1.49 |
| 570 | 1.27 | 1.43 | 1.52 |
| 600 | 1.30 | 1.47 | 1.55 |

Example 5

Isoelectric Point Measurements

Figure 6:
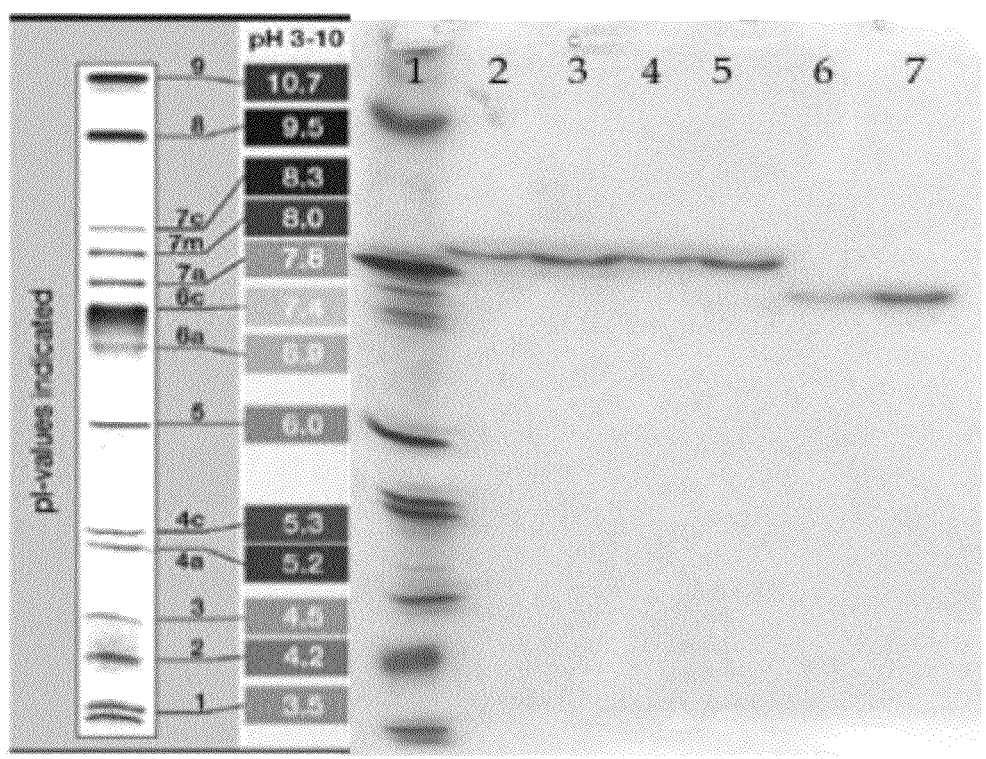
FIG. 6 shows a peptide induced change of the FoL PI

The samples prepared in Example 4 were loaded to a Nowex gel IEF 3-10. Lane 1: Marker. Lane 2: Sample 1 (10 μL). Lane 3: Sample 1 (20 μL). Lane 4: Sample 2 (10 μL). Lane 5: Sample 2 (20 μL). Lane 6: Sample 3 (10 μL). Lane 7: Sample 3 (20 μL). A photo of the gel is shown in FIG. 6. The gel revealed that addition of the peptide caused a change in pI due to bands (lane 6 and 7) which had a lower pI than samples with peptide (lane 2-5). This is a clear indication of binding of the peptide to the enzyme.

Example 6

Activity of TLL and FoL in a Lecithin Plate Assay

A lecithin plate without Triton-X 100 was prepared as described in the Materials and Methods. The same amounts based on $OD_{A280}$ of purified TLL and FoL was added to the holes: TLL to the two top holes, FoL to the two bottom holes; left holes (lower concentration, $OD_{A280}$ equal to 0.2); right holes (higher concentration, $OD_{A280}$ equal to 0.5). After 20 hours of incubation FoL exhibited a 7/10 mm clearing zone at the lower/higher concentration. TLL did not show a clearing zone.

TABLE 7

Lecithin plate assay. Clearing zone diameter after 20 hours incubation measured in mm (milimeters). The enzymes were dosed equally based on $OD_{A280}$.

| $OD_{A280}$ | TLL | FoL |
| --- | --- | --- |
| 0.2 | 0 mm | 7 mm |
| 0.5 | 0 mm | 10 mm |

Example 7

How to Modify the Alpha-Helix in Monellin to Generate a Polypeptide Having Phospholipase Inhibitory Activity The recently solved structure of the *Fusarium graminearum*, also known as *Gibberella zeae*, phospholipase has shown that the C-terminal peptide normally cleaved for maturation of the enzyme was present in the structure. This peptide adopts an alpha-helical structure and packs against the catalytic domain of the phospholipase. The peptide has been shown to inhibit the phospholipase activity against small esters.

Monellin is a sugar tasting protein from the African serendipity berry. The structure of Monellin consists of a long partially exposed alpha-helix packed perpendicularly against a 5-stranded beta-sheet. The presence of the solvent accessible alpha-helix makes the protein well suited for the purpose of modifying the alpha-helix in the attempt of transferring the inhibitory properties of the C-terminal peptide of the *Fusarium oxysporum* lipase (FoL), which is a very close homologue of *Fusarium graminearum* lipase (FGL). Two different Monellin variants were designed as FoL inhibitors.

Variant summary: Two variants were found after analyzing all the possible ways of superimposing the C-terminal peptide alpha-helix of FoL onto the alpha-helix of Monellin. In selection of the variants the visual inspection focused on; a) maximizing the alignment of the alpha-helix of Monellin with the C-terminal peptide residues that interact with the catalytic domain of the lipase; and b) minimizing the conflicts of other parts of Monellin with the catalytic domain. Two different possibilities of superimposing the helices either matching the N to C-terminal direction (parallel) or inverting it (anti-parallel) were identified.

Sequence/structure: The sequence of Monellin used on this study is shown in FIG. 2 (second line) together with the secondary structure (first line) as calculated by the program Dictionary of Secondary Structure Prediction (DSSP) published by W. Kabsch and C. Sander, Biopolymers (1983) 22:2577-2637. The b/B refer to beta-strands, the a/A refer to alpha-helices. The RCSB PDB file used for the superpositions was 1IV7.

Variants: Two Monellin variants were the result of this study. They are described in what follows.

MON1 variant: When the superposition where of the lipase peptide alpha-helix is aligned parallel to the Monellin alpha-helix the amino acid substitutions F11E+Q13K+N14L+L15V+K17Y+F18V+N24Y+K25V+I74A+E77R+R82G+R83G are to be made. These substitutions will mimic the interaction of the peptide with the lipase catalytic domain and eliminate possible conflicts of the remaining parts of the molecules. The complete sequence of MON1 is shown in FIG. 6 where the substituted amino acids are boldfaced in red. It may be necessary to change P10 into a leucine (P10L) but it is foreseen that this change will be detrimental to the overall stability of Monellin.

MON2 variant: When the superposition of the lipase peptide alpha-helix is aligned anti-parallel to the Monellin alpha-helix the amino acid substitutions F11Y+Q13N+N14L+K17A+F18L+K25H+F34V+R81G+R84G are to be made. These substitutions will mimic the interaction of the lipase peptide with the lipase catalytic domain and eliminate possible conflicts of the remaining parts of the molecule. The complete sequence of MON2 is shown in FIG. 7 where the substituted amino-acids are boldfaced in red.

Example 8

Inhibitory Effect of Various Peptides on FoL Wildtype and FoL Variant I207E

Enzyme assay: The substrate used for these experiments was para-nitropenyl (p-NP) butyrate (N9876 Sigma Aldrich). A substrate stock solution was prepared by adding 18 μL of p-NP butyrate to 1 ml of 2-propanol giving a 100 mM stock solution. The working solution was prepared by diluting 500 μL stock solution in final volume of 50 mL 500 mM phosphate pH 7, 0.4% triton X-100. 40 μL of the enzyme 38 ng/mL in 500 mM phosphate pH 7, 0.4% triton X-100, was pre-incubated with 20 μL of peptide having various concentrations giving peptide/lipase ratios from 0.5 to 1000 increasing with a factor of 2 through 12 steps. An enzyme substrate blank containing 60 μL was included. After pre-incubation in minimum 15 minutes, 100 μL of substrate was added and the reaction was followed in microtiter plate spectrophotometer (SPECTRAmax PLUS 384 from Molecular Devices) after an initial shaking (5 sec.) at room temperature. Colour development over time was monitored at $A_{405}$ (every 20 sec. for 30 minutes), measuring p-nitrophenol, one of the degradation products of p-NP butyrate, liberated by the hydrolysis.

Initial reaction rates (determined as the linear initial slope of $A_{405}$ plotted against time) were plotted against the logarithm to the inhibitor/lipase ratio. From the following model $IC_{50}$ values were determined:

$$v_0 = v_{max} + \frac{v_{min}}{1 + 10^{\frac{[peptide]}{[enzyme]} - IC_{50}}}$$

$v_0$ is the initial reaction rate, $v_{max}$ is the maximum rate, $v_{min}$ is the minimum reaction rate and $IC_{50}$ is the half maximal inhibitory concentration. GraphPad Prism (v.5.00, Mar. 12, 2007) from GraphPad Software, Inc. was used for regression.

% Inhibition is the percentage reduction in initial reaction rate where 0% inhibition is defined as the initial reaction rate without peptide.

TABLE 8

Peptide sequences tested. Synthetic peptides HPLC purified (>85% purity) were obtained from TAG Copenhagen A/S.

| Name | Design | Sequence |
|---|---|---|
| P0 | Wildtype | ATMTDAELEKKLNSYVQMDKEYVKNNQARS (SEQ ID NO: 23) |
| P1 | D291E | ATMTEAELEKKLNSYVQMDKEYVKNNQARS (SEQ ID NO: 24) |
| P2 | E295T | ATMTDAELTKKLNSYVQMDKEYVKNNQARS (SEQ ID NO: 25) |
| P3 | K297R | ATMTDAELEKRLNSYVQMDKEYVKNNQARS (SEQ ID NO: 26) |
| P4 | Y308E | ATMTDAELEKKLNSYVQMDKEEVKNNQARS (SEQ ID NO: 27) |
| P1' | D305A | ATMTDAELEKKLNSYVQMAKEYVKNNQARS (SEQ ID NO: 28) |

TABLE 9

The determined $IC_{50}$ values

| Name | P0 | P1 | P2 | P3 | P4 | P1' |
|---|---|---|---|---|---|---|
| FOL wt | 913 (555-1501) | Very low inhibition* | Very low inhibition* | 1561 (644-3782) | No inhibition | No inhibition |
| FOL I207E variant | 287[1] (208-397)[2] | 1009 (440-2314) | 782 (505-1210) | 301 (214-403) | Very low inhibition* | No inhibition |

[1]$IC_{50}$ value (half maximal inhibitory concentration).
[2]95% Confidence interval.
*IC50 > highest peptide excess tested Results: FIG. 8 shows how the initial reaction rates are altered by various peptide concentrations (A & B). Assuming 0% inhibition for the lowest concentration of peptide it is clear from (C) when plotting the curves for P0 that the FoL variant: I207E was better at binding the peptide than the wildtype enzyme.

Example 9

Inhibitory Effect of Various Peptides on TLL Wildtype and TLL Variants

Enzyme assay: As described above. Peptides P11 and P13 were tested in concentrations giving peptide/lipase ratios from 5 to 5000 increasing with a factor of 2 through 10 steps. Peptide P12 was tested in concentrations giving peptide/lipase ratios from 6 to 6000 increasing with a factor of 2 through 10 steps.

TABLE 10

Peptide sequences tested

| Name | Design | Sequence |
|---|---|---|
| P11 | L294V | ATMTDAEVEKKLNSYVQMDKEYVKNNQARS (SEQ ID NO: 29) |
| P12 | Q303N | ATMTDAELEKKLNSYVNMDKEYVKNNQARS (SEQ ID NO: 30) |
| P13 | K306A | ATMTDAELEKKLNSYVQMDAEYVKNNQARS (SEQ ID NO: 31) |

TABLE 11

IC$_{50}$ values for TLL variant N248G/Q249G/P250T/N251L/I252G/P253L

| TLL variant | P11 | P12 | P13 |
|---|---|---|---|
| N248G/Q249G/P250T/N251L/I252G/P253L | Very low inhibition* | 1688[1] (496-5745)[2] | 1716 (1403-2098) |

Figure 9:
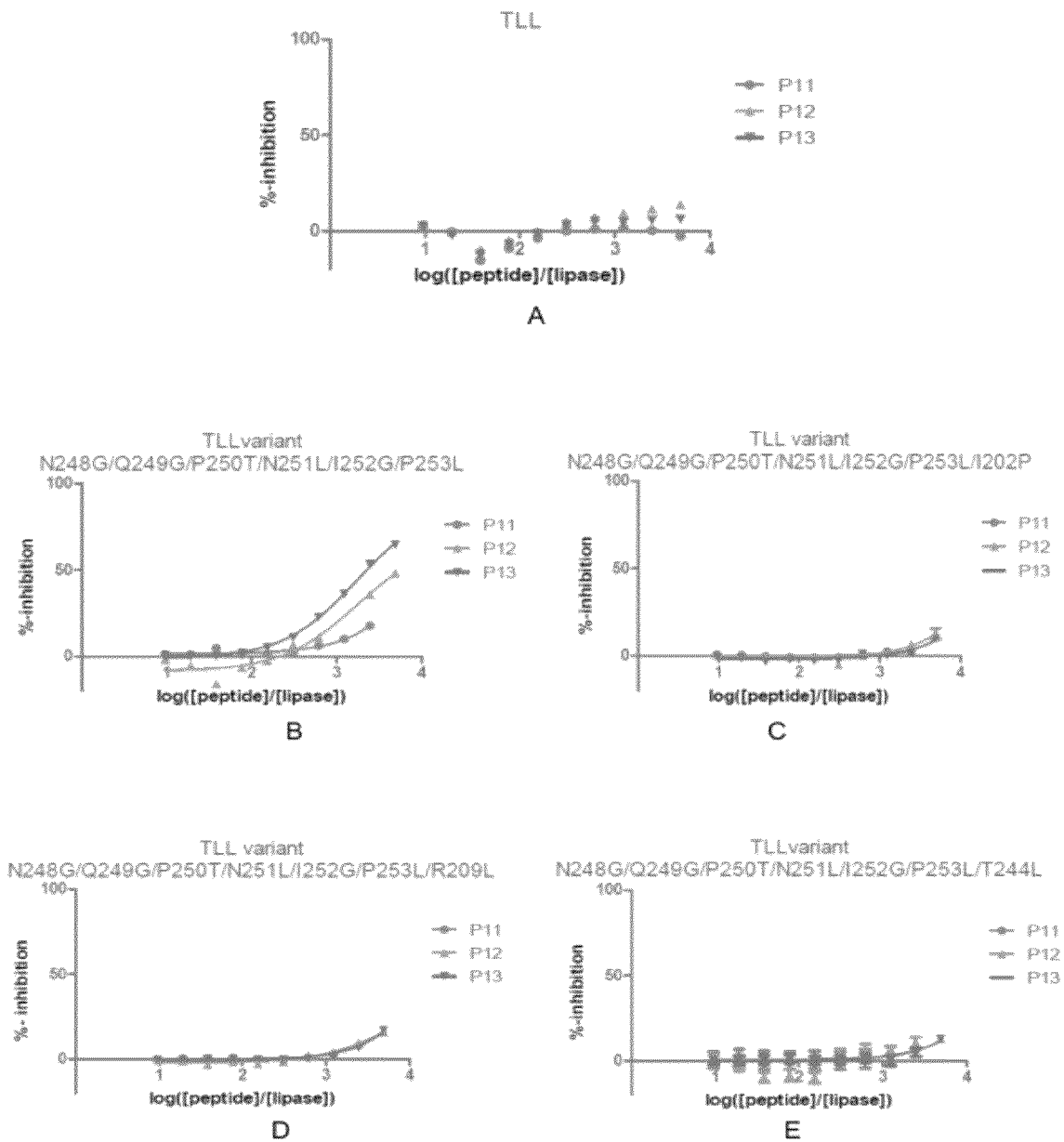
FIG. 9 shows the change in % inhibition for various peptides and lipases

[1] IC$_{50}$ value (half maximal inhibitory concentration).
[2] 95% Confidence interval.
*IC50 > highest peptide excess tested Results: FIG. 9 shows how the % inhibition is altered by various peptide concentrations (peptide blank is 0% inhibition).

APPENDIX 1

| Coordinates in Protein Data Bank (PDB) format of GZEL. | | | | | | | |
|---|---|---|---|---|---|---|---|
| ATOM | 1 | CB | ALA | 1 | 26.829 | 24.911 | 33.431 | 1.00 | 46.79 |
| ATOM | 2 | C | ALA | 1 | 28.010 | 24.831 | 31.273 | 1.00 | 51.75 |
| ATOM | 3 | O | ALA | 1 | 29.048 | 25.242 | 30.748 | 1.00 | 55.66 |
| ATOM | 4 | N | ALA | 1 | 29.275 | 24.764 | 33.312 | 1.00 | 48.96 |
| ATOM | 5 | CA | ALA | 1 | 28.005 | 24.323 | 32.689 | 1.00 | 49.44 |
| ATOM | 6 | N | VAL | 2 | 26.838 | 24.818 | 30.659 | 1.00 | 49.20 |
| ATOM | 7 | CA | VAL | 2 | 26.701 | 25.297 | 29.297 | 1.00 | 46.02 |
| ATOM | 8 | CB | VAL | 2 | 26.195 | 24.190 | 28.377 | 1.00 | 44.99 |
| ATOM | 9 | CG1 | VAL | 2 | 26.187 | 24.670 | 26.943 | 1.00 | 43.38 |
| ATOM | 10 | CG2 | VAL | 2 | 27.093 | 22.967 | 28.534 | 1.00 | 40.91 |
| ATOM | 11 | C | VAL | 2 | 25.705 | 26.444 | 29.321 | 1.00 | 45.79 |
| ATOM | 12 | O | VAL | 2 | 24.830 | 26.501 | 30.192 | 1.00 | 46.48 |
| ATOM | 13 | N | SER | 3 | 25.844 | 27.373 | 28.382 | 1.00 | 45.59 |
| ATOM | 14 | CA | SER | 3 | 24.951 | 28.533 | 28.326 | 1.00 | 45.63 |
| ATOM | 15 | CB | SER | 3 | 25.543 | 29.692 | 29.138 | 1.00 | 46.98 |
| ATOM | 16 | OG | SER | 3 | 24.691 | 30.821 | 29.139 | 1.00 | 50.89 |
| ATOM | 17 | C | SER | 3 | 24.738 | 28.971 | 26.886 | 1.00 | 42.84 |
| ATOM | 18 | O | SER | 3 | 25.100 | 28.256 | 25.949 | 1.00 | 46.23 |
| ATOM | 19 | N | VAL | 4 | 24.148 | 30.143 | 26.703 | 1.00 | 38.57 |
| ATOM | 20 | CA | VAL | 4 | 23.901 | 30.633 | 25.356 | 1.00 | 37.41 |
| ATOM | 21 | CB | VAL | 4 | 22.400 | 30.871 | 25.136 | 1.00 | 36.17 |
| ATOM | 22 | CG1 | VAL | 4 | 21.933 | 32.057 | 25.965 | 1.00 | 34.74 |
| ATOM | 23 | CG2 | VAL | 4 | 22.125 | 31.071 | 23.661 | 1.00 | 35.04 |
| ATOM | 24 | C | VAL | 4 | 24.671 | 31.941 | 25.171 | 1.00 | 36.25 |
| ATOM | 25 | O | VAL | 4 | 25.036 | 32.593 | 26.163 | 1.00 | 34.50 |
| ATOM | 26 | N | SER | 5 | 24.935 | 32.322 | 23.918 | 1.00 | 34.33 |
| ATOM | 27 | CA | SER | 5 | 25.664 | 33.559 | 23.655 | 1.00 | 34.34 |
| ATOM | 28 | CB | SER | 5 | 27.076 | 33.268 | 23.179 | 1.00 | 30.08 |
| ATOM | 29 | OG | SER | 5 | 27.086 | 32.928 | 21.806 | 1.00 | 23.67 |
| ATOM | 30 | C | SER | 5 | 25.032 | 34.490 | 22.627 | 1.00 | 35.94 |
| ATOM | 31 | O | SER | 5 | 24.066 | 34.149 | 21.921 | 1.00 | 38.21 |
| ATOM | 32 | N | THR | 6 | 25.631 | 35.668 | 22.536 | 1.00 | 35.10 |
| ATOM | 33 | CA | THR | 6 | 25.194 | 36.693 | 21.625 | 1.00 | 33.67 |
| ATOM | 34 | CB | THR | 6 | 26.131 | 37.887 | 21.716 | 1.00 | 33.12 |
| ATOM | 35 | OG1 | THR | 6 | 25.661 | 38.744 | 22.755 | 1.00 | 33.18 |
| ATOM | 36 | CG2 | THR | 6 | 26.203 | 38.662 | 20.385 | 1.00 | 34.10 |
| ATOM | 37 | C | THR | 6 | 25.198 | 36.161 | 20.219 | 1.00 | 34.02 |
| ATOM | 38 | O | THR | 6 | 24.183 | 36.172 | 19.528 | 1.00 | 37.02 |
| ATOM | 39 | N | THR | 7 | 26.360 | 35.692 | 19.801 | 1.00 | 36.77 |
| ATOM | 40 | CA | THR | 7 | 26.506 | 35.158 | 18.474 | 1.00 | 37.15 |
| ATOM | 41 | CB | THR | 7 | 27.972 | 35.059 | 18.119 | 1.00 | 38.00 |
| ATOM | 42 | OG1 | THR | 7 | 28.138 | 34.070 | 17.104 | 1.00 | 42.94 |
| ATOM | 43 | CG2 | THR | 7 | 28.796 | 34.694 | 19.333 | 1.00 | 35.45 |
| ATOM | 44 | C | THR | 7 | 25.850 | 33.788 | 18.346 | 1.00 | 37.14 |
| ATOM | 45 | O | THR | 7 | 25.545 | 33.333 | 17.241 | 1.00 | 35.92 |
| ATOM | 46 | N | ASP | 8 | 25.655 | 33.121 | 19.479 | 1.00 | 35.56 |

APPENDIX 1-continued

Coordinates in Protein Data Bank (PDB) format of GZEL.

| ATOM | 47 | CA | ASP | 8 | 25.005 | 31.824 | 19.478 | 1.00 | 36.26 |
|---|---|---|---|---|---|---|---|---|---|
| ATOM | 48 | CB | ASP | 8 | 25.069 | 31.157 | 20.859 | 1.00 | 37.91 |
| ATOM | 49 | CG | ASP | 8 | 26.118 | 30.044 | 20.930 | 1.00 | 42.07 |
| ATOM | 50 | OD1 | ASP | 8 | 26.845 | 29.821 | 19.926 | 1.00 | 42.80 |
| ATOM | 51 | OD2 | ASP | 8 | 26.207 | 29.385 | 21.992 | 1.00 | 40.71 |
| ATOM | 52 | C | ASP | 8 | 23.565 | 32.055 | 19.084 | 1.00 | 34.39 |
| ATOM | 53 | O | ASP | 8 | 23.020 | 31.297 | 18.295 | 1.00 | 32.33 |
| ATOM | 54 | N | PHE | 9 | 22.956 | 33.110 | 19.612 | 1.00 | 33.82 |
| ATOM | 55 | CA | PHE | 9 | 21.576 | 33.396 | 19.262 | 1.00 | 34.15 |
| ATOM | 56 | CB | PHE | 9 | 21.000 | 34.468 | 20.165 | 1.00 | 32.06 |
| ATOM | 57 | CG | PHE | 9 | 19.502 | 34.518 | 20.138 | 1.00 | 31.29 |
| ATOM | 58 | CD1 | PHE | 9 | 18.766 | 33.459 | 20.656 | 1.00 | 29.36 |
| ATOM | 59 | CD2 | PHE | 9 | 18.827 | 35.611 | 19.581 | 1.00 | 30.22 |
| ATOM | 60 | CE1 | PHE | 9 | 17.367 | 33.478 | 20.631 | 1.00 | 31.11 |
| ATOM | 61 | CE2 | PHE | 9 | 17.453 | 35.651 | 19.544 | 1.00 | 31.35 |
| ATOM | 62 | CZ | PHE | 9 | 16.705 | 34.571 | 20.072 | 1.00 | 34.10 |
| ATOM | 63 | C | PHE | 9 | 21.463 | 33.865 | 17.817 | 1.00 | 35.20 |
| ATOM | 64 | O | PHE | 9 | 20.526 | 33.515 | 17.095 | 1.00 | 37.15 |
| ATOM | 65 | N | GLY | 10 | 22.430 | 34.674 | 17.406 | 1.00 | 35.16 |
| ATOM | 66 | CA | GLY | 10 | 22.443 | 35.182 | 16.049 | 1.00 | 34.12 |
| ATOM | 67 | C | GLY | 10 | 22.435 | 34.027 | 15.085 | 1.00 | 31.88 |
| ATOM | 68 | O | GLY | 10 | 21.608 | 33.975 | 14.180 | 1.00 | 31.31 |
| ATOM | 69 | N | ASN | 11 | 23.367 | 33.098 | 15.289 | 1.00 | 32.62 |
| ATOM | 70 | CA | ASN | 11 | 23.474 | 31.915 | 14.446 | 1.00 | 32.09 |
| ATOM | 71 | CB | ASN | 11 | 24.500 | 30.936 | 15.000 | 1.00 | 30.29 |
| ATOM | 72 | CG | ASN | 11 | 25.918 | 31.372 | 14.715 | 1.00 | 27.15 |
| ATOM | 73 | OD1 | ASN | 11 | 26.167 | 32.066 | 13.732 | 1.00 | 25.09 |
| ATOM | 74 | ND2 | ASN | 11 | 26.855 | 30.960 | 15.560 | 1.00 | 20.33 |
| ATOM | 75 | C | ASN | 11 | 22.148 | 31.206 | 14.360 | 1.00 | 32.33 |
| ATOM | 76 | O | ASN | 11 | 21.715 | 30.830 | 13.262 | 1.00 | 34.04 |
| ATOM | 77 | N | PHE | 12 | 21.524 | 31.021 | 15.527 | 1.00 | 30.36 |
| ATOM | 78 | CA | PHE | 12 | 20.215 | 30.371 | 15.624 | 1.00 | 32.00 |
| ATOM | 79 | CB | PHE | 12 | 19.626 | 30.516 | 17.051 | 1.00 | 29.79 |
| ATOM | 80 | CG | PHE | 12 | 20.365 | 29.735 | 18.124 | 1.00 | 24.06 |
| ATOM | 81 | CD1 | PHE | 12 | 21.479 | 28.953 | 17.813 | 1.00 | 24.09 |
| ATOM | 82 | CD2 | PHE | 12 | 19.955 | 29.795 | 19.464 | 1.00 | 22.95 |
| ATOM | 83 | CE1 | PHE | 12 | 22.165 | 28.254 | 18.817 | 1.00 | 20.49 |
| ATOM | 84 | CE2 | PHE | 12 | 20.659 | 29.079 | 20.467 | 1.00 | 21.55 |
| ATOM | 85 | CZ | PHE | 12 | 21.754 | 28.321 | 20.123 | 1.00 | 20.63 |
| ATOM | 86 | C | PHE | 12 | 19.276 | 31.053 | 14.613 | 1.00 | 31.42 |
| ATOM | 87 | O | PHE | 12 | 18.788 | 30.434 | 13.656 | 1.00 | 33.69 |
| ATOM | 88 | N | LYS | 13 | 19.056 | 32.343 | 14.824 | 1.00 | 28.13 |
| ATOM | 89 | CA | LYS | 13 | 18.178 | 33.097 | 13.968 | 1.00 | 24.06 |
| ATOM | 90 | CB | LYS | 13 | 18.120 | 34.542 | 14.443 | 1.00 | 24.85 |
| ATOM | 91 | CG | LYS | 13 | 17.469 | 34.664 | 15.785 | 1.00 | 26.16 |
| ATOM | 92 | CD | LYS | 13 | 17.143 | 36.111 | 16.115 | 1.00 | 31.82 |
| ATOM | 93 | CE | LYS | 13 | 16.040 | 36.686 | 15.214 | 1.00 | 34.72 |
| ATOM | 94 | NZ | LYS | 13 | 15.847 | 38.173 | 15.401 | 1.00 | 35.98 |
| ATOM | 95 | C | LYS | 13 | 18.612 | 33.053 | 12.532 | 1.00 | 21.70 |
| ATOM | 96 | O | LYS | 13 | 17.809 | 33.258 | 11.617 | 1.00 | 23.96 |
| ATOM | 97 | N | PHE | 14 | 19.882 | 32.787 | 12.311 | 1.00 | 22.50 |
| ATOM | 98 | CA | PHE | 14 | 20.338 | 32.800 | 10.948 | 1.00 | 22.03 |
| ATOM | 99 | CB | PHE | 14 | 21.809 | 33.188 | 10.876 | 1.00 | 20.84 |
| ATOM | 100 | CG | PHE | 14 | 22.375 | 33.054 | 9.508 | 1.00 | 23.35 |
| ATOM | 101 | CD1 | PHE | 14 | 21.949 | 33.893 | 8.479 | 1.00 | 16.32 |
| ATOM | 102 | CD2 | PHE | 14 | 23.269 | 32.027 | 9.212 | 1.00 | 25.22 |
| ATOM | 103 | CE1 | PHE | 14 | 22.398 | 33.700 | 7.183 | 1.00 | 20.53 |
| ATOM | 104 | CE2 | PHE | 14 | 23.722 | 31.836 | 7.895 | 1.00 | 24.23 |
| ATOM | 105 | CZ | PHE | 14 | 23.286 | 32.668 | 6.892 | 1.00 | 23.06 |
| ATOM | 106 | C | PHE | 14 | 20.155 | 31.508 | 10.185 | 1.00 | 20.08 |
| ATOM | 107 | O | PHE | 14 | 19.757 | 31.528 | 9.014 | 1.00 | 18.56 |
| ATOM | 108 | N | TYR | 15 | 20.469 | 30.388 | 10.820 | 1.00 | 22.14 |
| ATOM | 109 | CA | TYR | 15 | 20.383 | 29.145 | 10.100 | 1.00 | 28.79 |
| ATOM | 110 | CB | TYR | 15 | 21.181 | 28.078 | 10.854 | 1.00 | 28.20 |
| ATOM | 111 | CG | TYR | 15 | 22.677 | 28.326 | 10.692 | 1.00 | 29.94 |
| ATOM | 112 | CD1 | TYR | 15 | 23.498 | 28.492 | 11.792 | 1.00 | 31.99 |
| ATOM | 113 | CE1 | TYR | 15 | 24.884 | 28.755 | 11.653 | 1.00 | 32.66 |
| ATOM | 114 | CD2 | TYR | 15 | 23.259 | 28.430 | 9.428 | 1.00 | 31.55 |
| ATOM | 115 | CE2 | TYR | 15 | 24.628 | 28.692 | 9.269 | 1.00 | 33.72 |
| ATOM | 116 | CZ | TYR | 15 | 25.442 | 28.850 | 10.394 | 1.00 | 33.86 |
| ATOM | 117 | OH | TYR | 15 | 26.807 | 29.062 | 10.294 | 1.00 | 28.91 |
| ATOM | 118 | C | TYR | 15 | 18.997 | 28.681 | 9.672 | 1.00 | 30.43 |
| ATOM | 119 | O | TYR | 15 | 18.874 | 28.025 | 8.639 | 1.00 | 28.40 |
| ATOM | 120 | N | ILE | 16 | 17.944 | 29.024 | 10.409 | 1.00 | 30.41 |
| ATOM | 121 | CA | ILE | 16 | 16.630 | 28.580 | 9.957 | 1.00 | 30.84 |
| ATOM | 122 | CB | ILE | 16 | 15.471 | 29.079 | 10.830 | 1.00 | 31.23 |
| ATOM | 123 | CG2 | ILE | 16 | 14.975 | 27.958 | 11.664 | 1.00 | 28.44 |
| ATOM | 124 | CG1 | ILE | 16 | 15.886 | 30.291 | 11.656 | 1.00 | 32.82 |

APPENDIX 1-continued

Coordinates in Protein Data Bank (PDB) format of GZEL.

| ATOM | 125 | CD1 | ILE | 16 | 15.349 | 31.590 | 11.107 | 1.00 | 33.34 |
|------|-----|-----|-----|----|--------|--------|--------|------|-------|
| ATOM | 126 | C   | ILE | 16 | 16.366 | 29.035 | 8.540  | 1.00 | 31.82 |
| ATOM | 127 | O   | ILE | 16 | 15.580 | 28.419 | 7.830  | 1.00 | 34.26 |
| ATOM | 128 | N   | GLN | 17 | 17.016 | 30.108 | 8.105  | 1.00 | 30.85 |
| ATOM | 129 | CA  | GLN | 17 | 16.775 | 30.575 | 6.742  | 1.00 | 28.53 |
| ATOM | 130 | CB  | GLN | 17 | 17.574 | 31.858 | 6.463  | 1.00 | 30.13 |
| ATOM | 131 | CG  | GLN | 17 | 17.234 | 32.992 | 7.473  | 1.00 | 30.83 |
| ATOM | 132 | CD  | GLN | 17 | 17.579 | 34.397 | 6.964  | 1.00 | 32.84 |
| ATOM | 133 | OE1 | GLN | 17 | 17.582 | 35.348 | 7.733  | 1.00 | 28.29 |
| ATOM | 134 | NE2 | GLN | 17 | 17.854 | 34.528 | 5.664  | 1.00 | 34.81 |
| ATOM | 135 | C   | GLN | 17 | 17.122 | 29.456 | 5.772  | 1.00 | 26.12 |
| ATOM | 136 | O   | GLN | 17 | 16.461 | 29.257 | 4.771  | 1.00 | 22.90 |
| ATOM | 137 | N   | HIS | 18 | 18.157 | 28.699 | 6.096  | 1.00 | 24.71 |
| ATOM | 138 | CA  | HIS | 18 | 18.554 | 27.574 | 5.260  | 1.00 | 26.07 |
| ATOM | 139 | CB  | HIS | 18 | 19.952 | 27.134 | 5.596  | 1.00 | 25.26 |
| ATOM | 140 | CG  | HIS | 18 | 20.996 | 27.922 | 4.894  | 1.00 | 26.41 |
| ATOM | 141 | CD2 | HIS | 18 | 21.394 | 27.907 | 3.603  | 1.00 | 25.37 |
| ATOM | 142 | ND1 | HIS | 18 | 21.798 | 28.835 | 5.538  | 1.00 | 28.88 |
| ATOM | 143 | CE1 | HIS | 18 | 22.659 | 29.344 | 4.672  | 1.00 | 29.96 |
| ATOM | 144 | NE2 | HIS | 18 | 22.433 | 28.795 | 3.491  | 1.00 | 28.73 |
| ATOM | 145 | C   | HIS | 18 | 17.624 | 26.408 | 5.465  | 1.00 | 27.02 |
| ATOM | 146 | O   | HIS | 18 | 17.345 | 25.655 | 4.534  | 1.00 | 27.11 |
| ATOM | 147 | N   | GLY | 19 | 17.148 | 26.252 | 6.693  | 1.00 | 28.43 |
| ATOM | 148 | CA  | GLY | 19 | 16.217 | 25.178 | 6.943  | 1.00 | 29.45 |
| ATOM | 149 | C   | GLY | 19 | 14.979 | 25.390 | 6.083  | 1.00 | 31.53 |
| ATOM | 150 | O   | GLY | 19 | 14.518 | 24.461 | 5.417  | 1.00 | 34.43 |
| ATOM | 151 | N   | ALA | 20 | 14.464 | 26.624 | 6.090  | 1.00 | 28.21 |
| ATOM | 152 | CA  | ALA | 20 | 13.268 | 27.022 | 5.339  | 1.00 | 28.35 |
| ATOM | 153 | CB  | ALA | 20 | 12.785 | 28.396 | 5.826  | 1.00 | 26.16 |
| ATOM | 154 | C   | ALA | 20 | 13.547 | 27.086 | 3.842  | 1.00 | 29.16 |
| ATOM | 155 | O   | ALA | 20 | 12.654 | 26.891 | 3.004  | 1.00 | 33.64 |
| ATOM | 156 | N   | ALA | 21 | 14.798 | 27.390 | 3.520  | 1.00 | 27.87 |
| ATOM | 157 | CA  | ALA | 21 | 15.241 | 27.493 | 2.145  | 1.00 | 25.44 |
| ATOM | 158 | CB  | ALA | 21 | 16.668 | 28.040 | 2.104  | 1.00 | 19.43 |
| ATOM | 159 | C   | ALA | 21 | 15.187 | 26.105 | 1.511  | 1.00 | 26.54 |
| ATOM | 160 | O   | ALA | 21 | 14.754 | 25.954 | 0.365  | 1.00 | 29.36 |
| ATOM | 161 | N   | ALA | 22 | 15.620 | 25.092 | 2.263  | 1.00 | 27.19 |
| ATOM | 162 | CA  | ALA | 22 | 15.639 | 23.730 | 1.758  | 1.00 | 28.51 |
| ATOM | 163 | CB  | ALA | 22 | 15.989 | 22.789 | 2.858  | 1.00 | 26.37 |
| ATOM | 164 | C   | ALA | 22 | 14.276 | 23.376 | 1.184  | 1.00 | 32.45 |
| ATOM | 165 | O   | ALA | 22 | 14.164 | 22.491 | 0.317  | 1.00 | 33.17 |
| ATOM | 166 | N   | TYR | 23 | 13.250 | 24.079 | 1.669  | 1.00 | 34.80 |
| ATOM | 167 | CA  | TYR | 23 | 11.878 | 23.856 | 1.240  | 1.00 | 35.46 |
| ATOM | 168 | CB  | TYR | 23 | 10.900 | 24.500 | 2.230  | 1.00 | 31.16 |
| ATOM | 169 | CG  | TYR | 23 | 10.567 | 23.607 | 3.423  | 1.00 | 31.27 |
| ATOM | 170 | CD1 | TYR | 23 | 9.927  | 22.370 | 3.254  | 1.00 | 29.95 |
| ATOM | 171 | CE1 | TYR | 23 | 9.624  | 21.533 | 4.367  | 1.00 | 24.00 |
| ATOM | 172 | CD2 | TYR | 23 | 10.901 | 23.987 | 4.718  | 1.00 | 28.94 |
| ATOM | 173 | CE2 | TYR | 23 | 10.615 | 23.163 | 5.817  | 1.00 | 27.14 |
| ATOM | 174 | CZ  | TYR | 23 | 9.979  | 21.948 | 5.642  | 1.00 | 24.07 |
| ATOM | 175 | OH  | TYR | 23 | 9.709  | 21.174 | 6.755  | 1.00 | 30.00 |
| ATOM | 176 | C   | TYR | 23 | 11.574 | 24.334 | −0.171 | 1.00 | 38.29 |
| ATOM | 177 | O   | TYR | 23 | 10.434 | 24.227 | −0.628 | 1.00 | 39.77 |
| ATOM | 178 | N   | CYS | 24 | 12.566 | 24.873 | −0.867 | 1.00 | 40.13 |
| ATOM | 179 | CA  | CYS | 24 | 12.300 | 25.303 | −2.227 | 1.00 | 43.23 |
| ATOM | 180 | C   | CYS | 24 | 13.517 | 25.301 | −3.116 | 1.00 | 42.88 |
| ATOM | 181 | O   | CYS | 24 | 13.401 | 25.294 | −4.330 | 1.00 | 42.12 |
| ATOM | 182 | CB  | CYS | 24 | 11.628 | 26.679 | −2.240 | 1.00 | 47.63 |
| ATOM | 183 | SG  | CYS | 24 | 12.447 | 27.997 | −1.288 | 1.00 | 56.39 |
| ATOM | 184 | N   | ASN | 25 | 14.691 | 25.287 | −2.514 | 1.00 | 42.45 |
| ATOM | 185 | CA  | ASN | 25 | 15.906 | 25.271 | −3.304 | 1.00 | 44.76 |
| ATOM | 186 | CB  | ASN | 25 | 16.952 | 26.149 | −2.642 | 1.00 | 43.87 |
| ATOM | 187 | CG  | ASN | 25 | 16.533 | 27.586 | −2.612 | 1.00 | 48.58 |
| ATOM | 188 | OD1 | ASN | 25 | 15.624 | 27.974 | −1.875 | 1.00 | 48.53 |
| ATOM | 189 | ND2 | ASN | 25 | 17.171 | 28.391 | −3.443 | 1.00 | 52.09 |
| ATOM | 190 | C   | ASN | 25 | 16.412 | 23.852 | −3.460 | 1.00 | 45.88 |
| ATOM | 191 | O   | ASN | 25 | 17.475 | 23.613 | −4.039 | 1.00 | 46.08 |
| ATOM | 192 | N   | SER | 26 | 15.610 | 22.917 | −2.965 | 1.00 | 48.46 |
| ATOM | 193 | CA  | SER | 26 | 15.940 | 21.509 | −2.998 | 1.00 | 49.56 |
| ATOM | 194 | CB  | SER | 26 | 14.972 | 20.760 | −2.085 | 1.00 | 51.09 |
| ATOM | 195 | OG  | SER | 26 | 13.680 | 21.347 | −2.136 | 1.00 | 54.46 |
| ATOM | 196 | C   | SER | 26 | 15.885 | 20.973 | −4.417 | 1.00 | 48.64 |
| ATOM | 197 | O   | SER | 26 | 16.054 | 19.769 | −4.651 | 1.00 | 46.39 |
| ATOM | 198 | N   | GLU | 27 | 15.665 | 21.886 | −5.359 | 1.00 | 48.70 |
| ATOM | 199 | CA  | GLU | 27 | 15.558 | 21.526 | −6.754 | 1.00 | 47.85 |
| ATOM | 200 | CB  | GLU | 27 | 14.123 | 21.687 | −7.187 | 1.00 | 50.86 |
| ATOM | 201 | CG  | GLU | 27 | 13.741 | 20.727 | −8.260 | 1.00 | 54.11 |
| ATOM | 202 | CD  | GLU | 27 | 13.588 | 19.339 | −7.708 | 1.00 | 53.46 |

APPENDIX 1-continued

Coordinates in Protein Data Bank (PDB) format of GZEL.

| ATOM | 203 | OE1 | GLU | 27 | 12.499 | 19.046 | −7.165 | 1.00 | 48.31 |
|---|---|---|---|---|---|---|---|---|---|
| ATOM | 204 | OE2 | GLU | 27 | 14.565 | 18.558 | −7.799 | 1.00 | 55.78 |
| ATOM | 205 | C | GLU | 27 | 16.426 | 22.410 | −7.623 | 1.00 | 46.15 |
| ATOM | 206 | O | GLU | 27 | 16.583 | 22.165 | −8.818 | 1.00 | 45.46 |
| ATOM | 207 | N | ALA | 28 | 16.979 | 23.448 | −7.010 | 1.00 | 45.36 |
| ATOM | 208 | CA | ALA | 28 | 17.821 | 24.404 | −7.712 | 1.00 | 45.38 |
| ATOM | 209 | CB | ALA | 28 | 18.254 | 25.493 | −6.762 | 1.00 | 46.93 |
| ATOM | 210 | C | ALA | 28 | 19.040 | 23.804 | −8.395 | 1.00 | 45.46 |
| ATOM | 211 | O | ALA | 28 | 19.693 | 22.904 | −7.868 | 1.00 | 45.96 |
| ATOM | 212 | N | PRO | 29 | 19.361 | 24.314 | −9.593 | 1.00 | 43.34 |
| ATOM | 213 | CD | PRO | 29 | 18.585 | 25.318 | −10.336 | 1.00 | 43.59 |
| ATOM | 214 | CA | PRO | 29 | 20.499 | 23.860 | −10.392 | 1.00 | 39.84 |
| ATOM | 215 | CB | PRO | 29 | 20.199 | 24.422 | −11.789 | 1.00 | 40.87 |
| ATOM | 216 | CG | PRO | 29 | 18.731 | 24.809 | −11.738 | 1.00 | 43.29 |
| ATOM | 217 | C | PRO | 29 | 21.768 | 24.456 | −9.814 | 1.00 | 36.35 |
| ATOM | 218 | O | PRO | 29 | 21.745 | 25.532 | −9.218 | 1.00 | 32.62 |
| ATOM | 219 | N | ALA | 30 | 22.879 | 23.760 | −9.981 | 1.00 | 34.74 |
| ATOM | 220 | CA | ALA | 30 | 24.118 | 24.291 | −9.462 | 1.00 | 40.14 |
| ATOM | 221 | CB | ALA | 30 | 25.293 | 23.443 | −9.913 | 1.00 | 39.49 |
| ATOM | 222 | C | ALA | 30 | 24.224 | 25.704 | −10.015 | 1.00 | 43.07 |
| ATOM | 223 | O | ALA | 30 | 23.557 | 26.041 | −10.999 | 1.00 | 45.14 |
| ATOM | 224 | N | GLY | 31 | 25.039 | 26.532 | −9.366 | 1.00 | 43.67 |
| ATOM | 225 | CA | GLY | 31 | 25.209 | 27.903 | −9.812 | 1.00 | 44.09 |
| ATOM | 226 | C | GLY | 31 | 24.044 | 28.817 | −9.486 | 1.00 | 45.12 |
| ATOM | 227 | O | GLY | 31 | 24.216 | 30.036 | −9.426 | 1.00 | 45.37 |
| ATOM | 228 | N | ALA | 32 | 22.861 | 28.236 | −9.275 | 1.00 | 45.29 |
| ATOM | 229 | CA | ALA | 32 | 21.663 | 29.012 | −8.942 | 1.00 | 44.96 |
| ATOM | 230 | CB | ALA | 32 | 20.427 | 28.091 | −8.837 | 1.00 | 46.26 |
| ATOM | 231 | C | ALA | 32 | 21.874 | 29.754 | −7.626 | 1.00 | 44.27 |
| ATOM | 232 | O | ALA | 32 | 22.799 | 29.449 | −6.871 | 1.00 | 45.48 |
| ATOM | 233 | N | LYS | 33 | 21.014 | 30.731 | −7.362 | 1.00 | 44.05 |
| ATOM | 234 | CA | LYS | 33 | 21.096 | 31.530 | −6.147 | 1.00 | 43.46 |
| ATOM | 235 | CB | LYS | 33 | 20.903 | 33.007 | −6.469 | 1.00 | 45.85 |
| ATOM | 236 | CG | LYS | 33 | 21.975 | 33.588 | −7.362 | 1.00 | 46.87 |
| ATOM | 237 | CD | LYS | 33 | 23.287 | 33.640 | −6.609 | 1.00 | 48.03 |
| ATOM | 238 | CE | LYS | 33 | 24.349 | 34.400 | −7.378 | 1.00 | 48.31 |
| ATOM | 239 | NZ | LYS | 33 | 25.524 | 34.723 | −6.507 | 1.00 | 47.98 |
| ATOM | 240 | C | LYS | 33 | 20.041 | 31.120 | −5.157 | 1.00 | 42.61 |
| ATOM | 241 | O | LYS | 33 | 18.853 | 31.089 | −5.472 | 1.00 | 44.51 |
| ATOM | 242 | N | VAL | 34 | 20.480 | 30.820 | −3.947 | 1.00 | 41.96 |
| ATOM | 243 | CA | VAL | 34 | 19.559 | 30.423 | −2.906 | 1.00 | 40.22 |
| ATOM | 244 | CB | VAL | 34 | 20.314 | 30.132 | −1.607 | 1.00 | 39.03 |
| ATOM | 245 | CG1 | VAL | 34 | 19.333 | 29.774 | −0.516 | 1.00 | 39.34 |
| ATOM | 246 | CG2 | VAL | 34 | 21.301 | 28.982 | −1.835 | 1.00 | 37.52 |
| ATOM | 247 | C | VAL | 34 | 18.553 | 31.554 | −2.731 | 1.00 | 41.33 |
| ATOM | 248 | O | VAL | 34 | 18.917 | 32.711 | −2.492 | 1.00 | 41.11 |
| ATOM | 249 | N | THR | 35 | 17.284 | 31.206 | −2.879 | 1.00 | 43.13 |
| ATOM | 250 | CA | THR | 35 | 16.242 | 32.187 | −2.801 | 1.00 | 46.82 |
| ATOM | 251 | CB | THR | 35 | 15.904 | 32.677 | −4.215 | 1.00 | 48.83 |
| ATOM | 252 | OG1 | THR | 35 | 15.010 | 33.792 | −4.143 | 1.00 | 55.17 |
| ATOM | 253 | CG2 | THR | 35 | 15.253 | 31.559 | −4.996 | 1.00 | 48.30 |
| ATOM | 254 | C | THR | 35 | 14.987 | 31.629 | −2.153 | 1.00 | 47.64 |
| ATOM | 255 | O | THR | 35 | 14.723 | 30.432 | −2.197 | 1.00 | 50.05 |
| ATOM | 256 | N | CYS | 36 | 14.209 | 32.525 | −1.561 | 1.00 | 47.99 |
| ATOM | 257 | CA | CYS | 36 | 12.974 | 32.160 | −0.895 | 1.00 | 47.27 |
| ATOM | 258 | C | CYS | 36 | 11.993 | 33.270 | −1.071 | 1.00 | 49.06 |
| ATOM | 259 | O | CYS | 36 | 12.351 | 34.443 | −1.147 | 1.00 | 51.86 |
| ATOM | 260 | CB | CYS | 36 | 13.206 | 31.961 | 0.599 | 1.00 | 47.51 |
| ATOM | 261 | SG | CYS | 36 | 14.721 | 31.004 | 0.946 | 1.00 | 46.80 |
| ATOM | 262 | N | SER | 37 | 10.738 | 32.873 | −1.122 | 1.00 | 50.29 |
| ATOM | 263 | CA | SER | 37 | 9.657 | 33.811 | −1.253 | 1.00 | 51.64 |
| ATOM | 264 | CB | SER | 37 | 8.606 | 33.282 | −2.224 | 1.00 | 51.71 |
| ATOM | 265 | OG | SER | 37 | 7.920 | 32.176 | −1.671 | 1.00 | 51.99 |
| ATOM | 266 | C | SER | 37 | 9.047 | 33.954 | 0.132 | 1.00 | 52.79 |
| ATOM | 267 | O | SER | 37 | 9.227 | 33.081 | 1.009 | 1.00 | 54.99 |
| ATOM | 268 | N | GLY | 38 | 8.313 | 35.049 | 0.319 | 1.00 | 52.11 |
| ATOM | 269 | CA | GLY | 38 | 7.683 | 35.300 | 1.601 | 1.00 | 47.78 |
| ATOM | 270 | C | GLY | 38 | 8.741 | 35.668 | 2.616 | 1.00 | 46.33 |
| ATOM | 271 | O | GLY | 38 | 8.597 | 35.336 | 3.799 | 1.00 | 41.87 |
| ATOM | 272 | N | ASN | 39 | 9.794 | 36.347 | 2.142 | 1.00 | 46.02 |
| ATOM | 273 | CA | ASN | 39 | 10.905 | 36.774 | 2.986 | 1.00 | 43.85 |
| ATOM | 274 | CB | ASN | 39 | 10.435 | 37.873 | 3.941 | 1.00 | 47.51 |
| ATOM | 275 | CG | ASN | 39 | 11.282 | 39.114 | 3.842 | 1.00 | 54.53 |
| ATOM | 276 | OD1 | ASN | 39 | 12.286 | 39.258 | 4.551 | 1.00 | 56.71 |
| ATOM | 277 | ND2 | ASN | 39 | 10.902 | 40.017 | 2.938 | 1.00 | 55.69 |
| ATOM | 278 | C | ASN | 39 | 11.422 | 35.574 | 3.762 | 1.00 | 41.94 |
| ATOM | 279 | O | ASN | 39 | 11.950 | 35.703 | 4.881 | 1.00 | 38.41 |
| ATOM | 280 | N | GLY | 40 | 11.274 | 34.406 | 3.143 | 1.00 | 41.26 |

APPENDIX 1-continued

Coordinates in Protein Data Bank (PDB) format of GZEL.

| ATOM | 281 | CA  | GLY | 40 | 11.689 | 33.183 | 3.785  | 1.00 | 39.14 |
|------|-----|-----|-----|----|--------|--------|--------|------|-------|
| ATOM | 282 | C   | GLY | 40 | 13.131 | 33.124 | 4.234  | 1.00 | 37.57 |
| ATOM | 283 | O   | GLY | 40 | 13.427 | 32.461 | 5.228  | 1.00 | 38.05 |
| ATOM | 284 | N   | CYS | 41 | 14.025 | 33.809 | 3.521  | 1.00 | 37.14 |
| ATOM | 285 | CA  | CYS | 41 | 15.449 | 33.756 | 3.851  | 1.00 | 36.29 |
| ATOM | 286 | C   | CYS | 41 | 16.257 | 34.924 | 3.300  | 1.00 | 37.23 |
| ATOM | 287 | O   | CYS | 41 | 17.256 | 34.731 | 2.617  | 1.00 | 36.42 |
| ATOM | 288 | CB  | CYS | 41 | 16.028 | 32.456 | 3.305  | 1.00 | 33.97 |
| ATOM | 289 | SG  | CYS | 41 | 16.100 | 32.411 | 1.482  | 1.00 | 36.33 |
| ATOM | 290 | N   | PRO | 42 | 15.850 | 36.153 | 3.621  | 1.00 | 38.20 |
| ATOM | 291 | CD  | PRO | 42 | 14.779 | 36.487 | 4.576  | 1.00 | 39.84 |
| ATOM | 292 | CA  | PRO | 42 | 16.540 | 37.356 | 3.148  | 1.00 | 38.13 |
| ATOM | 293 | CB  | PRO | 42 | 15.715 | 38.485 | 3.766  | 1.00 | 37.35 |
| ATOM | 294 | CG  | PRO | 42 | 15.177 | 37.862 | 5.027  | 1.00 | 37.04 |
| ATOM | 295 | C   | PRO | 42 | 18.047 | 37.480 | 3.424  | 1.00 | 38.39 |
| ATOM | 296 | O   | PRO | 42 | 18.790 | 37.903 | 2.548  | 1.00 | 38.45 |
| ATOM | 297 | N   | THR | 43 | 18.504 | 37.126 | 4.622  | 1.00 | 38.67 |
| ATOM | 298 | CA  | THR | 43 | 19.931 | 37.235 | 4.932  | 1.00 | 38.85 |
| ATOM | 299 | CB  | THR | 43 | 20.251 | 36.818 | 6.395  | 1.00 | 36.92 |
| ATOM | 300 | OG1 | THR | 43 | 19.613 | 37.727 | 7.299  | 1.00 | 37.95 |
| ATOM | 301 | CG2 | THR | 43 | 21.753 | 36.853 | 6.653  | 1.00 | 33.96 |
| ATOM | 302 | C   | THR | 43 | 20.686 | 36.334 | 3.993  | 1.00 | 38.46 |
| ATOM | 303 | O   | THR | 43 | 21.789 | 36.636 | 3.556  | 1.00 | 39.61 |
| ATOM | 304 | N   | VAL | 44 | 20.081 | 35.209 | 3.684  | 1.00 | 38.02 |
| ATOM | 305 | CA  | VAL | 44 | 20.730 | 34.302 | 2.792  | 1.00 | 39.52 |
| ATOM | 306 | CB  | VAL | 44 | 19.982 | 32.988 | 2.750  | 1.00 | 36.82 |
| ATOM | 307 | CG1 | VAL | 44 | 20.601 | 32.105 | 1.712  | 1.00 | 37.04 |
| ATOM | 308 | CG2 | VAL | 44 | 20.028 | 32.321 | 4.106  | 1.00 | 36.16 |
| ATOM | 309 | C   | VAL | 44 | 20.794 | 34.949 | 1.412  | 1.00 | 43.60 |
| ATOM | 310 | O   | VAL | 44 | 21.843 | 34.950 | 0.771  | 1.00 | 41.94 |
| ATOM | 311 | N   | GLN | 45 | 19.682 | 35.516 | 0.957  | 1.00 | 47.86 |
| ATOM | 312 | CA  | GLN | 45 | 19.684 | 36.166 | −0.347 | 1.00 | 50.53 |
| ATOM | 313 | CB  | GLN | 45 | 18.267 | 36.548 | −0.780 | 1.00 | 46.99 |
| ATOM | 314 | CG  | GLN | 45 | 17.327 | 35.370 | −0.912 | 1.00 | 49.29 |
| ATOM | 315 | CD  | GLN | 45 | 15.924 | 35.790 | −1.305 | 1.00 | 50.89 |
| ATOM | 316 | OE1 | GLN | 45 | 15.396 | 36.774 | −0.795 | 1.00 | 54.31 |
| ATOM | 317 | NE2 | GLN | 45 | 15.311 | 35.044 | −2.205 | 1.00 | 47.74 |
| ATOM | 318 | C   | GLN | 45 | 20.568 | 37.405 | −0.289 | 1.00 | 52.82 |
| ATOM | 319 | O   | GLN | 45 | 21.341 | 37.667 | −1.207 | 1.00 | 54.98 |
| ATOM | 320 | N   | SER | 46 | 20.462 | 38.164 | 0.795  | 1.00 | 54.53 |
| ATOM | 321 | CA  | SER | 46 | 21.278 | 39.360 | 0.946  | 1.00 | 54.05 |
| ATOM | 322 | CB  | SER | 46 | 21.162 | 39.907 | 2.356  | 1.00 | 52.75 |
| ATOM | 323 | OG  | SER | 46 | 22.332 | 40.647 | 2.655  | 1.00 | 52.40 |
| ATOM | 324 | C   | SER | 46 | 22.737 | 39.045 | 0.667  | 1.00 | 53.72 |
| ATOM | 325 | O   | SER | 46 | 23.455 | 39.812 | 0.033  | 1.00 | 52.04 |
| ATOM | 326 | N   | ASN | 47 | 23.170 | 37.907 | 1.180  | 1.00 | 54.08 |
| ATOM | 327 | CA  | ASN | 47 | 24.524 | 37.462 | 0.975  | 1.00 | 54.09 |
| ATOM | 328 | CB  | ASN | 47 | 24.926 | 36.519 | 2.094  | 1.00 | 52.99 |
| ATOM | 329 | CG  | ASN | 47 | 24.669 | 37.109 | 3.446  | 1.00 | 55.12 |
| ATOM | 330 | OD1 | ASN | 47 | 24.826 | 36.447 | 4.464  | 1.00 | 55.92 |
| ATOM | 331 | ND2 | ASN | 47 | 24.267 | 38.376 | 3.470  | 1.00 | 56.97 |
| ATOM | 332 | C   | ASN | 47 | 24.483 | 36.722 | −0.335 | 1.00 | 55.62 |
| ATOM | 333 | O   | ASN | 47 | 23.409 | 36.481 | −0.895 | 1.00 | 55.92 |
| ATOM | 334 | N   | GLY | 48 | 25.651 | 36.338 | −0.815 | 1.00 | 55.14 |
| ATOM | 335 | CA  | GLY | 48 | 25.706 | 35.629 | −2.071 | 1.00 | 53.83 |
| ATOM | 336 | C   | GLY | 48 | 25.619 | 34.127 | −1.991 | 1.00 | 51.96 |
| ATOM | 337 | O   | GLY | 48 | 26.424 | 33.435 | −2.596 | 1.00 | 54.44 |
| ATOM | 338 | N   | ALA | 49 | 24.632 | 33.615 | −1.269 | 1.00 | 49.83 |
| ATOM | 339 | CA  | ALA | 49 | 24.465 | 32.166 | −1.130 | 1.00 | 47.17 |
| ATOM | 340 | CB  | ALA | 49 | 23.393 | 31.863 | −0.106 | 1.00 | 44.77 |
| ATOM | 341 | C   | ALA | 49 | 24.108 | 31.506 | −2.458 | 1.00 | 45.91 |
| ATOM | 342 | O   | ALA | 49 | 23.130 | 31.879 | −3.108 | 1.00 | 44.92 |
| ATOM | 343 | N   | THR | 50 | 24.895 | 30.513 | −2.855 | 1.00 | 44.61 |
| ATOM | 344 | CA  | THR | 50 | 24.658 | 29.827 | −4.119 | 1.00 | 45.57 |
| ATOM | 345 | CB  | THR | 50 | 25.711 | 30.252 | −5.137 | 1.00 | 44.64 |
| ATOM | 346 | OG1 | THR | 50 | 27.016 | 30.057 | −4.572 | 1.00 | 48.93 |
| ATOM | 347 | CG2 | THR | 50 | 25.543 | 31.714 | −5.484 | 1.00 | 44.18 |
| ATOM | 348 | C   | THR | 50 | 24.689 | 28.303 | −3.973 | 1.00 | 44.90 |
| ATOM | 349 | O   | THR | 50 | 25.323 | 27.774 | −3.058 | 1.00 | 47.41 |
| ATOM | 350 | N   | ILE | 51 | 24.001 | 27.606 | −4.878 | 1.00 | 41.51 |
| ATOM | 351 | CA  | ILE | 51 | 23.939 | 26.147 | −4.854 | 1.00 | 40.26 |
| ATOM | 352 | CB  | ILE | 51 | 22.705 | 25.608 | −5.608 | 1.00 | 40.04 |
| ATOM | 353 | CG2 | ILE | 51 | 22.656 | 24.083 | −5.524 | 1.00 | 40.44 |
| ATOM | 354 | CG1 | ILE | 51 | 21.431 | 26.191 | −5.012 | 1.00 | 44.06 |
| ATOM | 355 | CD1 | ILE | 51 | 20.980 | 27.438 | −5.720 | 1.00 | 43.76 |
| ATOM | 356 | C   | ILE | 51 | 25.155 | 25.502 | −5.491 | 1.00 | 39.87 |
| ATOM | 357 | O   | ILE | 51 | 25.649 | 25.955 | −6.523 | 1.00 | 42.31 |
| ATOM | 358 | N   | VAL | 52 | 25.631 | 24.429 | −4.877 | 1.00 | 38.22 |

APPENDIX 1-continued

Coordinates in Protein Data Bank (PDB) format of GZEL.

| ATOM | 359 | CA | VAL | 52 | 26.763 | 23.712 | −5.415 | 1.00 | 35.17 |
|---|---|---|---|---|---|---|---|---|---|
| ATOM | 360 | CB | VAL | 52 | 27.711 | 23.308 | −4.299 | 1.00 | 33.49 |
| ATOM | 361 | CG1 | VAL | 52 | 28.920 | 22.570 | −4.869 | 1.00 | 34.02 |
| ATOM | 362 | CG2 | VAL | 52 | 28.152 | 24.553 | −3.549 | 1.00 | 29.71 |
| ATOM | 363 | C | VAL | 52 | 26.144 | 22.485 | −6.076 | 1.00 | 35.33 |
| ATOM | 364 | O | VAL | 52 | 26.728 | 21.887 | −7.001 | 1.00 | 36.26 |
| ATOM | 365 | N | ALA | 53 | 24.936 | 22.144 | −5.619 | 1.00 | 35.25 |
| ATOM | 366 | CA | ALA | 53 | 24.194 | 21.003 | −6.152 | 1.00 | 35.42 |
| ATOM | 367 | CB | ALA | 53 | 25.073 | 19.748 | −6.117 | 1.00 | 31.66 |
| ATOM | 368 | C | ALA | 53 | 22.951 | 20.793 | −5.293 | 1.00 | 33.55 |
| ATOM | 369 | O | ALA | 53 | 22.942 | 21.153 | −4.115 | 1.00 | 35.15 |
| ATOM | 370 | N | SER | 54 | 21.890 | 20.247 | −5.874 | 1.00 | 32.33 |
| ATOM | 371 | CA | SER | 54 | 20.688 | 19.973 | −5.084 | 1.00 | 31.79 |
| ATOM | 372 | CB | SER | 54 | 19.502 | 20.832 | −5.524 | 1.00 | 30.57 |
| ATOM | 373 | OG | SER | 54 | 19.105 | 20.503 | −6.840 | 1.00 | 37.05 |
| ATOM | 374 | C | SER | 54 | 20.383 | 18.505 | −5.309 | 1.00 | 31.23 |
| ATOM | 375 | O | SER | 54 | 20.939 | 17.883 | −6.230 | 1.00 | 27.55 |
| ATOM | 376 | N | PHE | 55 | 19.501 | 17.939 | −4.500 | 1.00 | 32.84 |
| ATOM | 377 | CA | PHE | 55 | 19.243 | 16.526 | −4.654 | 1.00 | 35.43 |
| ATOM | 378 | CB | PHE | 55 | 20.399 | 15.741 | −4.053 | 1.00 | 35.14 |
| ATOM | 379 | CG | PHE | 55 | 20.922 | 16.322 | −2.761 | 1.00 | 32.14 |
| ATOM | 380 | CD1 | PHE | 55 | 22.222 | 16.856 | −2.704 | 1.00 | 29.42 |
| ATOM | 381 | CD2 | PHE | 55 | 20.155 | 16.305 | −1.599 | 1.00 | 30.22 |
| ATOM | 382 | CE1 | PHE | 55 | 22.745 | 17.352 | −1.520 | 1.00 | 25.73 |
| ATOM | 383 | CE2 | PHE | 55 | 20.693 | 16.810 | −0.398 | 1.00 | 31.85 |
| ATOM | 384 | CZ | PHE | 55 | 21.978 | 17.325 | −0.368 | 1.00 | 29.09 |
| ATOM | 385 | C | PHE | 55 | 17.979 | 16.116 | −3.975 | 1.00 | 35.04 |
| ATOM | 386 | O | PHE | 55 | 17.518 | 16.777 | −3.037 | 1.00 | 39.64 |
| ATOM | 387 | N | THR | 56 | 17.429 | 15.000 | −4.436 | 1.00 | 29.99 |
| ATOM | 388 | CA | THR | 56 | 16.191 | 14.488 | −3.864 | 1.00 | 28.55 |
| ATOM | 389 | CB | THR | 56 | 14.945 | 15.096 | −4.590 | 1.00 | 27.79 |
| ATOM | 390 | OG1 | THR | 56 | 14.733 | 14.425 | −5.844 | 1.00 | 23.97 |
| ATOM | 391 | CG2 | THR | 56 | 15.178 | 16.600 | −4.870 | 1.00 | 21.19 |
| ATOM | 392 | C | THR | 56 | 16.129 | 12.958 | −3.945 | 1.00 | 27.76 |
| ATOM | 393 | O | THR | 56 | 16.540 | 12.352 | −4.945 | 1.00 | 27.35 |
| ATOM | 394 | N | GLY | 57 | 15.659 | 12.336 | −2.869 | 1.00 | 27.18 |
| ATOM | 395 | CA | GLY | 57 | 15.530 | 10.890 | −2.856 | 1.00 | 28.45 |
| ATOM | 396 | C | GLY | 57 | 14.097 | 10.554 | −3.204 | 1.00 | 29.19 |
| ATOM | 397 | O | GLY | 57 | 13.209 | 10.576 | −2.352 | 1.00 | 28.30 |
| ATOM | 398 | N | SER | 58 | 13.874 | 10.243 | −4.475 | 1.00 | 31.31 |
| ATOM | 399 | CA | SER | 58 | 12.547 | 9.912 | −4.978 | 1.00 | 34.45 |
| ATOM | 400 | CB | SER | 58 | 12.654 | 9.347 | −6.397 | 1.00 | 38.20 |
| ATOM | 401 | OG | SER | 58 | 11.381 | 9.224 | −7.010 | 1.00 | 44.69 |
| ATOM | 402 | C | SER | 58 | 11.858 | 8.901 | −4.076 | 1.00 | 33.61 |
| ATOM | 403 | O | SER | 58 | 10.735 | 9.126 | −3.620 | 1.00 | 34.55 |
| ATOM | 404 | N | LYS | 59 | 12.535 | 7.796 | −3.810 | 1.00 | 34.29 |
| ATOM | 405 | CA | LYS | 59 | 11.974 | 6.761 | −2.968 | 1.00 | 34.68 |
| ATOM | 406 | CB | LYS | 59 | 12.943 | 5.587 | −2.921 | 1.00 | 36.22 |
| ATOM | 407 | CG | LYS | 59 | 12.562 | 4.459 | −1.966 | 1.00 | 38.49 |
| ATOM | 408 | CD | LYS | 59 | 13.605 | 3.338 | −2.000 | 1.00 | 48.21 |
| ATOM | 409 | CE | LYS | 59 | 13.141 | 2.110 | −1.216 | 1.00 | 54.13 |
| ATOM | 410 | NZ | LYS | 59 | 14.126 | 0.972 | −1.246 | 1.00 | 54.56 |
| ATOM | 411 | C | LYS | 59 | 11.644 | 7.199 | −1.549 | 1.00 | 33.98 |
| ATOM | 412 | O | LYS | 59 | 10.735 | 6.654 | −0.921 | 1.00 | 39.25 |
| ATOM | 413 | N | THR | 60 | 12.352 | 8.193 | −1.033 | 1.00 | 32.34 |
| ATOM | 414 | CA | THR | 60 | 12.114 | 8.569 | 0.347 | 1.00 | 29.15 |
| ATOM | 415 | CB | THR | 60 | 13.426 | 8.369 | 1.109 | 1.00 | 27.10 |
| ATOM | 416 | OG1 | THR | 60 | 13.175 | 7.767 | 2.378 | 1.00 | 23.98 |
| ATOM | 417 | CG2 | THR | 60 | 14.143 | 9.696 | 1.268 | 1.00 | 29.07 |
| ATOM | 418 | C | THR | 60 | 11.520 | 9.963 | 0.636 | 1.00 | 30.25 |
| ATOM | 419 | O | THR | 60 | 11.184 | 10.270 | 1.779 | 1.00 | 28.21 |
| ATOM | 420 | N | GLY | 61 | 11.381 | 10.804 | −0.384 | 1.00 | 30.45 |
| ATOM | 421 | CA | GLY | 61 | 10.815 | 12.119 | −0.148 | 1.00 | 29.54 |
| ATOM | 422 | C | GLY | 61 | 11.822 | 13.108 | 0.398 | 1.00 | 31.39 |
| ATOM | 423 | O | GLY | 61 | 11.553 | 14.299 | 0.458 | 1.00 | 34.11 |
| ATOM | 424 | N | ILE | 62 | 12.989 | 12.640 | 0.808 | 1.00 | 29.86 |
| ATOM | 425 | CA | ILE | 62 | 13.961 | 13.583 | 1.294 | 1.00 | 28.85 |
| ATOM | 426 | CB | ILE | 62 | 15.203 | 12.887 | 1.857 | 1.00 | 29.86 |
| ATOM | 427 | CG2 | ILE | 62 | 15.952 | 12.192 | 0.729 | 1.00 | 30.75 |
| ATOM | 428 | CG1 | ILE | 62 | 16.091 | 13.922 | 2.572 | 1.00 | 30.47 |
| ATOM | 429 | CD1 | ILE | 62 | 15.475 | 14.557 | 3.844 | 1.00 | 24.98 |
| ATOM | 430 | C | ILE | 62 | 14.373 | 14.495 | 0.140 | 1.00 | 30.26 |
| ATOM | 431 | O | ILE | 62 | 14.013 | 14.278 | −1.018 | 1.00 | 30.97 |
| ATOM | 432 | N | GLY | 63 | 15.130 | 15.526 | 0.481 | 1.00 | 29.70 |
| ATOM | 433 | CA | GLY | 63 | 15.599 | 16.488 | −0.492 | 1.00 | 29.18 |
| ATOM | 434 | C | GLY | 63 | 16.466 | 17.450 | 0.281 | 1.00 | 30.92 |
| ATOM | 435 | O | GLY | 63 | 16.366 | 17.524 | 1.516 | 1.00 | 32.28 |
| ATOM | 436 | N | GLY | 64 | 17.309 | 18.186 | −0.437 | 1.00 | 30.23 |

APPENDIX 1-continued

Coordinates in Protein Data Bank (PDB) format of GZEL.

| ATOM | 437 | CA | GLY | 64 | 18.192 | 19.141 | 0.201 | 1.00 | 31.31 |
|---|---|---|---|---|---|---|---|---|---|
| ATOM | 438 | C | GLY | 64 | 19.222 | 19.699 | −0.759 | 1.00 | 32.75 |
| ATOM | 439 | O | GLY | 64 | 19.257 | 19.312 | −1.937 | 1.00 | 35.66 |
| ATOM | 440 | N | TYR | 65 | 20.084 | 20.579 | −0.251 | 1.00 | 31.95 |
| ATOM | 441 | CA | TYR | 65 | 21.113 | 21.206 | −1.075 | 1.00 | 32.66 |
| ATOM | 442 | CB | TYR | 65 | 20.546 | 22.488 | −1.709 | 1.00 | 34.11 |
| ATOM | 443 | CG | TYR | 65 | 20.241 | 23.601 | −0.703 | 1.00 | 30.58 |
| ATOM | 444 | CD1 | TYR | 65 | 21.260 | 24.429 | −0.204 | 1.00 | 29.89 |
| ATOM | 445 | CE1 | TYR | 65 | 20.991 | 25.404 | 0.765 | 1.00 | 31.16 |
| ATOM | 446 | CD2 | TYR | 65 | 18.946 | 23.791 | −0.203 | 1.00 | 31.70 |
| ATOM | 447 | CE2 | TYR | 65 | 18.682 | 24.762 | 0.767 | 1.00 | 31.85 |
| ATOM | 448 | CZ | TYR | 65 | 19.704 | 25.567 | 1.251 | 1.00 | 33.02 |
| ATOM | 449 | OH | TYR | 65 | 19.436 | 26.519 | 2.234 | 1.00 | 30.17 |
| ATOM | 450 | C | TYR | 65 | 22.384 | 21.544 | −0.295 | 1.00 | 31.93 |
| ATOM | 451 | O | TYR | 65 | 22.420 | 21.458 | 0.946 | 1.00 | 33.75 |
| ATOM | 452 | N | VAL | 66 | 23.425 | 21.898 | −1.050 | 1.00 | 31.26 |
| ATOM | 453 | CA | VAL | 66 | 24.730 | 22.308 | −0.519 | 1.00 | 29.99 |
| ATOM | 454 | CB | VAL | 66 | 25.879 | 21.384 | −0.995 | 1.00 | 25.14 |
| ATOM | 455 | CG1 | VAL | 66 | 27.229 | 21.928 | −0.486 | 1.00 | 19.75 |
| ATOM | 456 | CG2 | VAL | 66 | 25.653 | 19.983 | −0.517 | 1.00 | 19.11 |
| ATOM | 457 | C | VAL | 66 | 24.977 | 23.683 | −1.138 | 1.00 | 32.47 |
| ATOM | 458 | O | VAL | 66 | 24.944 | 23.819 | −2.378 | 1.00 | 34.11 |
| ATOM | 459 | N | ALA | 67 | 25.229 | 24.688 | −0.297 | 1.00 | 34.55 |
| ATOM | 460 | CA | ALA | 67 | 25.456 | 26.034 | −0.794 | 1.00 | 36.86 |
| ATOM | 461 | CB | ALA | 67 | 24.248 | 26.883 | −0.501 | 1.00 | 37.43 |
| ATOM | 462 | C | ALA | 67 | 26.691 | 26.686 | −0.205 | 1.00 | 38.04 |
| ATOM | 463 | O | ALA | 67 | 27.185 | 26.266 | 0.847 | 1.00 | 37.89 |
| ATOM | 464 | N | THR | 68 | 27.142 | 27.746 | −0.877 | 1.00 | 38.87 |
| ATOM | 465 | CA | THR | 68 | 28.320 | 28.515 | −0.477 | 1.00 | 41.49 |
| ATOM | 466 | CB | THR | 68 | 29.374 | 28.482 | −1.555 | 1.00 | 40.24 |
| ATOM | 467 | OG1 | THR | 68 | 28.781 | 28.909 | −2.786 | 1.00 | 39.38 |
| ATOM | 468 | CG2 | THR | 68 | 29.916 | 27.078 | −1.695 | 1.00 | 37.17 |
| ATOM | 469 | C | THR | 68 | 27.974 | 29.971 | −0.209 | 1.00 | 44.07 |
| ATOM | 470 | O | THR | 68 | 27.303 | 30.619 | −1.007 | 1.00 | 45.44 |
| ATOM | 471 | N | ASP | 69 | 28.481 | 30.476 | 0.914 | 1.00 | 46.41 |
| ATOM | 472 | CA | ASP | 69 | 28.240 | 31.844 | 1.379 | 1.00 | 48.43 |
| ATOM | 473 | CB | ASP | 69 | 27.760 | 31.808 | 2.834 | 1.00 | 52.61 |
| ATOM | 474 | CG | ASP | 69 | 26.780 | 32.927 | 3.167 | 1.00 | 56.38 |
| ATOM | 475 | OD1 | ASP | 69 | 27.148 | 34.118 | 3.048 | 1.00 | 56.17 |
| ATOM | 476 | OD2 | ASP | 69 | 25.634 | 32.602 | 3.556 | 1.00 | 58.58 |
| ATOM | 477 | C | ASP | 69 | 29.493 | 32.716 | 1.294 | 1.00 | 48.33 |
| ATOM | 478 | O | ASP | 69 | 30.354 | 32.686 | 2.182 | 1.00 | 49.35 |
| ATOM | 479 | N | PRO | 70 | 29.611 | 33.507 | 0.221 | 1.00 | 46.85 |
| ATOM | 480 | CD | PRO | 70 | 28.598 | 33.759 | −0.816 | 1.00 | 45.47 |
| ATOM | 481 | CA | PRO | 70 | 30.773 | 34.384 | 0.052 | 1.00 | 47.08 |
| ATOM | 482 | CB | PRO | 70 | 30.425 | 35.181 | −1.210 | 1.00 | 46.69 |
| ATOM | 483 | CG | PRO | 70 | 28.929 | 35.155 | −1.241 | 1.00 | 45.84 |
| ATOM | 484 | C | PRO | 70 | 30.991 | 35.281 | 1.276 | 1.00 | 47.53 |
| ATOM | 485 | O | PRO | 70 | 32.110 | 35.455 | 1.749 | 1.00 | 47.58 |
| ATOM | 486 | N | THR | 71 | 29.895 | 35.833 | 1.782 | 1.00 | 46.80 |
| ATOM | 487 | CA | THR | 71 | 29.901 | 36.723 | 2.938 | 1.00 | 45.48 |
| ATOM | 488 | CB | THR | 71 | 28.501 | 37.315 | 3.177 | 1.00 | 43.99 |
| ATOM | 489 | OG1 | THR | 71 | 28.104 | 38.086 | 2.041 | 1.00 | 40.66 |
| ATOM | 490 | CG2 | THR | 71 | 28.497 | 38.181 | 4.408 | 1.00 | 43.58 |
| ATOM | 491 | C | THR | 71 | 30.312 | 36.029 | 4.231 | 1.00 | 45.79 |
| ATOM | 492 | O | THR | 71 | 31.178 | 36.506 | 4.960 | 1.00 | 45.02 |
| ATOM | 493 | N | ARG | 72 | 29.671 | 34.904 | 4.521 | 1.00 | 46.99 |
| ATOM | 494 | CA | ARG | 72 | 29.954 | 34.171 | 5.746 | 1.00 | 47.70 |
| ATOM | 495 | CB | ARG | 72 | 28.724 | 33.384 | 6.159 | 1.00 | 48.08 |
| ATOM | 496 | CG | ARG | 72 | 27.681 | 34.206 | 6.859 | 1.00 | 48.15 |
| ATOM | 497 | CD | ARG | 72 | 26.521 | 33.312 | 7.196 | 1.00 | 46.29 |
| ATOM | 498 | NE | ARG | 72 | 25.995 | 33.592 | 8.524 | 1.00 | 46.49 |
| ATOM | 499 | CZ | ARG | 72 | 26.452 | 33.057 | 9.651 | 1.00 | 44.95 |
| ATOM | 500 | NH1 | ARG | 72 | 27.457 | 32.193 | 9.625 | 1.00 | 50.14 |
| ATOM | 501 | NH2 | ARG | 72 | 25.905 | 33.400 | 10.809 | 1.00 | 41.99 |
| ATOM | 502 | C | ARG | 72 | 31.143 | 33.217 | 5.681 | 1.00 | 46.99 |
| ATOM | 503 | O | ARG | 72 | 31.549 | 32.655 | 6.709 | 1.00 | 44.85 |
| ATOM | 504 | N | LYS | 73 | 31.698 | 33.035 | 4.484 | 1.00 | 46.91 |
| ATOM | 505 | CA | LYS | 73 | 32.822 | 32.128 | 4.308 | 1.00 | 46.89 |
| ATOM | 506 | CB | LYS | 73 | 34.098 | 32.703 | 4.929 | 1.00 | 51.74 |
| ATOM | 507 | CG | LYS | 73 | 34.809 | 33.782 | 4.112 | 1.00 | 57.40 |
| ATOM | 508 | CD | LYS | 73 | 36.162 | 34.081 | 4.783 | 1.00 | 63.05 |
| ATOM | 509 | CE | LYS | 73 | 37.203 | 34.577 | 3.777 | 1.00 | 67.22 |
| ATOM | 510 | NZ | LYS | 73 | 38.607 | 34.596 | 4.319 | 1.00 | 69.40 |
| ATOM | 511 | C | LYS | 73 | 32.516 | 30.792 | 4.968 | 1.00 | 44.83 |
| ATOM | 512 | O | LYS | 73 | 33.140 | 30.419 | 5.969 | 1.00 | 42.64 |
| ATOM | 513 | N | GLU | 74 | 31.544 | 30.081 | 4.409 | 1.00 | 42.80 |
| ATOM | 514 | CA | GLU | 74 | 31.164 | 28.781 | 4.926 | 1.00 | 41.44 |

APPENDIX 1-continued

Coordinates in Protein Data Bank (PDB) format of GZEL.

| ATOM | 515 | CB | GLU | 74 | 30.311 | 28.923 | 6.191 | 1.00 | 41.39 |
|---|---|---|---|---|---|---|---|---|---|
| ATOM | 516 | CG | GLU | 74 | 28.989 | 29.654 | 5.992 | 1.00 | 40.80 |
| ATOM | 517 | CD | GLU | 74 | 28.215 | 29.819 | 7.295 | 1.00 | 41.18 |
| ATOM | 518 | OE1 | GLU | 74 | 26.988 | 30.036 | 7.239 | 1.00 | 37.73 |
| ATOM | 519 | OE2 | GLU | 74 | 28.831 | 29.738 | 8.376 | 1.00 | 41.62 |
| ATOM | 520 | C | GLU | 74 | 30.393 | 27.999 | 3.876 | 1.00 | 39.97 |
| ATOM | 521 | O | GLU | 74 | 30.014 | 28.534 | 2.825 | 1.00 | 39.67 |
| ATOM | 522 | N | ILE | 75 | 30.181 | 26.723 | 4.179 | 1.00 | 37.40 |
| ATOM | 523 | CA | ILE | 75 | 29.464 | 25.807 | 3.309 | 1.00 | 33.79 |
| ATOM | 524 | CB | ILE | 75 | 30.418 | 24.715 | 2.753 | 1.00 | 33.51 |
| ATOM | 525 | CG2 | ILE | 75 | 29.679 | 23.821 | 1.766 | 1.00 | 33.40 |
| ATOM | 526 | CG1 | ILE | 75 | 31.626 | 25.362 | 2.062 | 1.00 | 34.17 |
| ATOM | 527 | CD1 | ILE | 75 | 32.723 | 24.362 | 1.645 | 1.00 | 32.76 |
| ATOM | 528 | C | ILE | 75 | 28.394 | 25.135 | 4.157 | 1.00 | 31.88 |
| ATOM | 529 | O | ILE | 75 | 28.711 | 24.432 | 5.127 | 1.00 | 30.16 |
| ATOM | 530 | N | VAL | 76 | 27.130 | 25.354 | 3.806 | 1.00 | 29.47 |
| ATOM | 531 | CA | VAL | 76 | 26.043 | 24.736 | 4.571 | 1.00 | 30.29 |
| ATOM | 532 | CB | VAL | 76 | 24.930 | 25.758 | 4.986 | 1.00 | 29.82 |
| ATOM | 533 | CG1 | VAL | 76 | 25.539 | 27.145 | 5.281 | 1.00 | 25.34 |
| ATOM | 534 | CG2 | VAL | 76 | 23.870 | 25.815 | 3.913 | 1.00 | 29.32 |
| ATOM | 535 | C | VAL | 76 | 25.363 | 23.627 | 3.767 | 1.00 | 29.05 |
| ATOM | 536 | O | VAL | 76 | 25.384 | 23.655 | 2.523 | 1.00 | 32.60 |
| ATOM | 537 | N | VAL | 77 | 24.757 | 22.668 | 4.484 | 1.00 | 29.82 |
| ATOM | 538 | CA | VAL | 77 | 24.037 | 21.517 | 3.879 | 1.00 | 29.11 |
| ATOM | 539 | CB | VAL | 77 | 24.688 | 20.162 | 4.261 | 1.00 | 27.37 |
| ATOM | 540 | CG1 | VAL | 77 | 24.313 | 19.102 | 3.250 | 1.00 | 24.87 |
| ATOM | 541 | CG2 | VAL | 77 | 26.179 | 20.302 | 4.359 | 1.00 | 25.61 |
| ATOM | 542 | C | VAL | 77 | 22.619 | 21.486 | 4.429 | 1.00 | 28.13 |
| ATOM | 543 | O | VAL | 77 | 22.412 | 21.080 | 5.576 | 1.00 | 29.04 |
| ATOM | 544 | N | SER | 78 | 21.649 | 21.894 | 3.618 | 1.00 | 27.68 |
| ATOM | 545 | CA | SER | 78 | 20.267 | 21.957 | 4.083 | 1.00 | 29.69 |
| ATOM | 546 | CB | SER | 78 | 19.669 | 23.313 | 3.737 | 1.00 | 29.26 |
| ATOM | 547 | OG | SER | 78 | 20.187 | 24.292 | 4.582 | 1.00 | 35.26 |
| ATOM | 548 | C | SER | 78 | 19.333 | 20.870 | 3.580 | 1.00 | 28.37 |
| ATOM | 549 | O | SER | 78 | 19.176 | 20.652 | 2.375 | 1.00 | 32.05 |
| ATOM | 550 | N | PHE | 79 | 18.686 | 20.195 | 4.509 | 1.00 | 26.09 |
| ATOM | 551 | CA | PHE | 79 | 17.774 | 19.148 | 4.120 | 1.00 | 27.58 |
| ATOM | 552 | CB | PHE | 79 | 18.086 | 17.899 | 4.894 | 1.00 | 27.89 |
| ATOM | 553 | CG | PHE | 79 | 19.512 | 17.483 | 4.792 | 1.00 | 23.20 |
| ATOM | 554 | CD1 | PHE | 79 | 20.499 | 18.090 | 5.561 | 1.00 | 23.22 |
| ATOM | 555 | CD2 | PHE | 79 | 19.868 | 16.445 | 3.954 | 1.00 | 22.33 |
| ATOM | 556 | CE1 | PHE | 79 | 21.813 | 17.649 | 5.495 | 1.00 | 23.58 |
| ATOM | 557 | CE2 | PHE | 79 | 21.172 | 16.006 | 3.886 | 1.00 | 21.16 |
| ATOM | 558 | CZ | PHE | 79 | 22.143 | 16.605 | 4.659 | 1.00 | 22.90 |
| ATOM | 559 | C | PHE | 79 | 16.411 | 19.660 | 4.471 | 1.00 | 30.97 |
| ATOM | 560 | O | PHE | 79 | 16.260 | 20.394 | 5.467 | 1.00 | 31.30 |
| ATOM | 561 | N | ARG | 80 | 15.419 | 19.272 | 3.675 | 1.00 | 34.09 |
| ATOM | 562 | CA | ARG | 80 | 14.069 | 19.757 | 3.884 | 1.00 | 37.31 |
| ATOM | 563 | CB | ARG | 80 | 13.423 | 20.015 | 2.541 | 1.00 | 39.96 |
| ATOM | 564 | CG | ARG | 80 | 13.054 | 18.739 | 1.827 | 1.00 | 44.84 |
| ATOM | 565 | CD | ARG | 80 | 12.388 | 19.015 | 0.509 | 1.00 | 43.90 |
| ATOM | 566 | NE | ARG | 80 | 11.986 | 17.775 | −0.140 | 1.00 | 44.13 |
| ATOM | 567 | CZ | ARG | 80 | 11.652 | 17.692 | −1.421 | 1.00 | 47.81 |
| ATOM | 568 | NH1 | ARG | 80 | 11.673 | 18.779 | −2.185 | 1.00 | 47.38 |
| ATOM | 569 | NH2 | ARG | 80 | 11.308 | 16.522 | −1.943 | 1.00 | 50.47 |
| ATOM | 570 | C | ARG | 80 | 13.176 | 18.819 | 4.674 | 1.00 | 38.95 |
| ATOM | 571 | O | ARG | 80 | 13.176 | 17.603 | 4.441 | 1.00 | 38.69 |
| ATOM | 572 | N | GLY | 81 | 12.381 | 19.397 | 5.573 | 1.00 | 40.20 |
| ATOM | 573 | CA | GLY | 81 | 11.482 | 18.604 | 6.393 | 1.00 | 42.83 |
| ATOM | 574 | C | GLY | 81 | 10.232 | 18.077 | 5.687 | 1.00 | 45.60 |
| ATOM | 575 | O | GLY | 81 | 10.196 | 17.974 | 4.443 | 1.00 | 46.04 |
| ATOM | 576 | N | SER | 82 | 9.207 | 17.739 | 6.475 | 1.00 | 48.26 |
| ATOM | 577 | CA | SER | 82 | 7.961 | 17.210 | 5.937 | 1.00 | 51.78 |
| ATOM | 578 | CB | SER | 82 | 7.335 | 16.244 | 6.947 | 1.00 | 53.73 |
| ATOM | 579 | OG | SER | 82 | 6.254 | 15.513 | 6.393 | 1.00 | 58.63 |
| ATOM | 580 | C | SER | 82 | 6.998 | 18.348 | 5.632 | 1.00 | 53.53 |
| ATOM | 581 | O | SER | 82 | 6.751 | 19.219 | 6.471 | 1.00 | 54.68 |
| ATOM | 582 | N | ILE | 83 | 6.464 | 18.339 | 4.420 | 1.00 | 52.86 |
| ATOM | 583 | CA | ILE | 83 | 5.522 | 19.355 | 4.003 | 1.00 | 52.55 |
| ATOM | 584 | CB | ILE | 83 | 5.488 | 19.443 | 2.479 | 1.00 | 53.58 |
| ATOM | 585 | CG2 | ILE | 83 | 6.841 | 19.896 | 1.979 | 1.00 | 53.86 |
| ATOM | 586 | CG1 | ILE | 83 | 5.133 | 18.077 | 1.885 | 1.00 | 53.41 |
| ATOM | 587 | CD1 | ILE | 83 | 5.129 | 18.011 | 0.381 | 1.00 | 53.83 |
| ATOM | 588 | C | ILE | 83 | 4.157 | 18.946 | 4.527 | 1.00 | 52.26 |
| ATOM | 589 | O | ILE | 83 | 3.168 | 19.677 | 4.375 | 1.00 | 51.93 |
| ATOM | 590 | N | ASN | 84 | 4.122 | 17.770 | 5.153 | 1.00 | 48.94 |
| ATOM | 591 | CA | ASN | 84 | 2.888 | 17.229 | 5.711 | 1.00 | 46.21 |
| ATOM | 592 | CB | ASN | 84 | 2.353 | 16.135 | 4.805 | 1.00 | 46.90 |

APPENDIX 1-continued

Coordinates in Protein Data Bank (PDB) format of GZEL.

| | | | | | | | | |
|---|---|---|---|---|---|---|---|---|
| ATOM | 593 | CG | ASN | 84 | 0.855 | 15.998 | 4.902 | 1.00 | 49.97 |
| ATOM | 594 | OD1 | ASN | 84 | 0.271 | 16.163 | 5.985 | 1.00 | 51.10 |
| ATOM | 595 | ND2 | ASN | 84 | 0.213 | 15.695 | 3.765 | 1.00 | 46.93 |
| ATOM | 596 | C | ASN | 84 | 3.133 | 16.649 | 7.097 | 1.00 | 44.37 |
| ATOM | 597 | O | ASN | 84 | 2.867 | 15.489 | 7.354 | 1.00 | 44.26 |
| ATOM | 598 | N | ILE | 85 | 3.629 | 17.473 | 8.001 | 1.00 | 38.99 |
| ATOM | 599 | CA | ILE | 85 | 3.945 | 17.006 | 9.341 | 1.00 | 33.20 |
| ATOM | 600 | CB | ILE | 85 | 4.619 | 18.087 | 10.145 | 1.00 | 28.90 |
| ATOM | 601 | CG2 | ILE | 85 | 3.577 | 19.113 | 10.608 | 1.00 | 27.23 |
| ATOM | 602 | CG1 | ILE | 85 | 5.455 | 17.418 | 11.242 | 1.00 | 25.20 |
| ATOM | 603 | CD1 | ILE | 85 | 6.778 | 16.808 | 10.681 | 1.00 | 20.62 |
| ATOM | 604 | C | ILE | 85 | 2.826 | 16.453 | 10.207 | 1.00 | 32.57 |
| ATOM | 605 | O | ILE | 85 | 3.035 | 15.504 | 10.955 | 1.00 | 32.52 |
| ATOM | 606 | N | ARG | 86 | 1.641 | 17.037 | 10.143 | 1.00 | 35.06 |
| ATOM | 607 | CA | ARG | 86 | 0.577 | 16.497 | 10.963 | 1.00 | 38.21 |
| ATOM | 608 | CB | ARG | 86 | −0.723 | 17.259 | 10.755 | 1.00 | 42.23 |
| ATOM | 609 | CG | ARG | 86 | −1.836 | 16.354 | 10.257 | 1.00 | 51.70 |
| ATOM | 610 | CD | ARG | 86 | −3.214 | 16.998 | 10.318 | 1.00 | 54.87 |
| ATOM | 611 | NE | ARG | 86 | −4.172 | 16.168 | 11.047 | 1.00 | 53.16 |
| ATOM | 612 | CZ | ARG | 86 | −4.345 | 16.211 | 12.362 | 1.00 | 54.60 |
| ATOM | 613 | NH1 | ARG | 86 | −3.623 | 17.049 | 13.092 | 1.00 | 54.61 |
| ATOM | 614 | NH2 | ARG | 86 | −5.237 | 15.419 | 12.944 | 1.00 | 52.09 |
| ATOM | 615 | C | ARG | 86 | 0.410 | 15.056 | 10.502 | 1.00 | 38.35 |
| ATOM | 616 | O | ARG | 86 | 0.181 | 14.158 | 11.289 | 1.00 | 37.91 |
| ATOM | 617 | N | ASN | 87 | 0.543 | 14.844 | 9.205 | 1.00 | 39.43 |
| ATOM | 618 | CA | ASN | 87 | 0.421 | 13.510 | 8.652 | 1.00 | 41.29 |
| ATOM | 619 | CB | ASN | 87 | 0.679 | 13.544 | 7.145 | 1.00 | 45.33 |
| ATOM | 620 | CG | ASN | 87 | 0.464 | 12.198 | 6.486 | 1.00 | 48.42 |
| ATOM | 621 | OD1 | ASN | 87 | 0.764 | 12.021 | 5.305 | 1.00 | 48.98 |
| ATOM | 622 | ND2 | ASN | 87 | −0.065 | 11.239 | 7.245 | 1.00 | 50.03 |
| ATOM | 623 | C | ASN | 87 | 1.425 | 12.569 | 9.312 | 1.00 | 39.38 |
| ATOM | 624 | O | ASN | 87 | 1.049 | 11.532 | 9.870 | 1.00 | 40.50 |
| ATOM | 625 | N | TRP | 88 | 2.701 | 12.951 | 9.236 | 1.00 | 38.35 |
| ATOM | 626 | CA | TRP | 88 | 3.797 | 12.170 | 9.792 | 1.00 | 33.00 |
| ATOM | 627 | CB | TRP | 88 | 5.113 | 12.961 | 9.750 | 1.00 | 28.10 |
| ATOM | 628 | CG | TRP | 88 | 6.309 | 12.112 | 10.132 | 1.00 | 28.88 |
| ATOM | 629 | CD2 | TRP | 88 | 6.975 | 12.066 | 11.400 | 1.00 | 23.66 |
| ATOM | 630 | CE2 | TRP | 88 | 7.932 | 11.005 | 11.333 | 1.00 | 24.60 |
| ATOM | 631 | CE3 | TRP | 88 | 6.859 | 12.808 | 12.589 | 1.00 | 24.28 |
| ATOM | 632 | CD1 | TRP | 88 | 6.878 | 11.128 | 9.373 | 1.00 | 28.94 |
| ATOM | 633 | NE1 | TRP | 88 | 7.850 | 10.452 | 10.085 | 1.00 | 22.39 |
| ATOM | 634 | CZ2 | TRP | 88 | 8.765 | 10.672 | 12.416 | 1.00 | 23.76 |
| ATOM | 635 | CZ3 | TRP | 88 | 7.697 | 12.478 | 13.675 | 1.00 | 25.97 |
| ATOM | 636 | CH2 | TRP | 88 | 8.636 | 11.413 | 13.572 | 1.00 | 24.75 |
| ATOM | 637 | C | TRP | 88 | 3.509 | 11.800 | 11.228 | 1.00 | 33.22 |
| ATOM | 638 | O | TRP | 88 | 3.827 | 10.697 | 11.681 | 1.00 | 34.17 |
| ATOM | 639 | N | LEU | 89 | 2.919 | 12.731 | 11.957 | 1.00 | 33.69 |
| ATOM | 640 | CA | LEU | 89 | 2.629 | 12.450 | 13.334 | 1.00 | 35.69 |
| ATOM | 641 | CB | LEU | 89 | 2.199 | 13.726 | 14.056 | 1.00 | 34.51 |
| ATOM | 642 | CG | LEU | 89 | 3.267 | 14.770 | 14.425 | 1.00 | 31.52 |
| ATOM | 643 | CD1 | LEU | 89 | 2.615 | 15.814 | 15.303 | 1.00 | 31.01 |
| ATOM | 644 | CD2 | LEU | 89 | 4.415 | 14.153 | 15.183 | 1.00 | 27.75 |
| ATOM | 645 | C | LEU | 89 | 1.570 | 11.372 | 13.464 | 1.00 | 37.12 |
| ATOM | 646 | O | LEU | 89 | 1.710 | 10.463 | 14.264 | 1.00 | 42.41 |
| ATOM | 647 | N | THR | 90 | 0.513 | 11.444 | 12.676 | 1.00 | 35.52 |
| ATOM | 648 | CA | THR | 90 | −0.531 | 10.444 | 12.799 | 1.00 | 33.89 |
| ATOM | 649 | CB | THR | 90 | −1.687 | 10.772 | 11.895 | 1.00 | 32.79 |
| ATOM | 650 | OG1 | THR | 90 | −1.228 | 10.778 | 10.538 | 1.00 | 29.17 |
| ATOM | 651 | CG2 | THR | 90 | −2.254 | 12.129 | 12.274 | 1.00 | 31.57 |
| ATOM | 652 | C | THR | 90 | −0.053 | 9.039 | 12.484 | 1.00 | 34.21 |
| ATOM | 653 | O | THR | 90 | −0.640 | 8.065 | 12.958 | 1.00 | 34.70 |
| ATOM | 654 | N | ASN | 91 | 1.009 | 8.933 | 11.694 | 1.00 | 33.44 |
| ATOM | 655 | CA | ASN | 91 | 1.540 | 7.628 | 11.326 | 1.00 | 34.05 |
| ATOM | 656 | CB | ASN | 91 | 2.364 | 7.747 | 10.067 | 1.00 | 34.95 |
| ATOM | 657 | CG | ASN | 91 | 1.503 | 7.962 | 8.866 | 1.00 | 40.50 |
| ATOM | 658 | OD1 | ASN | 91 | 1.972 | 8.382 | 7.816 | 1.00 | 44.74 |
| ATOM | 659 | ND2 | ASN | 91 | 0.213 | 7.666 | 9.011 | 1.00 | 45.23 |
| ATOM | 660 | C | ASN | 91 | 2.354 | 6.954 | 12.389 | 1.00 | 33.80 |
| ATOM | 661 | O | ASN | 91 | 2.441 | 5.731 | 12.403 | 1.00 | 34.95 |
| ATOM | 662 | N | LEU | 92 | 2.945 | 7.751 | 13.275 | 1.00 | 34.11 |
| ATOM | 663 | CA | LEU | 92 | 3.774 | 7.242 | 14.370 | 1.00 | 34.02 |
| ATOM | 664 | CB | LEU | 92 | 2.956 | 6.320 | 15.281 | 1.00 | 33.05 |
| ATOM | 665 | CG | LEU | 92 | 1.686 | 7.011 | 15.761 | 1.00 | 31.66 |
| ATOM | 666 | CD1 | LEU | 92 | 0.976 | 6.160 | 16.793 | 1.00 | 28.13 |
| ATOM | 667 | CD2 | LEU | 92 | 2.073 | 8.343 | 16.363 | 1.00 | 34.00 |
| ATOM | 668 | C | LEU | 92 | 5.005 | 6.488 | 13.878 | 1.00 | 35.56 |
| ATOM | 669 | O | LEU | 92 | 5.248 | 5.342 | 14.288 | 1.00 | 34.71 |
| ATOM | 670 | N | ASP | 93 | 5.774 | 7.139 | 13.014 | 1.00 | 36.76 |

APPENDIX 1-continued

Coordinates in Protein Data Bank (PDB) format of GZEL.

| ATOM | 671 | CA | ASP | 93 | 6.973 | 6.547 | 12.451 | 1.00 | 37.90 |
|---|---|---|---|---|---|---|---|---|---|
| ATOM | 672 | CB | ASP | 93 | 7.515 | 7.500 | 11.393 | 1.00 | 38.96 |
| ATOM | 673 | CG | ASP | 93 | 8.548 | 6.850 | 10.505 | 1.00 | 42.87 |
| ATOM | 674 | OD1 | ASP | 93 | 9.435 | 6.144 | 11.044 | 1.00 | 43.52 |
| ATOM | 675 | OD2 | ASP | 93 | 8.474 | 7.044 | 9.266 | 1.00 | 41.91 |
| ATOM | 676 | C | ASP | 93 | 8.016 | 6.325 | 13.555 | 1.00 | 38.75 |
| ATOM | 677 | O | ASP | 93 | 8.795 | 7.234 | 13.849 | 1.00 | 38.67 |
| ATOM | 678 | N | PHE | 94 | 8.052 | 5.131 | 14.146 | 1.00 | 37.65 |
| ATOM | 679 | CA | PHE | 94 | 9.001 | 4.886 | 15.217 | 1.00 | 36.97 |
| ATOM | 680 | CB | PHE | 94 | 8.246 | 4.562 | 16.488 | 1.00 | 33.98 |
| ATOM | 681 | CG | PHE | 94 | 7.409 | 5.684 | 16.988 | 1.00 | 36.52 |
| ATOM | 682 | CD1 | PHE | 94 | 6.436 | 5.455 | 17.943 | 1.00 | 34.84 |
| ATOM | 683 | CD2 | PHE | 94 | 7.621 | 6.981 | 16.537 | 1.00 | 37.51 |
| ATOM | 684 | CE1 | PHE | 94 | 5.681 | 6.496 | 18.450 | 1.00 | 36.25 |
| ATOM | 685 | CE2 | PHE | 94 | 6.874 | 8.046 | 17.032 | 1.00 | 39.25 |
| ATOM | 686 | CZ | PHE | 94 | 5.894 | 7.800 | 18.002 | 1.00 | 39.66 |
| ATOM | 687 | C | PHE | 94 | 10.042 | 3.804 | 14.992 | 1.00 | 35.93 |
| ATOM | 688 | O | PHE | 94 | 11.111 | 3.828 | 15.619 | 1.00 | 34.66 |
| ATOM | 689 | N | ASP | 95 | 9.755 | 2.861 | 14.110 | 1.00 | 33.05 |
| ATOM | 690 | CA | ASP | 95 | 10.693 | 1.789 | 13.893 | 1.00 | 32.72 |
| ATOM | 691 | CB | ASP | 95 | 10.241 | 1.010 | 12.705 | 1.00 | 33.93 |
| ATOM | 692 | CG | ASP | 95 | 8.985 | 0.249 | 13.001 | 1.00 | 38.39 |
| ATOM | 693 | OD1 | ASP | 95 | 8.254 | 0.678 | 13.919 | 1.00 | 36.80 |
| ATOM | 694 | OD2 | ASP | 95 | 8.719 | −0.770 | 12.331 | 1.00 | 38.25 |
| ATOM | 695 | C | ASP | 95 | 12.137 | 2.191 | 13.759 | 1.00 | 33.61 |
| ATOM | 696 | O | ASP | 95 | 12.480 | 3.217 | 13.188 | 1.00 | 32.88 |
| ATOM | 697 | N | GLN | 96 | 13.004 | 1.368 | 14.311 | 1.00 | 32.68 |
| ATOM | 698 | CA | GLN | 96 | 14.394 | 1.698 | 14.224 | 1.00 | 33.14 |
| ATOM | 699 | CB | GLN | 96 | 14.902 | 2.281 | 15.537 | 1.00 | 31.37 |
| ATOM | 700 | CG | GLN | 96 | 15.216 | 1.274 | 16.638 | 1.00 | 32.76 |
| ATOM | 701 | CD | GLN | 96 | 15.964 | 1.910 | 17.834 | 1.00 | 33.37 |
| ATOM | 702 | OE1 | GLN | 96 | 15.507 | 2.895 | 18.410 | 1.00 | 29.23 |
| ATOM | 703 | NE2 | GLN | 96 | 17.108 | 1.338 | 18.203 | 1.00 | 32.04 |
| ATOM | 704 | C | GLN | 96 | 15.293 | 0.574 | 13.808 | 1.00 | 35.47 |
| ATOM | 705 | O | GLN | 96 | 15.246 | −0.536 | 14.324 | 1.00 | 32.06 |
| ATOM | 706 | N | ASP | 97 | 16.116 | 0.904 | 12.830 | 1.00 | 37.28 |
| ATOM | 707 | CA | ASP | 97 | 17.110 | 0.002 | 12.296 | 1.00 | 39.67 |
| ATOM | 708 | CB | ASP | 97 | 17.446 | 0.371 | 10.858 | 1.00 | 39.54 |
| ATOM | 709 | CG | ASP | 97 | 16.723 | −0.484 | 9.871 | 1.00 | 42.24 |
| ATOM | 710 | OD1 | ASP | 97 | 16.978 | −0.344 | 8.656 | 1.00 | 43.67 |
| ATOM | 711 | OD2 | ASP | 97 | 15.897 | −1.305 | 10.318 | 1.00 | 48.30 |
| ATOM | 712 | C | ASP | 97 | 18.369 | 0.129 | 13.121 | 1.00 | 39.69 |
| ATOM | 713 | O | ASP | 97 | 18.495 | 1.016 | 13.964 | 1.00 | 41.13 |
| ATOM | 714 | N | GLU | 98 | 19.305 | −0.764 | 12.859 | 1.00 | 37.69 |
| ATOM | 715 | CA | GLU | 98 | 20.550 | −0.728 | 13.566 | 1.00 | 36.93 |
| ATOM | 716 | CB | GLU | 98 | 21.158 | −2.108 | 13.605 | 1.00 | 39.43 |
| ATOM | 717 | CG | GLU | 98 | 20.107 | −3.147 | 13.842 | 1.00 | 45.29 |
| ATOM | 718 | CD | GLU | 98 | 20.688 | −4.508 | 14.065 | 1.00 | 50.89 |
| ATOM | 719 | OE1 | GLU | 98 | 19.909 | −5.488 | 14.117 | 1.00 | 52.97 |
| ATOM | 720 | OE2 | GLU | 98 | 21.925 | −4.597 | 14.191 | 1.00 | 54.27 |
| ATOM | 721 | C | GLU | 98 | 21.418 | 0.206 | 12.765 | 1.00 | 33.23 |
| ATOM | 722 | O | GLU | 98 | 21.154 | 0.454 | 11.584 | 1.00 | 32.06 |
| ATOM | 723 | N | CYS | 99 | 22.450 | 0.743 | 13.400 | 1.00 | 32.71 |
| ATOM | 724 | CA | CYS | 99 | 23.351 | 1.665 | 12.722 | 1.00 | 34.26 |
| ATOM | 725 | C | CYS | 99 | 24.782 | 1.212 | 13.008 | 1.00 | 34.77 |
| ATOM | 726 | O | CYS | 99 | 25.023 | 0.504 | 13.991 | 1.00 | 34.87 |
| ATOM | 727 | CB | CYS | 99 | 23.106 | 3.078 | 13.232 | 1.00 | 34.11 |
| ATOM | 728 | SG | CYS | 99 | 24.557 | 3.884 | 13.952 | 1.00 | 42.37 |
| ATOM | 729 | N | SER | 100 | 25.729 | 1.587 | 12.153 | 1.00 | 36.04 |
| ATOM | 730 | CA | SER | 100 | 27.114 | 1.170 | 12.362 | 1.00 | 35.94 |
| ATOM | 731 | CB | SER | 100 | 27.615 | 0.358 | 11.161 | 1.00 | 34.65 |
| ATOM | 732 | OG | SER | 100 | 27.789 | 1.156 | 9.992 | 1.00 | 36.00 |
| ATOM | 733 | C | SER | 100 | 28.042 | 2.355 | 12.599 | 1.00 | 38.47 |
| ATOM | 734 | O | SER | 100 | 29.095 | 2.473 | 11.960 | 1.00 | 41.79 |
| ATOM | 735 | N | LEU | 101 | 27.653 | 3.231 | 13.518 | 1.00 | 37.61 |
| ATOM | 736 | CA | LEU | 101 | 28.451 | 4.405 | 13.822 | 1.00 | 36.68 |
| ATOM | 737 | CB | LEU | 101 | 27.554 | 5.635 | 13.906 | 1.00 | 37.98 |
| ATOM | 738 | CG | LEU | 101 | 27.063 | 6.258 | 12.595 | 1.00 | 37.48 |
| ATOM | 739 | CD1 | LEU | 101 | 25.893 | 7.176 | 12.923 | 1.00 | 36.78 |
| ATOM | 740 | CD2 | LEU | 101 | 28.187 | 7.031 | 11.888 | 1.00 | 37.90 |
| ATOM | 741 | C | LEU | 101 | 29.163 | 4.187 | 15.145 | 1.00 | 34.88 |
| ATOM | 742 | O | LEU | 101 | 30.266 | 4.728 | 15.380 | 1.00 | 32.30 |
| ATOM | 743 | N | THR | 102 | 28.527 | 3.388 | 15.999 | 1.00 | 33.47 |
| ATOM | 744 | CA | THR | 102 | 29.081 | 3.077 | 17.302 | 1.00 | 37.75 |
| ATOM | 745 | CB | THR | 102 | 28.696 | 4.148 | 18.342 | 1.00 | 37.45 |
| ATOM | 746 | OG1 | THR | 102 | 29.294 | 5.394 | 17.975 | 1.00 | 42.24 |
| ATOM | 747 | CG2 | THR | 102 | 29.187 | 3.760 | 19.748 | 1.00 | 37.29 |
| ATOM | 748 | C | THR | 102 | 28.526 | 1.738 | 17.737 | 1.00 | 39.39 |

APPENDIX 1-continued

Coordinates in Protein Data Bank (PDB) format of GZEL.

| ATOM | 749 | O | THR | 102 | 27.515 | 1.267 | 17.189 | 1.00 | 43.35 |
|------|-----|-----|-----|-----|--------|--------|--------|------|-------|
| ATOM | 750 | N | SER | 103 | 29.196 | 1.127 | 18.708 | 1.00 | 39.79 |
| ATOM | 751 | CA | SER | 103 | 28.766 | −0.149 | 19.226 | 1.00 | 41.28 |
| ATOM | 752 | CB | SER | 103 | 29.656 | −0.555 | 20.386 | 1.00 | 42.67 |
| ATOM | 753 | OG | SER | 103 | 29.204 | −1.767 | 20.957 | 1.00 | 45.02 |
| ATOM | 754 | C | SER | 103 | 27.326 | −0.085 | 19.708 | 1.00 | 39.98 |
| ATOM | 755 | O | SER | 103 | 26.935 | 0.866 | 20.384 | 1.00 | 41.43 |
| ATOM | 756 | N | GLY | 104 | 26.544 | −1.104 | 19.366 | 1.00 | 38.48 |
| ATOM | 757 | CA | GLY | 104 | 25.156 | −1.144 | 19.796 | 1.00 | 38.43 |
| ATOM | 758 | C | GLY | 104 | 24.331 | 0.069 | 19.411 | 1.00 | 36.76 |
| ATOM | 759 | O | GLY | 104 | 23.406 | 0.449 | 20.137 | 1.00 | 34.83 |
| ATOM | 760 | N | CYS | 105 | 24.652 | 0.649 | 18.254 | 1.00 | 36.77 |
| ATOM | 761 | CA | CYS | 105 | 23.970 | 1.838 | 17.733 | 1.00 | 35.81 |
| ATOM | 762 | C | CYS | 105 | 22.632 | 1.565 | 17.036 | 1.00 | 34.27 |
| ATOM | 763 | O | CYS | 105 | 22.562 | 0.759 | 16.086 | 1.00 | 35.72 |
| ATOM | 764 | CB | CYS | 105 | 24.904 | 2.575 | 16.759 | 1.00 | 37.31 |
| ATOM | 765 | SG | CYS | 105 | 24.192 | 4.053 | 15.956 | 1.00 | 41.61 |
| ATOM | 766 | N | GLY | 106 | 21.580 | 2.241 | 17.513 | 1.00 | 32.57 |
| ATOM | 767 | CA | GLY | 106 | 20.264 | 2.088 | 16.918 | 1.00 | 29.70 |
| ATOM | 768 | C | GLY | 106 | 19.841 | 3.398 | 16.282 | 1.00 | 28.51 |
| ATOM | 769 | O | GLY | 106 | 20.227 | 4.469 | 16.751 | 1.00 | 24.97 |
| ATOM | 770 | N | VAL | 107 | 19.043 | 3.323 | 15.222 | 1.00 | 27.72 |
| ATOM | 771 | CA | VAL | 107 | 18.612 | 4.522 | 14.529 | 1.00 | 25.88 |
| ATOM | 772 | CB | VAL | 107 | 19.608 | 4.900 | 13.424 | 1.00 | 24.77 |
| ATOM | 773 | CG1 | VAL | 107 | 19.527 | 3.891 | 12.307 | 1.00 | 24.43 |
| ATOM | 774 | CG2 | VAL | 107 | 19.328 | 6.308 | 12.927 | 1.00 | 27.27 |
| ATOM | 775 | C | VAL | 107 | 17.240 | 4.345 | 13.906 | 1.00 | 26.16 |
| ATOM | 776 | O | VAL | 107 | 16.821 | 3.226 | 13.586 | 1.00 | 26.91 |
| ATOM | 777 | N | HIS | 108 | 16.561 | 5.481 | 13.751 | 1.00 | 22.68 |
| ATOM | 778 | CA | HIS | 108 | 15.239 | 5.558 | 13.176 | 1.00 | 21.88 |
| ATOM | 779 | CB | HIS | 108 | 14.657 | 6.930 | 13.459 | 1.00 | 18.95 |
| ATOM | 780 | CG | HIS | 108 | 13.354 | 7.185 | 12.773 | 1.00 | 18.23 |
| ATOM | 781 | CD2 | HIS | 108 | 12.114 | 7.404 | 13.274 | 1.00 | 16.34 |
| ATOM | 782 | ND1 | HIS | 108 | 13.233 | 7.242 | 11.399 | 1.00 | 15.06 |
| ATOM | 783 | CE1 | HIS | 108 | 11.971 | 7.486 | 11.084 | 1.00 | 16.78 |
| ATOM | 784 | NE2 | HIS | 108 | 11.272 | 7.588 | 12.203 | 1.00 | 18.04 |
| ATOM | 785 | C | HIS | 108 | 15.336 | 5.338 | 11.687 | 1.00 | 24.47 |
| ATOM | 786 | O | HIS | 108 | 15.754 | 6.225 | 10.945 | 1.00 | 28.53 |
| ATOM | 787 | N | SER | 109 | 14.933 | 4.151 | 11.259 | 1.00 | 26.53 |
| ATOM | 788 | CA | SER | 109 | 14.971 | 3.767 | 9.846 | 1.00 | 26.33 |
| ATOM | 789 | CB | SER | 109 | 13.901 | 2.718 | 9.596 | 1.00 | 25.81 |
| ATOM | 790 | OG | SER | 109 | 14.122 | 1.617 | 10.464 | 1.00 | 30.40 |
| ATOM | 791 | C | SER | 109 | 14.800 | 4.902 | 8.855 | 1.00 | 24.40 |
| ATOM | 792 | O | SER | 109 | 15.747 | 5.278 | 8.155 | 1.00 | 23.43 |
| ATOM | 793 | N | GLY | 110 | 13.575 | 5.416 | 8.805 | 1.00 | 23.31 |
| ATOM | 794 | CA | GLY | 110 | 13.244 | 6.506 | 7.921 | 1.00 | 25.96 |
| ATOM | 795 | C | GLY | 110 | 14.392 | 7.453 | 7.742 | 1.00 | 26.60 |
| ATOM | 796 | O | GLY | 110 | 15.010 | 7.515 | 6.689 | 1.00 | 27.43 |
| ATOM | 797 | N | PHE | 111 | 14.693 | 8.183 | 8.798 | 1.00 | 24.09 |
| ATOM | 798 | CA | PHE | 111 | 15.773 | 9.159 | 8.742 | 1.00 | 23.35 |
| ATOM | 799 | CB | PHE | 111 | 16.105 | 9.663 | 10.139 | 1.00 | 22.88 |
| ATOM | 800 | CG | PHE | 111 | 14.912 | 10.175 | 10.893 | 1.00 | 20.11 |
| ATOM | 801 | CD1 | PHE | 111 | 13.822 | 10.729 | 10.213 | 1.00 | 16.75 |
| ATOM | 802 | CD2 | PHE | 111 | 14.885 | 10.152 | 12.287 | 1.00 | 17.31 |
| ATOM | 803 | CE1 | PHE | 111 | 12.731 | 11.251 | 10.926 | 1.00 | 17.67 |
| ATOM | 804 | CE2 | PHE | 111 | 13.797 | 10.676 | 12.986 | 1.00 | 19.96 |
| ATOM | 805 | CZ | PHE | 111 | 12.731 | 11.221 | 12.308 | 1.00 | 19.28 |
| ATOM | 806 | C | PHE | 111 | 17.031 | 8.596 | 8.086 | 1.00 | 24.50 |
| ATOM | 807 | O | PHE | 111 | 17.600 | 9.218 | 7.188 | 1.00 | 23.12 |
| ATOM | 808 | N | GLN | 112 | 17.452 | 7.407 | 8.501 | 1.00 | 24.02 |
| ATOM | 809 | CA | GLN | 112 | 18.649 | 6.815 | 7.921 | 1.00 | 26.60 |
| ATOM | 810 | CB | GLN | 112 | 19.051 | 5.555 | 8.677 | 1.00 | 26.33 |
| ATOM | 811 | CG | GLN | 112 | 20.212 | 4.850 | 8.021 | 1.00 | 26.25 |
| ATOM | 812 | CD | GLN | 112 | 21.011 | 4.000 | 8.981 | 1.00 | 29.74 |
| ATOM | 813 | OE1 | GLN | 112 | 21.443 | 2.894 | 8.639 | 1.00 | 35.31 |
| ATOM | 814 | NE2 | GLN | 112 | 21.243 | 4.519 | 10.180 | 1.00 | 34.04 |
| ATOM | 815 | C | GLN | 112 | 18.516 | 6.488 | 6.435 | 1.00 | 27.78 |
| ATOM | 816 | O | GLN | 112 | 19.436 | 6.745 | 5.647 | 1.00 | 29.45 |
| ATOM | 817 | N | ASN | 113 | 17.371 | 5.938 | 6.041 | 1.00 | 28.08 |
| ATOM | 818 | CA | ASN | 113 | 17.175 | 5.596 | 4.639 | 1.00 | 28.43 |
| ATOM | 819 | CB | ASN | 113 | 15.839 | 4.901 | 4.424 | 1.00 | 28.41 |
| ATOM | 820 | CG | ASN | 113 | 15.871 | 3.451 | 4.863 | 1.00 | 30.04 |
| ATOM | 821 | OD1 | ASN | 113 | 16.792 | 2.700 | 4.496 | 1.00 | 30.46 |
| ATOM | 822 | ND2 | ASN | 113 | 14.865 | 3.040 | 5.643 | 1.00 | 28.40 |
| ATOM | 823 | C | ASN | 113 | 17.233 | 6.841 | 3.803 | 1.00 | 28.99 |
| ATOM | 824 | O | ASN | 113 | 17.865 | 6.880 | 2.759 | 1.00 | 33.51 |
| ATOM | 825 | N | ALA | 114 | 16.554 | 7.869 | 4.279 | 1.00 | 28.45 |
| ATOM | 826 | CA | ALA | 114 | 16.527 | 9.145 | 3.583 | 1.00 | 27.49 |

APPENDIX 1-continued

Coordinates in Protein Data Bank (PDB) format of GZEL.

| ATOM | 827 | CB  | ALA | 114 | 15.801 | 10.171 | 4.405  | 1.00 | 26.03 |
| ---- | --- | --- | --- | --- | ------ | ------ | ------ | ---- | ----- |
| ATOM | 828 | C   | ALA | 114 | 17.950 | 9.609  | 3.343  | 1.00 | 27.35 |
| ATOM | 829 | O   | ALA | 114 | 18.299 | 10.023 | 2.241  | 1.00 | 29.80 |
| ATOM | 830 | N   | TRP | 115 | 18.767 | 9.532  | 4.391  | 1.00 | 23.62 |
| ATOM | 831 | CA  | TRP | 115 | 20.155 | 9.952  | 4.323  | 1.00 | 21.51 |
| ATOM | 832 | CB  | TRP | 115 | 20.875 | 9.730  | 5.652  | 1.00 | 21.64 |
| ATOM | 833 | CG  | TRP | 115 | 22.372 | 9.888  | 5.533  | 1.00 | 20.35 |
| ATOM | 834 | CD2 | TRP | 115 | 23.087 | 10.970 | 4.903  | 1.00 | 19.79 |
| ATOM | 835 | CE2 | TRP | 115 | 24.474 | 10.687 | 5.036  | 1.00 | 18.85 |
| ATOM | 836 | CE3 | TRP | 115 | 22.691 | 12.146 | 4.247  | 1.00 | 17.80 |
| ATOM | 837 | CD1 | TRP | 115 | 23.321 | 9.029  | 5.998  | 1.00 | 20.04 |
| ATOM | 838 | NE1 | TRP | 115 | 24.593 | 9.500  | 5.700  | 1.00 | 17.55 |
| ATOM | 839 | CZ2 | TRP | 115 | 25.456 | 11.537 | 4.543  | 1.00 | 17.95 |
| ATOM | 840 | CZ3 | TRP | 115 | 23.672 | 12.994 | 3.756  | 1.00 | 18.83 |
| ATOM | 841 | CH2 | TRP | 115 | 25.042 | 12.681 | 3.909  | 1.00 | 21.55 |
| ATOM | 842 | C   | TRP | 115 | 20.868 | 9.144  | 3.295  | 1.00 | 23.16 |
| ATOM | 843 | O   | TRP | 115 | 21.623 | 9.663  | 2.471  | 1.00 | 27.46 |
| ATOM | 844 | N   | ASN | 116 | 20.658 | 7.846  | 3.386  | 1.00 | 23.42 |
| ATOM | 845 | CA  | ASN | 116 | 21.304 | 6.953  | 2.465  | 1.00 | 24.21 |
| ATOM | 846 | CB  | ASN | 116 | 21.030 | 5.516  | 2.849  | 1.00 | 24.03 |
| ATOM | 847 | CG  | ASN | 116 | 21.676 | 5.150  | 4.132  | 1.00 | 29.29 |
| ATOM | 848 | OD1 | ASN | 116 | 22.717 | 5.687  | 4.481  | 1.00 | 31.97 |
| ATOM | 849 | ND2 | ASN | 116 | 21.080 | 4.218  | 4.844  | 1.00 | 33.01 |
| ATOM | 850 | C   | ASN | 116 | 20.836 | 7.172  | 1.052  | 1.00 | 23.56 |
| ATOM | 851 | O   | ASN | 116 | 21.567 | 6.937  | 0.093  | 1.00 | 22.94 |
| ATOM | 852 | N   | GLU | 117 | 19.604 | 7.614  | 0.897  | 1.00 | 20.73 |
| ATOM | 853 | CA  | GLU | 117 | 19.146 | 7.772  | −0.454 | 1.00 | 22.57 |
| ATOM | 854 | CB  | GLU | 117 | 17.640 | 8.002  | −0.509 | 1.00 | 21.79 |
| ATOM | 855 | CG  | GLU | 117 | 17.137 | 7.876  | −1.925 | 1.00 | 27.82 |
| ATOM | 856 | CD  | GLU | 117 | 15.642 | 7.790  | −2.017 | 1.00 | 28.18 |
| ATOM | 857 | OE1 | GLU | 117 | 15.136 | 7.453  | −3.110 | 1.00 | 28.56 |
| ATOM | 858 | OE2 | GLU | 117 | 14.979 | 8.066  | −1.000 | 1.00 | 27.41 |
| ATOM | 859 | C   | GLU | 117 | 19.849 | 8.891  | −1.180 | 1.00 | 22.98 |
| ATOM | 860 | O   | GLU | 117 | 19.907 | 8.890  | −2.413 | 1.00 | 22.77 |
| ATOM | 861 | N   | ILE | 118 | 20.433 | 9.812  | −0.421 | 1.00 | 24.29 |
| ATOM | 862 | CA  | ILE | 118 | 21.056 | 10.989 | −1.017 | 1.00 | 24.36 |
| ATOM | 863 | CB  | ILE | 118 | 20.160 | 12.210 | −0.739 | 1.00 | 23.50 |
| ATOM | 864 | CG2 | ILE | 118 | 18.679 | 11.913 | −1.178 | 1.00 | 17.72 |
| ATOM | 865 | CG1 | ILE | 118 | 20.229 | 12.521 | 0.768  | 1.00 | 23.92 |
| ATOM | 866 | CD1 | ILE | 118 | 19.649 | 13.873 | 1.188  | 1.00 | 24.45 |
| ATOM | 867 | C   | ILE | 118 | 22.470 | 11.302 | −0.500 | 1.00 | 27.82 |
| ATOM | 868 | O   | ILE | 118 | 23.083 | 12.301 | −0.893 | 1.00 | 27.76 |
| ATOM | 869 | N   | SER | 119 | 22.989 | 10.455 | 0.384  | 1.00 | 28.69 |
| ATOM | 870 | CA  | SER | 119 | 24.321 | 10.676 | 0.972  | 1.00 | 31.82 |
| ATOM | 871 | CB  | SER | 119 | 24.707 | 9.487  | 1.842  | 1.00 | 31.79 |
| ATOM | 872 | OG  | SER | 119 | 24.796 | 8.321  | 1.064  | 1.00 | 31.33 |
| ATOM | 873 | C   | SER | 119 | 25.459 | 10.952 | −0.015 | 1.00 | 31.63 |
| ATOM | 874 | O   | SER | 119 | 26.269 | 11.845 | 0.191  | 1.00 | 32.58 |
| ATOM | 875 | N   | ALA | 120 | 25.508 | 10.187 | −1.095 | 1.00 | 30.64 |
| ATOM | 876 | CA  | ALA | 120 | 26.563 | 10.324 | −2.104 | 1.00 | 31.31 |
| ATOM | 877 | CB  | ALA | 120 | 26.414 | 9.246  | −3.178 | 1.00 | 32.77 |
| ATOM | 878 | C   | ALA | 120 | 26.633 | 11.678 | −2.769 | 1.00 | 30.92 |
| ATOM | 879 | O   | ALA | 120 | 27.681 | 12.311 | −2.810 | 1.00 | 32.49 |
| ATOM | 880 | N   | ALA | 121 | 25.499 | 12.115 | −3.290 | 1.00 | 28.48 |
| ATOM | 881 | CA  | ALA | 121 | 25.396 | 13.411 | −3.954 | 1.00 | 23.95 |
| ATOM | 882 | CB  | ALA | 121 | 24.007 | 13.605 | −4.511 | 1.00 | 22.70 |
| ATOM | 883 | C   | ALA | 121 | 25.681 | 14.490 | −2.958 | 1.00 | 23.32 |
| ATOM | 884 | O   | ALA | 121 | 26.352 | 15.466 | −3.250 | 1.00 | 20.59 |
| ATOM | 885 | N   | ALA | 122 | 25.151 | 14.282 | −1.765 | 1.00 | 23.65 |
| ATOM | 886 | CA  | ALA | 122 | 25.323 | 15.216 | −0.668 | 1.00 | 25.49 |
| ATOM | 887 | CB  | ALA | 122 | 24.650 | 14.670 | 0.571  | 1.00 | 25.06 |
| ATOM | 888 | C   | ALA | 122 | 26.803 | 15.400 | −0.407 | 1.00 | 26.41 |
| ATOM | 889 | O   | ALA | 122 | 27.327 | 16.507 | −0.423 | 1.00 | 24.84 |
| ATOM | 890 | N   | THR | 123 | 27.481 | 14.285 | −0.194 | 1.00 | 24.70 |
| ATOM | 891 | CA  | THR | 123 | 28.904 | 14.297 | 0.068  | 1.00 | 26.60 |
| ATOM | 892 | CB  | THR | 123 | 29.406 | 12.912 | 0.185  | 1.00 | 26.27 |
| ATOM | 893 | OG1 | THR | 123 | 28.622 | 12.238 | 1.168  | 1.00 | 28.89 |
| ATOM | 894 | CG2 | THR | 123 | 30.873 | 12.916 | 0.569  | 1.00 | 23.09 |
| ATOM | 895 | C   | THR | 123 | 29.748 | 14.970 | −0.989 | 1.00 | 29.08 |
| ATOM | 896 | O   | THR | 123 | 30.545 | 15.869 | −0.698 | 1.00 | 29.71 |
| ATOM | 897 | N   | ALA | 124 | 29.591 | 14.494 | −2.213 | 1.00 | 29.51 |
| ATOM | 898 | CA  | ALA | 124 | 30.335 | 15.033 | −3.317 | 1.00 | 30.04 |
| ATOM | 899 | CB  | ALA | 124 | 29.850 | 14.428 | −4.590 | 1.00 | 28.86 |
| ATOM | 900 | C   | ALA | 124 | 30.214 | 16.536 | −3.384 | 1.00 | 31.99 |
| ATOM | 901 | O   | ALA | 124 | 31.229 | 17.231 | −3.494 | 1.00 | 32.89 |
| ATOM | 902 | N   | ALA | 125 | 28.978 | 17.032 | −3.324 | 1.00 | 32.86 |
| ATOM | 903 | CA  | ALA | 125 | 28.732 | 18.470 | −3.390 | 1.00 | 32.71 |
| ATOM | 904 | CB  | ALA | 125 | 27.257 | 18.762 | −3.214 | 1.00 | 29.72 |

APPENDIX 1-continued

Coordinates in Protein Data Bank (PDB) format of GZEL.

| ATOM | 905 | C | ALA | 125 | 29.548 | 19.196 | −2.316 | 1.00 | 36.27 |
|---|---|---|---|---|---|---|---|---|---|
| ATOM | 906 | O | ALA | 125 | 30.168 | 20.230 | −2.585 | 1.00 | 38.52 |
| ATOM | 907 | N | VAL | 126 | 29.556 | 18.648 | −1.106 | 1.00 | 37.28 |
| ATOM | 908 | CA | VAL | 126 | 30.299 | 19.247 | −0.015 | 1.00 | 37.15 |
| ATOM | 909 | CB | VAL | 126 | 30.080 | 18.467 | 1.271 | 1.00 | 35.30 |
| ATOM | 910 | CG1 | VAL | 126 | 30.905 | 19.081 | 2.376 | 1.00 | 31.71 |
| ATOM | 911 | CG2 | VAL | 126 | 28.620 | 18.467 | 1.628 | 1.00 | 37.20 |
| ATOM | 912 | C | VAL | 126 | 31.788 | 19.281 | −0.316 | 1.00 | 39.89 |
| ATOM | 913 | O | VAL | 126 | 32.500 | 20.211 | 0.078 | 1.00 | 39.87 |
| ATOM | 914 | N | ALA | 127 | 32.263 | 18.246 | −0.997 | 1.00 | 41.11 |
| ATOM | 915 | CA | ALA | 127 | 33.666 | 18.176 | −1.340 | 1.00 | 41.91 |
| ATOM | 916 | CB | ALA | 127 | 33.964 | 16.836 | −1.939 | 1.00 | 38.95 |
| ATOM | 917 | C | ALA | 127 | 33.971 | 19.272 | −2.336 | 1.00 | 42.35 |
| ATOM | 918 | O | ALA | 127 | 34.782 | 20.147 | −2.112 | 1.00 | 43.45 |
| ATOM | 919 | N | LYS | 128 | 33.270 | 19.189 | −3.449 | 1.00 | 42.74 |
| ATOM | 920 | CA | LYS | 128 | 33.376 | 20.124 | −4.552 | 1.00 | 45.06 |
| ATOM | 921 | CB | LYS | 128 | 32.173 | 19.946 | −5.493 | 1.00 | 46.03 |
| ATOM | 922 | CG | LYS | 128 | 32.162 | 20.899 | −6.664 | 1.00 | 45.30 |
| ATOM | 923 | CD | LYS | 128 | 31.018 | 20.569 | −7.617 | 1.00 | 43.76 |
| ATOM | 924 | CE | LYS | 128 | 31.086 | 21.435 | −8.866 | 1.00 | 42.90 |
| ATOM | 925 | NZ | LYS | 128 | 30.055 | 21.041 | −9.865 | 1.00 | 47.44 |
| ATOM | 926 | C | LYS | 128 | 33.445 | 21.580 | −4.124 | 1.00 | 47.18 |
| ATOM | 927 | O | LYS | 128 | 34.218 | 22.365 | −4.688 | 1.00 | 48.16 |
| ATOM | 928 | N | ALA | 129 | 32.619 | 21.947 | −3.149 | 1.00 | 46.89 |
| ATOM | 929 | CA | ALA | 129 | 32.568 | 23.327 | −2.681 | 1.00 | 48.47 |
| ATOM | 930 | CB | ALA | 129 | 31.176 | 23.649 | −2.202 | 1.00 | 50.70 |
| ATOM | 931 | C | ALA | 129 | 33.556 | 23.554 | −1.564 | 1.00 | 48.47 |
| ATOM | 932 | O | ALA | 129 | 33.724 | 24.664 | −1.069 | 1.00 | 49.52 |
| ATOM | 933 | N | ARG | 130 | 34.216 | 22.481 | −1.173 | 1.00 | 47.79 |
| ATOM | 934 | CA | ARG | 130 | 35.177 | 22.533 | −0.091 | 1.00 | 47.18 |
| ATOM | 935 | CB | ARG | 130 | 35.056 | 21.238 | 0.708 | 1.00 | 46.27 |
| ATOM | 936 | CG | ARG | 130 | 35.996 | 21.101 | 1.866 | 1.00 | 45.34 |
| ATOM | 937 | CD | ARG | 130 | 35.303 | 21.237 | 3.216 | 1.00 | 45.42 |
| ATOM | 938 | NE | ARG | 130 | 36.154 | 20.722 | 4.292 | 1.00 | 46.95 |
| ATOM | 939 | CZ | ARG | 130 | 36.532 | 19.446 | 4.379 | 1.00 | 47.21 |
| ATOM | 940 | NH1 | ARG | 130 | 36.125 | 18.578 | 3.455 | 1.00 | 49.67 |
| ATOM | 941 | NH2 | ARG | 130 | 37.316 | 19.030 | 5.374 | 1.00 | 47.17 |
| ATOM | 942 | C | ARG | 130 | 36.569 | 22.695 | −0.688 | 1.00 | 47.32 |
| ATOM | 943 | O | ARG | 130 | 37.481 | 23.265 | −0.085 | 1.00 | 46.83 |
| ATOM | 944 | N | LYS | 131 | 36.699 | 22.182 | −1.900 | 1.00 | 47.02 |
| ATOM | 945 | CA | LYS | 131 | 37.927 | 22.234 | −2.665 | 1.00 | 47.60 |
| ATOM | 946 | CB | LYS | 131 | 37.898 | 21.096 | −3.683 | 1.00 | 48.24 |
| ATOM | 947 | CG | LYS | 131 | 38.905 | 21.171 | −4.797 | 1.00 | 49.97 |
| ATOM | 948 | CD | LYS | 131 | 38.712 | 20.006 | −5.773 | 1.00 | 51.12 |
| ATOM | 949 | CE | LYS | 131 | 39.616 | 20.100 | −7.012 | 1.00 | 54.18 |
| ATOM | 950 | NZ | LYS | 131 | 41.091 | 20.138 | −6.750 | 1.00 | 52.50 |
| ATOM | 951 | C | LYS | 131 | 37.935 | 23.590 | −3.358 | 1.00 | 46.50 |
| ATOM | 952 | O | LYS | 131 | 38.974 | 24.205 | −3.565 | 1.00 | 45.65 |
| ATOM | 953 | N | ALA | 132 | 36.745 | 24.057 | −3.703 | 1.00 | 46.55 |
| ATOM | 954 | CA | ALA | 132 | 36.596 | 25.338 | −4.366 | 1.00 | 46.83 |
| ATOM | 955 | CB | ALA | 132 | 35.250 | 25.412 | −5.040 | 1.00 | 46.52 |
| ATOM | 956 | C | ALA | 132 | 36.734 | 26.481 | −3.392 | 1.00 | 47.29 |
| ATOM | 957 | O | ALA | 132 | 37.140 | 27.564 | −3.742 | 1.00 | 48.72 |
| ATOM | 958 | N | ASN | 133 | 36.393 | 26.237 | −2.149 | 1.00 | 47.56 |
| ATOM | 959 | CA | ASN | 133 | 36.475 | 27.290 | −1.167 | 1.00 | 47.89 |
| ATOM | 960 | CB | ASN | 133 | 35.073 | 27.831 | −0.904 | 1.00 | 47.13 |
| ATOM | 961 | CG | ASN | 133 | 34.379 | 28.258 | −2.180 | 1.00 | 44.88 |
| ATOM | 962 | OD1 | ASN | 133 | 34.762 | 29.251 | −2.797 | 1.00 | 46.01 |
| ATOM | 963 | ND2 | ASN | 133 | 33.365 | 27.501 | −2.594 | 1.00 | 42.65 |
| ATOM | 964 | C | ASN | 133 | 37.088 | 26.709 | 0.084 | 1.00 | 51.35 |
| ATOM | 965 | O | ASN | 133 | 36.428 | 26.587 | 1.115 | 1.00 | 54.41 |
| ATOM | 966 | N | PRO | 134 | 38.379 | 26.354 | 0.004 | 1.00 | 52.07 |
| ATOM | 967 | CD | PRO | 134 | 39.241 | 26.711 | −1.139 | 1.00 | 51.41 |
| ATOM | 968 | CA | PRO | 134 | 39.175 | 25.765 | 1.082 | 1.00 | 51.27 |
| ATOM | 969 | CB | PRO | 134 | 40.543 | 25.589 | 0.429 | 1.00 | 50.94 |
| ATOM | 970 | CG | PRO | 134 | 40.598 | 26.756 | −0.500 | 1.00 | 53.24 |
| ATOM | 971 | C | PRO | 134 | 39.248 | 26.523 | 2.416 | 1.00 | 52.11 |
| ATOM | 972 | O | PRO | 134 | 39.540 | 25.917 | 3.452 | 1.00 | 54.28 |
| ATOM | 973 | N | SER | 135 | 38.995 | 27.829 | 2.417 | 1.00 | 51.79 |
| ATOM | 974 | CA | SER | 135 | 39.048 | 28.568 | 3.681 | 1.00 | 49.81 |
| ATOM | 975 | CB | SER | 135 | 39.238 | 30.065 | 3.427 | 1.00 | 48.81 |
| ATOM | 976 | OG | SER | 135 | 38.140 | 30.602 | 2.716 | 1.00 | 44.30 |
| ATOM | 977 | C | SER | 135 | 37.760 | 28.354 | 4.469 | 1.00 | 48.48 |
| ATOM | 978 | O | SER | 135 | 37.769 | 28.345 | 5.707 | 1.00 | 48.39 |
| ATOM | 979 | N | PHE | 136 | 36.660 | 28.178 | 3.734 | 1.00 | 46.17 |
| ATOM | 980 | CA | PHE | 136 | 35.320 | 27.980 | 4.295 | 1.00 | 44.62 |
| ATOM | 981 | CB | PHE | 136 | 34.335 | 27.829 | 3.135 | 1.00 | 44.25 |
| ATOM | 982 | CG | PHE | 136 | 34.154 | 29.083 | 2.324 | 1.00 | 43.96 |

APPENDIX 1-continued

Coordinates in Protein Data Bank (PDB) format of GZEL.

| ATOM | 983 | CD1 | PHE | 136 | 35.249 | 29.862 | 1.966 | 1.00 | 44.47 |
|---|---|---|---|---|---|---|---|---|---|
| ATOM | 984 | CD2 | PHE | 136 | 32.883 | 29.499 | 1.930 | 1.00 | 45.10 |
| ATOM | 985 | CE1 | PHE | 136 | 35.079 | 31.039 | 1.232 | 1.00 | 45.46 |
| ATOM | 986 | CE2 | PHE | 136 | 32.707 | 30.675 | 1.195 | 1.00 | 47.14 |
| ATOM | 987 | CZ | PHE | 136 | 33.805 | 31.443 | 0.850 | 1.00 | 46.31 |
| ATOM | 988 | C | PHE | 136 | 35.167 | 26.799 | 5.266 | 1.00 | 43.26 |
| ATOM | 989 | O | PHE | 136 | 35.839 | 25.768 | 5.133 | 1.00 | 42.48 |
| ATOM | 990 | N | LYS | 137 | 34.298 | 26.969 | 6.259 | 1.00 | 42.74 |
| ATOM | 991 | CA | LYS | 137 | 34.016 | 25.918 | 7.240 | 1.00 | 45.31 |
| ATOM | 992 | CB | LYS | 137 | 33.944 | 26.514 | 8.642 | 1.00 | 47.43 |
| ATOM | 993 | CG | LYS | 137 | 33.075 | 27.753 | 8.724 | 1.00 | 50.73 |
| ATOM | 994 | CD | LYS | 137 | 33.088 | 28.321 | 10.120 | 1.00 | 54.00 |
| ATOM | 995 | CE | LYS | 137 | 32.294 | 29.614 | 10.197 | 1.00 | 56.52 |
| ATOM | 996 | NZ | LYS | 137 | 32.838 | 30.691 | 9.310 | 1.00 | 54.83 |
| ATOM | 997 | C | LYS | 137 | 32.664 | 25.315 | 6.843 | 1.00 | 43.52 |
| ATOM | 998 | O | LYS | 137 | 31.980 | 25.863 | 5.978 | 1.00 | 43.49 |
| ATOM | 999 | N | VAL | 138 | 32.271 | 24.207 | 7.467 | 1.00 | 40.21 |
| ATOM | 1000 | CA | VAL | 138 | 31.014 | 23.569 | 7.100 | 1.00 | 39.86 |
| ATOM | 1001 | CB | VAL | 138 | 31.236 | 22.126 | 6.677 | 1.00 | 39.80 |
| ATOM | 1002 | CG1 | VAL | 138 | 30.044 | 21.660 | 5.858 | 1.00 | 37.32 |
| ATOM | 1003 | CG2 | VAL | 138 | 32.524 | 21.995 | 5.912 | 1.00 | 38.61 |
| ATOM | 1004 | C | VAL | 138 | 29.934 | 23.540 | 8.169 | 1.00 | 38.40 |
| ATOM | 1005 | O | VAL | 138 | 30.222 | 23.430 | 9.357 | 1.00 | 39.54 |
| ATOM | 1006 | N | VAL | 139 | 28.685 | 23.595 | 7.715 | 1.00 | 36.50 |
| ATOM | 1007 | CA | VAL | 139 | 27.528 | 23.559 | 8.596 | 1.00 | 38.24 |
| ATOM | 1008 | CB | VAL | 139 | 26.933 | 24.956 | 8.791 | 1.00 | 39.41 |
| ATOM | 1009 | CG1 | VAL | 139 | 25.652 | 24.858 | 9.596 | 1.00 | 38.25 |
| ATOM | 1010 | CG2 | VAL | 139 | 27.942 | 25.850 | 9.487 | 1.00 | 40.77 |
| ATOM | 1011 | C | VAL | 139 | 26.437 | 22.642 | 8.051 | 1.00 | 36.49 |
| ATOM | 1012 | O | VAL | 139 | 26.124 | 22.650 | 6.866 | 1.00 | 39.45 |
| ATOM | 1013 | N | SER | 140 | 25.835 | 21.869 | 8.937 | 1.00 | 32.14 |
| ATOM | 1014 | CA | SER | 140 | 24.792 | 20.936 | 8.552 | 1.00 | 29.04 |
| ATOM | 1015 | CB | SER | 140 | 25.181 | 19.543 | 9.042 | 1.00 | 24.02 |
| ATOM | 1016 | OG | SER | 140 | 24.210 | 18.589 | 8.703 | 1.00 | 29.12 |
| ATOM | 1017 | C | SER | 140 | 23.510 | 21.413 | 9.222 | 1.00 | 28.02 |
| ATOM | 1018 | O | SER | 140 | 23.397 | 21.358 | 10.441 | 1.00 | 27.82 |
| ATOM | 1019 | N | VAL | 141 | 22.553 | 21.874 | 8.417 | 1.00 | 27.82 |
| ATOM | 1020 | CA | VAL | 141 | 21.281 | 22.399 | 8.907 | 1.00 | 30.87 |
| ATOM | 1021 | CB | VAL | 141 | 21.111 | 23.883 | 8.420 | 1.00 | 29.90 |
| ATOM | 1022 | CG1 | VAL | 141 | 19.865 | 24.527 | 9.022 | 1.00 | 28.75 |
| ATOM | 1023 | CG2 | VAL | 141 | 22.348 | 24.679 | 8.798 | 1.00 | 33.17 |
| ATOM | 1024 | C | VAL | 141 | 20.074 | 21.550 | 8.485 | 1.00 | 33.03 |
| ATOM | 1025 | O | VAL | 141 | 20.176 | 20.659 | 7.644 | 1.00 | 35.84 |
| ATOM | 1026 | N | GLY | 142 | 18.933 | 21.848 | 9.104 | 1.00 | 32.70 |
| ATOM | 1027 | CA | GLY | 142 | 17.686 | 21.152 | 8.838 | 1.00 | 30.09 |
| ATOM | 1028 | C | GLY | 142 | 16.645 | 21.396 | 9.923 | 1.00 | 29.65 |
| ATOM | 1029 | O | GLY | 142 | 16.960 | 21.411 | 11.111 | 1.00 | 31.37 |
| ATOM | 1030 | N | HIS | 143 | 15.399 | 21.590 | 9.496 | 1.00 | 26.39 |
| ATOM | 1031 | CA | HIS | 143 | 14.269 | 21.829 | 10.399 | 1.00 | 19.33 |
| ATOM | 1032 | CB | HIS | 143 | 13.491 | 23.102 | 10.017 | 1.00 | 19.62 |
| ATOM | 1033 | CG | HIS | 143 | 12.026 | 23.054 | 10.359 | 1.00 | 20.09 |
| ATOM | 1034 | CD2 | HIS | 143 | 11.352 | 23.478 | 11.459 | 1.00 | 18.21 |
| ATOM | 1035 | ND1 | HIS | 143 | 11.070 | 22.536 | 9.506 | 1.00 | 21.83 |
| ATOM | 1036 | CE1 | HIS | 143 | 9.872 | 22.646 | 10.062 | 1.00 | 21.18 |
| ATOM | 1037 | NE2 | HIS | 143 | 10.017 | 23.216 | 11.248 | 1.00 | 20.26 |
| ATOM | 1038 | C | HIS | 143 | 13.315 | 20.672 | 10.321 | 1.00 | 18.40 |
| ATOM | 1039 | O | HIS | 143 | 13.069 | 20.129 | 9.238 | 1.00 | 19.89 |
| ATOM | 1040 | N | SER | 144 | 12.751 | 20.312 | 11.464 | 1.00 | 17.17 |
| ATOM | 1041 | CA | SER | 144 | 11.805 | 19.233 | 11.467 | 1.00 | 16.24 |
| ATOM | 1042 | CB | SER | 144 | 10.818 | 19.452 | 10.328 | 1.00 | 13.89 |
| ATOM | 1043 | OG | SER | 144 | 9.608 | 18.743 | 10.515 | 1.00 | 21.42 |
| ATOM | 1044 | C | SER | 144 | 12.578 | 17.950 | 11.231 | 1.00 | 17.37 |
| ATOM | 1045 | O | SER | 144 | 13.698 | 17.746 | 11.721 | 1.00 | 17.35 |
| ATOM | 1046 | N | LEU | 145 | 11.965 | 17.085 | 10.448 | 1.00 | 14.63 |
| ATOM | 1047 | CA | LEU | 145 | 12.564 | 15.820 | 10.130 | 1.00 | 16.67 |
| ATOM | 1048 | CB | LEU | 145 | 11.613 | 14.995 | 9.247 | 1.00 | 14.08 |
| ATOM | 1049 | CG | LEU | 145 | 10.177 | 14.808 | 9.767 | 1.00 | 15.88 |
| ATOM | 1050 | CD1 | LEU | 145 | 9.389 | 13.779 | 8.946 | 1.00 | 11.76 |
| ATOM | 1051 | CD2 | LEU | 145 | 10.246 | 14.399 | 11.216 | 1.00 | 14.25 |
| ATOM | 1052 | C | LEU | 145 | 13.834 | 16.173 | 9.373 | 1.00 | 19.50 |
| ATOM | 1053 | O | LEU | 145 | 14.886 | 15.546 | 9.557 | 1.00 | 18.82 |
| ATOM | 1054 | N | GLY | 146 | 13.733 | 17.204 | 8.537 | 1.00 | 19.28 |
| ATOM | 1055 | CA | GLY | 146 | 14.882 | 17.635 | 7.770 | 1.00 | 21.26 |
| ATOM | 1056 | C | GLY | 146 | 16.006 | 17.826 | 8.753 | 1.00 | 21.58 |
| ATOM | 1057 | O | GLY | 146 | 17.161 | 17.608 | 8.433 | 1.00 | 24.44 |
| ATOM | 1058 | N | GLY | 147 | 15.657 | 18.254 | 9.962 | 1.00 | 20.38 |
| ATOM | 1059 | CA | GLY | 147 | 16.656 | 18.427 | 11.002 | 1.00 | 22.70 |
| ATOM | 1060 | C | GLY | 147 | 17.203 | 17.074 | 11.425 | 1.00 | 23.22 |

APPENDIX 1-continued

Coordinates in Protein Data Bank (PDB) format of GZEL.

| ATOM | 1061 | O   | GLY | 147 | 18.411 | 16.899 | 11.618 | 1.00 | 17.17 |
|------|------|-----|-----|-----|--------|--------|--------|------|-------|
| ATOM | 1062 | N   | ALA | 148 | 16.295 | 16.107 | 11.569 | 1.00 | 24.83 |
| ATOM | 1063 | CA  | ALA | 148 | 16.682 | 14.750 | 11.955 | 1.00 | 26.11 |
| ATOM | 1064 | CB  | ALA | 148 | 15.499 | 13.795 | 11.842 | 1.00 | 26.21 |
| ATOM | 1065 | C   | ALA | 148 | 17.789 | 14.310 | 11.024 | 1.00 | 26.98 |
| ATOM | 1066 | O   | ALA | 148 | 18.944 | 14.236 | 11.415 | 1.00 | 26.77 |
| ATOM | 1067 | N   | VAL | 149 | 17.420 | 14.043 | 9.780  | 1.00 | 29.05 |
| ATOM | 1068 | CA  | VAL | 149 | 18.370 | 13.642 | 8.754  | 1.00 | 30.78 |
| ATOM | 1069 | CB  | VAL | 149 | 17.720 | 13.723 | 7.356  | 1.00 | 29.50 |
| ATOM | 1070 | CG1 | VAL | 149 | 17.139 | 15.107 | 7.141  | 1.00 | 36.38 |
| ATOM | 1071 | CG2 | VAL | 149 | 18.757 | 13.417 | 6.271  | 1.00 | 28.41 |
| ATOM | 1072 | C   | VAL | 149 | 19.631 | 14.520 | 8.758  | 1.00 | 32.09 |
| ATOM | 1073 | O   | VAL | 149 | 20.733 | 14.040 | 8.502  | 1.00 | 35.50 |
| ATOM | 1074 | N   | ALA | 150 | 19.476 | 15.808 | 9.052  | 1.00 | 31.81 |
| ATOM | 1075 | CA  | ALA | 150 | 20.627 | 16.720 | 9.050  | 1.00 | 31.91 |
| ATOM | 1076 | CB  | ALA | 150 | 20.188 | 18.142 | 9.407  | 1.00 | 31.19 |
| ATOM | 1077 | C   | ALA | 150 | 21.692 | 16.249 | 10.029 | 1.00 | 31.31 |
| ATOM | 1078 | O   | ALA | 150 | 22.876 | 16.480 | 9.838  | 1.00 | 31.99 |
| ATOM | 1079 | N   | THR | 151 | 21.262 | 15.571 | 11.075 | 1.00 | 31.04 |
| ATOM | 1080 | CA  | THR | 151 | 22.188 | 15.092 | 12.070 | 1.00 | 30.45 |
| ATOM | 1081 | CB  | THR | 151 | 21.442 | 14.612 | 13.316 | 1.00 | 31.26 |
| ATOM | 1082 | OG1 | THR | 151 | 20.654 | 15.683 | 13.847 | 1.00 | 35.05 |
| ATOM | 1083 | CG2 | THR | 151 | 22.430 | 14.179 | 14.369 | 1.00 | 31.46 |
| ATOM | 1084 | C   | THR | 151 | 23.070 | 13.961 | 11.573 | 1.00 | 30.95 |
| ATOM | 1085 | O   | THR | 151 | 24.291 | 14.020 | 11.709 | 1.00 | 30.80 |
| ATOM | 1086 | N   | LEU | 152 | 22.459 | 12.917 | 11.024 | 1.00 | 30.43 |
| ATOM | 1087 | CA  | LEU | 152 | 23.224 | 11.771 | 10.522 | 1.00 | 31.80 |
| ATOM | 1088 | CB  | LEU | 152 | 22.307 | 10.750 | 9.829  | 1.00 | 25.27 |
| ATOM | 1089 | CG  | LEU | 152 | 21.276 | 10.058 | 10.721 | 1.00 | 19.74 |
| ATOM | 1090 | CD1 | LEU | 152 | 20.542 | 8.952  | 10.000 | 1.00 | 19.66 |
| ATOM | 1091 | CD2 | LEU | 152 | 22.004 | 9.488  | 11.878 | 1.00 | 19.81 |
| ATOM | 1092 | C   | LEU | 152 | 24.246 | 12.282 | 9.527  | 1.00 | 33.94 |
| ATOM | 1093 | O   | LEU | 152 | 25.437 | 11.976 | 9.593  | 1.00 | 35.31 |
| ATOM | 1094 | N   | ALA | 153 | 23.754 | 13.101 | 8.617  | 1.00 | 33.85 |
| ATOM | 1095 | CA  | ALA | 153 | 24.590 | 13.692 | 7.597  | 1.00 | 33.67 |
| ATOM | 1096 | CB  | ALA | 153 | 23.795 | 14.716 | 6.823  | 1.00 | 36.30 |
| ATOM | 1097 | C   | ALA | 153 | 25.798 | 14.339 | 8.247  | 1.00 | 32.20 |
| ATOM | 1098 | O   | ALA | 153 | 26.896 | 14.239 | 7.745  | 1.00 | 33.42 |
| ATOM | 1099 | N   | GLY | 154 | 25.596 | 14.994 | 9.381  | 1.00 | 33.09 |
| ATOM | 1100 | CA  | GLY | 154 | 26.712 | 15.630 | 10.048 | 1.00 | 33.71 |
| ATOM | 1101 | C   | GLY | 154 | 27.637 | 14.570 | 10.590 | 1.00 | 34.42 |
| ATOM | 1102 | O   | GLY | 154 | 28.830 | 14.546 | 10.293 | 1.00 | 34.11 |
| ATOM | 1103 | N   | ALA | 155 | 27.065 | 13.682 | 11.394 | 1.00 | 35.16 |
| ATOM | 1104 | CA  | ALA | 155 | 27.815 | 12.602 | 12.020 | 1.00 | 37.79 |
| ATOM | 1105 | CB  | ALA | 155 | 26.855 | 11.612 | 12.635 | 1.00 | 36.39 |
| ATOM | 1106 | C   | ALA | 155 | 28.685 | 11.902 | 10.991 | 1.00 | 37.41 |
| ATOM | 1107 | O   | ALA | 155 | 29.902 | 11.805 | 11.120 | 1.00 | 36.20 |
| ATOM | 1108 | N   | ASN | 156 | 28.030 | 11.406 | 9.960  | 1.00 | 37.07 |
| ATOM | 1109 | CA  | ASN | 156 | 28.730 | 10.721 | 8.917  | 1.00 | 36.66 |
| ATOM | 1110 | CB  | ASN | 156 | 27.715 | 10.144 | 7.937  | 1.00 | 35.94 |
| ATOM | 1111 | CG  | ASN | 156 | 27.170 | 8.813  | 8.410  | 1.00 | 37.19 |
| ATOM | 1112 | OD1 | ASN | 156 | 27.823 | 7.782  | 8.257  | 1.00 | 41.36 |
| ATOM | 1113 | ND2 | ASN | 156 | 25.986 | 8.828  | 9.007  | 1.00 | 38.22 |
| ATOM | 1114 | C   | ASN | 156 | 29.732 | 11.640 | 8.235  | 1.00 | 38.00 |
| ATOM | 1115 | O   | ASN | 156 | 30.905 | 11.295 | 8.117  | 1.00 | 39.70 |
| ATOM | 1116 | N   | LEU | 157 | 29.302 | 12.825 | 7.815  | 1.00 | 36.33 |
| ATOM | 1117 | CA  | LEU | 157 | 30.231 | 13.721 | 7.125  | 1.00 | 30.00 |
| ATOM | 1118 | CB  | LEU | 157 | 29.610 | 15.104 | 6.865  | 1.00 | 26.41 |
| ATOM | 1119 | CG  | LEU | 157 | 29.181 | 15.474 | 5.424  | 1.00 | 26.33 |
| ATOM | 1120 | CD1 | LEU | 157 | 30.071 | 14.777 | 4.412  | 1.00 | 24.41 |
| ATOM | 1121 | CD2 | LEU | 157 | 27.761 | 15.069 | 5.167  | 1.00 | 26.08 |
| ATOM | 1122 | C   | LEU | 157 | 31.477 | 13.857 | 7.973  | 1.00 | 30.24 |
| ATOM | 1123 | O   | LEU | 157 | 32.600 | 13.744 | 7.491  | 1.00 | 29.89 |
| ATOM | 1124 | N   | ARG | 158 | 31.255 | 14.058 | 9.261  | 1.00 | 29.77 |
| ATOM | 1125 | CA  | ARG | 158 | 32.345 | 14.195 | 10.194 | 1.00 | 32.79 |
| ATOM | 1126 | CB  | ARG | 158 | 31.820 | 14.192 | 11.645 | 1.00 | 33.07 |
| ATOM | 1127 | CG  | ARG | 158 | 30.861 | 15.331 | 12.023 | 1.00 | 32.85 |
| ATOM | 1128 | CD  | ARG | 158 | 31.088 | 15.717 | 13.489 | 1.00 | 35.95 |
| ATOM | 1129 | NE  | ARG | 158 | 29.886 | 16.070 | 14.260 | 1.00 | 38.94 |
| ATOM | 1130 | CZ  | ARG | 158 | 29.346 | 17.287 | 14.342 | 1.00 | 39.79 |
| ATOM | 1131 | NH1 | ARG | 158 | 28.259 | 17.469 | 15.082 | 1.00 | 32.39 |
| ATOM | 1132 | NH2 | ARG | 158 | 29.875 | 18.323 | 13.686 | 1.00 | 40.89 |
| ATOM | 1133 | C   | ARG | 158 | 33.320 | 13.037 | 9.998  | 1.00 | 35.98 |
| ATOM | 1134 | O   | ARG | 158 | 34.485 | 13.250 | 9.709  | 1.00 | 40.19 |
| ATOM | 1135 | N   | ILE | 159 | 32.835 | 11.805 | 10.136 | 1.00 | 36.99 |
| ATOM | 1136 | CA  | ILE | 159 | 33.708 | 10.632 | 10.014 | 1.00 | 36.27 |
| ATOM | 1137 | CB  | ILE | 159 | 32.963 | 9.267  | 10.118 | 1.00 | 36.24 |
| ATOM | 1138 | CG2 | ILE | 159 | 32.042 | 9.259  | 11.325 | 1.00 | 30.70 |

APPENDIX 1-continued

Coordinates in Protein Data Bank (PDB) format of GZEL.

| ATOM | 1139 | CG1 | ILE | 159 | 32.157 | 8.994 | 8.855 | 1.00 | 41.45 |
|---|---|---|---|---|---|---|---|---|---|
| ATOM | 1140 | CD1 | ILE | 159 | 31.199 | 7.805 | 9.010 | 1.00 | 48.56 |
| ATOM | 1141 | C | ILE | 159 | 34.394 | 10.661 | 8.692 | 1.00 | 37.10 |
| ATOM | 1142 | O | ILE | 159 | 35.466 | 10.073 | 8.528 | 1.00 | 39.04 |
| ATOM | 1143 | N | GLY | 160 | 33.759 | 11.341 | 7.744 | 1.00 | 39.77 |
| ATOM | 1144 | CA | GLY | 160 | 34.332 | 11.467 | 6.421 | 1.00 | 45.59 |
| ATOM | 1145 | C | GLY | 160 | 35.558 | 12.367 | 6.464 | 1.00 | 49.14 |
| ATOM | 1146 | O | GLY | 160 | 36.290 | 12.512 | 5.491 | 1.00 | 49.04 |
| ATOM | 1147 | N | GLY | 161 | 35.797 | 12.974 | 7.614 | 1.00 | 49.77 |
| ATOM | 1148 | CA | GLY | 161 | 36.940 | 13.847 | 7.732 | 1.00 | 49.94 |
| ATOM | 1149 | C | GLY | 161 | 36.429 | 15.241 | 7.928 | 1.00 | 48.63 |
| ATOM | 1150 | O | GLY | 161 | 36.604 | 15.837 | 8.982 | 1.00 | 51.78 |
| ATOM | 1151 | N | THR | 162 | 35.758 | 15.752 | 6.914 | 1.00 | 45.61 |
| ATOM | 1152 | CA | THR | 162 | 35.227 | 17.098 | 6.992 | 1.00 | 43.42 |
| ATOM | 1153 | CB | THR | 162 | 34.318 | 17.391 | 5.828 | 1.00 | 43.68 |
| ATOM | 1154 | OG1 | THR | 162 | 33.204 | 18.157 | 6.298 | 1.00 | 46.49 |
| ATOM | 1155 | CG2 | THR | 162 | 33.854 | 16.105 | 5.195 | 1.00 | 44.15 |
| ATOM | 1156 | C | THR | 162 | 34.454 | 17.394 | 8.273 | 1.00 | 42.04 |
| ATOM | 1157 | O | THR | 162 | 33.408 | 16.801 | 8.550 | 1.00 | 40.79 |
| ATOM | 1158 | N | PRO | 163 | 34.988 | 18.311 | 9.082 | 1.00 | 41.64 |
| ATOM | 1159 | CD | PRO | 163 | 36.376 | 18.797 | 8.979 | 1.00 | 39.68 |
| ATOM | 1160 | CA | PRO | 163 | 34.380 | 18.718 | 10.346 | 1.00 | 42.23 |
| ATOM | 1161 | CB | PRO | 163 | 35.560 | 19.279 | 11.134 | 1.00 | 43.75 |
| ATOM | 1162 | CG | PRO | 163 | 36.438 | 19.839 | 10.054 | 1.00 | 44.13 |
| ATOM | 1163 | C | PRO | 163 | 33.229 | 19.703 | 10.165 | 1.00 | 40.16 |
| ATOM | 1164 | O | PRO | 163 | 33.223 | 20.565 | 9.275 | 1.00 | 37.11 |
| ATOM | 1165 | N | LEU | 164 | 32.267 | 19.559 | 11.067 | 1.00 | 40.42 |
| ATOM | 1166 | CA | LEU | 164 | 31.031 | 20.322 | 11.051 | 1.00 | 38.72 |
| ATOM | 1167 | CB | LEU | 164 | 29.883 | 19.434 | 10.632 | 1.00 | 35.75 |
| ATOM | 1168 | CG | LEU | 164 | 29.691 | 19.202 | 9.166 | 1.00 | 33.13 |
| ATOM | 1169 | CD1 | LEU | 164 | 28.838 | 17.977 | 9.033 | 1.00 | 37.44 |
| ATOM | 1170 | CD2 | LEU | 164 | 29.047 | 20.412 | 8.519 | 1.00 | 29.26 |
| ATOM | 1171 | C | LEU | 164 | 30.579 | 20.917 | 12.349 | 1.00 | 38.94 |
| ATOM | 1172 | O | LEU | 164 | 31.271 | 20.888 | 13.368 | 1.00 | 42.10 |
| ATOM | 1173 | N | ASP | 165 | 29.346 | 21.407 | 12.258 | 1.00 | 40.82 |
| ATOM | 1174 | CA | ASP | 165 | 28.593 | 22.013 | 13.326 | 1.00 | 39.97 |
| ATOM | 1175 | CB | ASP | 165 | 28.921 | 23.491 | 13.494 | 1.00 | 41.99 |
| ATOM | 1176 | CG | ASP | 165 | 29.864 | 23.743 | 14.638 | 1.00 | 45.08 |
| ATOM | 1177 | OD1 | ASP | 165 | 29.907 | 22.907 | 15.571 | 1.00 | 47.09 |
| ATOM | 1178 | OD2 | ASP | 165 | 30.550 | 24.786 | 14.610 | 1.00 | 46.42 |
| ATOM | 1179 | C | ASP | 165 | 27.193 | 21.882 | 12.776 | 1.00 | 38.60 |
| ATOM | 1180 | O | ASP | 165 | 26.868 | 22.451 | 11.732 | 1.00 | 40.54 |
| ATOM | 1181 | N | ILE | 166 | 26.368 | 21.124 | 13.486 | 1.00 | 33.75 |
| ATOM | 1182 | CA | ILE | 166 | 24.983 | 20.891 | 13.096 | 1.00 | 30.12 |
| ATOM | 1183 | CB | ILE | 166 | 24.577 | 19.449 | 13.398 | 1.00 | 27.81 |
| ATOM | 1184 | CG2 | ILE | 166 | 23.165 | 19.180 | 12.900 | 1.00 | 28.09 |
| ATOM | 1185 | CG1 | ILE | 166 | 25.580 | 18.499 | 12.731 | 1.00 | 27.25 |
| ATOM | 1186 | CD1 | ILE | 166 | 25.524 | 17.076 | 13.276 | 1.00 | 16.32 |
| ATOM | 1187 | C | ILE | 166 | 24.012 | 21.806 | 13.813 | 1.00 | 28.19 |
| ATOM | 1188 | O | ILE | 166 | 24.072 | 21.950 | 15.037 | 1.00 | 28.70 |
| ATOM | 1189 | N | TYR | 167 | 23.120 | 22.409 | 13.030 | 1.00 | 26.22 |
| ATOM | 1190 | CA | TYR | 167 | 22.085 | 23.310 | 13.529 | 1.00 | 29.29 |
| ATOM | 1191 | CB | TYR | 167 | 22.225 | 24.703 | 12.915 | 1.00 | 29.15 |
| ATOM | 1192 | CG | TYR | 167 | 23.295 | 25.581 | 13.541 | 1.00 | 29.82 |
| ATOM | 1193 | CD1 | TYR | 167 | 24.634 | 25.451 | 13.193 | 1.00 | 31.46 |
| ATOM | 1194 | CE1 | TYR | 167 | 25.618 | 26.271 | 13.778 | 1.00 | 33.38 |
| ATOM | 1195 | CD2 | TYR | 167 | 22.956 | 26.547 | 14.490 | 1.00 | 31.23 |
| ATOM | 1196 | CE2 | TYR | 167 | 23.917 | 27.362 | 15.082 | 1.00 | 31.33 |
| ATOM | 1197 | CZ | TYR | 167 | 25.250 | 27.224 | 14.726 | 1.00 | 32.94 |
| ATOM | 1198 | OH | TYR | 167 | 26.198 | 28.032 | 15.329 | 1.00 | 33.66 |
| ATOM | 1199 | C | TYR | 167 | 20.713 | 22.756 | 13.155 | 1.00 | 30.93 |
| ATOM | 1200 | O | TYR | 167 | 20.380 | 22.642 | 11.977 | 1.00 | 31.73 |
| ATOM | 1201 | N | THR | 168 | 19.917 | 22.429 | 14.163 | 1.00 | 33.46 |
| ATOM | 1202 | CA | THR | 168 | 18.592 | 21.866 | 13.950 | 1.00 | 34.18 |
| ATOM | 1203 | CB | THR | 168 | 18.564 | 20.428 | 14.427 | 1.00 | 34.56 |
| ATOM | 1204 | OG1 | THR | 168 | 19.567 | 20.266 | 15.439 | 1.00 | 36.47 |
| ATOM | 1205 | CG2 | THR | 168 | 18.855 | 19.470 | 13.274 | 1.00 | 35.43 |
| ATOM | 1206 | C | THR | 168 | 17.494 | 22.643 | 14.659 | 1.00 | 34.34 |
| ATOM | 1207 | O | THR | 168 | 17.718 | 23.310 | 15.667 | 1.00 | 37.07 |
| ATOM | 1208 | N | TYR | 169 | 16.294 | 22.535 | 14.106 | 1.00 | 33.59 |
| ATOM | 1209 | CA | TYR | 169 | 15.132 | 23.227 | 14.615 | 1.00 | 31.03 |
| ATOM | 1210 | CB | TYR | 169 | 14.839 | 24.434 | 13.726 | 1.00 | 26.08 |
| ATOM | 1211 | CG | TYR | 169 | 16.037 | 25.332 | 13.525 | 1.00 | 27.60 |
| ATOM | 1212 | CD1 | TYR | 169 | 17.109 | 24.930 | 12.739 | 1.00 | 30.90 |
| ATOM | 1213 | CE1 | TYR | 169 | 18.217 | 25.762 | 12.533 | 1.00 | 31.53 |
| ATOM | 1214 | CD2 | TYR | 169 | 16.094 | 26.587 | 14.112 | 1.00 | 28.88 |
| ATOM | 1215 | CE2 | TYR | 169 | 17.191 | 27.438 | 13.916 | 1.00 | 31.16 |
| ATOM | 1216 | CZ | TYR | 169 | 18.254 | 27.023 | 13.116 | 1.00 | 33.28 |

APPENDIX 1-continued

Coordinates in Protein Data Bank (PDB) format of GZEL.

| ATOM | 1217 | OH | TYR | 169 | 19.323 | 27.867 | 12.846 | 1.00 | 32.19 |
|---|---|---|---|---|---|---|---|---|---|
| ATOM | 1218 | C | TYR | 169 | 13.924 | 22.322 | 14.662 | 1.00 | 32.69 |
| ATOM | 1219 | O | TYR | 169 | 13.402 | 21.904 | 13.631 | 1.00 | 31.23 |
| ATOM | 1220 | N | GLY | 170 | 13.486 | 22.034 | 15.879 | 1.00 | 32.73 |
| ATOM | 1221 | CA | GLY | 170 | 12.320 | 21.196 | 16.067 | 1.00 | 31.89 |
| ATOM | 1222 | C | GLY | 170 | 12.510 | 19.828 | 15.448 | 1.00 | 31.16 |
| ATOM | 1223 | O | GLY | 170 | 11.592 | 19.282 | 14.834 | 1.00 | 30.48 |
| ATOM | 1224 | N | SER | 171 | 13.709 | 19.271 | 15.601 | 1.00 | 29.94 |
| ATOM | 1225 | CA | SER | 171 | 13.999 | 17.953 | 15.043 | 1.00 | 29.41 |
| ATOM | 1226 | CB | SER | 171 | 15.504 | 17.797 | 14.760 | 1.00 | 31.96 |
| ATOM | 1227 | OG | SER | 171 | 16.189 | 17.109 | 15.813 | 1.00 | 28.95 |
| ATOM | 1228 | C | SER | 171 | 13.568 | 16.897 | 16.050 | 1.00 | 27.43 |
| ATOM | 1229 | O | SER | 171 | 13.529 | 17.136 | 17.262 | 1.00 | 30.66 |
| ATOM | 1230 | N | PRO | 172 | 13.209 | 15.723 | 15.565 | 1.00 | 24.19 |
| ATOM | 1231 | CD | PRO | 172 | 12.982 | 15.315 | 14.175 | 1.00 | 24.16 |
| ATOM | 1232 | CA | PRO | 172 | 12.799 | 14.693 | 16.513 | 1.00 | 25.27 |
| ATOM | 1233 | CB | PRO | 172 | 11.906 | 13.802 | 15.667 | 1.00 | 22.48 |
| ATOM | 1234 | CG | PRO | 172 | 12.570 | 13.861 | 14.337 | 1.00 | 26.34 |
| ATOM | 1235 | C | PRO | 172 | 14.071 | 13.995 | 17.006 | 1.00 | 26.93 |
| ATOM | 1236 | O | PRO | 172 | 15.165 | 14.277 | 16.481 | 1.00 | 25.21 |
| ATOM | 1237 | N | ARG | 173 | 13.950 | 13.122 | 18.015 | 1.00 | 24.87 |
| ATOM | 1238 | CA | ARG | 173 | 15.117 | 12.387 | 18.509 | 1.00 | 19.89 |
| ATOM | 1239 | CB | ARG | 173 | 14.741 | 11.481 | 19.651 | 1.00 | 16.72 |
| ATOM | 1240 | CG | ARG | 173 | 14.075 | 12.137 | 20.827 | 1.00 | 13.01 |
| ATOM | 1241 | CD | ARG | 173 | 14.184 | 11.214 | 22.011 | 1.00 | 18.41 |
| ATOM | 1242 | NE | ARG | 173 | 13.775 | 11.943 | 23.200 | 1.00 | 22.47 |
| ATOM | 1243 | CZ | ARG | 173 | 12.516 | 12.251 | 23.482 | 1.00 | 22.00 |
| ATOM | 1244 | NH1 | ARG | 173 | 12.229 | 12.936 | 24.577 | 1.00 | 18.05 |
| ATOM | 1245 | NH2 | ARG | 173 | 11.545 | 11.841 | 22.684 | 1.00 | 23.39 |
| ATOM | 1246 | C | ARG | 173 | 15.482 | 11.515 | 17.327 | 1.00 | 20.52 |
| ATOM | 1247 | O | ARG | 173 | 14.565 | 11.012 | 16.689 | 1.00 | 21.15 |
| ATOM | 1248 | N | VAL | 174 | 16.770 | 11.306 | 17.024 | 1.00 | 22.47 |
| ATOM | 1249 | CA | VAL | 174 | 17.135 | 10.497 | 15.827 | 1.00 | 25.15 |
| ATOM | 1250 | CB | VAL | 174 | 18.144 | 11.313 | 14.881 | 1.00 | 23.04 |
| ATOM | 1251 | CG1 | VAL | 174 | 18.336 | 12.735 | 15.425 | 1.00 | 22.73 |
| ATOM | 1252 | CG2 | VAL | 174 | 19.469 | 10.612 | 14.772 | 1.00 | 24.59 |
| ATOM | 1253 | C | VAL | 174 | 17.621 | 9.020 | 16.017 | 1.00 | 26.28 |
| ATOM | 1254 | O | VAL | 174 | 17.560 | 8.223 | 15.067 | 1.00 | 26.79 |
| ATOM | 1255 | N | GLY | 175 | 18.063 | 8.650 | 17.225 | 1.00 | 30.71 |
| ATOM | 1256 | CA | GLY | 175 | 18.513 | 7.281 | 17.478 | 1.00 | 32.37 |
| ATOM | 1257 | C | GLY | 175 | 18.428 | 6.893 | 18.942 | 1.00 | 32.98 |
| ATOM | 1258 | O | GLY | 175 | 17.602 | 7.406 | 19.686 | 1.00 | 35.87 |
| ATOM | 1259 | N | ASN | 176 | 19.285 | 5.971 | 19.359 | 1.00 | 30.86 |
| ATOM | 1260 | CA | ASN | 176 | 19.302 | 5.535 | 20.747 | 1.00 | 31.73 |
| ATOM | 1261 | CB | ASN | 176 | 19.361 | 4.007 | 20.873 | 1.00 | 28.19 |
| ATOM | 1262 | CG | ASN | 176 | 20.700 | 3.408 | 20.428 | 1.00 | 30.78 |
| ATOM | 1263 | OD1 | ASN | 176 | 20.915 | 2.203 | 20.552 | 1.00 | 28.67 |
| ATOM | 1264 | ND2 | ASN | 176 | 21.592 | 4.238 | 19.907 | 1.00 | 35.19 |
| ATOM | 1265 | C | ASN | 176 | 20.475 | 6.123 | 21.488 | 1.00 | 32.41 |
| ATOM | 1266 | O | ASN | 176 | 21.370 | 6.776 | 20.926 | 1.00 | 32.01 |
| ATOM | 1267 | N | THR | 177 | 20.452 | 5.888 | 22.779 | 1.00 | 31.20 |
| ATOM | 1268 | CA | THR | 177 | 21.497 | 6.359 | 23.660 | 1.00 | 35.00 |
| ATOM | 1269 | CB | THR | 177 | 21.510 | 5.478 | 24.861 | 1.00 | 33.97 |
| ATOM | 1270 | OG1 | THR | 177 | 20.534 | 4.443 | 24.654 | 1.00 | 40.81 |
| ATOM | 1271 | CG2 | THR | 177 | 21.141 | 6.276 | 26.090 | 1.00 | 34.76 |
| ATOM | 1272 | C | THR | 177 | 22.889 | 6.430 | 23.069 | 1.00 | 36.41 |
| ATOM | 1273 | O | THR | 177 | 23.475 | 7.492 | 23.025 | 1.00 | 38.30 |
| ATOM | 1274 | N | GLN | 178 | 23.423 | 5.309 | 22.605 | 1.00 | 36.58 |
| ATOM | 1275 | CA | GLN | 178 | 24.776 | 5.343 | 22.045 | 1.00 | 38.33 |
| ATOM | 1276 | CB | GLN | 178 | 25.380 | 3.928 | 21.855 | 1.00 | 37.70 |
| ATOM | 1277 | CG | GLN | 178 | 24.401 | 2.867 | 21.458 | 1.00 | 37.39 |
| ATOM | 1278 | CD | GLN | 178 | 23.795 | 2.165 | 22.668 | 1.00 | 38.56 |
| ATOM | 1279 | OE1 | GLN | 178 | 24.497 | 1.494 | 23.415 | 1.00 | 37.40 |
| ATOM | 1280 | NE2 | GLN | 178 | 22.486 | 2.312 | 22.857 | 1.00 | 36.48 |
| ATOM | 1281 | C | GLN | 178 | 24.882 | 6.124 | 20.748 | 1.00 | 36.06 |
| ATOM | 1282 | O | GLN | 178 | 25.936 | 6.708 | 20.448 | 1.00 | 35.15 |
| ATOM | 1283 | N | LEU | 179 | 23.821 | 6.163 | 19.963 | 1.00 | 31.34 |
| ATOM | 1284 | CA | LEU | 179 | 23.972 | 6.929 | 18.753 | 1.00 | 31.50 |
| ATOM | 1285 | CB | LEU | 179 | 22.786 | 6.691 | 17.840 | 1.00 | 28.66 |
| ATOM | 1286 | CG | LEU | 179 | 22.690 | 7.609 | 16.631 | 1.00 | 27.94 |
| ATOM | 1287 | CD1 | LEU | 179 | 23.680 | 7.207 | 15.572 | 1.00 | 29.06 |
| ATOM | 1288 | CD2 | LEU | 179 | 21.302 | 7.507 | 16.072 | 1.00 | 33.99 |
| ATOM | 1289 | C | LEU | 179 | 24.061 | 8.405 | 19.175 | 1.00 | 34.01 |
| ATOM | 1290 | O | LEU | 179 | 25.032 | 9.111 | 18.845 | 1.00 | 33.60 |
| ATOM | 1291 | N | ALA | 180 | 23.061 | 8.856 | 19.935 | 1.00 | 34.29 |
| ATOM | 1292 | CA | ALA | 180 | 23.013 | 10.245 | 20.375 | 1.00 | 34.25 |
| ATOM | 1293 | CB | ALA | 180 | 21.878 | 10.440 | 21.312 | 1.00 | 31.38 |
| ATOM | 1294 | C | ALA | 180 | 24.291 | 10.650 | 21.067 | 1.00 | 35.98 |

APPENDIX 1-continued

Coordinates in Protein Data Bank (PDB) format of GZEL.

| ATOM | 1295 | O | ALA | 180 | 24.757 | 11.779 | 20.946 | 1.00 | 39.76 |
|---|---|---|---|---|---|---|---|---|---|
| ATOM | 1296 | N | ALA | 181 | 24.831 | 9.722 | 21.836 | 1.00 | 34.88 |
| ATOM | 1297 | CA | ALA | 181 | 26.039 | 9.966 | 22.583 | 1.00 | 31.64 |
| ATOM | 1298 | CB | ALA | 181 | 26.369 | 8.771 | 23.380 | 1.00 | 28.24 |
| ATOM | 1299 | C | ALA | 181 | 27.139 | 10.249 | 21.632 | 1.00 | 32.31 |
| ATOM | 1300 | O | ALA | 181 | 27.818 | 11.261 | 21.713 | 1.00 | 30.45 |
| ATOM | 1301 | N | PHE | 182 | 27.311 | 9.311 | 20.729 | 1.00 | 33.84 |
| ATOM | 1302 | CA | PHE | 182 | 28.338 | 9.409 | 19.721 | 1.00 | 37.67 |
| ATOM | 1303 | CB | PHE | 182 | 28.038 | 8.399 | 18.634 | 1.00 | 35.24 |
| ATOM | 1304 | CG | PHE | 182 | 29.006 | 8.421 | 17.513 | 1.00 | 32.23 |
| ATOM | 1305 | CD1 | PHE | 182 | 28.581 | 8.744 | 16.230 | 1.00 | 35.37 |
| ATOM | 1306 | CD2 | PHE | 182 | 30.325 | 8.027 | 17.709 | 1.00 | 31.11 |
| ATOM | 1307 | CE1 | PHE | 182 | 29.453 | 8.658 | 15.150 | 1.00 | 35.57 |
| ATOM | 1308 | CE2 | PHE | 182 | 31.203 | 7.937 | 16.629 | 1.00 | 32.35 |
| ATOM | 1309 | CZ | PHE | 182 | 30.764 | 8.252 | 15.351 | 1.00 | 34.57 |
| ATOM | 1310 | C | PHE | 182 | 28.412 | 10.809 | 19.123 | 1.00 | 40.35 |
| ATOM | 1311 | O | PHE | 182 | 29.431 | 11.500 | 19.216 | 1.00 | 40.89 |
| ATOM | 1312 | N | VAL | 183 | 27.308 | 11.226 | 18.527 | 1.00 | 38.30 |
| ATOM | 1313 | CA | VAL | 183 | 27.235 | 12.529 | 17.917 | 1.00 | 39.18 |
| ATOM | 1314 | CB | VAL | 183 | 25.866 | 12.741 | 17.393 | 1.00 | 40.72 |
| ATOM | 1315 | CG1 | VAL | 183 | 25.790 | 14.058 | 16.649 | 1.00 | 39.25 |
| ATOM | 1316 | CG2 | VAL | 183 | 25.507 | 11.552 | 16.530 | 1.00 | 37.39 |
| ATOM | 1317 | C | VAL | 183 | 27.534 | 13.621 | 18.919 | 1.00 | 38.88 |
| ATOM | 1318 | O | VAL | 183 | 28.213 | 14.600 | 18.622 | 1.00 | 39.49 |
| ATOM | 1319 | N | SER | 184 | 27.014 | 13.457 | 20.119 | 1.00 | 37.57 |
| ATOM | 1320 | CA | SER | 184 | 27.251 | 14.452 | 21.126 | 1.00 | 37.92 |
| ATOM | 1321 | CB | SER | 184 | 26.554 | 14.053 | 22.413 | 1.00 | 34.90 |
| ATOM | 1322 | OG | SER | 184 | 25.169 | 14.191 | 22.253 | 1.00 | 31.35 |
| ATOM | 1323 | C | SER | 184 | 28.740 | 14.599 | 21.370 | 1.00 | 40.95 |
| ATOM | 1324 | O | SER | 184 | 29.262 | 15.713 | 21.453 | 1.00 | 43.53 |
| ATOM | 1325 | N | ASN | 185 | 29.417 | 13.463 | 21.459 | 1.00 | 42.49 |
| ATOM | 1326 | CA | ASN | 185 | 30.838 | 13.428 | 21.749 | 1.00 | 43.30 |
| ATOM | 1327 | CB | ASN | 185 | 31.129 | 12.154 | 22.478 | 1.00 | 46.28 |
| ATOM | 1328 | CG | ASN | 185 | 30.120 | 11.904 | 23.542 | 1.00 | 51.12 |
| ATOM | 1329 | OD1 | ASN | 185 | 29.977 | 12.708 | 24.455 | 1.00 | 51.56 |
| ATOM | 1330 | ND2 | ASN | 185 | 29.390 | 10.809 | 23.430 | 1.00 | 56.16 |
| ATOM | 1331 | C | ASN | 185 | 31.714 | 13.526 | 20.554 | 1.00 | 43.01 |
| ATOM | 1332 | O | ASN | 185 | 32.880 | 13.173 | 20.592 | 1.00 | 43.68 |
| ATOM | 1333 | N | GLN | 186 | 31.137 | 13.981 | 19.469 | 1.00 | 39.81 |
| ATOM | 1334 | CA | GLN | 186 | 31.917 | 14.138 | 18.283 | 1.00 | 39.03 |
| ATOM | 1335 | CB | GLN | 186 | 31.058 | 13.959 | 17.041 | 1.00 | 39.39 |
| ATOM | 1336 | CG | GLN | 186 | 31.029 | 12.570 | 16.476 | 1.00 | 36.32 |
| ATOM | 1337 | CD | GLN | 186 | 30.509 | 12.574 | 15.068 | 1.00 | 35.86 |
| ATOM | 1338 | OE1 | GLN | 186 | 30.888 | 11.732 | 14.255 | 1.00 | 39.13 |
| ATOM | 1339 | NE2 | GLN | 186 | 29.627 | 13.522 | 14.764 | 1.00 | 35.55 |
| ATOM | 1340 | C | GLN | 186 | 32.454 | 15.541 | 18.324 | 1.00 | 39.42 |
| ATOM | 1341 | O | GLN | 186 | 31.866 | 16.437 | 18.926 | 1.00 | 41.40 |
| ATOM | 1342 | N | ALA | 187 | 33.605 | 15.724 | 17.710 | 1.00 | 38.62 |
| ATOM | 1343 | CA | ALA | 187 | 34.194 | 17.042 | 17.666 | 1.00 | 38.34 |
| ATOM | 1344 | CB | ALA | 187 | 35.438 | 17.030 | 16.788 | 1.00 | 37.50 |
| ATOM | 1345 | C | ALA | 187 | 33.118 | 17.938 | 17.069 | 1.00 | 39.50 |
| ATOM | 1346 | O | ALA | 187 | 32.374 | 17.532 | 16.150 | 1.00 | 38.37 |
| ATOM | 1347 | N | GLY | 188 | 33.012 | 19.146 | 17.615 | 1.00 | 39.42 |
| ATOM | 1348 | CA | GLY | 188 | 32.009 | 20.067 | 17.114 | 1.00 | 38.11 |
| ATOM | 1349 | C | GLY | 188 | 30.737 | 20.118 | 17.950 | 1.00 | 35.77 |
| ATOM | 1350 | O | GLY | 188 | 30.613 | 19.421 | 18.987 | 1.00 | 35.70 |
| ATOM | 1351 | N | GLY | 189 | 29.789 | 20.939 | 17.500 | 1.00 | 33.30 |
| ATOM | 1352 | CA | GLY | 189 | 28.548 | 21.082 | 18.230 | 1.00 | 34.89 |
| ATOM | 1353 | C | GLY | 189 | 27.280 | 20.762 | 17.472 | 1.00 | 35.30 |
| ATOM | 1354 | O | GLY | 189 | 27.213 | 20.843 | 16.233 | 1.00 | 36.66 |
| ATOM | 1355 | N | GLU | 190 | 26.271 | 20.397 | 18.261 | 1.00 | 34.26 |
| ATOM | 1356 | CA | GLU | 190 | 24.926 | 20.036 | 17.802 | 1.00 | 30.13 |
| ATOM | 1357 | CB | GLU | 190 | 24.568 | 18.609 | 18.250 | 1.00 | 29.94 |
| ATOM | 1358 | CG | GLU | 190 | 25.555 | 17.509 | 17.877 | 1.00 | 30.77 |
| ATOM | 1359 | CD | GLU | 190 | 26.936 | 17.697 | 18.461 | 1.00 | 32.53 |
| ATOM | 1360 | OE1 | GLU | 190 | 27.052 | 17.995 | 19.673 | 1.00 | 34.56 |
| ATOM | 1361 | OE2 | GLU | 190 | 27.905 | 17.523 | 17.695 | 1.00 | 32.05 |
| ATOM | 1362 | C | GLU | 190 | 23.988 | 20.987 | 18.552 | 1.00 | 25.52 |
| ATOM | 1363 | O | GLU | 190 | 23.506 | 20.631 | 19.645 | 1.00 | 25.60 |
| ATOM | 1364 | N | TYR | 191 | 23.747 | 22.178 | 18.012 | 1.00 | 23.84 |
| ATOM | 1365 | CA | TYR | 191 | 22.868 | 23.104 | 18.689 | 1.00 | 26.80 |
| ATOM | 1366 | CB | TYR | 191 | 23.167 | 24.539 | 18.295 | 1.00 | 29.71 |
| ATOM | 1367 | CG | TYR | 191 | 24.614 | 24.924 | 18.207 | 1.00 | 32.88 |
| ATOM | 1368 | CD1 | TYR | 191 | 25.198 | 25.723 | 19.184 | 1.00 | 33.47 |
| ATOM | 1369 | CE1 | TYR | 191 | 26.526 | 26.132 | 19.071 | 1.00 | 33.90 |
| ATOM | 1370 | CD2 | TYR | 191 | 25.390 | 24.537 | 17.119 | 1.00 | 35.22 |
| ATOM | 1371 | CE2 | TYR | 191 | 26.702 | 24.938 | 16.997 | 1.00 | 38.47 |
| ATOM | 1372 | CZ | TYR | 191 | 27.265 | 25.737 | 17.967 | 1.00 | 37.34 |

APPENDIX 1-continued

Coordinates in Protein Data Bank (PDB) format of GZEL.

| ATOM | 1373 | OH  | TYR | 191 | 28.561 | 26.167 | 17.795 | 1.00 | 41.52 |
|------|------|-----|-----|-----|--------|--------|--------|------|-------|
| ATOM | 1374 | C   | TYR | 191 | 21.482 | 22.789 | 18.188 | 1.00 | 27.01 |
| ATOM | 1375 | O   | TYR | 191 | 21.111 | 23.265 | 17.118 | 1.00 | 30.00 |
| ATOM | 1376 | N   | ARG | 192 | 20.721 | 21.970 | 18.912 | 1.00 | 23.47 |
| ATOM | 1377 | CA  | ARG | 192 | 19.363 | 21.697 | 18.466 | 1.00 | 23.80 |
| ATOM | 1378 | CB  | ARG | 192 | 18.966 | 20.213 | 18.555 | 1.00 | 23.43 |
| ATOM | 1379 | CG  | ARG | 192 | 18.894 | 19.585 | 19.917 | 1.00 | 26.56 |
| ATOM | 1380 | CD  | ARG | 192 | 18.227 | 18.215 | 19.805 | 1.00 | 29.50 |
| ATOM | 1381 | NE  | ARG | 192 | 17.268 | 17.990 | 20.884 | 1.00 | 30.31 |
| ATOM | 1382 | CZ  | ARG | 192 | 17.598 | 17.672 | 22.130 | 1.00 | 32.33 |
| ATOM | 1383 | NH1 | ARG | 192 | 16.654 | 17.501 | 23.046 | 1.00 | 33.74 |
| ATOM | 1384 | NH2 | ARG | 192 | 18.863 | 17.492 | 22.449 | 1.00 | 35.07 |
| ATOM | 1385 | C   | ARG | 192 | 18.448 | 22.558 | 19.290 | 1.00 | 22.85 |
| ATOM | 1386 | O   | ARG | 192 | 18.488 | 22.540 | 20.542 | 1.00 | 22.61 |
| ATOM | 1387 | N   | VAL | 193 | 17.670 | 23.352 | 18.554 | 1.00 | 20.52 |
| ATOM | 1388 | CA  | VAL | 193 | 16.726 | 24.306 | 19.117 | 1.00 | 24.71 |
| ATOM | 1389 | CB  | VAL | 193 | 16.760 | 25.635 | 18.307 | 1.00 | 25.59 |
| ATOM | 1390 | CG1 | VAL | 193 | 15.771 | 26.629 | 18.888 | 1.00 | 23.22 |
| ATOM | 1391 | CG2 | VAL | 193 | 18.191 | 26.227 | 18.280 | 1.00 | 26.47 |
| ATOM | 1392 | C   | VAL | 193 | 15.284 | 23.782 | 19.106 | 1.00 | 28.05 |
| ATOM | 1393 | O   | VAL | 193 | 14.845 | 23.158 | 18.111 | 1.00 | 32.43 |
| ATOM | 1394 | N   | THR | 194 | 14.564 | 24.055 | 20.205 | 1.00 | 29.93 |
| ATOM | 1395 | CA  | THR | 194 | 13.166 | 23.659 | 20.383 | 1.00 | 32.80 |
| ATOM | 1396 | CB  | THR | 194 | 13.009 | 22.586 | 21.494 | 1.00 | 33.39 |
| ATOM | 1397 | OG1 | THR | 194 | 13.570 | 23.052 | 22.734 | 1.00 | 34.60 |
| ATOM | 1398 | CG2 | THR | 194 | 13.700 | 21.316 | 21.074 | 1.00 | 35.77 |
| ATOM | 1399 | C   | THR | 194 | 12.253 | 24.844 | 20.728 | 1.00 | 33.73 |
| ATOM | 1400 | O   | THR | 194 | 12.623 | 25.790 | 21.432 | 1.00 | 34.75 |
| ATOM | 1401 | N   | ASN | 195 | 11.022 | 24.762 | 20.258 | 1.00 | 33.87 |
| ATOM | 1402 | CA  | ASN | 195 | 10.076 | 25.835 | 20.492 | 1.00 | 36.33 |
| ATOM | 1403 | CB  | ASN | 195 | 9.586  | 26.345 | 19.132 | 1.00 | 36.77 |
| ATOM | 1404 | CG  | ASN | 195 | 8.726  | 27.574 | 19.232 | 1.00 | 37.55 |
| ATOM | 1405 | OD1 | ASN | 195 | 8.810  | 28.352 | 20.193 | 1.00 | 32.92 |
| ATOM | 1406 | ND2 | ASN | 195 | 7.896  | 27.773 | 18.213 | 1.00 | 33.28 |
| ATOM | 1407 | C   | ASN | 195 | 8.911  | 25.443 | 21.395 | 1.00 | 36.22 |
| ATOM | 1408 | O   | ASN | 195 | 8.031  | 24.664 | 21.002 | 1.00 | 33.64 |
| ATOM | 1409 | N   | ALA | 196 | 8.931  | 25.979 | 22.617 | 1.00 | 37.74 |
| ATOM | 1410 | CA  | ALA | 196 | 7.864  | 25.730 | 23.592 | 1.00 | 39.36 |
| ATOM | 1411 | CB  | ALA | 196 | 6.670  | 26.666 | 23.303 | 1.00 | 42.05 |
| ATOM | 1412 | C   | ALA | 196 | 7.377  | 24.271 | 23.670 | 1.00 | 40.34 |
| ATOM | 1413 | O   | ALA | 196 | 8.135  | 23.373 | 24.112 | 1.00 | 43.70 |
| ATOM | 1414 | N   | LYS | 197 | 6.117  | 24.049 | 23.265 | 1.00 | 38.99 |
| ATOM | 1415 | CA  | LYS | 197 | 5.503  | 22.726 | 23.292 | 1.00 | 35.84 |
| ATOM | 1416 | CB  | LYS | 197 | 4.137  | 22.823 | 23.920 | 1.00 | 33.03 |
| ATOM | 1417 | CG  | LYS | 197 | 4.182  | 23.206 | 25.348 | 1.00 | 36.10 |
| ATOM | 1418 | CD  | LYS | 197 | 2.794  | 23.473 | 25.836 | 1.00 | 37.51 |
| ATOM | 1419 | CE  | LYS | 197 | 2.783  | 23.551 | 27.342 | 1.00 | 39.85 |
| ATOM | 1420 | NZ  | LYS | 197 | 3.163  | 22.223 | 27.944 | 1.00 | 43.96 |
| ATOM | 1421 | C   | LYS | 197 | 5.366  | 22.066 | 21.930 | 1.00 | 36.67 |
| ATOM | 1422 | O   | LYS | 197 | 4.373  | 21.373 | 21.679 | 1.00 | 38.07 |
| ATOM | 1423 | N   | ASP | 198 | 6.351  | 22.295 | 21.055 | 1.00 | 34.49 |
| ATOM | 1424 | CA  | ASP | 198 | 6.384  | 21.686 | 19.717 | 1.00 | 32.29 |
| ATOM | 1425 | CB  | ASP | 198 | 7.708  | 22.032 | 19.013 | 1.00 | 29.09 |
| ATOM | 1426 | CG  | ASP | 198 | 7.882  | 21.302 | 17.701 | 1.00 | 26.03 |
| ATOM | 1427 | OD1 | ASP | 198 | 7.062  | 20.409 | 17.414 | 1.00 | 23.23 |
| ATOM | 1428 | OD2 | ASP | 198 | 8.845  | 21.615 | 16.969 | 1.00 | 21.49 |
| ATOM | 1429 | C   | ASP | 198 | 6.333  | 20.180 | 20.033 | 1.00 | 33.21 |
| ATOM | 1430 | O   | ASP | 198 | 7.153  | 19.676 | 20.809 | 1.00 | 36.31 |
| ATOM | 1431 | N   | PRO | 199 | 5.384  | 19.438 | 19.442 | 1.00 | 31.90 |
| ATOM | 1432 | CD  | PRO | 199 | 4.208  | 19.890 | 18.679 | 1.00 | 33.69 |
| ATOM | 1433 | CA  | PRO | 199 | 5.302  | 18.004 | 19.740 | 1.00 | 31.80 |
| ATOM | 1434 | CB  | PRO | 199 | 3.859  | 17.676 | 19.408 | 1.00 | 30.13 |
| ATOM | 1435 | CG  | PRO | 199 | 3.581  | 18.575 | 18.252 | 1.00 | 30.92 |
| ATOM | 1436 | C   | PRO | 199 | 6.266  | 17.016 | 19.090 | 1.00 | 34.31 |
| ATOM | 1437 | O   | PRO | 199 | 6.313  | 15.856 | 19.490 | 1.00 | 37.03 |
| ATOM | 1438 | N   | VAL | 200 | 7.038  | 17.451 | 18.102 | 1.00 | 32.02 |
| ATOM | 1439 | CA  | VAL | 200 | 7.952  | 16.525 | 17.429 | 1.00 | 33.55 |
| ATOM | 1440 | CB  | VAL | 200 | 8.140  | 16.879 | 15.896 | 1.00 | 31.45 |
| ATOM | 1441 | CG1 | VAL | 200 | 7.679  | 18.286 | 15.609 | 1.00 | 26.24 |
| ATOM | 1442 | CG2 | VAL | 200 | 9.603  | 16.708 | 15.471 | 1.00 | 26.07 |
| ATOM | 1443 | C   | VAL | 200 | 9.314  | 16.342 | 18.080 | 1.00 | 36.82 |
| ATOM | 1444 | O   | VAL | 200 | 9.900  | 15.254 | 18.026 | 1.00 | 36.73 |
| ATOM | 1445 | N   | PRO | 201 | 9.843  | 17.398 | 18.704 | 1.00 | 39.43 |
| ATOM | 1446 | CD  | PRO | 201 | 9.432  | 18.809 | 18.677 | 1.00 | 40.66 |
| ATOM | 1447 | CA  | PRO | 201 | 11.152 | 17.259 | 19.341 | 1.00 | 38.84 |
| ATOM | 1448 | CB  | PRO | 201 | 11.466 | 18.682 | 19.778 | 1.00 | 35.83 |
| ATOM | 1449 | CG  | PRO | 201 | 10.765 | 19.504 | 18.729 | 1.00 | 38.37 |
| ATOM | 1450 | C   | PRO | 201 | 11.121 | 16.280 | 20.507 | 1.00 | 38.72 |

APPENDIX 1-continued

Coordinates in Protein Data Bank (PDB) format of GZEL.

| ATOM | 1451 | O | PRO | 201 | 12.136 | 16.029 | 21.137 | 1.00 | 41.44 |
|------|------|------|-----|-----|--------|--------|--------|------|-------|
| ATOM | 1452 | N | ARG | 202 | 9.944 | 15.735 | 20.791 | 1.00 | 38.20 |
| ATOM | 1453 | CA | ARG | 202 | 9.810 | 14.778 | 21.865 | 1.00 | 33.59 |
| ATOM | 1454 | CB | ARG | 202 | 8.833 | 15.287 | 22.943 | 1.00 | 31.21 |
| ATOM | 1455 | CG | ARG | 202 | 7.619 | 16.100 | 22.527 | 1.00 | 26.21 |
| ATOM | 1456 | CD | ARG | 202 | 6.651 | 16.096 | 23.704 | 1.00 | 28.07 |
| ATOM | 1457 | NE | ARG | 202 | 5.721 | 17.221 | 23.771 | 1.00 | 32.08 |
| ATOM | 1458 | CZ | ARG | 202 | 4.543 | 17.282 | 23.145 | 1.00 | 31.23 |
| ATOM | 1459 | NH1 | ARG | 202 | 3.782 | 18.357 | 23.293 | 1.00 | 33.90 |
| ATOM | 1460 | NH2 | ARG | 202 | 4.112 | 16.286 | 22.372 | 1.00 | 30.66 |
| ATOM | 1461 | C | ARG | 202 | 9.406 | 13.419 | 21.309 | 1.00 | 32.52 |
| ATOM | 1462 | O | ARG | 202 | 8.807 | 12.575 | 22.004 | 1.00 | 35.11 |
| ATOM | 1463 | N | LEU | 203 | 9.773 | 13.204 | 20.048 | 1.00 | 29.82 |
| ATOM | 1464 | CA | LEU | 203 | 9.481 | 11.946 | 19.380 | 1.00 | 25.27 |
| ATOM | 1465 | CB | LEU | 203 | 8.263 | 12.104 | 18.460 | 1.00 | 24.76 |
| ATOM | 1466 | CG | LEU | 203 | 6.964 | 12.372 | 19.219 | 1.00 | 25.85 |
| ATOM | 1467 | CD1 | LEU | 203 | 5.883 | 12.703 | 18.207 | 1.00 | 20.27 |
| ATOM | 1468 | CD2 | LEU | 203 | 6.585 | 11.156 | 20.109 | 1.00 | 19.33 |
| ATOM | 1469 | C | LEU | 203 | 10.706 | 11.514 | 18.572 | 1.00 | 21.60 |
| ATOM | 1470 | O | LEU | 203 | 11.471 | 12.352 | 18.074 | 1.00 | 19.99 |
| ATOM | 1471 | N | PRO | 204 | 10.948 | 10.200 | 18.489 | 1.00 | 18.93 |
| ATOM | 1472 | CD | PRO | 204 | 11.765 | 9.581 | 17.427 | 1.00 | 17.45 |
| ATOM | 1473 | CA | PRO | 204 | 10.098 | 9.203 | 19.144 | 1.00 | 20.16 |
| ATOM | 1474 | CB | PRO | 204 | 10.572 | 7.888 | 18.516 | 1.00 | 21.98 |
| ATOM | 1475 | CG | PRO | 204 | 11.007 | 8.301 | 17.141 | 1.00 | 16.12 |
| ATOM | 1476 | C | PRO | 204 | 10.234 | 9.215 | 20.685 | 1.00 | 18.91 |
| ATOM | 1477 | O | PRO | 204 | 11.176 | 9.789 | 21.239 | 1.00 | 15.54 |
| ATOM | 1478 | N | PRO | 205 | 9.299 | 8.554 | 21.388 | 1.00 | 19.35 |
| ATOM | 1479 | CD | PRO | 205 | 8.213 | 7.738 | 20.823 | 1.00 | 20.56 |
| ATOM | 1480 | CA | PRO | 205 | 9.278 | 8.477 | 22.850 | 1.00 | 21.21 |
| ATOM | 1481 | CB | PRO | 205 | 8.091 | 7.555 | 23.131 | 1.00 | 19.58 |
| ATOM | 1482 | CG | PRO | 205 | 7.212 | 7.756 | 21.945 | 1.00 | 19.74 |
| ATOM | 1483 | C | PRO | 205 | 10.561 | 7.919 | 23.442 | 1.00 | 24.31 |
| ATOM | 1484 | O | PRO | 205 | 11.210 | 7.055 | 22.842 | 1.00 | 27.43 |
| ATOM | 1485 | N | LEU | 206 | 10.924 | 8.411 | 24.624 | 1.00 | 24.15 |
| ATOM | 1486 | CA | LEU | 206 | 12.115 | 7.908 | 25.284 | 1.00 | 26.76 |
| ATOM | 1487 | CB | LEU | 206 | 12.329 | 8.538 | 26.663 | 1.00 | 25.72 |
| ATOM | 1488 | CG | LEU | 206 | 12.816 | 9.977 | 26.831 | 1.00 | 28.25 |
| ATOM | 1489 | CD1 | LEU | 206 | 13.274 | 10.191 | 28.268 | 1.00 | 26.97 |
| ATOM | 1490 | CD2 | LEU | 206 | 13.970 | 10.252 | 25.873 | 1.00 | 29.72 |
| ATOM | 1491 | C | LEU | 206 | 11.864 | 6.431 | 25.493 | 1.00 | 28.70 |
| ATOM | 1492 | O | LEU | 206 | 12.751 | 5.607 | 25.218 | 1.00 | 32.61 |
| ATOM | 1493 | N | ILE | 207 | 10.654 | 6.101 | 25.968 | 1.00 | 30.14 |
| ATOM | 1494 | CA | ILE | 207 | 10.296 | 4.714 | 26.248 | 1.00 | 31.14 |
| ATOM | 1495 | CB | ILE | 207 | 8.799 | 4.556 | 26.569 | 1.00 | 28.18 |
| ATOM | 1496 | CG2 | ILE | 207 | 8.463 | 5.299 | 27.868 | 1.00 | 26.68 |
| ATOM | 1497 | CG1 | ILE | 207 | 7.966 | 5.038 | 25.387 | 1.00 | 26.98 |
| ATOM | 1498 | CD1 | ILE | 207 | 6.479 | 4.718 | 25.510 | 1.00 | 32.66 |
| ATOM | 1499 | C | ILE | 207 | 10.653 | 3.767 | 25.103 | 1.00 | 33.97 |
| ATOM | 1500 | O | ILE | 207 | 10.739 | 2.543 | 25.309 | 1.00 | 34.93 |
| ATOM | 1501 | N | PHE | 208 | 10.864 | 4.317 | 23.904 | 1.00 | 34.47 |
| ATOM | 1502 | CA | PHE | 208 | 11.213 | 3.473 | 22.771 | 1.00 | 33.35 |
| ATOM | 1503 | CB | PHE | 208 | 10.242 | 3.743 | 21.597 | 1.00 | 33.97 |
| ATOM | 1504 | CG | PHE | 208 | 8.801 | 3.322 | 21.882 | 1.00 | 37.81 |
| ATOM | 1505 | CD1 | PHE | 208 | 7.728 | 4.050 | 21.361 | 1.00 | 36.85 |
| ATOM | 1506 | CD2 | PHE | 208 | 8.518 | 2.225 | 22.716 | 1.00 | 38.73 |
| ATOM | 1507 | CE1 | PHE | 208 | 6.393 | 3.706 | 21.672 | 1.00 | 35.52 |
| ATOM | 1508 | CE2 | PHE | 208 | 7.182 | 1.871 | 23.032 | 1.00 | 38.10 |
| ATOM | 1509 | CZ | PHE | 208 | 6.124 | 2.623 | 22.504 | 1.00 | 37.46 |
| ATOM | 1510 | C | PHE | 208 | 12.702 | 3.627 | 22.394 | 1.00 | 30.91 |
| ATOM | 1511 | O | PHE | 208 | 13.085 | 3.557 | 21.230 | 1.00 | 33.03 |
| ATOM | 1512 | N | GLY | 209 | 13.530 | 3.813 | 23.422 | 1.00 | 27.41 |
| ATOM | 1513 | CA | GLY | 209 | 14.977 | 3.902 | 23.270 | 1.00 | 27.70 |
| ATOM | 1514 | C | GLY | 209 | 15.564 | 5.177 | 22.712 | 1.00 | 29.53 |
| ATOM | 1515 | O | GLY | 209 | 16.769 | 5.436 | 22.851 | 1.00 | 29.48 |
| ATOM | 1516 | N | TYR | 210 | 14.718 | 5.962 | 22.055 | 1.00 | 29.56 |
| ATOM | 1517 | CA | TYR | 210 | 15.154 | 7.198 | 21.451 | 1.00 | 29.10 |
| ATOM | 1518 | CB | TYR | 210 | 14.054 | 7.729 | 20.544 | 1.00 | 28.00 |
| ATOM | 1519 | CG | TYR | 210 | 13.904 | 6.928 | 19.253 | 1.00 | 28.06 |
| ATOM | 1520 | CD1 | TYR | 210 | 14.611 | 7.283 | 18.093 | 1.00 | 26.44 |
| ATOM | 1521 | CE1 | TYR | 210 | 14.454 | 6.564 | 16.884 | 1.00 | 25.01 |
| ATOM | 1522 | CD2 | TYR | 210 | 13.043 | 5.829 | 19.181 | 1.00 | 22.49 |
| ATOM | 1523 | CE2 | TYR | 210 | 12.881 | 5.099 | 17.980 | 1.00 | 24.49 |
| ATOM | 1524 | CZ | TYR | 210 | 13.585 | 5.477 | 16.839 | 1.00 | 26.12 |
| ATOM | 1525 | OH | TYR | 210 | 13.400 | 4.789 | 15.654 | 1.00 | 28.95 |
| ATOM | 1526 | C | TYR | 210 | 15.564 | 8.211 | 22.506 | 1.00 | 30.17 |
| ATOM | 1527 | O | TYR | 210 | 14.879 | 8.419 | 23.530 | 1.00 | 31.17 |
| ATOM | 1528 | N | ARG | 211 | 16.716 | 8.818 | 22.230 | 1.00 | 29.17 |

APPENDIX 1-continued

Coordinates in Protein Data Bank (PDB) format of GZEL.

| ATOM | 1529 | CA | ARG | 211 | 17.357 | 9.805 | 23.082 | 1.00 | 27.79 |
|------|------|-----|-----|-----|--------|--------|--------|------|-------|
| ATOM | 1530 | CB | ARG | 211 | 18.591 | 9.177 | 23.707 | 1.00 | 26.76 |
| ATOM | 1531 | CG | ARG | 211 | 18.308 | 7.871 | 24.418 | 1.00 | 30.07 |
| ATOM | 1532 | CD | ARG | 211 | 17.554 | 8.140 | 25.688 | 1.00 | 28.13 |
| ATOM | 1533 | NE | ARG | 211 | 16.471 | 7.194 | 25.872 | 1.00 | 31.44 |
| ATOM | 1534 | CZ | ARG | 211 | 16.342 | 6.426 | 26.945 | 1.00 | 37.43 |
| ATOM | 1535 | NH1 | ARG | 211 | 17.240 | 6.511 | 27.912 | 1.00 | 38.25 |
| ATOM | 1536 | NH2 | ARG | 211 | 15.323 | 5.576 | 27.053 | 1.00 | 39.38 |
| ATOM | 1537 | C | ARG | 211 | 17.789 | 10.976 | 22.206 | 1.00 | 29.96 |
| ATOM | 1538 | O | ARG | 211 | 17.767 | 10.860 | 20.969 | 1.00 | 35.98 |
| ATOM | 1539 | N | HIS | 212 | 18.196 | 12.080 | 22.837 | 1.00 | 28.81 |
| ATOM | 1540 | CA | HIS | 212 | 18.632 | 13.264 | 22.116 | 1.00 | 27.59 |
| ATOM | 1541 | CB | HIS | 212 | 17.826 | 14.468 | 22.586 | 1.00 | 25.29 |
| ATOM | 1542 | CG | HIS | 212 | 16.632 | 14.782 | 21.733 | 1.00 | 21.16 |
| ATOM | 1543 | CD2 | HIS | 212 | 15.329 | 14.985 | 22.051 | 1.00 | 18.56 |
| ATOM | 1544 | ND1 | HIS | 212 | 16.727 | 14.996 | 20.374 | 1.00 | 19.29 |
| ATOM | 1545 | CE1 | HIS | 212 | 15.538 | 15.314 | 19.892 | 1.00 | 19.37 |
| ATOM | 1546 | NE2 | HIS | 212 | 14.671 | 15.313 | 20.889 | 1.00 | 18.19 |
| ATOM | 1547 | C | HIS | 212 | 20.115 | 13.592 | 22.258 | 1.00 | 29.89 |
| ATOM | 1548 | O | HIS | 212 | 20.858 | 12.902 | 22.948 | 1.00 | 32.67 |
| ATOM | 1549 | N | THR | 213 | 20.533 | 14.653 | 21.568 | 1.00 | 32.51 |
| ATOM | 1550 | CA | THR | 213 | 21.915 | 15.151 | 21.609 | 1.00 | 34.41 |
| ATOM | 1551 | CB | THR | 213 | 22.434 | 15.671 | 20.251 | 1.00 | 35.45 |
| ATOM | 1552 | OG1 | THR | 213 | 21.376 | 16.357 | 19.565 | 1.00 | 36.52 |
| ATOM | 1553 | CG2 | THR | 213 | 22.991 | 14.545 | 19.421 | 1.00 | 38.69 |
| ATOM | 1554 | C | THR | 213 | 21.929 | 16.359 | 22.518 | 1.00 | 35.02 |
| ATOM | 1555 | O | THR | 213 | 21.008 | 17.165 | 22.518 | 1.00 | 33.04 |
| ATOM | 1556 | N | SER | 214 | 22.998 | 16.511 | 23.266 | 1.00 | 35.79 |
| ATOM | 1557 | CA | SER | 214 | 23.068 | 17.627 | 24.161 | 1.00 | 37.40 |
| ATOM | 1558 | CB | SER | 214 | 23.556 | 17.122 | 25.514 | 1.00 | 37.51 |
| ATOM | 1559 | OG | SER | 214 | 23.560 | 18.133 | 26.501 | 1.00 | 42.60 |
| ATOM | 1560 | C | SER | 214 | 23.990 | 18.694 | 23.575 | 1.00 | 37.69 |
| ATOM | 1561 | O | SER | 214 | 24.931 | 18.390 | 22.842 | 1.00 | 39.04 |
| ATOM | 1562 | N | PRO | 215 | 23.699 | 19.968 | 23.857 | 1.00 | 36.66 |
| ATOM | 1563 | CD | PRO | 215 | 24.595 | 21.111 | 23.606 | 1.00 | 36.17 |
| ATOM | 1564 | CA | PRO | 215 | 22.562 | 20.383 | 24.677 | 1.00 | 35.16 |
| ATOM | 1565 | CB | PRO | 215 | 23.032 | 21.699 | 25.252 | 1.00 | 34.57 |
| ATOM | 1566 | CG | PRO | 215 | 23.761 | 22.286 | 24.085 | 1.00 | 34.47 |
| ATOM | 1567 | C | PRO | 215 | 21.286 | 20.568 | 23.879 | 1.00 | 35.43 |
| ATOM | 1568 | O | PRO | 215 | 21.129 | 20.049 | 22.773 | 1.00 | 34.55 |
| ATOM | 1569 | N | GLU | 216 | 20.389 | 21.341 | 24.469 | 1.00 | 36.14 |
| ATOM | 1570 | CA | GLU | 216 | 19.101 | 21.651 | 23.885 | 1.00 | 35.35 |
| ATOM | 1571 | CB | GLU | 216 | 18.015 | 20.782 | 24.504 | 1.00 | 34.93 |
| ATOM | 1572 | CG | GLU | 216 | 16.632 | 21.260 | 24.130 | 1.00 | 31.58 |
| ATOM | 1573 | CD | GLU | 216 | 15.537 | 20.628 | 24.973 | 1.00 | 34.98 |
| ATOM | 1574 | OE1 | GLU | 216 | 15.723 | 19.485 | 25.463 | 1.00 | 41.04 |
| ATOM | 1575 | OE2 | GLU | 216 | 14.474 | 21.272 | 25.133 | 1.00 | 34.46 |
| ATOM | 1576 | C | GLU | 216 | 18.804 | 23.099 | 24.211 | 1.00 | 33.66 |
| ATOM | 1577 | O | GLU | 216 | 18.693 | 23.478 | 25.375 | 1.00 | 32.94 |
| ATOM | 1578 | N | TYR | 217 | 18.686 | 23.913 | 23.179 | 1.00 | 33.09 |
| ATOM | 1579 | CA | TYR | 217 | 18.392 | 25.326 | 23.361 | 1.00 | 34.95 |
| ATOM | 1580 | CB | TYR | 217 | 19.200 | 26.134 | 22.364 | 1.00 | 34.01 |
| ATOM | 1581 | CG | TYR | 217 | 20.689 | 25.910 | 22.489 | 1.00 | 35.10 |
| ATOM | 1582 | CD1 | TYR | 217 | 21.300 | 24.776 | 21.947 | 1.00 | 35.08 |
| ATOM | 1583 | CE1 | TYR | 217 | 22.681 | 24.583 | 22.053 | 1.00 | 33.58 |
| ATOM | 1584 | CD2 | TYR | 217 | 21.495 | 26.841 | 23.148 | 1.00 | 36.42 |
| ATOM | 1585 | CE2 | TYR | 217 | 22.869 | 26.653 | 23.263 | 1.00 | 33.49 |
| ATOM | 1586 | CZ | TYR | 217 | 23.453 | 25.523 | 22.710 | 1.00 | 32.43 |
| ATOM | 1587 | OH | TYR | 217 | 24.803 | 25.332 | 22.805 | 1.00 | 31.62 |
| ATOM | 1588 | C | TYR | 217 | 16.904 | 25.537 | 23.158 | 1.00 | 35.97 |
| ATOM | 1589 | O | TYR | 217 | 16.422 | 25.725 | 22.050 | 1.00 | 37.11 |
| ATOM | 1590 | N | TRP | 218 | 16.175 | 25.475 | 24.260 | 1.00 | 33.94 |
| ATOM | 1591 | CA | TRP | 218 | 14.720 | 25.597 | 24.245 | 1.00 | 33.34 |
| ATOM | 1592 | CB | TRP | 218 | 14.125 | 24.729 | 25.356 | 1.00 | 35.12 |
| ATOM | 1593 | CG | TRP | 218 | 12.660 | 24.733 | 25.456 | 1.00 | 31.18 |
| ATOM | 1594 | CD2 | TRP | 218 | 11.908 | 24.884 | 26.658 | 1.00 | 27.18 |
| ATOM | 1595 | CE2 | TRP | 218 | 10.545 | 24.649 | 26.342 | 1.00 | 27.19 |
| ATOM | 1596 | CE3 | TRP | 218 | 12.252 | 25.190 | 27.981 | 1.00 | 26.15 |
| ATOM | 1597 | CD1 | TRP | 218 | 11.755 | 24.437 | 24.467 | 1.00 | 32.33 |
| ATOM | 1598 | NE1 | TRP | 218 | 10.474 | 24.377 | 24.997 | 1.00 | 29.27 |
| ATOM | 1599 | CZ2 | TRP | 218 | 9.536 | 24.706 | 27.299 | 1.00 | 23.07 |
| ATOM | 1600 | CZ3 | TRP | 218 | 11.253 | 25.246 | 28.925 | 1.00 | 28.57 |
| ATOM | 1601 | CH2 | TRP | 218 | 9.909 | 25.005 | 28.582 | 1.00 | 27.07 |
| ATOM | 1602 | C | TRP | 218 | 14.215 | 27.006 | 24.385 | 1.00 | 32.24 |
| ATOM | 1603 | O | TRP | 218 | 14.706 | 27.785 | 25.218 | 1.00 | 30.36 |
| ATOM | 1604 | N | LEU | 219 | 13.223 | 27.316 | 23.553 | 1.00 | 32.03 |
| ATOM | 1605 | CA | LEU | 219 | 12.606 | 28.635 | 23.539 | 1.00 | 30.96 |
| ATOM | 1606 | CB | LEU | 219 | 12.153 | 28.992 | 22.130 | 1.00 | 24.86 |

APPENDIX 1-continued

Coordinates in Protein Data Bank (PDB) format of GZEL.

| ATOM | 1607 | CG  | LEU | 219 | 13.219 | 29.035 | 21.047 | 1.00 | 22.19 |
|------|------|-----|-----|-----|--------|--------|--------|------|-------|
| ATOM | 1608 | CD1 | LEU | 219 | 12.604 | 29.413 | 19.702 | 1.00 | 23.26 |
| ATOM | 1609 | CD2 | LEU | 219 | 14.294 | 30.024 | 21.451 | 1.00 | 23.32 |
| ATOM | 1610 | C   | LEU | 219 | 11.413 | 28.623 | 24.477 | 1.00 | 32.11 |
| ATOM | 1611 | O   | LEU | 219 | 10.383 | 28.003 | 24.199 | 1.00 | 31.03 |
| ATOM | 1612 | N   | SER | 220 | 11.574 | 29.320 | 25.591 | 1.00 | 34.19 |
| ATOM | 1613 | CA  | SER | 220 | 10.558 | 29.391 | 26.622 | 1.00 | 38.20 |
| ATOM | 1614 | CB  | SER | 220 | 11.232 | 29.675 | 27.975 | 1.00 | 40.51 |
| ATOM | 1615 | OG  | SER | 220 | 10.283 | 29.951 | 28.990 | 1.00 | 42.19 |
| ATOM | 1616 | C   | SER | 220 | 9.519  | 30.468 | 26.290 | 1.00 | 41.27 |
| ATOM | 1617 | O   | SER | 220 | 9.816  | 31.686 | 26.314 | 1.00 | 43.55 |
| ATOM | 1618 | N   | GLY | 221 | 8.309  | 30.004 | 25.974 | 1.00 | 42.71 |
| ATOM | 1619 | CA  | GLY | 221 | 7.228  | 30.901 | 25.630 | 1.00 | 44.34 |
| ATOM | 1620 | C   | GLY | 221 | 5.993  | 30.125 | 25.231 | 1.00 | 47.07 |
| ATOM | 1621 | O   | GLY | 221 | 5.641  | 29.130 | 25.880 | 1.00 | 48.33 |
| ATOM | 1622 | N   | SER | 222 | 5.335  | 30.570 | 24.162 | 1.00 | 47.78 |
| ATOM | 1623 | CA  | SER | 222 | 4.119  | 29.914 | 23.686 | 1.00 | 48.39 |
| ATOM | 1624 | CB  | SER | 222 | 2.896  | 30.819 | 23.912 | 1.00 | 48.99 |
| ATOM | 1625 | OG  | SER | 222 | 3.179  | 32.187 | 23.647 | 1.00 | 46.46 |
| ATOM | 1626 | C   | SER | 222 | 4.209  | 29.520 | 22.208 | 1.00 | 51.09 |
| ATOM | 1627 | O   | SER | 222 | 4.290  | 28.326 | 21.861 | 1.00 | 55.36 |
| ATOM | 1628 | N   | ASP | 223 | 4.181  | 30.530 | 21.340 | 1.00 | 51.73 |
| ATOM | 1629 | CA  | ASP | 223 | 4.269  | 30.334 | 19.895 | 1.00 | 51.72 |
| ATOM | 1630 | CB  | ASP | 223 | 3.077  | 29.475 | 19.432 | 1.00 | 46.28 |
| ATOM | 1631 | CG  | ASP | 223 | 2.848  | 29.517 | 17.926 | 1.00 | 44.22 |
| ATOM | 1632 | OD1 | ASP | 223 | 3.763  | 29.198 | 17.126 | 1.00 | 46.70 |
| ATOM | 1633 | OD2 | ASP | 223 | 1.719  | 29.867 | 17.539 | 1.00 | 38.38 |
| ATOM | 1634 | C   | ASP | 223 | 4.337  | 31.703 | 19.161 | 1.00 | 54.87 |
| ATOM | 1635 | O   | ASP | 223 | 3.716  | 32.693 | 19.587 | 1.00 | 55.13 |
| ATOM | 1636 | N   | LYS | 224 | 5.158  | 31.733 | 18.104 | 1.00 | 56.32 |
| ATOM | 1637 | CA  | LYS | 224 | 5.412  | 32.878 | 17.221 | 1.00 | 53.02 |
| ATOM | 1638 | CB  | LYS | 224 | 4.626  | 34.108 | 17.650 | 1.00 | 52.74 |
| ATOM | 1639 | CG  | LYS | 224 | 3.137  | 33.957 | 17.404 | 1.00 | 56.80 |
| ATOM | 1640 | CD  | LYS | 224 | 2.804  | 33.708 | 15.933 | 1.00 | 57.03 |
| ATOM | 1641 | CE  | LYS | 224 | 1.290  | 33.534 | 15.740 | 1.00 | 53.19 |
| ATOM | 1642 | NZ  | LYS | 224 | 0.831  | 33.475 | 14.322 | 1.00 | 50.36 |
| ATOM | 1643 | C   | LYS | 224 | 6.880  | 33.251 | 16.992 | 1.00 | 50.71 |
| ATOM | 1644 | O   | LYS | 224 | 7.801  | 32.547 | 17.395 | 1.00 | 49.91 |
| ATOM | 1645 | N   | ILE | 225 | 7.077  | 34.397 | 16.364 | 1.00 | 48.53 |
| ATOM | 1646 | CA  | ILE | 225 | 8.392  | 34.884 | 15.931 | 1.00 | 48.98 |
| ATOM | 1647 | CB  | ILE | 225 | 8.157  | 35.792 | 14.699 | 1.00 | 47.91 |
| ATOM | 1648 | CG2 | ILE | 225 | 9.461  | 36.175 | 14.035 | 1.00 | 50.91 |
| ATOM | 1649 | CG1 | ILE | 225 | 7.292  | 35.068 | 13.686 | 1.00 | 50.09 |
| ATOM | 1650 | CD1 | ILE | 225 | 6.841  | 35.963 | 12.570 | 1.00 | 52.31 |
| ATOM | 1651 | C   | ILE | 225 | 9.461  | 35.593 | 16.803 | 1.00 | 48.42 |
| ATOM | 1652 | O   | ILE | 225 | 10.666 | 35.340 | 16.627 | 1.00 | 47.48 |
| ATOM | 1653 | N   | ASP | 226 | 9.046  | 36.449 | 17.733 | 1.00 | 46.35 |
| ATOM | 1654 | CA  | ASP | 226 | 9.998  | 37.258 | 18.509 | 1.00 | 42.89 |
| ATOM | 1655 | CB  | ASP | 226 | 9.318  | 38.569 | 18.839 | 1.00 | 44.72 |
| ATOM | 1656 | CG  | ASP | 226 | 8.058  | 38.357 | 19.657 | 1.00 | 50.94 |
| ATOM | 1657 | OD1 | ASP | 226 | 7.807  | 37.187 | 20.044 | 1.00 | 51.85 |
| ATOM | 1658 | OD2 | ASP | 226 | 7.327  | 39.343 | 19.919 | 1.00 | 51.91 |
| ATOM | 1659 | C   | ASP | 226 | 10.749 | 36.823 | 19.770 | 1.00 | 40.29 |
| ATOM | 1660 | O   | ASP | 226 | 10.907 | 37.650 | 20.674 | 1.00 | 36.29 |
| ATOM | 1661 | N   | TYR | 227 | 11.241 | 35.592 | 19.864 | 1.00 | 38.05 |
| ATOM | 1662 | CA  | TYR | 227 | 11.970 | 35.268 | 21.087 | 1.00 | 35.65 |
| ATOM | 1663 | CB  | TYR | 227 | 12.205 | 33.787 | 21.223 | 1.00 | 31.14 |
| ATOM | 1664 | CG  | TYR | 227 | 10.979 | 32.944 | 21.408 | 1.00 | 23.94 |
| ATOM | 1665 | CD1 | TYR | 227 | 10.268 | 32.458 | 20.310 | 1.00 | 22.52 |
| ATOM | 1666 | CE1 | TYR | 227 | 9.253  | 31.538 | 20.467 | 1.00 | 18.28 |
| ATOM | 1667 | CD2 | TYR | 227 | 10.619 | 32.502 | 22.673 | 1.00 | 22.37 |
| ATOM | 1668 | CE2 | TYR | 227 | 9.607  | 31.579 | 22.834 | 1.00 | 20.84 |
| ATOM | 1669 | CZ  | TYR | 227 | 8.937  | 31.099 | 21.724 | 1.00 | 20.72 |
| ATOM | 1670 | OH  | TYR | 227 | 7.991  | 30.116 | 21.863 | 1.00 | 24.72 |
| ATOM | 1671 | C   | TYR | 227 | 13.324 | 35.961 | 21.059 | 1.00 | 34.93 |
| ATOM | 1672 | O   | TYR | 227 | 13.749 | 36.474 | 20.012 | 1.00 | 35.23 |
| ATOM | 1673 | N   | THR | 228 | 14.002 | 35.971 | 22.207 | 1.00 | 33.89 |
| ATOM | 1674 | CA  | THR | 228 | 15.312 | 36.619 | 22.306 | 1.00 | 33.29 |
| ATOM | 1675 | CB  | THR | 228 | 15.188 | 38.000 | 22.909 | 1.00 | 29.80 |
| ATOM | 1676 | OG1 | THR | 228 | 14.804 | 37.879 | 24.284 | 1.00 | 24.02 |
| ATOM | 1677 | CG2 | THR | 228 | 14.135 | 38.777 | 22.157 | 1.00 | 22.64 |
| ATOM | 1678 | C   | THR | 228 | 16.226 | 35.795 | 23.189 | 1.00 | 34.79 |
| ATOM | 1679 | O   | THR | 228 | 15.765 | 34.869 | 23.840 | 1.00 | 38.39 |
| ATOM | 1680 | N   | ILE | 229 | 17.509 | 36.142 | 23.241 | 1.00 | 34.44 |
| ATOM | 1681 | CA  | ILE | 229 | 18.451 | 35.355 | 24.030 | 1.00 | 37.75 |
| ATOM | 1682 | CB  | ILE | 229 | 19.835 | 36.044 | 24.181 | 1.00 | 39.09 |
| ATOM | 1683 | CG2 | ILE | 229 | 20.937 | 34.987 | 23.989 | 1.00 | 32.52 |
| ATOM | 1684 | CG1 | ILE | 229 | 19.995 | 37.178 | 23.154 | 1.00 | 42.61 |

APPENDIX 1-continued

Coordinates in Protein Data Bank (PDB) format of GZEL.

| ATOM | 1685 | CD1 | ILE | 229 | 21.396 | 37.800 | 23.068 | 1.00 | 45.25 |
|---|---|---|---|---|---|---|---|---|---|
| ATOM | 1686 | C | ILE | 229 | 17.932 | 35.044 | 25.414 | 1.00 | 39.33 |
| ATOM | 1687 | O | ILE | 229 | 18.148 | 33.960 | 25.952 | 1.00 | 39.91 |
| ATOM | 1688 | N | ASN | 230 | 17.195 | 35.991 | 25.971 | 1.00 | 42.05 |
| ATOM | 1689 | CA | ASN | 230 | 16.663 | 35.840 | 27.318 | 1.00 | 43.15 |
| ATOM | 1690 | CB | ASN | 230 | 16.427 | 37.216 | 27.905 | 1.00 | 44.81 |
| ATOM | 1691 | CG | ASN | 230 | 17.722 | 37.982 | 28.064 | 1.00 | 46.86 |
| ATOM | 1692 | OD1 | ASN | 230 | 17.718 | 39.201 | 28.182 | 1.00 | 44.52 |
| ATOM | 1693 | ND2 | ASN | 230 | 18.849 | 37.258 | 28.079 | 1.00 | 48.08 |
| ATOM | 1694 | C | ASN | 230 | 15.428 | 34.990 | 27.469 | 1.00 | 42.18 |
| ATOM | 1695 | O | ASN | 230 | 14.925 | 34.809 | 28.572 | 1.00 | 41.84 |
| ATOM | 1696 | N | ASP | 231 | 14.938 | 34.470 | 26.358 | 1.00 | 40.88 |
| ATOM | 1697 | CA | ASP | 231 | 13.763 | 33.623 | 26.385 | 1.00 | 40.09 |
| ATOM | 1698 | CB | ASP | 231 | 12.848 | 33.968 | 25.219 | 1.00 | 44.81 |
| ATOM | 1699 | CG | ASP | 231 | 12.537 | 35.435 | 25.148 | 1.00 | 45.26 |
| ATOM | 1700 | OD1 | ASP | 231 | 12.038 | 35.875 | 24.085 | 1.00 | 43.82 |
| ATOM | 1701 | OD2 | ASP | 231 | 12.793 | 36.137 | 26.153 | 1.00 | 48.49 |
| ATOM | 1702 | C | ASP | 231 | 14.259 | 32.200 | 26.220 | 1.00 | 38.80 |
| ATOM | 1703 | O | ASP | 231 | 13.479 | 31.276 | 26.031 | 1.00 | 36.46 |
| ATOM | 1704 | N | VAL | 232 | 15.574 | 32.029 | 26.263 | 1.00 | 37.12 |
| ATOM | 1705 | CA | VAL | 232 | 16.147 | 30.706 | 26.100 | 1.00 | 36.25 |
| ATOM | 1706 | CB | VAL | 232 | 17.434 | 30.762 | 25.227 | 1.00 | 34.82 |
| ATOM | 1707 | CG1 | VAL | 232 | 18.128 | 29.393 | 25.227 | 1.00 | 30.44 |
| ATOM | 1708 | CG2 | VAL | 232 | 17.070 | 31.144 | 23.803 | 1.00 | 30.02 |
| ATOM | 1709 | C | VAL | 232 | 16.449 | 29.999 | 27.428 | 1.00 | 37.79 |
| ATOM | 1710 | O | VAL | 232 | 16.680 | 30.642 | 28.469 | 1.00 | 39.93 |
| ATOM | 1711 | N | LYS | 233 | 16.400 | 28.668 | 27.384 | 1.00 | 37.60 |
| ATOM | 1712 | CA | LYS | 233 | 16.703 | 27.827 | 28.532 | 1.00 | 36.16 |
| ATOM | 1713 | CB | LYS | 233 | 15.435 | 27.145 | 29.060 | 1.00 | 37.40 |
| ATOM | 1714 | CG | LYS | 233 | 14.297 | 28.080 | 29.473 | 1.00 | 39.89 |
| ATOM | 1715 | CD | LYS | 233 | 14.501 | 28.672 | 30.863 | 1.00 | 43.04 |
| ATOM | 1716 | CE | LYS | 233 | 13.258 | 29.447 | 31.323 | 1.00 | 46.34 |
| ATOM | 1717 | NZ | LYS | 233 | 11.986 | 28.648 | 31.284 | 1.00 | 47.35 |
| ATOM | 1718 | C | LYS | 233 | 17.658 | 26.776 | 27.955 | 1.00 | 37.10 |
| ATOM | 1719 | O | LYS | 233 | 17.608 | 26.484 | 26.757 | 1.00 | 40.45 |
| ATOM | 1720 | N | VAL | 234 | 18.520 | 26.213 | 28.795 | 1.00 | 35.45 |
| ATOM | 1721 | CA | VAL | 234 | 19.472 | 25.203 | 28.346 | 1.00 | 31.04 |
| ATOM | 1722 | CB | VAL | 234 | 20.904 | 25.760 | 28.310 | 1.00 | 27.95 |
| ATOM | 1723 | CG1 | VAL | 234 | 21.888 | 24.667 | 27.894 | 1.00 | 27.27 |
| ATOM | 1724 | CG2 | VAL | 234 | 20.965 | 26.936 | 27.354 | 1.00 | 25.26 |
| ATOM | 1725 | C | VAL | 234 | 19.438 | 23.990 | 29.257 | 1.00 | 32.55 |
| ATOM | 1726 | O | VAL | 234 | 19.851 | 24.045 | 30.425 | 1.00 | 33.04 |
| ATOM | 1727 | N | CYS | 235 | 18.938 | 22.895 | 28.694 | 1.00 | 35.25 |
| ATOM | 1728 | CA | CYS | 235 | 18.781 | 21.619 | 29.391 | 1.00 | 38.31 |
| ATOM | 1729 | C | CYS | 235 | 19.860 | 20.670 | 28.841 | 1.00 | 37.75 |
| ATOM | 1730 | O | CYS | 235 | 20.025 | 20.522 | 27.620 | 1.00 | 39.24 |
| ATOM | 1731 | CB | CYS | 235 | 17.342 | 21.121 | 29.116 | 1.00 | 36.40 |
| ATOM | 1732 | SG | CYS | 235 | 16.413 | 22.533 | 28.396 | 1.00 | 49.33 |
| ATOM | 1733 | N | GLU | 236 | 20.631 | 20.055 | 29.732 | 1.00 | 37.70 |
| ATOM | 1734 | CA | GLU | 236 | 21.677 | 19.147 | 29.274 | 1.00 | 37.30 |
| ATOM | 1735 | CB | GLU | 236 | 23.026 | 19.544 | 29.886 | 1.00 | 35.33 |
| ATOM | 1736 | CG | GLU | 236 | 23.437 | 21.008 | 29.670 | 1.00 | 38.61 |
| ATOM | 1737 | CD | GLU | 236 | 24.837 | 21.314 | 30.211 | 1.00 | 37.96 |
| ATOM | 1738 | OE1 | GLU | 236 | 25.080 | 22.448 | 30.690 | 1.00 | 34.90 |
| ATOM | 1739 | OE2 | GLU | 236 | 25.699 | 20.416 | 30.147 | 1.00 | 34.80 |
| ATOM | 1740 | C | GLU | 236 | 21.332 | 17.687 | 29.612 | 1.00 | 37.87 |
| ATOM | 1741 | O | GLU | 236 | 20.639 | 17.415 | 30.606 | 1.00 | 40.11 |
| ATOM | 1742 | N | GLY | 237 | 21.785 | 16.753 | 28.769 | 1.00 | 36.80 |
| ATOM | 1743 | CA | GLY | 237 | 21.513 | 15.337 | 28.998 | 1.00 | 32.73 |
| ATOM | 1744 | C | GLY | 237 | 20.680 | 14.648 | 27.905 | 1.00 | 30.90 |
| ATOM | 1745 | O | GLY | 237 | 19.797 | 15.260 | 27.294 | 1.00 | 29.19 |
| ATOM | 1746 | N | ALA | 238 | 20.954 | 13.361 | 27.688 | 1.00 | 32.95 |
| ATOM | 1747 | CA | ALA | 238 | 20.284 | 12.512 | 26.691 | 1.00 | 32.90 |
| ATOM | 1748 | CB | ALA | 238 | 20.903 | 11.097 | 26.705 | 1.00 | 31.25 |
| ATOM | 1749 | C | ALA | 238 | 18.788 | 12.396 | 26.924 | 1.00 | 34.16 |
| ATOM | 1750 | O | ALA | 238 | 17.994 | 12.484 | 25.972 | 1.00 | 37.39 |
| ATOM | 1751 | N | ALA | 239 | 18.426 | 12.178 | 28.194 | 1.00 | 32.51 |
| ATOM | 1752 | CA | ALA | 239 | 17.028 | 12.037 | 28.623 | 1.00 | 33.61 |
| ATOM | 1753 | CB | ALA | 239 | 16.777 | 10.624 | 29.152 | 1.00 | 30.52 |
| ATOM | 1754 | C | ALA | 239 | 16.661 | 13.076 | 29.691 | 1.00 | 33.09 |
| ATOM | 1755 | O | ALA | 239 | 16.689 | 12.802 | 30.887 | 1.00 | 38.01 |
| ATOM | 1756 | N | ASN | 240 | 16.314 | 14.271 | 29.229 | 1.00 | 29.73 |
| ATOM | 1757 | CA | ASN | 240 | 15.958 | 15.402 | 30.079 | 1.00 | 28.09 |
| ATOM | 1758 | CB | ASN | 240 | 17.042 | 16.481 | 29.956 | 1.00 | 28.69 |
| ATOM | 1759 | CG | ASN | 240 | 16.675 | 17.762 | 30.674 | 1.00 | 29.76 |
| ATOM | 1760 | OD1 | ASN | 240 | 15.498 | 18.095 | 30.837 | 1.00 | 29.65 |
| ATOM | 1761 | ND2 | ASN | 240 | 17.682 | 18.498 | 31.097 | 1.00 | 32.23 |
| ATOM | 1762 | C | ASN | 240 | 14.614 | 15.959 | 29.593 | 1.00 | 27.56 |

APPENDIX 1-continued

Coordinates in Protein Data Bank (PDB) format of GZEL.

| ATOM | 1763 | O   | ASN | 240 | 14.485 | 16.335 | 28.421 | 1.00 | 32.63 |
| ATOM | 1764 | N   | LEU | 241 | 13.622 | 16.051 | 30.473 | 1.00 | 25.68 |
| ATOM | 1765 | CA  | LEU | 241 | 12.315 | 16.546 | 30.048 | 1.00 | 25.18 |
| ATOM | 1766 | CB  | LEU | 241 | 11.268 | 15.505 | 30.374 | 1.00 | 20.15 |
| ATOM | 1767 | CG  | LEU | 241 | 11.654 | 14.108 | 29.910 | 1.00 | 20.13 |
| ATOM | 1768 | CD1 | LEU | 241 | 10.667 | 13.096 | 30.438 | 1.00 | 19.46 |
| ATOM | 1769 | CD2 | LEU | 241 | 11.712 | 14.082 | 28.394 | 1.00 | 7.75  |
| ATOM | 1770 | C   | LEU | 241 | 11.957 | 17.837 | 30.735 | 1.00 | 28.61 |
| ATOM | 1771 | O   | LEU | 241 | 10.792 | 18.178 | 30.881 | 1.00 | 31.35 |
| ATOM | 1772 | N   | GLN | 242 | 12.974 | 18.550 | 31.177 | 1.00 | 31.34 |
| ATOM | 1773 | CA  | GLN | 242 | 12.761 | 19.798 | 31.875 | 1.00 | 31.71 |
| ATOM | 1774 | CB  | GLN | 242 | 14.002 | 20.174 | 32.671 | 1.00 | 32.22 |
| ATOM | 1775 | CG  | GLN | 242 | 14.327 | 19.140 | 33.687 | 1.00 | 35.19 |
| ATOM | 1776 | CD  | GLN | 242 | 13.107 | 18.781 | 34.520 | 1.00 | 36.20 |
| ATOM | 1777 | OE1 | GLN | 242 | 12.710 | 19.531 | 35.413 | 1.00 | 38.50 |
| ATOM | 1778 | NE2 | GLN | 242 | 12.503 | 17.634 | 34.225 | 1.00 | 37.34 |
| ATOM | 1779 | C   | GLN | 242 | 12.478 | 20.864 | 30.863 | 1.00 | 31.94 |
| ATOM | 1780 | O   | GLN | 242 | 12.335 | 22.027 | 31.213 | 1.00 | 33.10 |
| ATOM | 1781 | N   | CYS | 243 | 12.386 | 20.468 | 29.604 | 1.00 | 34.24 |
| ATOM | 1782 | CA  | CYS | 243 | 12.139 | 21.444 | 28.583 | 1.00 | 35.22 |
| ATOM | 1783 | C   | CYS | 243 | 11.105 | 21.019 | 27.577 | 1.00 | 34.96 |
| ATOM | 1784 | O   | CYS | 243 | 9.971  | 20.709 | 27.949 | 1.00 | 34.17 |
| ATOM | 1785 | CB  | CYS | 243 | 13.470 | 21.795 | 27.949 | 1.00 | 37.75 |
| ATOM | 1786 | SG  | CYS | 243 | 14.547 | 22.600 | 29.193 | 1.00 | 41.04 |
| ATOM | 1787 | N   | ASN | 244 | 11.465 | 21.029 | 26.301 | 1.00 | 32.89 |
| ATOM | 1788 | CA  | ASN | 244 | 10.493 | 20.637 | 25.280 | 1.00 | 32.64 |
| ATOM | 1789 | CB  | ASN | 244 | 11.122 | 20.572 | 23.886 | 1.00 | 32.57 |
| ATOM | 1790 | CG  | ASN | 244 | 10.185 | 19.952 | 22.854 | 1.00 | 30.96 |
| ATOM | 1791 | OD1 | ASN | 244 | 10.293 | 18.757 | 22.521 | 1.00 | 27.02 |
| ATOM | 1792 | ND2 | ASN | 244 | 9.245  | 20.759 | 22.352 | 1.00 | 27.59 |
| ATOM | 1793 | C   | ASN | 244 | 9.911  | 19.277 | 25.623 | 1.00 | 34.40 |
| ATOM | 1794 | O   | ASN | 244 | 8.724  | 19.175 | 25.935 | 1.00 | 36.59 |
| ATOM | 1795 | N   | GLY | 245 | 10.741 | 18.235 | 25.548 | 1.00 | 33.08 |
| ATOM | 1796 | CA  | GLY | 245 | 10.274 | 16.910 | 25.907 | 1.00 | 30.30 |
| ATOM | 1797 | C   | GLY | 245 | 9.784  | 17.150 | 27.307 | 1.00 | 30.36 |
| ATOM | 1798 | O   | GLY | 245 | 10.491 | 17.757 | 28.110 | 1.00 | 32.61 |
| ATOM | 1799 | N   | GLY | 246 | 8.584  | 16.696 | 27.616 | 1.00 | 29.59 |
| ATOM | 1800 | CA  | GLY | 246 | 8.062  | 16.949 | 28.942 | 1.00 | 29.91 |
| ATOM | 1801 | C   | GLY | 246 | 6.897  | 17.915 | 28.813 | 1.00 | 30.92 |
| ATOM | 1802 | O   | GLY | 246 | 6.141  | 18.122 | 29.771 | 1.00 | 28.51 |
| ATOM | 1803 | N   | THR | 247 | 6.751  | 18.512 | 27.626 | 1.00 | 31.78 |
| ATOM | 1804 | CA  | THR | 247 | 5.646  | 19.431 | 27.364 | 1.00 | 32.55 |
| ATOM | 1805 | CB  | THR | 247 | 6.039  | 20.521 | 26.378 | 1.00 | 29.13 |
| ATOM | 1806 | OG1 | THR | 247 | 6.538  | 19.917 | 25.181 | 1.00 | 34.76 |
| ATOM | 1807 | CG2 | THR | 247 | 7.099  | 21.402 | 26.966 | 1.00 | 28.24 |
| ATOM | 1808 | C   | THR | 247 | 4.496  | 18.637 | 26.748 | 1.00 | 35.15 |
| ATOM | 1809 | O   | THR | 247 | 4.673  | 17.468 | 26.373 | 1.00 | 32.84 |
| ATOM | 1810 | N   | LEU | 248 | 3.329  | 19.273 | 26.629 | 1.00 | 37.01 |
| ATOM | 1811 | CA  | LEU | 248 | 2.164  | 18.600 | 26.070 | 1.00 | 36.63 |
| ATOM | 1812 | CB  | LEU | 248 | 1.197  | 18.251 | 27.191 | 1.00 | 31.69 |
| ATOM | 1813 | CG  | LEU | 248 | 1.729  | 17.092 | 28.023 | 1.00 | 30.56 |
| ATOM | 1814 | CD1 | LEU | 248 | 0.903  | 16.929 | 29.279 | 1.00 | 27.80 |
| ATOM | 1815 | CD2 | LEU | 248 | 1.715  | 15.829 | 27.176 | 1.00 | 26.69 |
| ATOM | 1816 | C   | LEU | 248 | 1.433  | 19.380 | 24.990 | 1.00 | 37.81 |
| ATOM | 1817 | O   | LEU | 248 | 1.881  | 20.452 | 24.550 | 1.00 | 38.54 |
| ATOM | 1818 | N   | GLY | 249 | 0.314  | 18.818 | 24.541 | 1.00 | 38.01 |
| ATOM | 1819 | CA  | GLY | 249 | −0.462 | 19.488 | 23.520 | 1.00 | 39.37 |
| ATOM | 1820 | C   | GLY | 249 | −0.059 | 19.107 | 22.106 | 1.00 | 38.76 |
| ATOM | 1821 | O   | GLY | 249 | 0.797  | 18.238 | 21.873 | 1.00 | 37.04 |
| ATOM | 1822 | N   | LEU | 250 | −0.679 | 19.795 | 21.159 | 1.00 | 38.22 |
| ATOM | 1823 | CA  | LEU | 250 | −0.458 | 19.553 | 19.755 | 1.00 | 38.05 |
| ATOM | 1824 | CB  | LEU | 250 | −1.698 | 18.844 | 19.208 | 1.00 | 35.50 |
| ATOM | 1825 | CG  | LEU | 250 | −1.516 | 17.814 | 18.109 | 1.00 | 33.40 |
| ATOM | 1826 | CD1 | LEU | 250 | −2.861 | 17.207 | 17.780 | 1.00 | 36.98 |
| ATOM | 1827 | CD2 | LEU | 250 | −0.908 | 18.472 | 16.897 | 1.00 | 34.84 |
| ATOM | 1828 | C   | LEU | 250 | −0.265 | 20.916 | 19.091 | 1.00 | 36.02 |
| ATOM | 1829 | O   | LEU | 250 | −0.939 | 21.238 | 18.099 | 1.00 | 36.86 |
| ATOM | 1830 | N   | ASP | 251 | 0.667  | 21.703 | 19.629 | 1.00 | 34.80 |
| ATOM | 1831 | CA  | ASP | 251 | 0.918  | 23.027 | 19.088 | 1.00 | 33.81 |
| ATOM | 1832 | CB  | ASP | 251 | 1.550  | 23.921 | 20.160 | 1.00 | 31.99 |
| ATOM | 1833 | CG  | ASP | 251 | 1.572  | 25.398 | 19.764 | 1.00 | 33.18 |
| ATOM | 1834 | OD1 | ASP | 251 | 2.033  | 26.236 | 20.581 | 1.00 | 31.63 |
| ATOM | 1835 | OD2 | ASP | 251 | 1.131  | 25.724 | 18.638 | 1.00 | 35.47 |
| ATOM | 1836 | C   | ASP | 251 | 1.804  | 22.963 | 17.847 | 1.00 | 33.35 |
| ATOM | 1837 | O   | ASP | 251 | 2.873  | 23.571 | 17.806 | 1.00 | 36.22 |
| ATOM | 1838 | N   | ILE | 252 | 1.336  | 22.233 | 16.836 | 1.00 | 32.44 |
| ATOM | 1839 | CA  | ILE | 252 | 2.057  | 22.086 | 15.582 | 1.00 | 32.27 |
| ATOM | 1840 | CB  | ILE | 252 | 1.186  | 21.361 | 14.523 | 1.00 | 33.71 |

APPENDIX 1-continued

Coordinates in Protein Data Bank (PDB) format of GZEL.

| ATOM | 1841 | CG2 | ILE | 252 | 1.772 | 21.563 | 13.132 | 1.00 | 33.09 |
|---|---|---|---|---|---|---|---|---|---|
| ATOM | 1842 | CG1 | ILE | 252 | 1.076 | 19.862 | 14.853 | 1.00 | 35.60 |
| ATOM | 1843 | CD1 | ILE | 252 | 0.206 | 19.058 | 13.909 | 1.00 | 35.69 |
| ATOM | 1844 | C | ILE | 252 | 2.481 | 23.443 | 15.028 | 1.00 | 33.10 |
| ATOM | 1845 | O | ILE | 252 | 3.450 | 23.533 | 14.270 | 1.00 | 36.41 |
| ATOM | 1846 | N | ASP | 253 | 1.762 | 24.496 | 15.402 | 1.00 | 33.30 |
| ATOM | 1847 | CA | ASP | 253 | 2.099 | 25.833 | 14.936 | 1.00 | 31.11 |
| ATOM | 1848 | CB | ASP | 253 | 1.158 | 26.854 | 15.557 | 1.00 | 30.03 |
| ATOM | 1849 | CG | ASP | 253 | 0.521 | 27.751 | 14.520 | 1.00 | 34.22 |
| ATOM | 1850 | OD1 | ASP | 253 | −0.079 | 28.786 | 14.894 | 1.00 | 36.89 |
| ATOM | 1851 | OD2 | ASP | 253 | 0.619 | 27.415 | 13.320 | 1.00 | 37.40 |
| ATOM | 1852 | C | ASP | 253 | 3.528 | 26.169 | 15.348 | 1.00 | 29.66 |
| ATOM | 1853 | O | ASP | 253 | 4.332 | 26.690 | 14.566 | 1.00 | 28.81 |
| ATOM | 1854 | N | ALA | 254 | 3.817 | 25.855 | 16.603 | 1.00 | 26.55 |
| ATOM | 1855 | CA | ALA | 254 | 5.115 | 26.091 | 17.184 | 1.00 | 25.62 |
| ATOM | 1856 | CB | ALA | 254 | 5.140 | 25.564 | 18.598 | 1.00 | 20.85 |
| ATOM | 1857 | C | ALA | 254 | 6.196 | 25.405 | 16.345 | 1.00 | 29.11 |
| ATOM | 1858 | O | ALA | 254 | 7.213 | 26.018 | 15.997 | 1.00 | 31.34 |
| ATOM | 1859 | N | HIS | 255 | 5.986 | 24.137 | 16.013 | 1.00 | 27.36 |
| ATOM | 1860 | CA | HIS | 255 | 6.973 | 23.410 | 15.231 | 1.00 | 26.27 |
| ATOM | 1861 | CB | HIS | 255 | 6.428 | 22.033 | 14.880 | 1.00 | 24.83 |
| ATOM | 1862 | CG | HIS | 255 | 7.341 | 21.223 | 14.017 | 1.00 | 24.24 |
| ATOM | 1863 | CD2 | HIS | 255 | 7.154 | 20.674 | 12.790 | 1.00 | 23.27 |
| ATOM | 1864 | ND1 | HIS | 255 | 8.627 | 20.897 | 14.390 | 1.00 | 24.00 |
| ATOM | 1865 | CE1 | HIS | 255 | 9.193 | 20.185 | 13.431 | 1.00 | 21.55 |
| ATOM | 1866 | NE2 | HIS | 255 | 8.322 | 20.035 | 12.449 | 1.00 | 17.44 |
| ATOM | 1867 | C | HIS | 255 | 7.255 | 24.204 | 13.962 | 1.00 | 28.52 |
| ATOM | 1868 | O | HIS | 255 | 8.409 | 24.258 | 13.494 | 1.00 | 28.00 |
| ATOM | 1869 | N | LEU | 256 | 6.199 | 24.835 | 13.435 | 1.00 | 28.61 |
| ATOM | 1870 | CA | LEU | 256 | 6.265 | 25.621 | 12.207 | 1.00 | 28.55 |
| ATOM | 1871 | CB | LEU | 256 | 4.896 | 25.596 | 11.554 | 1.00 | 29.17 |
| ATOM | 1872 | CG | LEU | 256 | 4.695 | 24.226 | 10.899 | 1.00 | 33.99 |
| ATOM | 1873 | CD1 | LEU | 256 | 3.236 | 23.981 | 10.647 | 1.00 | 38.97 |
| ATOM | 1874 | CD2 | LEU | 256 | 5.494 | 24.144 | 9.599 | 1.00 | 35.28 |
| ATOM | 1875 | C | LEU | 256 | 6.749 | 27.045 | 12.359 | 1.00 | 29.39 |
| ATOM | 1876 | O | LEU | 256 | 6.735 | 27.824 | 11.410 | 1.00 | 31.07 |
| ATOM | 1877 | N | HIS | 257 | 7.185 | 27.371 | 13.567 | 1.00 | 29.83 |
| ATOM | 1878 | CA | HIS | 257 | 7.673 | 28.705 | 13.884 | 1.00 | 29.56 |
| ATOM | 1879 | CB | HIS | 257 | 6.605 | 29.480 | 14.656 | 1.00 | 32.53 |
| ATOM | 1880 | CG | HIS | 257 | 5.426 | 29.866 | 13.824 | 1.00 | 33.82 |
| ATOM | 1881 | CD2 | HIS | 257 | 4.196 | 29.316 | 13.713 | 1.00 | 30.44 |
| ATOM | 1882 | ND1 | HIS | 257 | 5.454 | 30.929 | 12.945 | 1.00 | 33.02 |
| ATOM | 1883 | CE1 | HIS | 257 | 4.289 | 31.017 | 12.329 | 1.00 | 29.43 |
| ATOM | 1884 | NE2 | HIS | 257 | 3.508 | 30.048 | 12.778 | 1.00 | 28.63 |
| ATOM | 1885 | C | HIS | 257 | 8.952 | 28.740 | 14.698 | 1.00 | 28.51 |
| ATOM | 1886 | O | HIS | 257 | 8.903 | 28.655 | 15.927 | 1.00 | 29.13 |
| ATOM | 1887 | N | TYR | 258 | 10.085 | 28.896 | 14.011 | 1.00 | 27.00 |
| ATOM | 1888 | CA | TYR | 258 | 11.407 | 29.000 | 14.646 | 1.00 | 25.03 |
| ATOM | 1889 | CB | TYR | 258 | 12.267 | 27.784 | 14.273 | 1.00 | 19.74 |
| ATOM | 1890 | CG | TYR | 258 | 11.874 | 26.563 | 15.076 | 1.00 | 17.11 |
| ATOM | 1891 | CD1 | TYR | 258 | 10.716 | 25.851 | 14.768 | 1.00 | 17.80 |
| ATOM | 1892 | CE1 | TYR | 258 | 10.301 | 24.765 | 15.565 | 1.00 | 19.70 |
| ATOM | 1893 | CD2 | TYR | 258 | 12.617 | 26.158 | 16.197 | 1.00 | 15.62 |
| ATOM | 1894 | CE2 | TYR | 258 | 12.216 | 25.074 | 16.977 | 1.00 | 18.52 |
| ATOM | 1895 | CZ | TYR | 258 | 11.060 | 24.380 | 16.660 | 1.00 | 21.26 |
| ATOM | 1896 | OH | TYR | 258 | 10.683 | 23.269 | 17.405 | 1.00 | 21.26 |
| ATOM | 1897 | C | TYR | 258 | 12.117 | 30.332 | 14.287 | 1.00 | 25.34 |
| ATOM | 1898 | O | TYR | 258 | 12.913 | 30.416 | 13.329 | 1.00 | 23.81 |
| ATOM | 1899 | N | PHE | 259 | 11.800 | 31.373 | 15.063 | 1.00 | 27.51 |
| ATOM | 1900 | CA | PHE | 259 | 12.347 | 32.716 | 14.846 | 1.00 | 30.42 |
| ATOM | 1901 | CB | PHE | 259 | 13.842 | 32.655 | 14.522 | 1.00 | 26.75 |
| ATOM | 1902 | CG | PHE | 259 | 14.682 | 32.157 | 15.645 | 1.00 | 27.90 |
| ATOM | 1903 | CD1 | PHE | 259 | 14.429 | 32.559 | 16.958 | 1.00 | 30.40 |
| ATOM | 1904 | CD2 | PHE | 259 | 15.769 | 31.325 | 15.401 | 1.00 | 29.77 |
| ATOM | 1905 | CE1 | PHE | 259 | 15.247 | 32.145 | 18.006 | 1.00 | 31.66 |
| ATOM | 1906 | CE2 | PHE | 259 | 16.604 | 30.904 | 16.472 | 1.00 | 25.94 |
| ATOM | 1907 | CZ | PHE | 259 | 16.335 | 31.317 | 17.760 | 1.00 | 27.26 |
| ATOM | 1908 | C | PHE | 259 | 11.610 | 33.315 | 13.658 | 1.00 | 32.76 |
| ATOM | 1909 | O | PHE | 259 | 11.661 | 34.518 | 13.400 | 1.00 | 35.13 |
| ATOM | 1910 | N | GLN | 260 | 10.913 | 32.462 | 12.932 | 1.00 | 31.61 |
| ATOM | 1911 | CA | GLN | 260 | 10.214 | 32.941 | 11.782 | 1.00 | 31.13 |
| ATOM | 1912 | CB | GLN | 260 | 11.229 | 33.310 | 10.703 | 1.00 | 27.17 |
| ATOM | 1913 | CG | GLN | 260 | 11.710 | 32.116 | 9.873 | 1.00 | 25.63 |
| ATOM | 1914 | CD | GLN | 260 | 12.849 | 32.468 | 8.940 | 1.00 | 26.16 |
| ATOM | 1915 | OE1 | GLN | 260 | 13.064 | 31.793 | 7.937 | 1.00 | 27.34 |
| ATOM | 1916 | NE2 | GLN | 260 | 13.598 | 33.520 | 9.275 | 1.00 | 31.37 |
| ATOM | 1917 | C | GLN | 260 | 9.352 | 31.798 | 11.323 | 1.00 | 34.49 |
| ATOM | 1918 | O | GLN | 260 | 9.301 | 30.750 | 11.950 | 1.00 | 35.38 |

APPENDIX 1-continued

Coordinates in Protein Data Bank (PDB) format of GZEL.

| | | | | | | | | |
|---|---|---|---|---|---|---|---|---|
| ATOM | 1919 | N | ALA | 261 | 8.657 | 32.008 | 10.218 | 1.00 | 36.41 |
| ATOM | 1920 | CA | ALA | 261 | 7.805 | 30.973 | 9.660 | 1.00 | 37.19 |
| ATOM | 1921 | CB | ALA | 261 | 6.737 | 31.591 | 8.766 | 1.00 | 34.82 |
| ATOM | 1922 | C | ALA | 261 | 8.657 | 29.993 | 8.852 | 1.00 | 40.12 |
| ATOM | 1923 | O | ALA | 261 | 9.423 | 30.386 | 7.961 | 1.00 | 37.41 |
| ATOM | 1924 | N | THR | 262 | 8.526 | 28.717 | 9.194 | 1.00 | 43.36 |
| ATOM | 1925 | CA | THR | 262 | 9.231 | 27.613 | 8.539 | 1.00 | 44.18 |
| ATOM | 1926 | CB | THR | 262 | 8.924 | 26.319 | 9.285 | 1.00 | 43.35 |
| ATOM | 1927 | OG1 | THR | 262 | 9.612 | 26.303 | 10.537 | 1.00 | 44.23 |
| ATOM | 1928 | CG2 | THR | 262 | 9.289 | 25.118 | 8.449 | 1.00 | 42.27 |
| ATOM | 1929 | C | THR | 262 | 8.739 | 27.416 | 7.097 | 1.00 | 46.97 |
| ATOM | 1930 | O | THR | 262 | 9.505 | 27.391 | 6.130 | 1.00 | 44.95 |
| ATOM | 1931 | N | ASP | 263 | 7.425 | 27.248 | 7.013 | 1.00 | 49.53 |
| ATOM | 1932 | CA | ASP | 263 | 6.660 | 27.035 | 5.798 | 1.00 | 48.98 |
| ATOM | 1933 | CB | ASP | 263 | 5.238 | 26.685 | 6.223 | 1.00 | 47.39 |
| ATOM | 1934 | CG | ASP | 263 | 4.644 | 27.730 | 7.170 | 1.00 | 50.68 |
| ATOM | 1935 | OD1 | ASP | 263 | 5.279 | 28.036 | 8.199 | 1.00 | 51.25 |
| ATOM | 1936 | OD2 | ASP | 263 | 3.542 | 28.255 | 6.887 | 1.00 | 53.12 |
| ATOM | 1937 | C | ASP | 263 | 6.635 | 28.246 | 4.847 | 1.00 | 49.91 |
| ATOM | 1938 | O | ASP | 263 | 5.878 | 28.258 | 3.876 | 1.00 | 50.87 |
| ATOM | 1939 | N | ALA | 264 | 7.464 | 29.253 | 5.107 | 1.00 | 48.36 |
| ATOM | 1940 | CA | ALA | 264 | 7.471 | 30.450 | 4.265 | 1.00 | 47.66 |
| ATOM | 1941 | CB | ALA | 264 | 8.601 | 31.406 | 4.678 | 1.00 | 46.98 |
| ATOM | 1942 | C | ALA | 264 | 7.615 | 30.083 | 2.797 | 1.00 | 48.80 |
| ATOM | 1943 | O | ALA | 264 | 6.810 | 30.519 | 1.961 | 1.00 | 46.94 |
| ATOM | 1944 | N | CYS | 265 | 8.621 | 29.261 | 2.488 | 1.00 | 52.02 |
| ATOM | 1945 | CA | CYS | 265 | 8.858 | 28.862 | 1.107 | 1.00 | 52.57 |
| ATOM | 1946 | C | CYS | 265 | 8.071 | 27.619 | 0.660 | 1.00 | 53.21 |
| ATOM | 1947 | O | CYS | 265 | 8.410 | 27.015 | −0.352 | 1.00 | 52.62 |
| ATOM | 1948 | CB | CYS | 265 | 10.356 | 28.641 | 0.894 | 1.00 | 51.98 |
| ATOM | 1949 | SG | CYS | 265 | 10.914 | 29.221 | −0.736 | 1.00 | 62.77 |
| ATOM | 1950 | N | SER | 266 | 7.016 | 27.256 | 1.397 | 1.00 | 55.18 |
| ATOM | 1951 | CA | SER | 266 | 6.186 | 26.076 | 1.094 | 1.00 | 55.25 |
| ATOM | 1952 | CB | SER | 266 | 5.315 | 26.296 | −0.163 | 1.00 | 55.01 |
| ATOM | 1953 | OG | SER | 266 | 6.059 | 26.313 | −1.376 | 1.00 | 53.51 |
| ATOM | 1954 | C | SER | 266 | 7.013 | 24.807 | 0.920 | 1.00 | 57.82 |
| ATOM | 1955 | O | SER | 266 | 6.771 | 23.800 | 1.592 | 1.00 | 58.50 |
| ATOM | 1956 | N | THR | 288 | −5.104 | 10.709 | 9.431 | 1.00 | 69.17 |
| ATOM | 1957 | CA | THR | 288 | −6.163 | 9.702 | 9.336 | 1.00 | 68.04 |
| ATOM | 1958 | CB | THR | 288 | −5.575 | 8.326 | 8.904 | 1.00 | 69.10 |
| ATOM | 1959 | OG1 | THR | 288 | −4.241 | 8.190 | 9.427 | 1.00 | 71.00 |
| ATOM | 1960 | CG2 | THR | 288 | −5.550 | 8.209 | 7.381 | 1.00 | 66.83 |
| ATOM | 1961 | C | THR | 288 | −6.897 | 9.563 | 10.669 | 1.00 | 66.62 |
| ATOM | 1962 | O | THR | 288 | −7.678 | 8.635 | 10.867 | 1.00 | 67.87 |
| ATOM | 1963 | N | MET | 289 | −6.637 | 10.504 | 11.573 | 1.00 | 63.79 |
| ATOM | 1964 | CA | MET | 289 | −7.267 | 10.517 | 12.887 | 1.00 | 59.84 |
| ATOM | 1965 | CB | MET | 289 | −6.376 | 9.822 | 13.911 | 1.00 | 60.37 |
| ATOM | 1966 | CG | MET | 289 | −5.070 | 10.549 | 14.185 | 1.00 | 58.53 |
| ATOM | 1967 | SD | MET | 289 | −4.097 | 9.750 | 15.488 | 1.00 | 55.89 |
| ATOM | 1968 | CE | MET | 289 | −3.213 | 8.434 | 14.513 | 1.00 | 53.56 |
| ATOM | 1969 | C | MET | 289 | −7.504 | 11.958 | 13.308 | 1.00 | 56.91 |
| ATOM | 1970 | O | MET | 289 | −6.766 | 12.851 | 12.911 | 1.00 | 56.23 |
| ATOM | 1971 | N | THR | 290 | −8.523 | 12.178 | 14.128 | 1.00 | 55.14 |
| ATOM | 1972 | CA | THR | 290 | −8.862 | 13.526 | 14.563 | 1.00 | 55.59 |
| ATOM | 1973 | CB | THR | 290 | −10.041 | 13.530 | 15.540 | 1.00 | 55.73 |
| ATOM | 1974 | OG1 | THR | 290 | −9.587 | 13.157 | 16.847 | 1.00 | 56.69 |
| ATOM | 1975 | CG2 | THR | 290 | −11.103 | 12.551 | 15.081 | 1.00 | 57.65 |
| ATOM | 1976 | C | THR | 290 | −7.722 | 14.275 | 15.228 | 1.00 | 55.10 |
| ATOM | 1977 | O | THR | 290 | −6.549 | 13.938 | 15.071 | 1.00 | 57.70 |
| ATOM | 1978 | N | ASP | 291 | −8.086 | 15.311 | 15.969 | 1.00 | 53.52 |
| ATOM | 1979 | CA | ASP | 291 | −7.113 | 16.122 | 16.666 | 1.00 | 53.03 |
| ATOM | 1980 | CB | ASP | 291 | −7.539 | 17.584 | 16.604 | 1.00 | 53.76 |
| ATOM | 1981 | CG | ASP | 291 | −6.579 | 18.435 | 15.798 | 1.00 | 53.50 |
| ATOM | 1982 | OD1 | ASP | 291 | −6.217 | 18.039 | 14.670 | 1.00 | 54.08 |
| ATOM | 1983 | OD2 | ASP | 291 | −6.186 | 19.509 | 16.294 | 1.00 | 53.04 |
| ATOM | 1984 | C | ASP | 291 | −7.032 | 15.648 | 18.108 | 1.00 | 53.15 |
| ATOM | 1985 | O | ASP | 291 | −5.974 | 15.205 | 18.567 | 1.00 | 50.18 |
| ATOM | 1986 | N | ALA | 292 | −8.164 | 15.732 | 18.807 | 1.00 | 54.12 |
| ATOM | 1987 | CA | ALA | 292 | −8.254 | 15.306 | 20.201 | 1.00 | 53.85 |
| ATOM | 1988 | CB | ALA | 292 | −9.705 | 15.131 | 20.603 | 1.00 | 55.19 |
| ATOM | 1989 | C | ALA | 292 | −7.540 | 13.988 | 20.293 | 1.00 | 52.42 |
| ATOM | 1990 | O | ALA | 292 | −6.840 | 13.687 | 21.244 | 1.00 | 53.42 |
| ATOM | 1991 | N | GLU | 293 | −7.749 | 13.198 | 19.264 | 1.00 | 52.24 |
| ATOM | 1992 | CA | GLU | 293 | −7.121 | 11.906 | 19.160 | 1.00 | 55.82 |
| ATOM | 1993 | CB | GLU | 293 | −7.529 | 11.259 | 17.837 | 1.00 | 59.67 |
| ATOM | 1994 | CG | GLU | 293 | −6.842 | 9.964 | 17.550 | 1.00 | 64.61 |
| ATOM | 1995 | CD | GLU | 293 | −7.295 | 8.872 | 18.483 | 1.00 | 67.82 |
| ATOM | 1996 | OE1 | GLU | 293 | −7.070 | 9.000 | 19.708 | 1.00 | 67.87 |

APPENDIX 1-continued

Coordinates in Protein Data Bank (PDB) format of GZEL.

| ATOM | 1997 | OE2 | GLU | 293 | −7.883 | 7.886 | 17.987 | 1.00 | 70.08 |
|---|---|---|---|---|---|---|---|---|---|
| ATOM | 1998 | C | GLU | 293 | −5.602 | 12.064 | 19.218 | 1.00 | 54.54 |
| ATOM | 1999 | O | GLU | 293 | −4.964 | 11.753 | 20.230 | 1.00 | 52.29 |
| ATOM | 2000 | N | LEU | 294 | −5.034 | 12.569 | 18.127 | 1.00 | 52.22 |
| ATOM | 2001 | CA | LEU | 294 | −3.594 | 12.745 | 18.036 | 1.00 | 49.88 |
| ATOM | 2002 | CB | LEU | 294 | −3.213 | 13.548 | 16.782 | 1.00 | 46.75 |
| ATOM | 2003 | CG | LEU | 294 | −1.734 | 13.465 | 16.357 | 1.00 | 46.25 |
| ATOM | 2004 | CD1 | LEU | 294 | −1.411 | 12.023 | 15.956 | 1.00 | 41.73 |
| ATOM | 2005 | CD2 | LEU | 294 | −1.450 | 14.414 | 15.187 | 1.00 | 45.50 |
| ATOM | 2006 | C | LEU | 294 | −3.012 | 13.418 | 19.262 | 1.00 | 49.36 |
| ATOM | 2007 | O | LEU | 294 | −1.936 | 13.061 | 19.715 | 1.00 | 48.76 |
| ATOM | 2008 | N | GLU | 295 | −3.714 | 14.397 | 19.810 | 1.00 | 49.05 |
| ATOM | 2009 | CA | GLU | 295 | −3.183 | 15.071 | 20.981 | 1.00 | 47.81 |
| ATOM | 2010 | CB | GLU | 295 | −4.094 | 16.204 | 21.408 | 1.00 | 48.38 |
| ATOM | 2011 | CG | GLU | 295 | −3.765 | 16.655 | 22.787 | 1.00 | 50.22 |
| ATOM | 2012 | CD | GLU | 295 | −4.643 | 17.782 | 23.219 | 1.00 | 52.29 |
| ATOM | 2013 | OE1 | GLU | 295 | −4.536 | 18.869 | 22.617 | 1.00 | 54.49 |
| ATOM | 2014 | OE2 | GLU | 295 | −5.450 | 17.580 | 24.154 | 1.00 | 52.86 |
| ATOM | 2015 | C | GLU | 295 | −3.055 | 14.084 | 22.126 | 1.00 | 46.68 |
| ATOM | 2016 | O | GLU | 295 | −2.019 | 14.009 | 22.801 | 1.00 | 45.14 |
| ATOM | 2017 | N | LYS | 296 | −4.129 | 13.341 | 22.352 | 1.00 | 45.98 |
| ATOM | 2018 | CA | LYS | 296 | −4.123 | 12.365 | 23.405 | 1.00 | 47.29 |
| ATOM | 2019 | CB | LYS | 296 | −5.454 | 11.633 | 23.432 | 1.00 | 47.12 |
| ATOM | 2020 | CG | LYS | 296 | −6.558 | 12.517 | 23.981 | 1.00 | 47.16 |
| ATOM | 2021 | CD | LYS | 296 | −7.900 | 11.809 | 24.010 | 1.00 | 50.91 |
| ATOM | 2022 | CE | LYS | 296 | −8.985 | 12.717 | 24.580 | 1.00 | 49.77 |
| ATOM | 2023 | NZ | LYS | 296 | −10.319 | 12.055 | 24.645 | 1.00 | 50.40 |
| ATOM | 2024 | C | LYS | 296 | −2.963 | 11.411 | 23.204 | 1.00 | 45.67 |
| ATOM | 2025 | O | LYS | 296 | −2.025 | 11.405 | 24.001 | 1.00 | 45.50 |
| ATOM | 2026 | N | LYS | 297 | −3.007 | 10.620 | 22.141 | 1.00 | 45.96 |
| ATOM | 2027 | CA | LYS | 297 | −1.927 | 9.678 | 21.894 | 1.00 | 46.33 |
| ATOM | 2028 | CB | LYS | 297 | −1.922 | 9.248 | 20.447 | 1.00 | 45.64 |
| ATOM | 2029 | CG | LYS | 297 | −3.017 | 8.264 | 20.143 | 1.00 | 49.76 |
| ATOM | 2030 | CD | LYS | 297 | −3.095 | 7.965 | 18.652 | 1.00 | 52.12 |
| ATOM | 2031 | CE | LYS | 297 | −4.241 | 7.000 | 18.307 | 1.00 | 53.58 |
| ATOM | 2032 | NZ | LYS | 297 | −4.433 | 6.842 | 16.829 | 1.00 | 55.41 |
| ATOM | 2033 | C | LYS | 297 | −0.578 | 10.252 | 22.236 | 1.00 | 45.70 |
| ATOM | 2034 | O | LYS | 297 | 0.164 | 9.692 | 23.040 | 1.00 | 45.62 |
| ATOM | 2035 | N | LEU | 298 | −0.275 | 11.392 | 21.639 | 1.00 | 43.91 |
| ATOM | 2036 | CA | LEU | 298 | 0.997 | 12.035 | 21.873 | 1.00 | 43.35 |
| ATOM | 2037 | CB | LEU | 298 | 1.104 | 13.280 | 21.030 | 1.00 | 42.24 |
| ATOM | 2038 | CG | LEU | 298 | 1.281 | 12.939 | 19.560 | 1.00 | 42.32 |
| ATOM | 2039 | CD1 | LEU | 298 | 1.715 | 14.203 | 18.864 | 1.00 | 40.59 |
| ATOM | 2040 | CD2 | LEU | 298 | 2.330 | 11.824 | 19.372 | 1.00 | 39.55 |
| ATOM | 2041 | C | LEU | 298 | 1.257 | 12.381 | 23.307 | 1.00 | 43.14 |
| ATOM | 2042 | O | LEU | 298 | 2.360 | 12.228 | 23.806 | 1.00 | 43.84 |
| ATOM | 2043 | N | ASN | 299 | 0.231 | 12.869 | 23.970 | 1.00 | 42.30 |
| ATOM | 2044 | CA | ASN | 299 | 0.369 | 13.215 | 25.367 | 1.00 | 40.09 |
| ATOM | 2045 | CB | ASN | 299 | −0.987 | 13.640 | 25.937 | 1.00 | 39.75 |
| ATOM | 2046 | CG | ASN | 299 | −1.236 | 15.126 | 25.817 | 1.00 | 39.45 |
| ATOM | 2047 | OD1 | ASN | 299 | −0.602 | 15.841 | 25.020 | 1.00 | 36.52 |
| ATOM | 2048 | ND2 | ASN | 299 | −2.182 | 15.604 | 26.610 | 1.00 | 39.54 |
| ATOM | 2049 | C | ASN | 299 | 0.845 | 11.952 | 26.061 | 1.00 | 39.47 |
| ATOM | 2050 | O | ASN | 299 | 1.896 | 11.917 | 26.688 | 1.00 | 39.95 |
| ATOM | 2051 | N | SER | 300 | 0.030 | 10.915 | 25.909 | 1.00 | 36.98 |
| ATOM | 2052 | CA | SER | 300 | 0.255 | 9.596 | 26.477 | 1.00 | 32.52 |
| ATOM | 2053 | CB | SER | 300 | −0.477 | 8.546 | 25.651 | 1.00 | 32.63 |
| ATOM | 2054 | OG | SER | 300 | 0.327 | 7.392 | 25.490 | 1.00 | 40.74 |
| ATOM | 2055 | C | SER | 300 | 1.725 | 9.242 | 26.529 | 1.00 | 31.83 |
| ATOM | 2056 | O | SER | 300 | 2.242 | 8.833 | 27.582 | 1.00 | 26.37 |
| ATOM | 2057 | N | TYR | 301 | 2.382 | 9.392 | 25.381 | 1.00 | 32.44 |
| ATOM | 2058 | CA | TYR | 301 | 3.793 | 9.096 | 25.255 | 1.00 | 33.17 |
| ATOM | 2059 | CB | TYR | 301 | 4.245 | 9.455 | 23.850 | 1.00 | 31.08 |
| ATOM | 2060 | CG | TYR | 301 | 3.738 | 8.476 | 22.832 | 1.00 | 31.92 |
| ATOM | 2061 | CD1 | TYR | 301 | 3.218 | 8.903 | 21.611 | 1.00 | 34.78 |
| ATOM | 2062 | CE1 | TYR | 301 | 2.692 | 7.981 | 20.684 | 1.00 | 35.21 |
| ATOM | 2063 | CD2 | TYR | 301 | 3.737 | 7.109 | 23.108 | 1.00 | 32.63 |
| ATOM | 2064 | CE2 | TYR | 301 | 3.220 | 6.183 | 22.202 | 1.00 | 33.64 |
| ATOM | 2065 | CZ | TYR | 301 | 2.693 | 6.625 | 20.993 | 1.00 | 36.58 |
| ATOM | 2066 | OH | TYR | 301 | 2.122 | 5.720 | 20.122 | 1.00 | 42.92 |
| ATOM | 2067 | C | TYR | 301 | 4.650 | 9.814 | 26.289 | 1.00 | 33.19 |
| ATOM | 2068 | O | TYR | 301 | 5.382 | 9.169 | 27.062 | 1.00 | 33.66 |
| ATOM | 2069 | N | VAL | 302 | 4.551 | 11.146 | 26.291 | 1.00 | 31.53 |
| ATOM | 2070 | CA | VAL | 302 | 5.309 | 11.986 | 27.207 | 1.00 | 31.88 |
| ATOM | 2071 | CB | VAL | 302 | 5.184 | 13.516 | 26.830 | 1.00 | 30.64 |
| ATOM | 2072 | CG1 | VAL | 302 | 3.806 | 13.804 | 26.245 | 1.00 | 34.62 |
| ATOM | 2073 | CG2 | VAL | 302 | 5.425 | 14.390 | 28.033 | 1.00 | 28.18 |
| ATOM | 2074 | C | VAL | 302 | 4.872 | 11.714 | 28.638 | 1.00 | 34.16 |

APPENDIX 1-continued

Coordinates in Protein Data Bank (PDB) format of GZEL.

| | | | | | | | | | |
|---|---|---|---|---|---|---|---|---|---|
| ATOM | 2075 | O | VAL | 302 | 5.579 | 12.060 | 29.582 | 1.00 | 35.35 |
| ATOM | 2076 | N | GLU | 303 | 3.725 | 11.075 | 28.822 | 1.00 | 37.44 |
| ATOM | 2077 | CA | GLU | 303 | 3.322 | 10.774 | 30.182 | 1.00 | 38.93 |
| ATOM | 2078 | CB | GLU | 303 | 1.814 | 10.559 | 30.249 | 1.00 | 41.44 |
| ATOM | 2079 | CG | GLU | 303 | 1.131 | 11.315 | 31.410 | 1.00 | 48.53 |
| ATOM | 2080 | CD | GLU | 303 | 1.164 | 12.848 | 31.252 | 1.00 | 53.98 |
| ATOM | 2081 | OE1 | GLU | 303 | 0.499 | 13.392 | 30.337 | 1.00 | 55.14 |
| ATOM | 2082 | OE2 | GLU | 303 | 1.861 | 13.520 | 32.046 | 1.00 | 56.20 |
| ATOM | 2083 | C | GLU | 303 | 4.094 | 9.512 | 30.572 | 1.00 | 38.83 |
| ATOM | 2084 | O | GLU | 303 | 4.418 | 9.294 | 31.745 | 1.00 | 41.64 |
| ATOM | 2085 | N | MET | 304 | 4.405 | 8.693 | 29.570 | 1.00 | 37.27 |
| ATOM | 2086 | CA | MET | 304 | 5.155 | 7.467 | 29.801 | 1.00 | 35.94 |
| ATOM | 2087 | CB | MET | 304 | 4.953 | 6.478 | 28.650 | 1.00 | 31.52 |
| ATOM | 2088 | CG | MET | 304 | 3.579 | 5.858 | 28.595 | 1.00 | 31.49 |
| ATOM | 2089 | SD | MET | 304 | 3.184 | 4.590 | 29.827 | 1.00 | 28.57 |
| ATOM | 2090 | CE | MET | 304 | 2.746 | 5.557 | 31.251 | 1.00 | 29.07 |
| ATOM | 2091 | C | MET | 304 | 6.632 | 7.809 | 29.934 | 1.00 | 37.54 |
| ATOM | 2092 | O | MET | 304 | 7.336 | 7.256 | 30.778 | 1.00 | 37.89 |
| ATOM | 2093 | N | ASP | 305 | 7.099 | 8.729 | 29.098 | 1.00 | 36.62 |
| ATOM | 2094 | CA | ASP | 305 | 8.494 | 9.138 | 29.142 | 1.00 | 36.97 |
| ATOM | 2095 | CB | ASP | 305 | 8.789 | 10.139 | 28.020 | 1.00 | 35.93 |
| ATOM | 2096 | CG | ASP | 305 | 8.797 | 9.478 | 26.641 | 1.00 | 35.21 |
| ATOM | 2097 | OD1 | ASP | 305 | 9.366 | 8.364 | 26.550 | 1.00 | 26.08 |
| ATOM | 2098 | OD2 | ASP | 305 | 8.256 | 10.063 | 25.663 | 1.00 | 35.03 |
| ATOM | 2099 | C | ASP | 305 | 8.830 | 9.727 | 30.507 | 1.00 | 36.38 |
| ATOM | 2100 | O | ASP | 305 | 9.907 | 9.521 | 31.037 | 1.00 | 36.84 |
| ATOM | 2101 | N | LYS | 306 | 7.878 | 10.407 | 31.112 | 1.00 | 34.64 |
| ATOM | 2102 | CA | LYS | 306 | 8.121 | 10.992 | 32.416 | 1.00 | 35.44 |
| ATOM | 2103 | CB | LYS | 306 | 7.036 | 12.016 | 32.739 | 1.00 | 34.65 |
| ATOM | 2104 | CG | LYS | 306 | 7.286 | 13.335 | 32.039 | 1.00 | 35.30 |
| ATOM | 2105 | CD | LYS | 306 | 6.029 | 14.155 | 31.857 | 1.00 | 42.10 |
| ATOM | 2106 | CE | LYS | 306 | 5.507 | 14.747 | 33.147 | 1.00 | 45.04 |
| ATOM | 2107 | NZ | LYS | 306 | 4.285 | 15.551 | 32.855 | 1.00 | 48.24 |
| ATOM | 2108 | C | LYS | 306 | 8.178 | 9.927 | 33.488 | 1.00 | 35.92 |
| ATOM | 2109 | O | LYS | 306 | 9.026 | 9.975 | 34.392 | 1.00 | 34.83 |
| ATOM | 2110 | N | GLU | 307 | 7.281 | 8.955 | 33.369 | 1.00 | 38.05 |
| ATOM | 2111 | CA | GLU | 307 | 7.209 | 7.871 | 34.334 | 1.00 | 41.32 |
| ATOM | 2112 | CB | GLU | 307 | 6.007 | 6.986 | 34.035 | 1.00 | 41.96 |
| ATOM | 2113 | CG | GLU | 307 | 5.559 | 6.166 | 35.230 | 1.00 | 44.27 |
| ATOM | 2114 | CD | GLU | 307 | 4.739 | 4.938 | 34.841 | 1.00 | 44.72 |
| ATOM | 2115 | OE1 | GLU | 307 | 3.890 | 5.025 | 33.925 | 1.00 | 42.09 |
| ATOM | 2116 | OE2 | GLU | 307 | 4.938 | 3.876 | 35.470 | 1.00 | 46.86 |
| ATOM | 2117 | C | GLU | 307 | 8.478 | 7.042 | 34.251 | 1.00 | 40.66 |
| ATOM | 2118 | O | GLU | 307 | 8.914 | 6.445 | 35.227 | 1.00 | 39.62 |
| ATOM | 2119 | N | TYR | 308 | 9.040 | 6.993 | 33.050 | 1.00 | 39.89 |
| ATOM | 2120 | CA | TYR | 308 | 10.271 | 6.265 | 32.795 | 1.00 | 38.66 |
| ATOM | 2121 | CB | TYR | 308 | 10.647 | 6.328 | 31.306 | 1.00 | 38.72 |
| ATOM | 2122 | CG | TYR | 308 | 11.998 | 5.698 | 30.995 | 1.00 | 35.82 |
| ATOM | 2123 | CD1 | TYR | 308 | 12.092 | 4.412 | 30.447 | 1.00 | 34.01 |
| ATOM | 2124 | CE1 | TYR | 308 | 13.326 | 3.802 | 30.244 | 1.00 | 33.27 |
| ATOM | 2125 | CD2 | TYR | 308 | 13.186 | 6.354 | 31.323 | 1.00 | 35.59 |
| ATOM | 2126 | CE2 | TYR | 308 | 14.430 | 5.744 | 31.126 | 1.00 | 35.52 |
| ATOM | 2127 | CZ | TYR | 308 | 14.494 | 4.468 | 30.592 | 1.00 | 35.24 |
| ATOM | 2128 | OH | TYR | 308 | 15.722 | 3.846 | 30.457 | 1.00 | 32.71 |
| ATOM | 2129 | C | TYR | 308 | 11.344 | 6.968 | 33.597 | 1.00 | 38.16 |
| ATOM | 2130 | O | TYR | 308 | 11.987 | 6.384 | 34.466 | 1.00 | 42.33 |
| ATOM | 2131 | N | ILE | 309 | 11.546 | 8.236 | 33.279 | 1.00 | 34.53 |
| ATOM | 2132 | CA | ILE | 309 | 12.539 | 9.008 | 33.978 | 1.00 | 33.96 |
| ATOM | 2133 | CB | ILE | 309 | 12.485 | 10.482 | 33.553 | 1.00 | 31.45 |
| ATOM | 2134 | CG2 | ILE | 309 | 12.843 | 11.392 | 34.737 | 1.00 | 28.90 |
| ATOM | 2135 | CG1 | ILE | 309 | 13.412 | 10.670 | 32.339 | 1.00 | 30.32 |
| ATOM | 2136 | CD1 | ILE | 309 | 13.436 | 12.066 | 31.764 | 1.00 | 34.28 |
| ATOM | 2137 | C | ILE | 309 | 12.345 | 8.877 | 35.466 | 1.00 | 35.18 |
| ATOM | 2138 | O | ILE | 309 | 13.295 | 8.668 | 36.212 | 1.00 | 33.45 |
| ATOM | 2139 | N | LYS | 310 | 11.103 | 8.981 | 35.897 | 1.00 | 38.85 |
| ATOM | 2140 | CA | LYS | 310 | 10.825 | 8.872 | 37.313 | 1.00 | 39.29 |
| ATOM | 2141 | CB | LYS | 310 | 9.323 | 8.894 | 37.541 | 1.00 | 37.16 |
| ATOM | 2142 | CG | LYS | 310 | 8.964 | 8.558 | 38.953 | 1.00 | 35.69 |
| ATOM | 2143 | CD | LYS | 310 | 7.641 | 7.848 | 38.996 | 1.00 | 38.63 |
| ATOM | 2144 | CE | LYS | 310 | 7.527 | 7.081 | 40.307 | 1.00 | 39.65 |
| ATOM | 2145 | NZ | LYS | 310 | 6.351 | 6.171 | 40.381 | 1.00 | 44.93 |
| ATOM | 2146 | C | LYS | 310 | 11.403 | 7.596 | 37.902 | 1.00 | 38.47 |
| ATOM | 2147 | O | LYS | 310 | 12.210 | 7.610 | 38.830 | 1.00 | 38.54 |
| ATOM | 2148 | N | THR | 311 | 10.972 | 6.491 | 37.330 | 1.00 | 38.54 |
| ATOM | 2149 | CA | THR | 311 | 11.370 | 5.180 | 37.784 | 1.00 | 38.10 |
| ATOM | 2150 | CB | THR | 311 | 10.551 | 4.112 | 37.056 | 1.00 | 37.44 |
| ATOM | 2151 | OG1 | THR | 311 | 10.847 | 2.832 | 37.622 | 1.00 | 42.06 |
| ATOM | 2152 | CG2 | THR | 311 | 10.868 | 4.114 | 35.559 | 1.00 | 33.19 |

APPENDIX 1-continued

Coordinates in Protein Data Bank (PDB) format of GZEL.

| ATOM | 2153 | C   | THR | 311 | 12.842 | 4.828 | 37.666 | 1.00 | 36.98 |
|------|------|-----|-----|-----|--------|-------|--------|------|-------|
| ATOM | 2154 | O   | THR | 311 | 13.253 | 3.757 | 38.093 | 1.00 | 38.27 |
| ATOM | 2155 | N   | HIS | 312 | 13.637 | 5.724 | 37.102 | 1.00 | 36.25 |
| ATOM | 2156 | CA  | HIS | 312 | 15.071 | 5.476 | 36.940 | 1.00 | 36.32 |
| ATOM | 2157 | CB  | HIS | 312 | 15.442 | 5.505 | 35.455 | 1.00 | 36.87 |
| ATOM | 2158 | CG  | HIS | 312 | 14.998 | 4.294 | 34.693 | 1.00 | 42.97 |
| ATOM | 2159 | CD2 | HIS | 312 | 13.776 | 3.730 | 34.531 | 1.00 | 46.21 |
| ATOM | 2160 | ND1 | HIS | 312 | 15.876 | 3.515 | 33.971 | 1.00 | 43.74 |
| ATOM | 2161 | CE1 | HIS | 312 | 15.217 | 2.522 | 33.396 | 1.00 | 45.94 |
| ATOM | 2162 | NE2 | HIS | 312 | 13.939 | 2.630 | 33.719 | 1.00 | 48.05 |
| ATOM | 2163 | C   | HIS | 312 | 15.893 | 6.520 | 37.693 | 1.00 | 34.17 |
| ATOM | 2164 | O   | HIS | 312 | 17.119 | 6.534 | 37.654 | 1.00 | 29.16 |
| ATOM | 2165 | N   | ALA | 313 | 15.195 | 7.398 | 38.389 | 1.00 | 34.95 |
| ATOM | 2166 | CA  | ALA | 313 | 15.841 | 8.461 | 39.137 | 1.00 | 37.67 |
| ATOM | 2167 | CB  | ALA | 313 | 14.808 | 9.133 | 40.053 | 1.00 | 33.12 |
| ATOM | 2168 | C   | ALA | 313 | 17.077 | 8.046 | 39.945 | 1.00 | 36.45 |
| ATOM | 2169 | O   | ALA | 313 | 18.137 | 8.654 | 39.811 | 1.00 | 35.64 |
| ATOM | 2170 | N   | SER | 314 | 16.935 | 7.006 | 40.763 | 1.00 | 35.30 |
| ATOM | 2171 | CA  | SER | 314 | 18.004 | 6.519 | 41.636 | 1.00 | 34.86 |
| ATOM | 2172 | CB  | SER | 314 | 17.387 | 5.751 | 42.799 | 1.00 | 32.67 |
| ATOM | 2173 | OG  | SER | 314 | 16.772 | 4.571 | 42.292 | 1.00 | 37.73 |
| ATOM | 2174 | C   | SER | 314 | 19.021 | 5.598 | 40.964 | 1.00 | 34.47 |
| ATOM | 2175 | O   | SER | 314 | 19.721 | 4.842 | 41.648 | 1.00 | 35.60 |
| ATOM | 2176 | N   | ARG | 315 | 19.110 | 5.661 | 39.643 | 1.00 | 34.13 |
| ATOM | 2177 | CA  | ARG | 315 | 20.026 | 4.801 | 38.923 | 1.00 | 33.01 |
| ATOM | 2178 | CB  | ARG | 315 | 19.315 | 4.214 | 37.709 | 1.00 | 30.87 |
| ATOM | 2179 | CG  | ARG | 315 | 18.160 | 3.289 | 38.078 | 1.00 | 33.01 |
| ATOM | 2180 | CD  | ARG | 315 | 18.596 | 1.841 | 38.115 | 1.00 | 30.79 |
| ATOM | 2181 | NE  | ARG | 315 | 18.950 | 1.363 | 36.782 | 1.00 | 27.06 |
| ATOM | 2182 | CZ  | ARG | 315 | 20.135 | 0.871 | 36.456 | 1.00 | 23.56 |
| ATOM | 2183 | NH1 | ARG | 315 | 21.079 | 0.788 | 37.372 | 1.00 | 19.72 |
| ATOM | 2184 | NH2 | ARG | 315 | 20.368 | 0.476 | 35.214 | 1.00 | 19.00 |
| ATOM | 2185 | C   | ARG | 315 | 21.316 | 5.486 | 38.508 | 1.00 | 36.88 |
| ATOM | 2186 | O   | ARG | 315 | 21.687 | 6.530 | 39.056 | 1.00 | 33.34 |
| ATOM | 2187 | N   | SER | 316 | 21.992 | 4.873 | 37.533 | 1.00 | 42.86 |
| ATOM | 2188 | CA  | SER | 316 | 23.281 | 5.337 | 36.997 | 1.00 | 44.60 |
| ATOM | 2189 | CB  | SER | 316 | 23.248 | 6.850 | 36.667 | 1.00 | 45.66 |
| ATOM | 2190 | OG  | SER | 316 | 24.311 | 7.227 | 35.802 | 1.00 | 45.23 |
| ATOM | 2191 | C   | SER | 316 | 24.329 | 5.034 | 38.070 | 1.00 | 44.35 |
| ATOM | 2192 | O   | SER | 316 | 25.091 | 4.052 | 37.885 | 1.00 | 46.99 |
| ATOM | 2193 | OXT | SER | 316 | 24.345 | 5.751 | 39.093 | 1.00 | 40.99 |

The invention claimed is:

1. An isolated peptide having phospholipase inhibitory activity, wherein the peptide has a length of at least 15 amino acids and less than 40 amino acids and the peptide is selected from the group consisting of:
   a) a peptide having at least 65% identity to residues 289-310 of SEQ ID NO: 1 or residues 154-175 of SEQ ID. NO: 10; and
   b) a peptide comprising a motif with the following amino acid sequence (SEQ ID NO: 32):

```
Met Thr Asp Xaa Xaa Leu Glu Xaa Lys Leu Asn Xaa Tyr
                5                   10

Val Xaa Xaa Asp Xaa Glu Tyr Xaa Lys
    15                  20
``` wherein Xaa at positions 4, 5, 8, 12, 15, 16, 18, and 21 are independently any amino acid.

2. The peptide of claim 1, which has at least 70% identity to residues 289-310 of SEQ ID NO: 1 or residues 154-175 of SEQ ID. NO: 10.

3. The peptide of claim 1, which has at least 75% identity to residues 289-310 of SEQ ID NO: 1 or residues 154-175 of SEQ ID. NO: 10.

4. The peptide of claim 1, which has at least 80% identity to residues 289-310 of SEQ ID NO: 1 or residues 154-175 of SEQ ID. NO: 10.

5. The peptide of claim 1, which has at least 85% identity to residues 289-310 of SEQ ID NO: 1 or residues 154-175 of SEQ ID. NO: 10.

6. The peptide of claim 1, which has at least 90% identity to residues 289-310 of SEQ ID NO: 1 or residues 154-175 of SEQ ID. NO: 10.

7. The peptide of claim 1, which has at least 95% identity to residues 289-310 of SEQ ID NO: 1 or residues 154-175 of SEQ ID. NO: 10.

8. The peptide of claim 1, which has at least 97% identity to residues 289-310 of SEQ ID NO: 1 or residues 154-175 of SEQ ID. NO: 10.

9. The peptide of claim 1, which has 100% identity to residues 289-310 of SEQ ID NO: 1 or residues 154-175 of SEQ ID. NO: 10.

10. The peptide of claim 6, which has a length of less than 35 amino acids.

11. The peptide of claim 6, which has a length of less than 30 amino acids.

12. The peptide of claim 6, which has a length of at least 20 amino acids.

13. The peptide of claim 6, which has a length of at least 25 amino acids.

14. The peptide of claim 1, having a secondary structure of an alpha helix.

15. The peptide of claim 1, which comprises the motif wherein
   Xaa at position 4 is A or E;
   Xaa at position 5 is E or Q;
   Xaa at position 8 is K or A;
   Xaa at position 12 is S or N;
   Xaa at position 15 is E, Q or A;
   Xaa at position 16 is L or M;
   Xaa at position 18 is K or Q; and/or
   Xaa at position 21 is I or V.

16. The peptide of claim 1, which comprises at least one amino acid substitution at a position corresponding to position D291; L294; E295; K297; L298; N299; Y301; D305; K306; Y308; or V309 of SEQ ID NO: 1.

17. The peptide according to claim 16, wherein the at least one amino acid substitution is selected from the group consisting of D291E; L294A; E295T,S; K297R; L298A; N299D,E; Y301W; D305A; K306R; Y308E,D; and V309I,N,Q.

18. A polypeptide comprising a lipase and the peptide of claim 1 as a C-terminal extension, wherein the polypeptide has a phospholipase activity below 50 PHLU/mg in a plate assay.

19. The polypeptide of claim 18, wherein the lipase has at least 75% identity to SEQ ID NO: 9.

20. The polypeptide of claim 18, wherein the lipase has at least 80% identity to SEQ ID NO: 9.

21. The polypeptide of claim 18, wherein the lipase has at least 85% identity to SEQ ID NO: 9.

22. The polypeptide of claim 18, wherein the lipase has at least 90% identity to SEQ ID NO: 9.

23. The polypeptide of claim 18, wherein the lipase has at least 95% identity to SEQ ID NO: 9.

* * * * *

UNITED STATES PATENT AND TRADEMARK OFFICE
CERTIFICATE OF CORRECTION

| | | |
|---|---|---|
| PATENT NO. | : 8,288,510 B2 | Page 1 of 1 |
| APPLICATION NO. | : 12/433266 | |
| DATED | : October 16, 2012 | |
| INVENTOR(S) | : de Maria et al. | |

It is certified that error appears in the above-identified patent and that said Letters Patent is hereby corrected as shown below:

On Title page Item (75) Inventors, in the first line:

Delete: "Leonardo de Naria" Insert -- Leonardo de Maria --

Signed and Sealed this
Fifteenth Day of January, 2013

David J. Kappos
*Director of the United States Patent and Trademark Office*

SEQUENCE LISTING

<160> NUMBER OF SEQ ID NOS: 32

<210> SEQ ID NO 1
<211> LENGTH: 316
<212> TYPE: PRT
<213> ORGANISM: Fusarium oxysporum

<400> SEQUENCE: 1

```
Ala Val Gly Val Thr Thr Thr Asp Phe Ser Asn Phe Lys Phe Tyr Ile
1               5                   10                  15

Gln His Gly Ala Ala Ala Tyr Cys Asn Ser Glu Ala Ala Gly Ser
            20                  25                  30

Lys Ile Thr Cys Ser Asn Asn Gly Cys Pro Thr Val Gln Gly Asn Gly
            35                  40                  45

Ala Thr Ile Val Thr Ser Phe Val Gly Ser Lys Thr Gly Ile Gly Gly
        50                  55                  60

Tyr Val Ala Thr Asp Ser Ala Arg Lys Glu Ile Val Ser Phe Arg
65                  70                  75                  80

Gly Ser Ile Asn Ile Arg Asn Trp Leu Thr Asn Leu Asp Phe Gly Gln
                85                  90                  95

Glu Asp Cys Ser Leu Val Ser Gly Cys Gly Val His Ser Gly Phe Gln
```

```
                  100                 105                 110
Arg Ala Trp Asn Glu Ile Ser Ser Gln Ala Thr Ala Ala Val Ala Ser
            115                 120                 125

Ala Arg Lys Ala Asn Pro Ser Phe Asn Val Ile Ser Thr Gly His Ser
130                 135                 140

Leu Gly Gly Ala Val Ala Val Leu Ala Ala Asn Leu Arg Val Gly
145                 150                 155                 160

Gly Thr Pro Val Asp Ile Tyr Thr Tyr Gly Ser Pro Arg Val Gly Asn
                165                 170                 175

Ala Gln Leu Ser Ala Phe Val Ser Asn Gln Ala Gly Gly Glu Tyr Arg
            180                 185                 190

Val Thr His Ala Asp Asp Pro Val Pro Arg Leu Pro Pro Leu Ile Phe
                195                 200                 205

Gly Tyr Arg His Thr Thr Pro Glu Phe Trp Leu Ser Gly Gly Gly Gly
210                 215                 220

Asp Lys Val Asp Tyr Thr Ile Ser Asp Val Lys Val Cys Glu Gly Ala
225                 230                 235                 240

Ala Asn Leu Gly Cys Asn Gly Gly Thr Leu Gly Leu Asp Ile Ala Ala
                245                 250                 255

His Leu His Tyr Phe Gln Ala Thr Asp Ala Cys Asn Ala Gly Gly Phe
            260                 265                 270

Ser Trp Arg Arg Tyr Arg Ser Ala Glu Ser Val Asp Lys Arg Ala Thr
            275                 280                 285

Met Thr Asp Ala Glu Leu Glu Lys Lys Leu Asn Ser Tyr Val Gln Met
290                 295                 300

Asp Lys Glu Tyr Val Lys Asn Asn Gln Ala Arg Ser
305                 310                 315

<210> SEQ ID NO 2
<211> LENGTH: 351
<212> TYPE: PRT
<213> ORGANISM: Fusarium graminearium

<400> SEQUENCE: 2

Met Arg Leu Leu Ser Leu Leu Ser Val Val Thr Leu Ala Val Ala Ser
1               5                   10                  15

Pro Leu Ser Val Glu Glu Tyr Ala Lys Ala Leu Asp Glu Arg Ala Val
            20                  25                  30

Ser Val Ser Thr Thr Asp Phe Gly Asn Phe Lys Phe Tyr Ile Gln His
        35                  40                  45

Gly Ala Ala Ala Tyr Cys Asn Ser Glu Ala Pro Ala Gly Ala Lys Val
    50                  55                  60

Thr Cys Ser Gly Asn Gly Cys Pro Thr Val Gln Ser Asn Gly Ala Thr
65                  70                  75                  80

Ile Val Ala Ser Phe Thr Gly Ser Lys Thr Gly Ile Gly Gly Tyr Val
                85                  90                  95

Ala Thr Asp Pro Thr Arg Lys Glu Ile Val Val Ser Phe Arg Gly Ser
            100                 105                 110

Ile Asn Ile Arg Asn Trp Leu Thr Asn Leu Asp Phe Asp Gln Asp Asp
        115                 120                 125

Cys Ser Leu Thr Ser Gly Cys Gly Val His Ser Gly Phe Gln Asn Ala
    130                 135                 140

Trp Asn Glu Ile Ser Ala Ala Thr Ala Ala Val Ala Lys Ala Arg
145                 150                 155                 160

Lys Ala Asn Pro Ser Phe Lys Val Val Ser Val Gly His Ser Leu Gly
```

```
            165                 170                 175
Gly Ala Val Ala Thr Leu Ala Gly Ala Asn Leu Arg Val Gly Gly Thr
        180                 185                 190

Pro Leu Asp Ile Tyr Thr Tyr Gly Ser Pro Arg Val Gly Asn Thr Gln
    195                 200                 205

Leu Ala Ala Phe Val Ser Asn Gln Ala Gly Gly Glu Phe Arg Val Thr
210                 215                 220

Asn Ala Lys Asp Pro Val Pro Arg Leu Pro Leu Ile Phe Gly Tyr
225                 230                 235                 240

Arg His Thr Ser Pro Glu Tyr Trp Leu Ser Gly Ser Gly Gly Asp Lys
                245                 250                 255

Ile Asp Tyr Thr Ile Asn Asp Val Lys Val Cys Glu Gly Ala Ala Asn
            260                 265                 270

Leu Gln Cys Asn Gly Gly Thr Leu Gly Leu Asp Ile Asp Ala His Leu
        275                 280                 285

His Tyr Phe Gln Ala Thr Asp Ala Cys Ser Ala Gly Gly Ile Ser Trp
    290                 295                 300

Arg Arg Tyr Arg Ser Ala Lys Arg Glu Ser Ile Ser Glu Arg Ala Thr
305                 310                 315                 320

Met Thr Asp Ala Glu Leu Glu Lys Lys Leu Asn Ser Tyr Val Glu Met
                325                 330                 335

Asp Lys Glu Tyr Ile Lys Thr His Ala Arg Pro Leu Ile Ile Val
            340                 345                 350

<210> SEQ ID NO 3
<211> LENGTH: 343
<212> TYPE: PRT
<213> ORGANISM: Nectria species

<400> SEQUENCE: 3

Met Arg Leu Leu Pro Ala Leu Ser Val Val Gly Val Ala Ser Ala Ala
1               5                   10                  15

Ser Ile Lys Ser Tyr Leu His Ala Phe Glu Glu Arg Ala Val Thr Val
            20                  25                  30

Thr Ser Gln Asn Leu Ala Asn Phe Lys Phe Tyr Val Gln His Ala Thr
        35                  40                  45

Ala Ala Tyr Cys Asn Tyr Asp Arg Ala Ala Gly Ala Leu Ile Ser Cys
    50                  55                  60

Ser Ser Asn Cys Pro Ser Ile Glu Ser Asn Ala Ala Lys Ile Val Gly
65                  70                  75                  80

Ser Phe Gly Gly Glu Asp Thr Gly Ile Ala Gly Tyr Val Ser Thr Asp
                85                  90                  95

Ala Thr Arg Lys Glu Ile Val Val Ser Ile Arg Gly Ser Ile Asn Val
            100                 105                 110

Arg Asn Trp Ile Thr Asn Leu Asp Phe Val Trp Ser Ser Cys Ser Asp
        115                 120                 125

Leu Ser Ser Asn Cys Lys Ala His Ala Gly Phe Lys Asp Ala Trp Asp
    130                 135                 140

Glu Ile Ser Thr Ala Ala Lys Ala Val Val Ser Ala Lys Lys Ala
145                 150                 155                 160

Asn Pro Ser Tyr Thr Ile Val Ala Thr Gly His Ser Leu Gly Gly Ala
                165                 170                 175

Val Ala Thr Leu Ala Ala Ala Tyr Ile Arg Ala Ala Gly Tyr Ser Val
            180                 185                 190

Asp Leu Tyr Thr Phe Gly Ser Pro Arg Val Gly Asn Asp Tyr Phe Ala
```

```
                  195                 200                 205
Asn Phe Val Thr Ser Gln Ala Gly Ala Glu Tyr Arg Val Thr His Leu
210                 215                 220
Asp Asp Pro Val Pro Arg Leu Pro Pro Ile Leu Phe Gly Tyr Arg His
225                 230                 235                 240
Thr Ser Pro Glu Tyr Trp Leu Ser Asn Gly Gly Ala Thr Thr Thr Thr
                245                 250                 255
Tyr Ser Leu Ser Asp Ile Val Val Cys Glu Gly Ile Ala Asn Thr Asp
            260                 265                 270
Cys Asn Ala Gly Thr Leu Gly Leu Asp Ile Ile Ala His Leu Ile Tyr
        275                 280                 285
Phe Gln Asp Thr Ser Ala Cys Asn Thr Gly Phe Thr Trp Lys Arg Asp
    290                 295                 300
Thr Leu Ser Asp Ala Glu Leu Glu Glu Met Val Asn Lys Trp Ala Glu
305                 310                 315                 320
Gln Asp Val Glu Tyr Val Ala Asn Leu Thr Thr Thr Ala Ser Lys Arg
                325                 330                 335
Trp Lys Gly Ala Val Ala Asn
                340

<210> SEQ ID NO 4
<211> LENGTH: 348
<212> TYPE: PRT
<213> ORGANISM: Nectria species

<400> SEQUENCE: 4

Met Leu Leu Leu Pro Leu Leu Ser Ala Ile Thr Leu Ala Val Ala Ser
1               5                   10                  15
Pro Val Ala Leu Glu Asp Tyr Ala Asn Ser Leu Glu Asp Arg Ala Val
                20                  25                  30
Gly Val Ser Thr Thr Asp Phe Gly Asn Phe Lys Phe Tyr Ile Gln His
            35                  40                  45
Gly Ala Ala Ala Tyr Cys Asn Ser Asp Ala Ser Ala Gly Ser Lys Ile
        50                  55                  60
Thr Cys Ser Asn Asn Gly Cys Pro Thr Ile Gln Ser Asn Gly Val Thr
65                  70                  75                  80
Val Val Ser Ser Phe Ile Gly Ser Lys Thr Gly Ile Gly Gly Tyr Val
                85                  90                  95
Ala Thr Asp Pro Ile Arg Lys Glu Ile Val Val Ser Ile Arg Gly Ser
            100                 105                 110
Ser Asn Ile Arg Asn Trp Leu Thr Asn Leu Asp Phe Gly Gln Ser Asp
        115                 120                 125
Cys Ser Leu Val Ser Gly Cys Gly Val His Thr Gly Phe Gln Asn Ala
    130                 135                 140
Trp Asn Glu Ile Ala Asn Gln Val Thr Ala Ala Val Ala Lys Ala Gln
145                 150                 155                 160
Lys Ala Asn Pro Ser Phe Lys Val Ile Ser Thr Gly His Ser Leu Gly
                165                 170                 175
Gly Ala Val Ala Val Leu Ala Gly Ala Asn Leu Arg Val Gly Gly Thr
            180                 185                 190
Pro Val Asp Ile Tyr Thr Tyr Gly Ala Pro Arg Val Gly Asn Ala Gln
        195                 200                 205
Leu Ser Ala Phe Ile Ser Asn Gln Ala Gly Gly Glu Tyr Arg Ile Thr
    210                 215                 220
His Ala Ala Asp Pro Val Pro Arg Leu Pro Pro Leu Ile Phe Gly Tyr
```

```
            225                 230                 235                 240
Arg His Thr Ser Pro Glu Phe Trp Leu Ser Gly Gly Ser Gly Ser Thr
                245                 250                 255

Ile Asp Tyr Thr Ile Asp Ser Val Lys Val Cys Glu Gly Ala Ala Asn
                260                 265                 270

Leu Gly Cys Asn Gly Gly Thr Leu Gly Leu Asp Ile Ile Ala His Leu
            275                 280                 285

His Tyr Phe Gln Ala Thr Asp Ala Cys Asn Val Leu Ser Ile Ser Trp
        290                 295                 300

Arg Arg Tyr Arg Ser Ala Ser Val Gly Val Asp Lys Arg Ala Thr
305                 310                 315                 320

Met Thr Asp Ala Glu Leu Glu Lys Lys Leu Asn Ser Tyr Val Glu Leu
                325                 330                 335

Asp Lys Glu Tyr Val Lys Asn His Gln Asn Arg Ser
                340                 345

<210> SEQ ID NO 5
<211> LENGTH: 318
<212> TYPE: PRT
<213> ORGANISM: Fusarium heterosporum

<400> SEQUENCE: 5

Ala Val Gly Val Thr Ser Thr Asp Phe Thr Asn Phe Lys Phe Tyr Ile
1               5                   10                  15

Gln His Gly Ala Ala Ala Tyr Cys Asn Ser Gly Thr Ala Ala Gly Ala
                20                  25                  30

Lys Ile Thr Cys Ser Asn Asn Gly Cys Pro Thr Ile Glu Ser Asn Gly
            35                  40                  45

Val Thr Val Val Ala Ser Phe Thr Gly Ser Lys Thr Gly Ile Gly Gly
        50                  55                  60

Tyr Val Ser Thr Asp Ser Ser Arg Lys Glu Ile Val Val Ala Ile Arg
65                  70                  75                  80

Gly Ser Ser Asn Ile Arg Asn Trp Leu Thr Asn Leu Asp Phe Asp Gln
                85                  90                  95

Ser Asp Cys Ser Leu Val Ser Gly Cys Gly Val His Ser Gly Phe Gln
            100                 105                 110

Asn Ala Trp Ala Glu Ile Ser Ala Gln Ala Ser Ala Ala Val Ala Lys
        115                 120                 125

Ala Arg Lys Ala Asn Pro Ser Phe Lys Val Val Ala Thr Gly His Ser
130                 135                 140

Leu Gly Gly Ala Val Ala Thr Leu Ser Ala Ala Asn Leu Arg Ala Ala
145                 150                 155                 160

Gly Thr Pro Val Asp Ile Tyr Thr Tyr Gly Ala Pro Arg Val Gly Asn
                165                 170                 175

Ala Ala Leu Ser Ala Phe Ile Ser Asn Gln Ala Gly Gly Glu Phe Arg
            180                 185                 190

Val Thr His Asp Lys Asp Pro Val Pro Arg Leu Pro Pro Leu Ile Phe
        195                 200                 205

Gly Tyr Arg His Thr Thr Pro Glu Tyr Trp Leu Ser Gly Gly Gly Gly
    210                 215                 220

Asp Lys Val Asp Tyr Ala Ile Ser Asp Val Lys Val Cys Glu Gly Ala
225                 230                 235                 240

Ala Asn Leu Met Cys Asn Gly Gly Thr Leu Gly Leu Asp Ile Asp Ala
                245                 250                 255

His Leu His Tyr Phe Gln Ala Thr Asp Ala Cys Asn Ala Gly Gly Phe
```

```
                260                 265                 270
Ser Trp Arg Arg Tyr Arg Ser Ala Lys Arg Glu Ser Ile Asp Lys Arg
        275                 280                 285

Ala Thr Met Thr Asp Ala Gln Leu Glu Ala Lys Leu Asn Ser Tyr Val
    290                 295                 300

Ala Met Asp Gln Glu Tyr Val Lys Thr His Gln Asn Arg Thr
305                 310                 315

<210> SEQ ID NO 6
<211> LENGTH: 352
<212> TYPE: PRT
<213> ORGANISM: Fusarium semitectum

<400> SEQUENCE: 6

Met Arg Val Leu Ser Leu Leu Ser Val Ala Thr Phe Ala Val Ala Ser
1               5                   10                  15

Pro Leu Ser Val Glu Asp Tyr Ala Lys Ala Leu Asp Glu Arg Ala Val
            20                  25                  30

Ala Val Ser Asn Gly Asp Phe Gly Asn Phe Lys Phe Tyr Ile Gln His
        35                  40                  45

Gly Ala Ser Tyr Cys Asn Ser Asn Ala Ala Ala Gly Ala Lys Ile
    50                  55                  60

Thr Cys Gly Asn Asn Gly Cys Pro Thr Val Gln Ser Asn Gly Ala Thr
65                  70                  75                  80

Ile Val Ala Ser Phe Thr Gly Ser Lys Thr Gly Ile Gly Gly Tyr Val
                85                  90                  95

Ser Thr Asp Ser Ser Arg Lys Glu Ile Val Leu Ser Val Arg Gly Ser
            100                 105                 110

Ile Asn Ile Arg Asn Trp Leu Thr Asn Leu Asp Phe Gly Gln Glu Asp
        115                 120                 125

Cys Ser Leu Thr Ser Gly Cys Gly Val His Ser Gly Phe Gln Asn Ala
130                 135                 140

Trp Lys Glu Ile Ser Ala Ala Thr Ala Ala Val Ala Lys Ala Arg
145                 150                 155                 160

Lys Ala Asn Pro Ser Phe Lys Val Ile Ala Thr Gly His Ser Leu Gly
                165                 170                 175

Gly Ala Val Ala Thr Leu Ala Gly Ala Asn Leu Arg Val Gly Gly Thr
            180                 185                 190

Pro Val Asp Ile Tyr Thr Tyr Gly Ser Pro Arg Val Gly Asn Ser Gln
        195                 200                 205

Leu Ala Gly Phe Ile Ser Asn Gln Ala Gly Gly Glu Phe Arg Val Thr
210                 215                 220

Asn Ala Lys Asp Pro Val Pro Arg Leu Pro Pro Leu Val Phe Gly Tyr
225                 230                 235                 240

Arg His Thr Ser Pro Glu Tyr Trp Leu Ser Gly Ala Gly Gly Asp Lys
                245                 250                 255

Val Asp Tyr Thr Ile Asn Asp Ile Lys Val Cys Glu Gly Ala Ala Asn
            260                 265                 270

Leu Lys Cys Asn Gly Gly Thr Leu Gly Leu Asp Ile Asp Ala His Leu
        275                 280                 285

His Tyr Phe Gln Glu Thr Asp Ala Cys Ser Gly Gly Ile Ser Trp
    290                 295                 300

Arg Ser Arg Arg Tyr Arg Ser Ala Lys Arg Glu Asp Ile Ser Glu Arg
305                 310                 315                 320

Ala Ala Pro Met Thr Asp Ala Glu Leu Glu Lys Lys Leu Asn Asn Tyr
```

```
                    325                 330                 335
Val Glu Met Asp Lys Glu Tyr Val Lys Asn Asn Ala Ala Arg Thr Ser
            340                 345                 350

<210> SEQ ID NO 7
<211> LENGTH: 333
<212> TYPE: PRT
<213> ORGANISM: Fusarium solani

<400> SEQUENCE: 7

Met His Leu Ile Leu Ser Ile Leu Ser Ile Ile Ala Phe Thr Ala Ala
1               5                   10                  15

Gly Pro Val Pro Ser Val Asp Glu Asn Thr Arg Val Leu Glu His Arg
            20                  25                  30

Ala Leu Thr Val Thr Thr Gln Asp Leu Ser Asn Phe Arg Phe Tyr Leu
        35                  40                  45

Gln His Ala Asp Ala Ala Tyr Cys Asn Phe Asn Thr Ala Val Gly Lys
    50                  55                  60

Pro Val His Cys Ser Ala Gly Asn Cys Pro Asp Ile Glu Lys Asp Ala
65                  70                  75                  80

Ala Ile Val Val Gly Ser Val Val Gly Thr Lys Gly Ile Gly Ala
                85                  90                  95

Tyr Val Ala Thr Asp Asn Ala Arg Lys Glu Ile Val Ser Val Arg
            100                 105                 110

Gly Ser Ile Asn Val Arg Asn Trp Ile Thr Asn Phe Asn Phe Gly Gln
        115                 120                 125

Lys Thr Cys Glu Leu Val Ala Gly Cys Gly Val His Thr Gly Phe Leu
    130                 135                 140

Asp Ala Trp Glu Glu Val Ala Ala Asn Val Lys Ala Ala Val Ser Ala
145                 150                 155                 160

Ala Lys Thr Ala Asn Pro Thr Phe Lys Phe Val Val Thr Gly His Ser
                165                 170                 175

Leu Gly Gly Ala Val Ala Thr Ile Ala Ala Ala Tyr Leu Arg Lys Asp
            180                 185                 190

Gly Phe Pro Phe Asp Leu Tyr Thr Tyr Gly Ser Pro Arg Val Gly Asn
        195                 200                 205

Asp Phe Phe Ala Asn Phe Val Thr Gln Gln Thr Gly Ala Glu Tyr Arg
    210                 215                 220

Val Thr His Gly Asp Asp Pro Val Pro Arg Leu Pro Pro Ile Val Phe
225                 230                 235                 240

Gly Tyr Arg His Thr Ser Pro Glu Tyr Trp Leu Asp Gly Gly Pro Leu
                245                 250                 255

Asp Lys Asp Tyr Thr Val Thr Glu Ile Lys Val Cys Glu Gly Met Ala
            260                 265                 270

Asn Val Met Cys Asn Gly Gly Thr Ile Gly Leu Asp Ile Leu Ala His
        275                 280                 285

Ile Thr Tyr Phe Gln Ser Met Ala Thr Cys Ala Pro Ile Ala Ile Pro
    290                 295                 300

Trp Lys Arg Asp Met Ser Asp Glu Glu Leu Glu Lys Lys Leu Thr Gln
305                 310                 315                 320

Tyr Ser Glu Met Asp Gln Glu Phe Val Lys Gln Met Thr
                325                 330

<210> SEQ ID NO 8
<211> LENGTH: 333
<212> TYPE: PRT
```

<213> ORGANISM: Fusarium solani

<400> SEQUENCE: 8

Met His Leu Ile Leu Ser Ile Leu Ser Ile Ile Ala Phe Thr Thr Ala
1               5                   10                  15

Gly Pro Val Pro Ser Val Asp Glu Asn Thr Arg Val Leu Glu His Arg
            20                  25                  30

Ala Val Thr Val Thr Thr Gln Asp Leu Ser Asn Phe Arg Phe Tyr Leu
        35                  40                  45

Gln His Ala Asp Ala Ala Tyr Cys Asn Phe Asp Thr Ala Val Gly Lys
    50                  55                  60

Pro Val His Cys Ser Ala Gly Asn Cys Pro Asp Val Glu Gln Asp Ala
65                  70                  75                  80

Ala Ile Val Val Gly Ser Val Val Gly Thr Lys Thr Gly Ile Gly Ala
                85                  90                  95

Tyr Val Ala Thr Asp Asn Ala Arg Lys Glu Ile Val Val Ser Val Arg
            100                 105                 110

Gly Ser Ile Asn Val Arg Asn Trp Ile Thr Asn Phe Asn Phe Gly Gln
        115                 120                 125

Lys Thr Cys Asp Leu Val Ala Gly Cys Gly Val His Thr Gly Phe Leu
    130                 135                 140

Asp Ala Trp Glu Glu Val Ala Ala Asn Ile Lys Ala Ala Val Ser Ala
145                 150                 155                 160

Ala Lys Thr Ala Asn Pro Thr Phe Lys Phe Val Ala Thr Gly His Ser
                165                 170                 175

Leu Gly Gly Ala Val Ala Thr Ile Ala Ala Ala Tyr Leu Arg Lys Asp
            180                 185                 190

Gly Phe Pro Phe Asp Leu Tyr Thr Tyr Gly Ser Pro Arg Val Gly Asn
        195                 200                 205

Asp Phe Phe Thr Asn Phe Val Thr Gln Gln Thr Gly Ala Glu Tyr Arg
    210                 215                 220

Val Thr His Gly Asp Asp Pro Val Pro Arg Leu Pro Pro Ile Val Phe
225                 230                 235                 240

Gly Tyr Arg His Thr Ser Pro Glu Tyr Trp Leu Asp Gly Gly Pro Leu
                245                 250                 255

Asp Lys Asp Tyr Thr Val Ser Glu Ile Lys Val Cys Glu Gly Met Ala
            260                 265                 270

Asn Val Met Cys Asn Gly Gly Thr Ile Gly Leu Asp Ile Leu Ala His
        275                 280                 285

Ile Thr Tyr Phe Gln Ser Met Ala Thr Cys Ala Pro Ile Ala Ile Pro
    290                 295                 300

Trp Lys Arg Asp Met Ser Asp Glu Glu Leu Glu Lys Lys Leu Thr Gln
305                 310                 315                 320

Tyr Ser Glu Met Asp Gln Glu Phe Val Lys Gln Met Thr
                325                 330

<210> SEQ ID NO 9
<211> LENGTH: 269
<212> TYPE: PRT
<213> ORGANISM: Thermomyces lanuginosus

<400> SEQUENCE: 9

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

```
Asn Ile Thr Cys Thr Gly Asn Ala Cys Pro Glu Val Glu Lys Ala Asp
            35                  40                  45

Ala Thr Phe Leu Tyr Ser Phe Glu Asp Ser Gly Val Gly Asp Val Thr
 50                  55                  60

Gly Phe Leu Ala Leu Asp Asn Thr Asn Lys Leu Ile Val Leu Ser Phe
 65                  70                  75                  80

Arg Gly Ser Arg Ser Ile Glu Asn Trp Ile Gly Asn Leu Asn Phe Asp
                 85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265

<210> SEQ ID NO 10
<211> LENGTH: 183
<212> TYPE: PRT
<213> ORGANISM: Fusarium venenatum

<400> SEQUENCE: 10

Met Lys Phe Ser Ala Thr Ile Leu Ser Leu Leu Pro Ala Val Leu Ala
 1               5                  10                  15

Leu Pro Thr Gly Glu Asp Ala Ser Val Ser Lys Arg Gln Ser Val Asn
                20                  25                  30

Thr Val Thr Asp Gln Leu Leu Phe Ser Val Thr Leu Pro Gln Phe Thr
            35                  40                  45

Ala Arg Arg Asn Ala Arg Asp Pro Pro Thr Val Asp Trp Thr Ser Asp
 50                  55                  60

Gly Cys Thr Ser Ser Pro Asp Asn Pro Phe Gly Phe Pro Phe Ile Pro
 65                  70                  75                  80

Ala Cys Asn Arg His Asp Phe Gly Tyr His Asn Tyr Arg Ala Gln Ser
                 85                  90                  95

Arg Phe Thr Val Ser Ala Lys Ser Arg Ile Asp Asn Asn Phe Lys Thr
            100                 105                 110

Asp Leu Tyr Phe Gln Cys Gln Ser Ser Val Ser Gly Val Cys Arg
        115                 120                 125

Ala Leu Ala Asp Val Tyr Phe Ala Ala Val Arg Ala Phe Gly Gly Asp
130                 135                 140
```

```
Asp Ala Thr Pro Gly Lys Arg Asp Glu Ala Leu Val Lys Glu Tyr Glu
145                 150                 155                 160

Lys Lys Val Glu Val Tyr Asn Lys Leu Val Glu Ala Gln Lys Lys
                165                 170                 175

Gly Asp Leu Pro Arg Leu Asp
            180

<210> SEQ ID NO 11
<211> LENGTH: 95
<212> TYPE: PRT
<213> ORGANISM: Artificial sequence
<220> FEATURE:
<223> OTHER INFORMATION: Plectasin

<400> SEQUENCE: 11

Met Gln Phe Thr Thr Ile Leu Ser Ile Gly Ile Thr Val Phe Gly Leu
1               5                   10                  15

Leu Asn Thr Gly Ala Phe Ala Ala Pro Gln Pro Val Pro Glu Ala Tyr
            20                  25                  30

Ala Val Ser Asp Pro Glu Ala His Pro Asp Asp Phe Ala Gly Met Asp
        35                  40                  45

Ala Asn Gln Leu Gln Lys Arg Gly Phe Gly Cys Asn Gly Pro Trp Asp
    50                  55                  60

Glu Asp Asp Met Gln Cys His Asn His Cys Lys Ser Ile Lys Gly Tyr
65                  70                  75                  80

Lys Gly Gly Tyr Cys Ala Lys Gly Gly Phe Val Cys Lys Cys Tyr
                85                  90                  95

<210> SEQ ID NO 12
<211> LENGTH: 96
<212> TYPE: PRT
<213> ORGANISM: Artificial sequence
<220> FEATURE:
<223> OTHER INFORMATION: Monellin

<400> SEQUENCE: 12

Gly Glu Trp Glu Ile Ile Asp Ile Gly Pro Phe Thr Gln Asn Leu Gly
1               5                   10                  15

Lys Phe Ala Val Asp Glu Glu Asn Lys Ile Gly Gln Tyr Gly Arg Leu
            20                  25                  30

Thr Phe Asn Lys Val Ile Arg Pro Cys Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Tyr Ala Ser Asp Lys Leu Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95

<210> SEQ ID NO 13
<211> LENGTH: 85
<212> TYPE: PRT
<213> ORGANISM: Artificial Sequence
<220> FEATURE:
<223> OTHER INFORMATION: Protegrin

<400> SEQUENCE: 13

Ala Leu Ser Tyr Arg Glu Ala Val Leu Arg Ala Val Asp Arg Leu Asn
1               5                   10                  15

Glu Gln Ser Ser Glu Ala Asn Leu Tyr Arg Leu Leu Glu Leu Asp Gly
```

```
                    20                  25                  30
Thr Pro Lys Pro Val Ser Phe Thr Val Lys Glu Thr Val Cys Pro Arg
                35                  40                  45

Pro Thr Arg Gln Pro Pro Glu Leu Cys Asp Phe Lys Glu Asn Gly Arg
            50                  55                  60

Val Lys Gln Cys Val Gly Thr Val Thr Leu Asp Pro Leu Asp Ile Thr
65                  70                  75                  80

Cys Asn Glu Val Gln
                85

<210> SEQ ID NO 14
<211> LENGTH: 110
<212> TYPE: PRT
<213> ORGANISM: Artificial Sequence
<220> FEATURE:
<223> OTHER INFORMATION: Barnase

<400> SEQUENCE: 14

Ala Gln Val Ile Asn Thr Phe Asp Gly Val Ala Asp Tyr Leu Gln Thr
1               5                   10                  15

Tyr His Lys Leu Pro Asp Asn Tyr Ile Thr Lys Ser Glu Ala Gln Ala
                20                  25                  30

Leu Gly Trp Val Ala Ser Lys Gly Asn Leu Ala Asp Val Ala Pro Gly
            35                  40                  45

Lys Ser Ile Gly Gly Asp Ile Phe Ser Asn Arg Glu Gly Lys Leu Pro
        50                  55                  60

Gly Lys Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
                100                 105                 110

<210> SEQ ID NO 15
<211> LENGTH: 122
<212> TYPE: PRT
<213> ORGANISM: Artificial sequence
<220> FEATURE:
<223> OTHER INFORMATION: Cystatin

<400> SEQUENCE: 15

Gly Ser Ala Ser Ala Gln Ser Arg Thr Leu Ala Gly Gly Ile His Ala
1               5                   10                  15

Thr Asp Leu Asn Asp Lys Ser Val Gln Arg Ala Leu Asp Phe Ala Ile
                20                  25                  30

Ser Glu Tyr Asn Lys Val Ile Asn Lys Asp Glu Tyr Tyr Ser Arg Pro
            35                  40                  45

Leu Gln Val Met Ala Ala Tyr Gln Gln Ile Val Gly Gly Val Asn Tyr
        50                  55                  60

Tyr Phe Asn Val Lys Phe Gly Arg Thr Thr Cys Thr Lys Ser Gln Pro
65                  70                  75                  80

Asn Leu Asp Asn Cys Pro Phe Asn Asp Gln Pro Lys Leu Lys Glu Glu
                85                  90                  95

Glu Phe Cys Ser Phe Gln Ile Asn Glu Val Pro Trp Glu Asp Lys Ile
                100                 105                 110

Ser Ile Leu Asn Tyr Lys Cys Arg Lys Val
            115                 120
```

```
<210> SEQ ID NO 16
<211> LENGTH: 139
<212> TYPE: PRT
<213> ORGANISM: Artificial sequence
<220> FEATURE:
<223> OTHER INFORMATION: Apolipoprotein E

<400> SEQUENCE: 16

Gln Arg Trp Glu Leu Ala Leu Gly Arg Phe Trp Asp Tyr Leu Arg Trp
1               5                   10                  15

Val Gln Thr Leu Ser Glu Gln Val Gln Glu Glu Leu Leu Ser Ser Gln
            20                  25                  30

Val Thr Gln Glu Leu Arg Ala Leu Met Asp Glu Thr Met Lys Glu Leu
        35                  40                  45

Lys Ala Tyr Lys Ser Glu Leu Glu Glu Gln Leu Thr Pro Val Ala Glu
    50                  55                  60

Glu Thr Arg Ala Arg Leu Ser Lys Glu Leu Gln Ala Ala Gln Ala Arg
65                  70                  75                  80

Leu Gly Ala Asp Met Glu Asp Val Arg Gly Arg Leu Val Gln Tyr Arg
                85                  90                  95

Gly Glu Val Gln Ala Met Leu Gly Gln Ser Thr Glu Glu Leu Arg Val
            100                 105                 110

Arg Leu Ala Ser His Leu Arg Lys Leu Arg Lys Arg Leu Leu Arg Asp
        115                 120                 125

Ala Asp Asp Leu Gln Lys Arg Leu Ala Val Tyr
    130                 135

<210> SEQ ID NO 17
<211> LENGTH: 95
<212> TYPE: PRT
<213> ORGANISM: Artificial sequence
<220> FEATURE:
<223> OTHER INFORMATION: MON1 is a variant of Monellin

<400> SEQUENCE: 17

Gly Glu Trp Glu Ile Ile Asp Ile Gly Pro Glu Thr Lys Leu Val Gly
1               5                   10                  15

Tyr Val Ala Val Asp Glu Glu Tyr Val Ile Gly Gln Tyr Gly Arg Leu
            20                  25                  30

Thr Phe Asn Lys Val Ile Arg Pro Cys Met Lys Lys Thr Ile Tyr Glu
        35                  40                  45

Glu Asn Phe Arg Glu Ile Lys Gly Tyr Glu Tyr Gln Leu Tyr Val Tyr
    50                  55                  60

Ala Ser Asp Lys Leu Phe Arg Ala Asp Ala Ser Arg Asp Tyr Lys Thr
65                  70                  75                  80

Gly Gly Gly Lys Leu Leu Arg Phe Asn Gly Pro Val Pro Pro Pro
                85                  90                  95

<210> SEQ ID NO 18
<211> LENGTH: 95
<212> TYPE: PRT
<213> ORGANISM: Artificial sequence
<220> FEATURE:
<223> OTHER INFORMATION: MON2 is a variant of Monellin

<400> SEQUENCE: 18

Gly Glu Trp Glu Ile Ile Asp Ile Gly Pro Tyr Thr Asn Leu Leu Gly
1               5                   10                  15

Ala Leu Ala Val Asp Glu Glu Asn His Ile Gly Gln Tyr Gly Arg Leu
            20                  25                  30
```

```
Thr Val Asn Lys Val Ile Arg Pro Cys Met Lys Lys Thr Ile Tyr Glu
             35                  40                  45

Glu Asn Phe Arg Glu Ile Lys Gly Tyr Glu Tyr Gln Leu Tyr Val Tyr
         50                  55                  60

Ala Ser Asp Lys Leu Phe Arg Ala Asp Ile Ser Glu Asp Tyr Lys Thr
 65                  70                  75                  80

Gly Gly Gly Lys Leu Leu Arg Phe Asn Gly Pro Val Pro Pro Pro
                 85                  90                  95

<210> SEQ ID NO 19
<211> LENGTH: 8
<212> TYPE: PRT
<213> ORGANISM: Artificial sequence
<220> FEATURE:
<223> OTHER INFORMATION: Synthetic construct

<400> SEQUENCE: 19

Asn Gln Pro Asn Ile Pro Asp Ile
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic construct

<400> SEQUENCE: 20

Asn Gly Gly Thr Leu Gly Leu Asp Ile
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic construct

<400> SEQUENCE: 21

Asn Gln Pro Asn Ile Pro
1               5

<210> SEQ ID NO 22
<211> LENGTH: 6
<212> TYPE: PRT
<213> ORGANISM: Artificial sequence
<220> FEATURE:
<223> OTHER INFORMATION: Synthetic construct

<400> SEQUENCE: 22

Gly Gly Thr Leu Gly Leu
1               5

<210> SEQ ID NO 23
<211> LENGTH: 30
<212> TYPE: PRT
<213> ORGANISM: Artificial sequence
<220> FEATURE:
<223> OTHER INFORMATION: Synthetic construct

<400> SEQUENCE: 23

Ala Thr Met Thr Asp Ala Glu Leu Glu Lys Lys Leu Asn Ser Tyr Val
1               5                   10                  15

Gln Met Asp Lys Glu Tyr Val Lys Asn Asn Gln Ala Arg Ser
             20                  25                  30
```

<210> SEQ ID NO 24
<211> LENGTH: 30
<212> TYPE: PRT
<213> ORGANISM: Artificial sequence
<220> FEATURE:
<223> OTHER INFORMATION: Synthetic construct

<400> SEQUENCE: 24

Ala Thr Met Thr Glu Ala Glu Leu Glu Lys Lys Leu Asn Ser Tyr Val
1               5                   10                  15

Gln Met Asp Lys Glu Tyr Val Lys Asn Asn Gln Ala Arg Ser
            20                  25                  30

<210> SEQ ID NO 25
<211> LENGTH: 30
<212> TYPE: PRT
<213> ORGANISM: Artificial sequence
<220> FEATURE:
<223> OTHER INFORMATION: Synthetic construct

<400> SEQUENCE: 25

Ala Thr Met Thr Asp Ala Glu Leu Thr Lys Lys Leu Asn Ser Tyr Val
1               5                   10                  15

Gln Met Asp Lys Glu Tyr Val Lys Asn Asn Gln Ala Arg Ser
            20                  25                  30

<210> SEQ ID NO 26
<211> LENGTH: 30
<212> TYPE: PRT
<213> ORGANISM: Artificial sequence
<220> FEATURE:
<223> OTHER INFORMATION: Synthetic construct

<400> SEQUENCE: 26

Ala Thr Met Thr Asp Ala Glu Leu Glu Lys Arg Leu Asn Ser Tyr Val
1               5                   10                  15

Gln Met Asp Lys Glu Tyr Val Lys Asn Asn Gln Ala Arg Ser
            20                  25                  30

<210> SEQ ID NO 27
<211> LENGTH: 30
<212> TYPE: PRT
<213> ORGANISM: Artificial sequence
<220> FEATURE:
<223> OTHER INFORMATION: Synthetic construct

<400> SEQUENCE: 27

Ala Thr Met Thr Asp Ala Glu Leu Glu Lys Lys Leu Asn Ser Tyr Val
1               5                   10                  15

Gln Met Asp Lys Glu Glu Val Lys Asn Asn Gln Ala Arg Ser
            20                  25                  30

<210> SEQ ID NO 28
<211> LENGTH: 30
<212> TYPE: PRT
<213> ORGANISM: Artificial sequence
<220> FEATURE:
<223> OTHER INFORMATION: Synthetic construct

<400> SEQUENCE: 28

Ala Thr Met Thr Asp Ala Glu Leu Glu Lys Lys Leu Asn Ser Tyr Val
1               5                   10                  15

Gln Met Ala Lys Glu Tyr Val Lys Asn Asn Gln Ala Arg Ser
            20                  25                  30

```
<210> SEQ ID NO 29
<211> LENGTH: 30
<212> TYPE: PRT
<213> ORGANISM: Artificial sequence
<220> FEATURE:
<223> OTHER INFORMATION: Synthetic construct

<400> SEQUENCE: 29

Ala Thr Met Thr Asp Ala Glu Val Glu Lys Lys Leu Asn Ser Tyr Val
1               5                   10                  15

Gln Met Asp Lys Glu Tyr Val Lys Asn Asn Gln Ala Arg Ser
            20                  25                  30

<210> SEQ ID NO 30
<211> LENGTH: 30
<212> TYPE: PRT
<213> ORGANISM: Artificial sequence
<220> FEATURE:
<223> OTHER INFORMATION: Synthetic construct

<400> SEQUENCE: 30

Ala Thr Met Thr Asp Ala Glu Leu Glu Lys Lys Leu Asn Ser Tyr Val
1               5                   10                  15

Asn Met Asp Lys Glu Tyr Val Lys Asn Asn Gln Ala Arg Ser
            20                  25                  30

<210> SEQ ID NO 31
<211> LENGTH: 30
<212> TYPE: PRT
<213> ORGANISM: Artificial sequence
<220> FEATURE:
<223> OTHER INFORMATION: Synthetic construct

<400> SEQUENCE: 31

Ala Thr Met Thr Asp Ala Glu Leu Glu Lys Lys Leu Asn Ser Tyr Val
1               5                   10                  15

Gln Met Asp Ala Glu Tyr Val Lys Asn Asn Gln Ala Arg Ser
            20                  25                  30

<210> SEQ ID NO 32
<211> LENGTH: 22
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
```

```
<400> SEQUENCE: 32

Met Thr Asp Xaa Xaa Leu Glu Xaa Lys Leu Asn Xaa Tyr Val Xaa Xaa
1               5                   10                  15

Asp Xaa Glu Tyr Xaa Lys
            20
```